United States Patent
Kupper et al.

(10) Patent No.: US 9,399,061 B2
(45) Date of Patent: Jul. 26, 2016

(54) METHODS FOR DETERMINING EFFICACY OF TNF-α INHIBITORS FOR TREATMENT OF RHEUMATOID ARTHRITIS

(75) Inventors: Hartmut Kupper, Mutterstadt (DE); Jeffrey D. Kent, Deerfield, IL (US); Mary A. Cifaldi, Gurnee, IL (US); John L. Perez, Doylestown, PA (US); Gerd R. Burmester, Berlin (DE); Philip Mease, Seattle, WA (US); Daniel J. Lovell, Cincinnati, OH (US); Edward Keystone, Toronto (CA); Arthur Kavanaugh, San Diego, CA (US)

(73) Assignee: ABBVIE BIOTECHNOLOGY LTD, Hamilton (BM)

( * ) Notice: Subject to any disclaimer, the term of this patent is extended or adjusted under 35 U.S.C. 154(b) by 0 days.

(21) Appl. No.: 11/786,442

(22) Filed: Apr. 10, 2007

(65) Prior Publication Data
US 2008/0166348 A1    Jul. 10, 2008

Related U.S. Application Data

(60) Provisional application No. 60/899,262, filed on Feb. 2, 2007, provisional application No. 60/815,489, filed on Jun. 20, 2006, provisional application No. 60/809,770, filed on May 30, 2006, provisional application No. 60/902,427, filed on Feb. 21, 2007, provisional application No. 60/790,909, filed on Apr. 10, 2006, provisional application No. 60/858,376, filed on Nov. 10, 2006, provisional application No. 60/909,683, filed on Apr. 2, 2007.

(51) Int. Cl.
*A61K 39/00* (2006.01)
*A61K 39/395* (2006.01)
*A61K 39/39* (2006.01)
*C07K 16/24* (2006.01)
*A61K 39/09* (2006.01)
*A61K 39/145* (2006.01)
*C12N 7/00* (2006.01)

(52) U.S. Cl.
CPC ............. *A61K 39/39* (2013.01); *A61K 39/092* (2013.01); *A61K 39/145* (2013.01); *A61K 39/3955* (2013.01); *C07K 16/241* (2013.01); *C12N 7/00* (2013.01); *A61K 2039/505* (2013.01); *A61K 2039/55516* (2013.01); *C07K 2316/96* (2013.01); *C07K 2317/21* (2013.01); *C07K 2317/30* (2013.01); *C12N 2760/16034* (2013.01); *C12N 2760/16071* (2013.01)

(58) Field of Classification Search
CPC ............. A61K 38/1774; A61K 2039/505; A61K 39/3955; A61K 39/395; A61K 38/191; A61K 47/48538; A61K 49/16; A61K 38/57; C07K 16/18; C07K 16/241; C07K 16/46; C07K 14/70503; C07K 16/00
See application file for complete search history.

(56) References Cited

U.S. PATENT DOCUMENTS

| | | |
|---|---|---|
| 5,231,024 A | 7/1993 | Moeller |
| 5,336,181 A | 8/1994 | Nakao et al. |
| 5,654,407 A | 8/1997 | Boyle |
| 5,656,272 A | 8/1997 | Le et al. |
| 5,698,195 A | 12/1997 | Le |
| 5,705,389 A | 1/1998 | Braham et al. |
| 5,795,967 A | 8/1998 | Aggarwal |
| 5,859,205 A | 1/1999 | Adair |
| 5,877,293 A | 3/1999 | Adair |
| 5,888,511 A | 3/1999 | Skurkovich |
| 5,929,212 A | 7/1999 | Jolliffe |
| 5,945,098 A | 8/1999 | Sarno |
| 5,994,510 A | 11/1999 | Adair |
| 6,015,557 A | 1/2000 | Tobinick |
| 6,024,938 A | 2/2000 | Corbo et al. |
| 6,090,382 A | 7/2000 | Salfeld |
| 6,171,586 B1 | 1/2001 | Lam et al. |
| 6,214,870 B1 | 4/2001 | McClure |
| 6,235,281 B1 | 5/2001 | Stenzel |
| 6,258,562 B1 | 7/2001 | Salfeld |
| 6,270,766 B1 | 8/2001 | Feldman |
| 6,372,715 B1 * | 4/2002 | Kaltwasser et al. ............. 514/2 |
| 6,379,666 B1 | 4/2002 | Tobinick |
| 6,419,944 B2 | 7/2002 | Tobinick |
| 6,423,321 B2 | 7/2002 | Tobinick |
| 6,448,380 B2 | 9/2002 | Rathjen |
| 6,451,983 B2 | 9/2002 | Rathjen |
| 6,498,237 B2 | 12/2002 | Rathjen |
| 6,509,015 B1 | 1/2003 | Salfeld |
| 6,537,549 B2 * | 3/2003 | Tobinick .................... 424/134.1 |

(Continued)

FOREIGN PATENT DOCUMENTS

| | | |
|---|---|---|
| CA | 2243459 | 8/1997 |
| CA | 2261630 | 2/1998 |

(Continued)

OTHER PUBLICATIONS

Bennett et al., Rheumatology 44:1026, 2005.*
Wolfe et al. 2005. J. Rheumatology 32:2410-2415.*
Brocq et al. 2004. Joint Bone Spine 71:601-603.*
Fransen et al. 2005. Clin. Exp. Rheum. 23(Suppl. 39):593-599.*
Ranganathan et al. 2003. Ann Rheum Dis. 62:4-9.*
Keystone et al. 2012. Rheumatology. 51:v48-v54.*
Abbott Laboratories "Humira (Adalimumab)," 2003, http://www.fda.gov/ohrms/dockets/ac/03/briefing/3930B1_02_A Abbott-Humira.pdf.

(Continued)

*Primary Examiner* — Shulamith H Shafer
(74) *Attorney, Agent, or Firm* — Foley Hoag LLP

(57) ABSTRACT

The invention provides methods, uses and compositions for the treatment of rheumatoid arthritis. The invention describes methods and uses for treating rheumatoid arthritis wherein a TNFα inhibitor, such as a human TNFα antibody, or antigen-binding portion thereof. Also described are methods for determining the efficacy of a TNFα inhibitor for treatment of rheumatoid arthritis in a subject.

6 Claims, 33 Drawing Sheets

(56) References Cited

U.S. PATENT DOCUMENTS

| | | |
|---|---|---|
| 6,562,006 B1 | 5/2003 | Hjertman et al. |
| 6,593,458 B1 | 7/2003 | Rathjen |
| 6,652,854 B2 | 11/2003 | Mohler et al. |
| 7,012,135 B2 | 3/2006 | Athwal |
| 7,070,775 B2 | 7/2006 | Le |
| 7,153,507 B2 * | 12/2006 | van de Winkel et al. .. 424/145.1 |
| 7,192,584 B2 | 3/2007 | Le |
| 7,223,394 B2 | 5/2007 | Salfeld et al. |
| 7,250,165 B2 | 7/2007 | Heavner et al. |
| 7,276,239 B2 | 10/2007 | Le |
| 7,541,031 B2 | 6/2009 | Salfeld et al. |
| 7,588,761 B2 | 9/2009 | Salfeld et al. |
| 7,863,426 B2 | 1/2011 | Wan et al. |
| 7,919,264 B2 | 4/2011 | Maksymowych et al. |
| 8,034,906 B2 | 10/2011 | Borhani |
| 8,092,998 B2 | 1/2012 | Stuhlmuller et al. |
| 8,093,045 B2 | 1/2012 | Pla et al. |
| 8,187,836 B2 | 5/2012 | Hsieh et al. |
| 8,197,813 B2 | 6/2012 | Salfeld et al. |
| 8,206,714 B2 | 6/2012 | Salfeld et al. |
| 8,216,583 B2 | 7/2012 | Kruase |
| 8,231,876 B2 | 7/2012 | Wan et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani |
| 8,455,219 B2 | 6/2013 | Hsieh |
| 8,636,704 B2 | 1/2014 | Shang et al. |
| 8,663,945 B2 | 3/2014 | Pla et al. |
| 8,679,061 B2 | 3/2014 | Julian et al. |
| 8,747,854 B2 | 6/2014 | Okun et al. |
| 8,753,633 B2 | 6/2014 | Salfeld et al. |
| 8,753,839 B2 | 6/2014 | Fraunhofer et al. |
| 2001/0004456 A1 | 6/2001 | Tobinick |
| 2001/0016195 A1 | 8/2001 | Tobinick |
| 2001/0021380 A1 | 9/2001 | Pluenneke |
| 2001/0026801 A1 | 10/2001 | Tobinick |
| 2002/0022720 A1 | 2/2002 | Le et al. |
| 2002/0114805 A1 | 8/2002 | Le |
| 2003/0012786 A1 | 1/2003 | Teoh |
| 2003/0049725 A1 * | 3/2003 | Heavner et al. .............. 435/69.1 |
| 2003/0092059 A1 | 5/2003 | Salfeld |
| 2003/0161828 A1 | 8/2003 | Abdekghany et al. |
| 2003/0206898 A1 | 11/2003 | Fischkoff |
| 2003/0219438 A1 | 11/2003 | Salfeld |
| 2003/0235585 A1 | 12/2003 | Fischkoff |
| 2004/0009172 A1 | 1/2004 | Fischkoff |
| 2004/0033228 A1 | 2/2004 | Krause |
| 2004/0120952 A1 | 6/2004 | Knight et al. |
| 2004/0126372 A1 | 7/2004 | Banerjee |
| 2004/0126373 A1 | 7/2004 | Banerjee |
| 2004/0131614 A1 | 7/2004 | Banerjee |
| 2004/0136989 A1 | 7/2004 | Banerjee |
| 2004/0136990 A1 | 7/2004 | Banerjee |
| 2004/0136991 A1 | 7/2004 | Banerjee |
| 2004/0151722 A1 | 8/2004 | Banerjee |
| 2004/0166111 A1 | 8/2004 | Kaymkcalan |
| 2004/0170626 A1 | 9/2004 | Schuurman |
| 2004/0219142 A1 | 11/2004 | Banerjee |
| 2005/0123541 A1 | 6/2005 | Heavner et al. |
| 2005/0249735 A1 | 11/2005 | Le et al. |
| 2005/0255104 A1 | 11/2005 | Le |
| 2005/0255532 A1 | 11/2005 | Ruben et al. |
| 2006/0009385 A1 | 1/2006 | Hoffman |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0153846 A1 | 7/2006 | Krause |
| 2006/0246073 A1 | 11/2006 | Knight et al. |
| 2007/0003548 A1 | 1/2007 | Heavner et al. |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0196373 A1 | 8/2007 | Le et al. |
| 2007/0202104 A1 | 8/2007 | Banerjee et al. |
| 2007/0249813 A1 | 10/2007 | Salfeld et al. |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0118496 A1 | 5/2008 | Medich |
| 2008/0131374 A1 | 6/2008 | Medich |
| 2008/0166348 A1 | 7/2008 | Kupper |
| 2008/0193466 A1 | 8/2008 | Banerjee |
| 2008/0227136 A1 | 9/2008 | Pla |
| 2008/0311043 A1 | 12/2008 | Hoffman |
| 2009/0017472 A1 | 1/2009 | Stuhlmuller |
| 2009/0028794 A1 | 1/2009 | Medich |
| 2009/0068172 A1 | 3/2009 | Kaymakcalan |
| 2009/0110679 A1 | 4/2009 | Li et al. |
| 2009/0123378 A1 | 5/2009 | Wong et al. |
| 2009/0155205 A1 | 6/2009 | Salfeld et al. |
| 2009/0226530 A1 | 9/2009 | Lassner |
| 2009/0258018 A1 | 10/2009 | Medich et al. |
| 2009/0271164 A1 | 10/2009 | Peng |
| 2009/0280065 A1 | 11/2009 | Willian |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong |
| 2010/0040630 A1 | 2/2010 | Elden |
| 2010/0278822 A1 | 11/2010 | Frauhofer |
| 2011/0171227 A1 | 7/2011 | Okun |
| 2012/0014956 A1 | 1/2012 | Kupper |
| 2012/0039900 A1 | 2/2012 | Stuhlmuller |
| 2012/0107783 A1 | 5/2012 | Julian et al. |
| 2012/0129185 A1 | 5/2012 | Maksymowych |
| 2012/0171123 A1 | 7/2012 | Medich |
| 2012/0177596 A1 | 7/2012 | Fischkoff |
| 2012/0258114 A1 | 10/2012 | Salfeld et al. |
| 2012/0282262 A1 | 11/2012 | Okun |
| 2012/0282270 A1 | 11/2012 | Krause |
| 2013/0004507 A1 | 1/2013 | Fischkoff |
| 2013/0028903 A1 | 1/2013 | Wan et al. |
| 2013/0115224 A1 | 5/2013 | Salfeld et al. |
| 2013/0122011 A1 | 5/2013 | Hoffman |
| 2013/0122018 A1 | 5/2013 | Salfeld et al. |
| 2013/0156760 A1 | 6/2013 | Fraunhofer |
| 2013/0195888 A1 | 8/2013 | Wang |
| 2013/0243763 A1 | 9/2013 | Banerjee |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0309242 A1 | 11/2013 | Wan et al. |
| 2013/0309309 A1 | 11/2013 | Borhani |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0344537 A1 | 12/2013 | Hsieh |
| 2014/0086929 A1 | 3/2014 | Krause |
| 2014/0086930 A1 | 3/2014 | Krause |
| 2014/0086931 A1 | 3/2014 | Krause |
| 2014/0127222 A1 | 5/2014 | Krause |
| 2014/0134674 A1 | 5/2014 | Pla et al. |
| 2014/0134675 A1 | 5/2014 | Pla et al. |

FOREIGN PATENT DOCUMENTS

| | | |
|---|---|---|
| CN | 1215407 A | 4/1999 |
| EP | 0492448 A1 | 7/1992 |
| EP | 0186833 B1 | 8/1992 |
| EP | 0212489 B1 | 1/1994 |
| EP | 0366043 B1 | 3/1994 |
| EP | 0101681 B1 | 12/1994 |
| EP | 0659766 A1 | 6/1995 |
| EP | 0351789 B1 | 11/1998 |
| EP | 0614984 B1 | 8/2001 |
| EP | 1174148 | 1/2002 |
| EP | 1254666 | 11/2002 |
| GB | 2279077 | 12/1994 |
| HU | 215242 | 7/1991 |
| HU | 211626 | 12/1995 |
| WO | WO 91/02078 A1 | 2/1991 |

(56) References Cited

FOREIGN PATENT DOCUMENTS

| | | |
|---|---|---|
| WO | WO 91/09967 A1 | 7/1991 |
| WO | WO 92/11383 A1 | 7/1992 |
| WO | WO 92/16553 A1 | 10/1992 |
| WO | WO 93/06213 A1 | 4/1993 |
| WO | WO 93/11793 A1 | 6/1993 |
| WO | WO 94/29347 A1 | 12/1994 |
| WO | WO 95/23813 A1 | 9/1995 |
| WO | WO 97/04801 | 2/1997 |
| WO | WO 97/29131 A1 | 8/1997 |
| WO | WO 98/05357 A1 | 2/1998 |
| WO | WO 98/56418 | 12/1998 |
| WO | WO 00/51637 | 9/2000 |
| WO | WO 01/00229 A1 | 1/2001 |
| WO | WO 01-37874 | 5/2001 |
| WO | WO 01-47554 | 7/2001 |
| WO | WO-01/62272 | 8/2001 |
| WO | WO 01/94585 | 12/2001 |
| WO | WO 02/12502 | 2/2002 |
| WO | WO 02/096461 | 12/2002 |
| WO | WO 02/100330 A2 | 12/2002 |
| WO | WO 03/016468 | 2/2003 |
| WO | WO 2004/053064 | 6/2004 |
| WO | WO 2006/041970 A2 | 4/2006 |

OTHER PUBLICATIONS

Abraham et al., "Efficacy and Safety of Monoclonal Antibody to Human Tumor Necrosis Factor a in Patients with Sepsis Syndrome," 1995, JAMA, 273 (12): 934-941.

Arthur et al., "Safety of self-injection of gold and methotrexate," 1999 J Rheumatol., 26(2): 302-5.

Asli, Bouchra et al., "Inhibition of Tumor Necrosis Factor a and Ankylosing Spondylitis," N. Engl. J. Med., Vo. 348 (4): 359-361.

Aulton, Pharmaceutics: The Science of Dosage Form Design, $2^{nd}$ Ed., 2001, pp. 275-288.

Avery RK, "Vaccination of the Immunosuppressed Adult Patient with Rheumatologic Disease," 1999, Rheum Dis Clin North Am, vol. 25(3): 567-84.

Awni WM, "Steady-State Pharmacokinetics (PK) of Adalimumab (Humira®) Following 40 mg Subutaneous (sc) Injection Every Other Week (eow) in Rheumatoid Arthritis Patients (RA) With and Without Methotrexate (MTX) Background Therapy," 2003, 48(9)(Suppl): S140 (Poster 255).

Bang & Keating, "Adalimumab: a review of its use in Rheumatoid Arthritis," 2004, Biodrugs 18(2): 121-139.

Bansback et al., "Cost Effectiveness of Adalimumab (Humiraä, Abbott) in the Treatment of Patients with Moderate to Severe Rheumatoid Arthritis (RA)", 2003, Arthritis Rheum., vol. 48 (Suppl. 9): S611.

Barbuto, "Production of Neutralizing Antibodies to Tumor Necrosis Factor by Human Tumor-Infiltrating B Lymphocytes," 1993, Proc. Am. Assoc. Cancer Res., 34:487, Abstr. 2904.

Barrera, "Effects of treatment with a fully human anti-tumour necrosis factor alpha monoclonal antibody on the local and systemic homeostasis of interleukin 1 and TNFalpha in patients with rheumatoid arthritis," 2001, Ann Rheum Dis, vol. 60:660-669.

Barrera et al., "Drug survival, efficacy and toxicity of monotherapy with a fully human anti-tumour necrosis factor-a antibody compared with methotrexate in long-standing rheumatoid arthritis," 2002, Rheumatology, vol. 41: 430-439.

Barrera et al., "Effect of a Fully Human Anti-TNF a Monoclonal Antibody on the Local and Systemic Expression of TNFa and IL-1b," 1999, Arthritis Rheum., vol. 42(9 Suppl.): S75.

Bendtzen, "Auto-antibodies to 1L-1a and TNFa in Normal Individuals and in Infectious and Immunoinflammatory Disorders," 1990, The physiological and Pathological Effects of Cytokines, 447-52.

Boeger, Ca.A. et al., "Treatment of anklyosing spondylitis with infliximab," 2001, Ann. Rheum Dis., vol. 60(12): 1159-1160.

Boekstegers et al., "Repeated administration of a F(ab')2 fragment of an anti-tumor recrosis factor alpha monoclonal antibody in patients with sever sepsis: effects on the cardiovascular system and cytokine levels," 1994, Shock, vol. 1(4): 237-245.

Bombardier C, "Pattern of DMARD use in a North American Cohort of Patients with Early Rheumatoid Arthritis (RA) (SONORA)." 2002, Arthritis Rheum, 46(9)(Suppl):S344(Abst 871).

Bobardieri S, Tzioufas AG, "Efficacy Evaluation of Adalimumab (Humira®) by Dose and Administration Route of Concomitant Methotrexate in Widespread Clinical Practice (REACT Trial." EULAR Annual Meeting, Jun. 8-11, 2005, Vienna, Austria (Poster SAT0061).

Bombardieri S, Tzioufas AG, McKenna, et al., Adalimumab (Humira®) Is Effective in Treating Patients with Rheumatoid Arthritis Who Previously Failed Etanercept and/or Infliximab in Real-Life Clinical Settings. Poster Presentation 294 at the 2005 Annual Scientific Meeting of the American College of Rheumatology, Nov. 2-17, 2005, San Diego, CA.

Borigini, "Innovative treatment approaches for rheumatoid arthritis. Combination therapy." 1995, Baillere's Clinical Rheumatology, vol. 9, No. 4, London, GB, pp. 698-710.

Boyle, "A Novel Monoclonal Human IgM Autoantibody which Binds Recombinant Human and Mouse Tumor Necrosis Factor-α," 1993, Cell. Immunol. 152: 556-68.

Boyle, "The B5 Monoclonal Human Autoantibody Binds to Cell Surface TNFα on Human Lymphoid Cells and Cell Lines and Appears to Recognize a Novel Epitope." 1993, Cell. Immunol., 152:569-81.

Brandt, Jan et al., "Successful Short Term Treatment of Severe Undifferentiated Spondyloarthropathy with the Anti-Tumor Necrosis Factor-α Monoclonal Antibody Infliximab." 2000, Arthritis & Rheumatism, vol. 43(6): 1346-1352.

Brandt, Jan et al. "Successful Treatment of Active Ankylosing Spondylitis with the Anti-Tumor Necrosis Factor α Monoclonal Antibody Infliximab" 2000, Arthritis & Rheumatism, vol. 43(6): 1346-1352.

Braun, J. et al., "Anti-TNFα: a new dimension in the pharmacotherapy of the spondyloarthropathies!?" 2000, Ann. Rheum. Dis., vol. 56(6): 404-407.

Braun, J. et al. "Anti-tumour necrosis factor α therapy for ankylosing spondylitis: international experience." 2000, Ann. Rheum. Dis., vol. 61(Suppl. III):iii51-iii60.

Braun, J. et al., "International ASAS consensus statement for the use of anti-tumour necrosis factor agents in patients with ankylosing spondylitis." 2003, Ann. Rheum. Dis., vol. 62:817-824.

Braun, J. et al., "Treatment of active ankylosing spondylitis with infliximab: a randomised controlled multicentre trial." 2002, The Lancet, vol. 359(9313):1187-1193.

Braun, Juergen et al., "Biologic therapies in the spondyloarthritis: new opportunities, new challenges." 2003, Current Opinion in Rheumatology, vol. 13:394-407.

Braun, Juergen et al., "Novel approaches in the treatment of ankylosing spondylitis and other spondyloarthritides." 2003, Expert Opin. Investig. Drugs., Vo 12(7):1097-1109.

Braun, Juergen et al., "Therapy of ankylosing spondylitis and other spondyloarthritides: established medical treatment, anti-TNF-α therapy and other novel approaches." 2002, Arthritis Res., vol. 4:307-321.

Braun, Juergen et al., "New Treatment options in spondyloarthropathies: increasing evidence for significant efficacy of anti-tumor necrosis factor therapy." 2001, Curr. Opin. Rheumatol., vol. 13:245-249.

Breban, M. et al., "Efficacy of infliximab in refractory ankylosing spondylitis: results of a six-month open-label study." 2002, Rheumatology, vol. 41:1280-1285.

Breedveld et al., "Sustained Efficacy over 5 Years with Adalimumab (Humiraa) in Patients with Active Rheumatoid Arthritis." 2003, Arhtritis Rheum., vol. 48(Suppl. 9): S118.

Breedveld et al., "Sustained Efficacy Over 4 Years with Adalimumab in Patients with Active Rheumatoid Arthritis." 2003, Ann. Rheum. Dis., vol. 62(Suppl. 1): 169.

Breedveld F. "The long-term efficacy and safety of adalimumab (D2E7), the fully human anti-tnf monoclonal antibody, in combination with methotrexate in the treatment of rheumatoid arthritis: Results of a 2 year study." 2002, J Clin Rheum 2002:8(Suppl):S46(Abst 20).

(56) References Cited

OTHER PUBLICATIONS

Breedveld FC, "The Fully Human Anti-TNF Antibody Adalimumab (D2E7) in Combination With Methotrexate (MTX) in the Treatment of Active Rheumatoid Arthritis: Results of a 2-Year Study." Presented at: The Annual Meeting of the European League Against Rheumatism (EULAR), Prague, Czech Republic, Jun. 2001.
Breedveld FC, Weisman MH, Kavanaugh AF, et al., "The Efficacy and Safety of Adalimumab (Humira®) Plus Methotrexate vs. Adalimumab Alone or Methotrexate Alone in the Early Treatment of Rheumatoid Arthritis (RA): 1- and 2-Year Results of the PREMIER Study." 2005 EULAR Annual Meeting, Jun. 8-11, 2005, Vienna Austria (Oral Presentation OP013).
Brekke et al., "Therapeutic Antibodies for Human Diseases at the Dawen of the Twenty-first Century." 2002, Nature, vol. 2:52-62.
Bresnihan et al., "The safety and efficacy of interleukin-1 receptor antagonist in the treatment of rheumatoid arthritis." 2001, Semin Arthritis Rheum., 30(5 Suppl 2):17-20.
Brocq et al., "Adalimumab in rheumatoid arthritis after failed infliximab and/or etanercept therapy: experience with 18 patients." 2004, Joint Bone Spine, 71: 601-603.
Bruno et al., "Bone metabolism changes during anti-TNF-alpha therapy in patients with active rheumatoid arthritis." 2006, Annals of the New York Academy of Science 1069: 420-427.
Buckley, "Calcium and vitamin D3 supplementation prevents bone loss in the spine secondary to low dose corticalsteroids in patients with rheumatoid arthritis." 1996, Annals of Internal Medicine 125(12): 961-968.
Burmester et al., "Effect of Dose Inerruptions on the Efficacy and Safety of Adalimumab in Patients with RA." 2003 Ann. Rheum. Dis., vol. 62(Suppl. 1) 192.
Burmester et al., Long-Term Efficacy and Safety of Adalimumab (D2E7) Monotherapy in Patients With DMARD-Refractory Rheumatoid Arthritis—Results From a 2-Year Study. 2002, Arthritis Rheum., vol. 46(9 Suppl.): S537.
Burmester et al., "Sustained Efficacy of Adalimumab Monotherapy for More than Four years in DMARD-Refractory RA." 2003 Ann. Rheum. Dis., vol. 62(Suppl.1): 192-3.
Burmester GR, Monteagudo Saez I, Malaise MG, et al., "Adalimumab (Humira®) is Effective in Patients who Have Previously Been Treated With TNF-Antagonists (Etanercept and/or Infliximab) in Widespread Clinical Practic: 12-Week Outcomes in the React Trial." 2005 EULAR Annual Meeting, Jun. 8-11, 2005, Vienna, Austria (Poster SAT0047).
Burmester GR, Monteagudo Saez I, Malaise MG, et al., "Adalimumab (Humira®) is Effective and Safe in Treating Rheumatoid Arthritis (RA) in Real-Life Clinical Practice: 1-Year Results of the ReAct Study." Poster Presentation 1436 at the 2005 Annual Scientific Meeting of the American College of Rheumatology, Nov. 12-17, 2005, San Diego, California.
Burmester GR, Wordsworth P, Mariett X, et al. Efficacy and Safety of Adalimumab (Humira) in European Clinical Practice: The ReAct Trial. (Rheumatology 2005; 44(Suppl 1): 123.) Oral Presentation OP62 at the BSR Annual Meeting, Apr. 21, 2005, Birmingham, UK.
Caporali et al., "Influenza may influence rheumatoid arthritis." 2000 J. Rheumatol. (Feb; 27(2): 553-4.
Carlin, et al., "A 50% Reduction in the Psoriasis Area and Severity Index (PASI 50) is a Clinically Significant Endpoint in the Assessment of Psoriasis." 2003 Journal of the American Academy of Dermatology, vol. 50(6):859-866.
Case, "Old and New Drugs Used in Rheumatoid Arthritis: A Historical Perspective: Part 2: The Newer Drugs and Drug Strategies," 2001 Am J Therapeutics 8(3):163-79.
Casset, Florence et al., "A peptide mimetic of an anti-CD4 monoclonal antibody by rational design." 2003 Biochemical and Biophysical Reserch Communication, 307: 198-205.
National Institutes of Health definition of the term "dose," 2009, nlm.nih.gov/medlineplus/mplusdictionary.html Nov. 23, 2009.
Chartash et al., "Adalimumab Improves Fatigue in patients with Active Rheumatoid Arthritis." 2003 Ann. Rheum. Dis., vol. 62(Suppl. 1):349.
Chen, "Epidemiology of Autommune reactions induced by vaccination." 2001 J Autoimmun. 16(3): 309-18.
Cherouvim, E.P. et all., "Infliximab Therapy for Patients With Active and Refractory Spondyloarthropathies at the Dose of 3 mg/kg, A 20-Month Open Treatment." 2004 Journal of Clinical Rheumatology, vol. 1094):162-168.
Chow, "Effect of monoclonal antibody on human tumor necrosis factor (TNF MAb) on TNFα, IL-1β, and IL-6 levels in patients with sepsis syndrome." 1994 Clinical Research, 42:2 299A.
Chung C., Sokka T, Pincus T, et al., "RA Patients in 4 Adalimumab Clinical Trials: 78% Have DAS of 5.1 or More, and 90% Have a Score of 5 or More on a Continuous Index of 3 Patient Questionnaire Scores for Physical Function, Pain and Global Status." 2005 EULAR Annual Meeting, Jun. 8-11, 2005, Vienna, Austria (Poster THU0263).
Cifaldi M, Sterz R, Dietz B, Chmiel J,Spencer-Green GT., "Criteria-based Interpretation of SF-36 Improvements from Adalimumab Plus Methotrexate (MTX) Combination Therapy Vs. MTX Alone in Early Rheumatoid Arthritis (RA)." 2005 ISPOR Eight Annual European Congress Contributed Presentation Abstracts. [Poster Presentation, Nov. 6, 2005, PAR19].
Cividino A., "Efficacy and Safety of Adalimumab (Humira®) in Canadian Clinical Practice. A Comparison of the Canadian and European Practice: The CanAct and the ReAct Trial." 2005 EULAR Annual Meeting, Jun. 8-11, 2005, Vienna Austria (Poster SAT0050).
Cleland, Jeffrey L. et al. A specific molar ratio of stabilizer to protein is required for storage stability of a lyophilized monoclonal antibody. 2001 Journal of Pharm. Sciences, vol. 90, No. 3: 310-321.
Cohen et al. Intersept: An international, multicenter, placebo-controlled trial of monoclonal anitbody to human tumor necrosis factor-a in patients with sepsis 1996 Crit Care Med, vol. 24(9):1431-1440.
Cohen SB, Kavanaugh AF, Emery P, et al. C-Reactive Protein Predicts Treatment Response to Adalimumab (Humira®) in Patients With Rheumatoid Arthritis. 2005 2005 EULAR Annual Meeting, Jun. 8-11, 2005, Vienna, Austria (Poster SAT0086).
Cox A directory of human germ-line $V_K$-segments reveals a strong bias in their usage 1994 Eur. J. Immunol., 24(2):827-36.
Database Geneseq Anti-TNF-alpha antibody heavy chain variable region. 1998 EBI accession No. GSP:AAW27569; Database accession No. AAW27569.
Database Geneseq Anti-TNF-alpha antibody light chain variable region. 1998EB1 accession No. GSP:AAW27568; Database accession No. AAW27568.
Dayer, Jean-Michel et al.Anti-TNF-α Therapy for Ankylosing Spondylitis—A Specific or Nonspecific Threatment?2002 N. Engl. J. Med., vol. 346(18):1399-1400.
De Keyser, Filip et al.Anti-TNF-alpha therapy in ankylosing spondylitis2006Cytokine, vol. 33:294-298.
den Broeder, "The Effect of D2E7, a new human anti-TNF a monoclonal antibody, on the oxidative burst of PMN in patients with RA." 1998 Arthritis and Rheumatism, vol. 41(9):S57.
den Broeder et al., "A Single Dose, Placebo Controlled Study of the Fully Human Anti-Tumor Necrosis Factor-a Antibody Adalimumab (D2E7) in Patients with Rheumatoid Arthritis." 2002The Journal of Rheumatology, vol. 29(11):2288-2298.
den Broeder et al., "Long term anti-tumour necrosis factor a monotherapy in rheumatoid arthritis: effect on radiological course and prognostic value of markers of cartilage turnover and endothelial activation." 2002 Ann. Rheum. Dis., vol. 61:311-318.
Dernis, E. et al., "Infliximab in spondylarthropathy—Influence on bone density." 2002 Clin. Exp. Rheumatol., vol. 20(Suppl. 28):S185-S186.
Dick, "Derivation of knee joint synovial perfusion. Using the Xenon. (133Xe) clearance technique." 1970 Annals of the Rheumatic Diseases, 29:131-134.
Dietz BM, Sterz R, Holtbrugge W, et al., "Adalimumab (Humira®) Monotherapy Significantly Improves Health Utility in Patients With Severe Rheumatoid Arthritis (RA)." 2005 EULAR Annual Meeting, Jun. 8-11, 2005, Vienna, Austria (Abstract of Poster Presentation FRI0451).
Dietz BM, Sterz R, Holtbrugge W, et al., "Adalimumab (Humira®) Monotherapy Significantly Improves Fatigue in Patients With Severe Rheumatoid Arthritis (RA)." 2005 EULAR Annual Meeting, Jun. 8-11, 2005, Vienna, Austria (Poster FRI0452).

(56) References Cited

OTHER PUBLICATIONS

Dietz BM, van de Putte LBA, Holtbrugge W, et al., "Adalimumab (Humira®) Monotherapy Provides Sustained Long-Term Improvement in Health Utility in Patients With Rheumatoid Arthritis (RA)." 2005 EULAR Annual Meeting, Jun. 8-11, 2005, Vienna, Austria (Poster FRI0453).

Dietz BM, van de Putte LBA, Holtbrugge W, et al., "Adalimumab (Humira®) Monotherapy Sustains Long-Term Improvements in Fatigue in Patients With Severe Rheumatoid Arthritis (RA)." 2005 EULAR Annual Meeting, Jun. 8-11, 2005, Vienna, Austria (Abstract of poster presentation).

Egan, "A randomized, single-blind, pharmacokinetic and doseresponse study of subcutaneous methotrexate, 15 and 25 MG/week, for refactory ulcerative colitis and Crohn's Disease." 1998 Gastroenterology, vol. 114(4):G3978.

Elliot, "Treatment of rheumatoid arthritis with chimeric monoclonal antibodies to tumor necrosis factor α." 1993 Arthritis & Rheumatism, 36(12):1681-90.

Emery et al., "Targeted therapies in rheumatoid arthritis: the need for action." 1999 Rheumatology (Oxford). 38(10):911-2.

Emery et al., "Changes in PRO-MMP-1 in Relation to Standard Measures of Disease Activity Over a 6 Month Treatment Period with Adalimumab (D2E7) in Rheumatoid Arthritis." 2001 Arthritis & Rheumatism, vol. 44(9):S215.

Emery et al., "Improvement in HAQ Disability in Rheumatoid Arthritis (RA) with Adalimumab (Humiraä) Based on Duration of Disease." 2003 Arthritis Rheum., vol. 48(Suppl. 9):S313.

Emery P, Schiff MH, Kalden JR, et al. "Major Clinical Response and Sustained Remission Over 4 Years in Patients With Rheumatoid Arthritis Treated With Adalimumab (Humira) Plus Methotrexate." 2005 Rheumatology 2005;44(Suppl 1):i25. Oral Presentation OP66 at the BSR Annual Meeting, Apr. 21, 2005, Birmingham, UK.

Emery P, van Riel PL, Cush JJ, et al., "Clinical Remission Achieved in the Early Treatment of Recent-Onset Rheumatoid Arthritis (RA): Subanalysis of the PREMIER Study." 2005 EULAR Annual Meeting, Jun. 8-11, 2005, Vienna, Austria (Abstract of Poster SAT0097).

Feldmann et al.. "Anti-TNFa Therapy of Rheumatoid Arthritis: What Have We Learned." 2001 Annu. Rev. Immunol., vol. 19:163-196.

Figini et al., "In Vitro Assembly of Repertoires of Antibody Chains on the Surface of Phage by Renaturation." 1994 J. Mol. Biol., vol. 239:68-78.

Fischer, "Anti-tumor necrosis factor antibodies (Infliximab) in the treatment of a patient with toxic epidermal necrolysis." 2002 Br. J. Dermatol. 146(4): 707-708.

Fomsgaard, "Auto-antibodies to Tumour Necrosis Factor α in Healthy Humans and Patients with Inflammatory Diseases and Gram-Negative Bacterial Infections." 1989 Scand. J. Immunol., 30:219-23.

Foot and Winter, "Antibody Framework Residues Affecting the Conformation of the Hypervariable Loops." 1992 J. Mol. Biol., vol. 224:487-490.

Foote, Jefferson et al., "Antibody Framework Residues Affecting the Conformation of the Hypervariable Loops." 1992 J. Mol. Biol., vol. 224:487-499.

Furst D, "Safety and Efficacy of Adalimumab (D2E7), a Fully Human Anti-TNF-α Monoclonal Antibody, Given in Combination with Standard Antirheumatic Therapy: Safety Trial of Adalimumab in Rheumatoid Arthritis (STAR)." 2002 "Arthritis Rheum; 46(9) (Suppl):S572 (Abst 1537)."

Furst DE, "Adalimumab, a Fully Human Anti-Tumor Necrosis Factor-a Monoclonal Antibody, and Concomitant Standard Antirheumatic Therapy for the Treatment of Rheumatoid Arthritis: Results of STAR (Safety Trial of Adalimumab in Rheumatoid Arthritis)." 2003 J Rheumatol, 30:2563-71.

Taber's Cyclopedic Medical Dictionary, ed. Thomas L Clayton, 17$^{th}$ edition, F.A. Davis Company, "intravenous injection" on pp. 1012-15. 1993.

Furst et al., "Improvement of the Individual ACR Components in ACR20 Responders in an Adalimumab (Humiraä) RA Clinical Trial." 2003 Arthritis Rheum., vol. 48(Suppl. 9):S106.

Furst et al., "TNF Blockade by the Fully Human Monoclonal Antibody Adalimumab (D2E7), in the Armada Trial Resuts in Decreases in Serum Matrix Metalloproteinase (MMP) Levels Along with Impressive Clinical Improvement in Refractory RA Patients." 2001 Arthritis Rheum., vol. 44(9 Suppl.):S215.

Genovese MC, Kavanaugh AF, Cohen SB, et al.. "The Relationship of Radiographic Progression to Clinical Response in Patients with Early RA Treated with Adalimumab (Humira®) Plus MTX or MTX Alone." 2005 Oral Presentation of Abstract 1178 at the 2005 Annual Scientific Meeting of the American College of Rheumatology, Nov. 12-17, 2005, San Diego, California.

Gorman, Jennifer D. et al., "Treatment of Ankylosing Spondylitis by Inhibition of Tumor Necrosis Factor α." 2002 The New England Journal of Medicine, vol. 346(18):1349-1356.

Goto, "Adalimumab." 2002 Japanese Journal of Clinical Medicine 60(12): 2384-2389.

Goto et al., "Adalimumab." 2002 Medline AC NLM12510366.

Granneman et al., "Pharmacokinetic/Pharmacodynamic (PK/PD) Relationships of Adalimumab (Humiraä, Abbott) in Rheumatoid Arthritis (RA) Patients during Phase II/III Clinical Trials." 2003 Arthritis. Rheum., vol. 48(Suppl. 9):S140.

Griffiths, "Human anti-self antibodies with high specificity from phage display libraries." 1993 The EMBO J., 12(2):725-34.

Guler-Yuksel M et al., "Changes in hand and generalised bone mineral density in patients with recent-onset rheumatoid arthritis." 2008 Annals of the Theumatic Diseases 68(3): 330-336.

Guillemin F, Mariette X, Contreras L, et al., "Adalimumab (Humira®) in Patients With Rheumatoid Arthritis Improves Quality of Life: Results From the ReAct Study in France." 2005 Poster Presentation Lu.27, Dec. 5, 2005, at the 18th Congress of the French Society of Rheumatology; abstract to be published (in French) in Revue du Rhumatisme Edition Française.

Hawkins et al., "Selection of Phage Antibodies by Binding Affinity Mimicking Affinity Maturation." 1992 J. Mol. Biol., vol. 226:889-896.

Hermann KGA, Scheel AK, Althoff C, et al., "Low-field magnetic resonance imaging for follow-up analysis of finger joint inflammation in patients with active rheumatoid arthritis receiving adalimumab." 2005 Abstract for presentation at 86th German Congress of Radiology, May 4-7, 2005, Berlin.

Hillgren A. et al., "Protection mechanism of Tween 80 during freeze-thawing of a model protein, LDH." 2002 International Journal of Pharmaceutics. vol. 237, No. 1-2: 57-69.

Hoff MY et al., "Adalimumab therapy reduces hand bone loss in early rheumatoid arthritis: explorative analyses from the PREMIER study." 2008 Annals of the Theumatic Diseases 68(7): 1171-1176.

Holler et al., "Modulation of Acute Graft-Versus-Host Disease After Allogeneic Bone Marrow Transplantation by Tumor Necrosis Factor a (TNFa) Release in the Course of Pretransplant Conditioning: Role of Conditioning Regimens and Prophylactic Application of a Monoclonal Antibody Neutralizing Human TNFa (MAK 195F)." 1995 Blood, vol. 86(3):890-899.

Hollinger, "Engineered antibody fragments and the rise of single domains." 2005 Nat Biotechnol., 23(9):1126-36.

Holt, L.J. et al., "Domain Antibodies: Proteins for Therapy." 2003Trends in Biotech, 21(11): 484-490.

Hoogenboom et al., "Converting rodent into human antibodies by guided selection." 1996 Antibody Engineering, Oxford University Press, Chpt. 8, pp. 169-185.

Horneff, G. et al. "TNF-α antagonists for the treatment of juvenile-onset spondyloarthritides." 2002 Clin. Exp. Rheumatol., vol. 20(Suppl. 28):S137-S142.

Hubert et al., "A 1-year case-control study in patients with rheumatoid arthritis indicates prevention of loss of bone mineral density in both responders and nonresponders to infliximab." 2007 Arthritis Research and Therapy 9(3): R61.

Huse, "Generation of a large combinatorial library of the immunoglobulin repertoire in phage lambda." 1989 Science, 246:1275-81.

Janeway, "The structure of a typical antibody molecule." 2001 Immunobiology, 5th Ed., Garland Science, p. 94-105.

(56) References Cited

OTHER PUBLICATIONS

Janeway et al., "The protein products of MHC class I and class II genes are highly polymorphic." 1997 Immunobiology, 3rd Edition, pp. 4:24-4:30.

Jespers et al., "Guiding the Selection of Human Antibodies from Phage Display Repertoires to a Single Epitope of an Antigen." 1994 Bio/Technology, vol. 12:899-903.

Kaiser, M.J. et al., "Efficacy of infliximab (Remicade®) in the treatment of spondyloarthropathies. Two case reports." 2001 Joint Bone Spine, vol. 68:525-527.

Kanakoudi-Tsakalidou, "Influenza vaccination in children with chronic rheumatic diseases and long-term immunosuppressive therapy." 2001 Clin. Exp. Rheumatol. vol. 19(5):589-94.

Kavanaugh A, "Immune Response is Not Affected by Adalimumab Therapy." 2003 Ann Rheum Dis 2003;62(Suppl I):169 (Poster THU0196).

Kavanaugh A, "Treatment With Adalimumab (D2E7) Does Not Affect Normal Immune Responsiveness." 2002 Arthritis Rheum 2002;46(9)(Suppl):S132 (Abst 259).

Kavanaugh et al., "The Armada Trial: 12-Month Efficacy and Safety of Combination Therapy with Adalimumab (D2E7), the First Fully Human Anti-TNF Monoclonal Antibody, and Methotrexate (MTX) in Patients with Active Rheumatoid Arthritis." 2002 Ann. Rheum. Dis., vol. 61(Suppl. I):S168.

Kaymakcalan et al., "Comparison of Adalimumab (D2E7), Infliximab, and Etanercept in the Prevention of Polyarthritis in the Transgene Murine Model of Rheumatoid Arthritis." 2002 Arthritis, Rheum., vol. 46(9 Suppl.):S304.

Kaymakcalan et al., "Murine Model for Assessing Adalimumab, Inflixmab, and Etanercept to Prevent Polyarthritis." 2003 Ann. Rheum. Dis., vol. 62(Suppl. 1):136-7.

Kempeni, "Preliminary Results of Early Clinical Trials with the Fully Human anti-TNF alpha Monoclonal Antibody D2E7." 1999 Ann Rheum Dis 58(Suppl 1):170-172.

Kempeni, "Update on D2E7: A Fully Human anti-Tumor Necrosis Factor alpha Monoclonal Antibody." 2000 Annals of the Rheumatic Diseases, 59(Suppl 1): i44-i45.

Kent JD, Pangan AL, Spencer-Green GT, et al., "Serious Infections in Patients with Rheumatoid Arthritis Who Participated in Adalimumab (Humira®) Clinical Trials." 2005 Poster Presentation 1454 at the 2005 Annual Scientific Meeting of the American College of Rheumatology, Nov. 12-17, 2005, San Diego, California.

Keystone, "Efficacy and safety of adalimumab (D2E7), the fully human anti-tnf monoclonal antibody, in MTX partial responders: Results of the 24-week ARMADA trial." 2002 JCR: Journal of Clinical Rheumatology, vol. 9(Suppl. 3):S69.

Keystone EC, Kavanaugh AF, Sharp JT, et al., "Inhibition of Radiographic Disease Progression in Patients With Long-Standing Rheumatoid Arthritis Treated with Adalimumab Plus Methotrexate for 5 Years." 2005 EULAR Annual Meeting, Jun. 8-11, 2005, Vienna, Austria (Poster THU0168).

Keystone EC, Kavanaugh AF, Sharp JT, et al., "Three Years of Adalimumab (Humira) Plus Methotrexate Therapy Sustains Radiographic Inhibition of Structural Damage in Patients with Long-Standing Rheumatoid Arthritis." 2005(Rheumatology 2005;44(Suppl 1):i71) Poster Presentation 132 at the BSR Annual Meeting, Apr. 20, 2005, Birmingham, UK.

Keystone et al., "Adalimumab Inhibits the Progression of Structural Joint Damage in Patients with Active RA." 2003 Ann. Rheum. Dis., vol. 62(Suppl. 1):64-5.

Keystone et al., "Response to Adalimumab in Patients with Early Versus Late Rheumatoid Arthritis (RA)." 2003 Ann. Rheum. Dis., vol. 62(Suppl. 1):170.

Keystone et al., "Sustained Radiographic Inhibition with Adalimumab (Humiraä) over 2 years in Patients with Long Standing Rheumatoid Arthritis (RA)." 2003 Arthritis Rheum., vol. 48(Suppl. 9):S315.

Keystone et al., "The Armada Trial: A Double-Blind Placebo Controlled Trial of the Fully Human Anti-TNF Monoclonal Antibody, Adalimumab (D2E7), in Patients with Active RA on Methotrexate (MTX)." 2001 Arthritis & Rheumatism, vol. 44(9):S213.

Keystone et al., "The Fully Human Anti-TNF Monoclonal Antibody, Adalimumab (D2E7), Dose Ranging Study: The 24-Week Clinical Results in Patients with Active RA on Methotrexate Therapy (The ARMADA Trial)." 2001 Presented at the Annual Meeting of the European League Against Rheumatoid Arthritis (EULAR), Prague, Czech Republic.

Keystone, E.C. et al., "Subgroup Analysis of Radiographic Progression in RA Patients with Moderate Disease Treated with Adalimumab (Humiraâ)." 2003 Ann. Rheum. Dis., vol. 62(Suppl. 1):169.

Kohn, "W1354: Infliximab in the Treatment of Severe Refractory Ulcerative Colitis." 2002 Gastroenterology 122: A615-A616.

Kreitman, "Efficacy of the anti-CD22 recombinant immunotoxin BL-22 in chemotherapy-resistant hairy cell leukemia." 2001 New Eng. J. Med. 345(4): 241-247.

Kremer, "Rational Use of New and Existing Disease-Modifying Agents in Rheumatoid Arthritis." 2001 Ann. Intern. Med., vol. 134:695-706.

Landewe R, van der Heijde DF, Burmester GR, et al., "Radiographic Improvement in Clinical Responders in the Early Treatment of Recent-Onset Rheumatoid Arthritis (RA): Subanlysis of the Premier Study." 2005 EULAR Annual Meeting, Jun. 8-11, 2005, Vienna, Austria (Poster SAT0099).

Lang U et al., "Increase in bone mineral density of patients with rheumatoid arthritis treated with anti-TNF-alpha antibody: a prospective open-label pilot study." 2005 Rheumatology (Oxford) 44(12): 1546-1548.

Lerner, "Antibodies without immunization." 1992 Science, 258:1313-14.

Leusch, "Failure to demonstrate TNFα-specific autoantibodies in human sera by ELISA and Western blot." 1991 J. Immunol. Methods, 139:145-47.

Lewis, "Use of alanine scanning mutagenesis to improve the affinity of an anti gp120 (HIV) antibody." 1994 J. Cell. Biochem., 18D:215.

Lipsky, "Infliximab and Methotrexate in the Treatment of Rheumatoid Arthritis." 2000 The New England Journal of Medicine, vol. 343:1594-1602.

Low, 1996 thesis extract, Cambridge University.

Low et al., "Mimicking Somatic Hypermutation: Affinity Maturation of Antibodies Displayed on Bacteriophage Using a Bacterial Mutator Strain." 1996 J. Mol. Biol., vol. 260:359-368.

MacCallum, Robert M. et al., "Antibody-antigen Interactions: Contact Analysis and Binding Site Topography." 1996 J. Mol. Biol., vol. 262:732-745.

Machold et al., "Adalimumab—a new TNF-a antibody for treatment of inflammatory joint disease." 2003 Expert Opin. Biol. Ther., vol. 3(2):351-360.

Maini R, "Infliximab (chimeric anti-tumour necrosis factor alpha monoclonal antibody) versus placebo in rheumatoid arthritis patients receiving concomitant methotrexate: a randomised phase III trial." 1999 Lancet, vol. 354:1932-1939.

Maksymowych, Walter P. et al., "Canadian Rheumatology Association Consensus on the Use of Anti-Tumour Necrosis Factor-α Directed Therapies in the Treatment of Spondyloarthritis." 2003 The Journal of Rheumatology, vol. 30:1356-1363.

Mariette X, Bijlsma JWJ, Herold M, et al., "Adalimumab (Humira®) is as Effective When Used With Other Concomitant DMARDS as When Used With Methotrexate in Treating Rheumatoid Arthritis in Widespread Clinical Practice: The REACT Study." 2005 EULAR Annual Meeting, Jun. 8-11, 2005, Vienna, Austria (Poster SAT0048).

Marks, "By-Passing Immunization: Building High Affinity Human Antibodies by Chain Shuffling." 1992 Biotechnology, vol. 10:779-783.

Marks, "By-passing immunization: Human antibodies from V-gene libraries displayed on phage." 1991 J. Mol. Biol. 222:581-97.

Marzo-Ortega, Helena et al., "Inhibition of tumor necrosis factor alpha and ankylosing spondylitis." 2003 New England Journal of Medicine, vol. 248(4):360-361.

Massarotti EM, "Treatment Patterns in Early-Onset Rheumatoid Arthritis (RA): Results from the Sonora Study." 2002 Ann Rheum Dis 2002;61(Suppl I);S93 (Abst THU0105).

(56) References Cited

OTHER PUBLICATIONS

McKenna F, Bombardieri S, Tzioufas AG, et al., "The ReAct Trial: Efficacy Evaluation of Adalimumab (Humira) in Patients Switching From Prior Biologic DMARD Therapies." 2005 (Rheumatology 2005;44(Suppl 1):i2. ) Oral Presentation OP3 at the BSR Annual Meeting, Apr. 19, 2005, Birmingham, UK.

Mease, "Tumor Necrosis Factor (TNF) in Psoriatic Arthritis: Pathophysiology and Treatment with TNF Inhibitors." 2002 Ann Rheum Dis. 61:298-304.

Medynski, "Phage Display: All Dressed Up and Ready to Role." 1994 Bio/Technology, vol. 12:1134-1136.

Mittendorf T, Sterz R, Greiner W, et al., "Effects of Adalimumab Monotherapy on Health Utility and Fatigue in Patients with Long-Standing, Severe Rheumatoid Arthritis (RA)." 2005 Value in Health 2005;8(3):342. Poster Presentation PAR9 at ISPOR 10th Annual International Meeting, May 17, 2005, Washington, DC.

Mittendorf T, Sterz R, Von der Schulenburg J, Kupper H, Cifaldi M, Dietz B., "Effects of Long-Term Adalimumab Therapy on Health Utility and Fatigue in Patients with Long-Standing, Severe Rheumatoid Arthritis (RA)—Results from a 3-Year Follow-Up Study." 2005 ISPOR Eighth Annual European Congress Contributed Presentation Abstracts. [Poster Presentation, Nov. 6, 2005, PAR20.].

Moller, "Monoclonal antibodies to human tumor necrosis factor α: in vitro and vivo application." 1990 Cytokine, 2(3):162-69.

Nilsson, "Antibody engineering." 1995 Current Opinion in Structural Biology, vol. 5:450-456.

Ogilvie, "Treatment of psoriatic arthritis with antitumour necrosis factor-alpha antibody clears skin lesions of psoriasis resistant to treatment with methotrexate." 2001 British Journal of Dermatology, vol. 144:587-58.

Older, "Can Immunization Precipitate Connective Tissue Disease? Report of Five Cases of Systemic Lupus Erythematosus and Review of the Literature." 1999 Semin Arthritis Rheum. 29(3):131-9.

Osborn et al., "From rodent reagents to human therapeutics using antibody guided selection." 2005 Methods, vol. 36:61-68.

Paul, "Immunogenicity and antigen structure." 1993 Fundamental Immunology, 3rd Edition; p. 242-295.

Paulus, "Relative Contributions of the Components of the American College of Rheumatology 20% Criteria for Improvement to Responder Status in Patients with Early Seropositive Rheumatoid Arthritis." 2000 Arthritis & Rheumatism vol. 43(12):2743-2750.

Pavelka K, Kvien TK, Cohen SB, et al., "Failure to Inhibit Radiographic Progression Within the First 6 Months of Therapy Leads to Worse Radiographic Outcomes at 2 Years." 2005 EULAR Annual Meeting, Jun. 8-11, 2005, Vienna, Austria (Poster SAT0088).

Pavelka K, Landewe R, Weisman MH, et al., "Radiographic Progression During the First 6 Months of Disease in Recent-Onset Rheumatoid Arthritis (RA): The Premier Study of Adalimumab (Humira®) Therapy in Early RA." 2005 EULAR Annual Meeting, Jun. 8-11, 2005, Vienna, Austria (Poster SAT0093).

Perez JL, Kupper H, Spencer-Green GT, et al., "Impact of Screening for Latent TB Prior to Initiating Anti-TNF Therapy in North America and Europe." 2005 EULAR Annual Meeting, Jun. 8-11, 2005, Vienna, Austria (Oral Presentation OP093).

Pham, T. et al., "Initiation of biological agents in patients with ankylosing spondylitis: results of a Delphi study by the ASAS Group." 2003 Ann. Rheum. Dis., vol. 62:812-816.

Pincus, "Combination Therapy with Multiple Disease-Modifying Antirheumatic Drugs in Rheumatoid Arthritis: A Preventive Strategy." 1999 Ann. Intern. Med., vol. 131:768-774.

Pincus T, Chung C, Sokka T, et al. "Routine, APGAR-Like Patient Index Datasheet" (RAPID): A Continuous Index of Patient Measures Discriminates Effectively Between Active and Placebo Treatments in 4 Adalimumab Clinical Trials. 2005 EULAR Annual Meeting, Jun. 8-11, 2005, Vienna, Austria (Poster SAT0046).

Queen et al., "A humanized antibody that binds to the interleukin 2 receptor." 1989 Proc. Natl. Acad. Sci. USA, vol. 86:10029-10033.

Rau, "Erfahrungen mit D2E7." 1999 Z. Rheumatol., vol. 58(Suppl. 1):1/21, S51.

Rau, "Erfahrungen mit D2E7." (Experiences with D2E7)2000Aktuelle Rheumatologie, vol. 25(3):83-88.

Rau, "Long Term Efficacy and Tolerability of Multiple i.v. Doses of the Fully Human anti-TNF Antibody D2E7 in Patients with Rheumatoid Arthritis." 1998 Arthritis Rheum vol. 41 (suppl):55 No. 137.

Rau, "Long-Term Treatment with the Fully Human Anti-TNF-Antibody D2E7 Slows Radiographic Disease Progression in Rheumatoid Arthritis." 1999 Arthritis and Rheumatism, vol. 42(9):S400.

Rau et al., "Adalimumab Inhibits Radiographic Disease Progression in Long-Standing, Rapidly Progressive Rheumatoid Arthritis." 2003 Ann. Rheum. Dis., vol. 62(Suppl. 1):191.

Rau et al., The English language translation of Rau et al. (Akt. Rheumatol., vol. 25:83-88 (2000))produced for the USPTO by the Mcelroy Translation Company, Jul. 2008, pp. 1-16.

Rau et al.,"Treatment with Adalimumab (D2E7), the Fully Human Anti-TNF Monoclonal Antibody, Slows Radiographic Disease Progression in Rheumatoid Arthritis: Results of a 12-Month Study." 2002 J. Clin. Rheum., vol. 8(Suppl.):S78.

Rau et al., "Wirkung and Vertraglichkeit wiederholter intravenoser Gaben des humanen anti-TNF Antikorpers D2E7 bei Patienten mit chronischer Polyarthritis." 1999 Z. Rheumatol., vol. 58(Suppl. 1):1/41, P12.

Rau R, "2.5-Year Treatment Results With Adalimumab (D2E7), The First Fully Human Anti-TNF Monoclonal Antibody, In Combination With Methotrexate in Active Rheumatoid Arthritis." 2002 Ann Rheum Dis 2002;61(Suppl I):S55 (Abst OP0073).

Rau R, "Adalimumab (a fully human anti-tumour necrosis factor a monoclonal antibody) in the treatment of active rheumatoid arthritis: the initial results of five trials." 2002 Ann. Rheum. Dis., vol. 61(Suppl. II):ii70-ii73.

Rau R, "Kombinationstherapie mit dem humanen Anti-TNF-Antikorper D2E7 and Methotrexat bei aktiver chronischer Polyarthritis (with English Translation)." 1999 Z Rheumatol (Suppl) 1999; 58: 1/35.

Prescribing Information for Humira (adalimumab) Injection, Solution for Subcutaneous use Initial U.S. Approval: 2002 (Updated Mar. 2009).

Office Actions cited during prosecution of U.S. Pat. No. 7,223,394 (U.S. Appl. No. 09/801,185 OA mailed on Sep. 9, 2002).

Reimold, Andreas M., "New Indications for Treatment of Chronic Inflammation by TNF-α Blockade." 2003 The American Journal of Medical Science, vol. 325(2):75-92.

Reinhart et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study." 1996 Crit. Care. Med., vol. 24(5):733-742.

Revicki et al., "Treatment with Adalimumab (D2E7), a Fully Human Anti-TNF Monoclonal Antibody, Improves Physical Function, Vitality, and Mental Health While Reducing Bodily Pain in Patients with Active Rheumatoid Arthritis (RA)." 2002 Arthritis Rheum., vol. 46(9 Suppl.):S537.

Riechmann et al., "Phage Display and Selection of a Site-Directed Randomized Single-Chain Antibody Fv Fragment for Its Affinity Improvement." 1993 Biochemistry, vol. 32:8848-8855.

Rinehart-Kim, "Alterations in the Gene Expression Profile of MCF-7 Breast Tumor Cells in Response to c-JUN." 2000 Int. J. Cancer, vol. 88(2):180-190.

Rudikoff, Stuart et al., "Single amino acid substitution altering antigen-binding specificity." 1982 Proc. Natl. Acad. Sci. USA, vol. 79:1979-1983.

Saidenberg-Kermanac'h N et al., "TNF-α antibodies and osteoprotegerin decrease systemic bone loss associated with inflammation through distinct mechanisms in collagen-induced arthritis." 2004 Bone, Pergamon Press., Oxford 35 (5): 1200-1207.

Salfeld et al., "Generation of Fully Human Anti-TNF Antibody D2E7." 1998 Arthritis Rheum., vol. 41(9 Suppl.):S57.

Sandborn, "Antitumor Necrosis Factor Therapy for Inflammatory Bowel Disease: C9 A Review of Agents, Pharmacology, Clinical Results, and Safety." 1999 Inflamm. Bowel Disease 5(2):199-33.

Sandborn et al., "An engineered human antibody to TNF (CDP571) for active Crohn's disease: a randomized double-blind placebo-controlled trial." 2001 Gastroenterology 120:1330-1338.

(56) References Cited

OTHER PUBLICATIONS

Santora, "Characterization of recombinant human monoclonal tissue necrosis factor-alpha antibody using cation-exchange HPLC and capillary isoelectric focusing." 1999 Analytical Biochem.vol. 275:98-108.

Santora et al., "Characterization of Noncovalent Complexes of Recombinant Human Monoclonal Antibody and Antigen Using Carbon Exchange, Size Exclusion Chromatography, and BIAcore." 2001 Analytical Biochemistry, vol. 299(2):119-129.

Schattenkirchner, "Efficacy and Tolerability of Weekly Subcutaneous Injections of the Fully Human Anti-TNF-Antibody D2E7 in Patients with Rheumatoid Arthritis—Results of a Phase I Study." 1998 Arthritis and Rheumatism, vol. 41(9):S57.

Schattenkirchner, "Long-term Use of the Fully Human Anti-TNF Antibody D2E7 in Combination With Methotrexate in Active Rheumatoid Arthritis." 2000 Arthritis Rheum 2000;43(9)(Suppl):S228.

Schattenkirchner et al., "Long-term Use of the Fully Human Anti-TNF Antibody Adalimumab (D2E7) in DMARD-refractory Rheumatoid Arthritis." 2001 Presented at: The Annual Meeting of the European League Against Rheumatism (EULAR), Prague, Czech Republic, Jun. 2001.

Schattenkirchner et al., "Phase-1-Studie zur Wirksamkeit und Vertraglichkeit wochentlicher subcutaner Injektionen des humanen Anti-TNF-Antikorpers D2E7 bei cP." 1999 Z. Rheumatol., vol. 58(Suppl. 1):1/42, P14.

Schiff et al., "Efficacy of Adalimumab Measured by the Disease Activity Score 28 (DAS28) and EULAR Response Criteria." 2003 Ann. Rheum. Dis., vol. 62(Suppl. 1):170.

Schiff et al., "Malignancies in Rheumatoid Arthritis (RA) Clinical Trials with Adalimumab (Humiraä)." 2003 Arthritis Rheum., vol. 48(Suppl. 9):S700.

Schiff et al., "Rates of Infection in Adalimumab Rheumatoid Arthritis Clinical Trials." 2003 Ann. Rheum. Dis., vol. 62(Suppl. 1):184.

Schiff MA, "Randomized, Controlled, Safety Trial of Adalimumab (D2E7), A Fully Human Anti-TNF Monoclonal Antibody, Given to RA Patients in Combination With Standard Rheumatologic Care: The STAR (Safety Trial of Adalimumab in Rheumatoid Arthritis) Trial." 2002 Ann Rheum Dis 2002;61(Suppl I):S169 (Abst FRI0028).

Schiff MH, "Sustained Efficacy of Adalimumab (Humira®) Plus Methotrexate (MTX) in Rheumatoid Arthritis (RA) Patients." 2003 Arthritis Rheum 2003;48(9)(Suppl):S314 (Poster 740).

Schiff MH, Breedveld FC, Weisman MH, et al., "Adalimumab (Humira®) Plus Methotrexate is Safe and Efficacious in Patients With Rheumatoid Arthritis Into the 7th Year of Therapy." 2005 EULAR Annual Meeting, Jun. 8-11, 2005, Vienna, Austria (Poster SAT0090).

Schiff MH, Burmester GR, Pangan AL, et al., "Safety of Adalimumab (Humira®) in Global Clinical Trials of Patients With Early vs. Long-Standing Rheumatoid Arthritis (RA)." 2005 EULAR Annual Meeting, Jun. 8-11, 2005, Vienna, Austria (Poster SAT0044).

Schnarr, S. et al., "Anti-tumour necrosis factor (TNF)-α therapy in undifferentiated spondyloarthropathy." 2002 Clin. Exp. Rheumatol., vol. 20(Suppl. 28):S126-S129.

Schoenfeld, "Vaccination and Autoimmunity—'Vaccinosis': A Dangerous Liaison?" 2000 Journal of Autoimmunity, 14(1):1-10.

Shergy, "Open label study to assess infliximab safety and timing of onset of clinical benefit among patients with rheumatoid arthritis." 2002 J. Rheumatol. 29(4): 667-677.

Sibilia, Combinaison de traitements de fond dans la polyarthrite rhumatoïde. 2002 Ann. Med. Interne, vol. 153(1):41-52.

Siegel et al., Evidence of Effects of a TNF Blocking Agent in ACR20 Non-Responders. 2003 Arthritis Rheum., vol. 48(Suppl. 9):S127.

Sieper, J. et al., "New treatment options in ankylosing spondylitis: a role for anti-TNFα therapy." 2001 Ann. Rheum., vol. 60:iii58-iii61.

Office Actions cited during prosecution of U.S. Appl. No. 10/163,657.

Smith, David Lloyd et al., "Ibuprofen in psoriatic arthritis." 1980 Arthritis Rheum., vol. 23(8):961-962.

Smolen et al., "A Comparison of the SDAI and DAS28 as Measures of Response in Adalimumab (Humiraä) Clinical Trials in Rheumatoid Arthritis (RA)." 2003 Arthritis Rheum., vol. 48(Suppl. 9):S107.

Smolen et al., "Objectives and Strategies for Rheumatoid Arthritis Therapy: Yesterday vs. Today." 2003 Drugs of Today, vol. 39(Suppl. B):3-8.

St Clair, "Therapy of rheumatoid arthritis: new developments and trends." 1999 Curr. Rheumatol.Rep. 1(2): 149-156.

Stockinger, "CD147." 1999 Protein Reviews on the Web, http://mpr.nci.nhi.gov/prow/guide/1397527348_g.htm, Oct. 14, 1999.

Stokes, David G. et al., "Potential of Tumor Necrosis Factor Neutralization Strategies in Rheumatologic Disorders Other Than Rheumatoid Arthritis." 2003 Seminars in Arthritis and Rheumatism, vol. 33(1):1-18.

Stone, Millicent et al., "Clinical and Imaging Correlates of Response to Treatment with Infliximab in Patients with Ankylosign Spondylitis." 2001 J. Rheumatol., vol. 28:1605-1614.

Strand et al., "Adalimumab Improves Health-related Quality of Life in Rheumatoid Arthritis Patients." 2003 Ann. Rheum. Dis., vol. 62(Suppl. 1):356.

Strand et al., "Improvement in Health-related Quality of Life, Health Utility, and Fatigue in Patients with Active Rheumatoid Arthritis (RA) on Adalimumab (Humiraä, Abbott) Therapy." 2003 Arthritis Rheum., vol. 48(Suppl. 9):S402.

Strand et al., "Treatment with Adalimumab (D2E7), a Fully Human Anti-TNF Monoclonal Antibody, Improves Physical Function and Health Related Quality of Life (HRQOL) in Patients with Active Rheumatoid Arthritis (RA)." 2002 Ann. Rheum. Dis., vol. 61(Suppl. I):S175.

Tan, "Improvement of Pyoderma gangrenosum and psoriasis associated with Crohn's Disease with anti-tumor necrosis factor alpha moniclonal antibody." 2001 Arch. Dematol. 137(7): 930-933.

Taylor, "Anti-tumor necrosis factor therapies." 2001 Current Opinion in Rheumatology, vol. 13:164-169.

The CDC Prevention and Control of Influenza Recommendations of the Advisory Committee on Immunization Practices2002MMWR, Apr. 12, 2002, vol. 51(RR-3):1-32.

The Lenercept Multiple Sclerosis Study Group and The University of British Columbia MS/MRI Analysis Group "TNF neutralization in MS: Results of a randomized, placebo-controlled multicenter study." 1999 Neurology 53: 457-465.

Thomas, "Taber's Cyclopedic Medical Dictionary." 1977 F.A. Davis Co., pp. S-118-S-119.

Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," 1996 J. Mol. Biol., vol. 256:77-88.

Tomlinson, "The repertoire of human germline VH sequences reveals about fifty groups of VH segments with different hypervariable loops." 1992 J. Mol. Biol., 227:776-798.

Tomlinson, "The structural repertoire of the human Vk domain." 1995 The EMBO J., 14(18):4628-38.

Tracey, "Tumor necrosis factor: A pleiotropic cytokine and therapeutic target." 1994 Annu. Rev. Med., 45:491-503.

Tripathi, M., "Essentials of Medical Pharmacology." 2003 Jaypee Brothers Medical Publishers (P) Ltd., 5th Ed., Ch.3:51-56.

Tugwell et al., "Adalimumab Improves Utility and Quality-adjusted Life Days in Rheumatoid Arthritis." 2003 Ann. Rheum. Dis., vol. 62(Suppl. 1):107-8.

Tugwell et al., "Relationship Between ACR Response and HRQL in Adalimumab Clinical Trials." 2003 Ann. Rheum. Dis., vol. 62(Suppl. 1):536.

U Møller Døhn et al., "Decreased signs of inflammation and no erosive progression on ultrasonography at 6 and 12 months in patients with rheumatoid arthritis in adalimumab and methotrexate combination therapy." 2010 EULAR 2010 from the Denmark IIS Study HUM 04-020 entitled: "Humira in rheumatoid arthritis—do bone erosions heal—an MRI CT and X-ray study (The HURRAH Study)".

U Møller Døhn et al., "Detection rates of bone erosions and estimation of erosion volume by ultrasonography in rheumatoid arthritis—a comparison with computed tomography." 2010 EULAR 2010 from

(56) References Cited

OTHER PUBLICATIONS the Denmark IIS Study HUM 04-020 entitled: "Humira in rheumatoid arthritis—do bone erosions heal—an MRI CT and X-ray study (The HURRAH Study)".
Vajdos, "Comprehensive Functional Maps of the Antigen-binding Site of an Anti-ErbB2 Antibody Obtained with Shotgun Scanning Mutagenesis." 2002 J Mol Biol 320(2):415-28.
Valle et al., "Infliximab." 2001 Expert Opinion on Pharmacotherapy, Ashley, London, UK, 2:1015-1025.
Van Assche, "Anti-TNF agents in Crohn's Disease." 2000 Expert Opin Investig. Drugs; 9(1):103-11.
van de Putte, "Efficacy of the fully human anti-TNF antibody D2E7 in rheumatoid arthritis." 1999 Arthritis and Rheumatism, vol. 42(9):5400.
van de Putte et al., "A Single Dose Placebo Controlled Phase I Study of the Fully Human Anti-TNF Antibody D2E7 in Patients with Rheumatoid Arthritis," 1998 Arthritis Rheum., vol. 41:S57.
van de Putte et al., "Adalimumab (D2E7) Monotherapy in the Treatment of Patients with Severely Active Rheumatoid Arthritis (RA)." 2002 Arthritis Rheum., vol. 46(9 Suppl.):S171.
van de Putte et al., "Adalimumab (D2E7), the Fully Human Anti-TNF Monoclonal Antibody, in the Treatment of Patients with Rheumatoid Arthritis Who Failed Previous DMARD Therapy: Efficacy and Safety Results from a 6-Month Phase III Study." 2002 JCR: Journal of Clinical Rheumatology, vol. 8(Suppl. 3):S89.
van de Putte et al., "Adaliumuab." 2003 TNFa-Inhibition in the Treatment of Rheumatoid Arthritis, MD Martin Dunitz, Larry W. Moreland, Ed., pp. 71-93.
van de Putte et al., "Efficacy and Safety of Adalimumab (D2E7), the First Fully Human Anti-TNF Monoclonal Antibody, in Patients with Rheumatoid Arthritis Who Failed Previous DMARD Therapy: 6-Month Results from a Phase III Study." 2002 Ann. Rheum. Dis., vol. 61(Suppl. 1):S168.
van de Putte et al., "Efficacy and safety of the fully human anti-tumour necrosis factor a monoclonal antibody adalimumbo (D2E7) in DMARD refractory patients with rheumatoid arthritis: a 12 week, phase II study." 2003 Ann. Rheum. Dis., vol. 62:1168-1177.
van de Putte et al., "Eine placebo-kontrollierte Phase-1-Studie des humanen Anti-TNF-Antikorpers D2E7 bei Patienten mit aktiver chronischer Polyarthritis." 1999 Z. Rheumatol., vol. 58(Suppl. 1):1/34, F19.
van de Putte et al., "One Year Efficacy Results of the Fully Human Anti-TNF Antibody D2E7 in Rheumatoid Arthritis." 2000 Arthritis Rheum., vol. 43(9 Suppl.):S269.
van de Putte et al., "Sustained 5-Year Efficacy of Adalimumab (Humiraä) Monotherapy in DMARD-Refractory rheumatoid arthritis (RA)." 2003 Arthritis Rheum., vol. 48(Suppl. 9):S314.
Department of Surgery, Univeristy of Toronto, Annual Report 1998-1999.
van de Putte, L.B.A. et al., "Efficacy and safety of adalimumab as monotherapy in patients with rheumatoid arthritis for whom previous disease modifying antirheumatic drug treatment has failed." 2004 Ann. Rheum. Dis., vol. 63:508-516.
Van den Bosch, Filip et al., "Crohn's disease associated with spondyloarthropathy: effect of TNF-α blockade with infliximab on articular symptoms." 2000 The Lancet, vol. 356(9244):1821-1822.
van der Bijl, Breedveld FC, Antoni CE, et al., "Adalimumab (Humira®) is Effective in Treating Patients With Rheumatoid Arthritis who Previously Failed Infliximab Treatment." 2005 EULAR Annual Meeting, Jun. 8-11, 2005, Vienna, Austria (Poster SAT0062).
van der Heijde DF, Landewe R, Sharp JT, et al., "Baseline CRP Concentrations Predict Radiographic Progression in MTX-Naïve Patients With Early RA: Subanalysis of the Premier Study." 2005 EULAR Annual Meeting, Jun. 8-11, 2005, Vienna, Austria (Poster SAT0085).
van der Heijde DMFM, Landewe RBM, Keystone EC, et al., "Adalimumab (Humira®) Plus MTX Prevents Nearly All Severe Radiographic Progression Observed with Methotrexate Monotherapy in Early, Aggressive Rheumatoid Arthritis." 2005 Poster Presentation 207 at the 2005 Annual Scientific Meeting of the American College of Rheumatology, Nov. 12-17, 2005, San Diego, California.
van der Poll et al., "Effect of postponed treatment with an anti-tumour necrosis factor (TNF) F(ab')2 fragment on endotoxin-induced cytokine and neutrophil responses in chimpanzees." 1995 Clin. Exp. Immunol., vol. 100:21-25.
van Riel et al., "Long-Term Treatment with Adalimumab (D2E7) Using Background Methotrexate in Active Rheumatoid Arthritis: Results of a 3 Year Study." 2002 Arthritis Rheum., vol. 46(9 Suppl.):S534.
Van Riel PL, "A Comparison of CRP and ESR to Measure the DAS28 in Adalimumab Clinical Trials." 2003 Ann Rheum Dis 2003;62(Suppl I):169-70 (Poster THU0199).
Van Vollenhoven R, Breeveld FC, Kavanaugh AF, et al., "The Clinical and Radiographic Efficacy of Every-Other-Week vs. Weekly Dosing Frequence of Adalimumab (Humira®) in the Treatment of Early Rhuematoid Arthritis (RA)." 2005 Poster Presentation 271 at the 2005 Annual Scientific Meeting of the American College of Rheumatology, Nov. 12-17, 2005 San Diego, California.
Vaughan et al., "Human antibodies by design." 1998 Nature Biotechnology, vol. 16:535-539.
Velagapudi et al., "Effect of Methotrexate (MTX) Coadministration on the Pharmacokinetics (PK) of Adalimumab (Humiraä, Abbott) Following a Single Intravenous (iv) Injection." 2003 Arthritis Rheum., vol. 48(Suppl. 9):S141.
Velagapudi R B, "Pharmacokinetics of Adalimumab (D2E7), a Fully Human Anti-TNF-α Monoclonal Antibody, Following a Single Intravenous Injection in Rheumatoid Arthritis Patients Treated with Methotrexate." 2002 Arthritis Rheum 2002;46(9)(Suppl):S133 (Abst 261).
Vis M et al., "Evaluation of bone mineral density, bone metabolism, osteoprotegerin and receptor activator of the NF kappa B ligand serum levels during treatment with infliximab in patients with rheumatoid arthritis." 2006 Ann Rheum Dis. 65(11):1495-1499.
Wailoo, "Modeling the cost effectiveness of etanercept, adalimumab and anakinra compared to infliximab in the treatment of patients with rheumatoid arthritis in the medicare program, final report." 2006 Agency for Healthcare Research and Quality, 1-74.
Ward et al., "Binding activities of a repertoire of single immunoglobulin variable domains secreted from *Escherichia coli*." 1989 Nature, vol. 341:544-546.
Weinblatt et al., "Adalimumab, a Fully Human Anti-Tumor Necrosis Factor a Monoclonal Antibody, for the Treatment of Rheumatoid Arthritis in Patients Taking Concomitant Methotrexate." 2003 Arthritis & Rheumatism, vol. 48(1):35-45.
Weinblatt et al., "The ARMADA Trial: Efficacy and Safety of Adalimumab in Patients with Active RA at 24 Months." 2003 Ann. Rheum. Dis., vol. 62(Suppl. 1):98.
Weinblatt et al., "The ARMADA Trial: Sustained Improvement and Tolerability in Long-Term Follow-Up of Patients Treated with Adalimumab (Humiraä)." 2003 Arthritis Rheum., vol. 48(Suppl. 9):S314.
Weinblatt ME, Keystone EC, Furst DE, et al., "Long-Term Efficacy, Remission, and Safety of Adalimumab (Humira®) Plus Methotrexate in Patients with Rheumatoid Arthritis in the ARMADA Trial." 2005 Poster Presentation 1497 at the 2005 Annual Scientific Meeting of the American College of Rheumatology, Nov. 12-17, 2005, San Diego, California.
Weinblatt ME, Keystone EC, Furst DE, et al., "The ARMADA Trial: Sustained Efficacy After Dose Reduction of Concomitant Methotrexate and/or Corticosteroids in Patients With Rheumatoid Arthritis Treated With Adalimumab (Humira®)." 2005 EULAR Annual Meeting, Jun. 8-11, 2005, Vienna, Austria (Poster SAT0083).
Weisman et al., "Efficacy, Pharmacokinetic, and Safety Assessment of Adalimumab, a Fully Human Anti-Tumor Necrosis Factor-Alpha Monoclonal Antibody, in Adults with Rheumatoid Arthritis Receiving Concomitant Methotrexate: A Pilot Study." 2003 Clinical Therapeutics; vol. 25(6):1700-21.
Weisman et al., "The Importance of Pain and the Impact of Adalimumab on Pain in RA Patients." 2003 Ann. Rheum. Dis., vol. 62(Suppl. 1):351.

(56) References Cited

OTHER PUBLICATIONS

Weisman MA, "Dose Escalation Study Designed to Demonstrate the Safety, Tolerability and Efficacy of the Fully Human Anti-TNF Antibody, D2E7, Given in Combination With Methotrexate (MTX) in Patients With Active RA." 2000 Arthritis Rheum 2000;43(9) (Suppl.):S391 (Abst 1948).
Weisman MH, Breedveld FC, Cifaldi MA, et al., "Improvements in Quality of Life Measures from Adalimumab (Humira®) Plus Methotrexate (MTX) Translate into Improved Physical Function and Less Fatigue in Patients with Early Rheumatoid Arthritis (RA)." 2005 Poster Presentation 1017 at the 2005 Annual Scientific Meeting of the American College of Rheumatology, Nov. 12-17, 2005, San Diego, California.
Weisman MH, Strand V, Cifaldi MA, et al., "Adalimumab (Humira®) Plus Methotrexate is Superior to MTX Alone in Improving Physical Function, as Measured by the SF-36, in Patients with Early Rheumatoid Arthritis." 2005 Poster Presentation 1018 at the 2005 Annual Scientific Meeting of the American College of Rheumatology, Nov. 12-17, 2005, San Diego, California.
Wellborne et al., "Adalimumab (D2E7), a Fully Human Anti-TNF-α Monoclonal Antibody, Improved Health-Related Quality of Life in Patients with Active Rheumatoid Arthritis Despite Concomitant Methotrexate Therapy." 2002 Arthritis Rheum., vol. 46(9 Suppl.):S518.
Wells et al., "Incidence of Injection-Site Reactions Associated with Adalimumab (D2E7) Give Subcutaneously for at Least 6 Months: A Retrospective Analysis of 4 Phase II/III Clinical Trials." 2002 Arthritis Rheum., vol. 46(9 Suppl.):S171.
Wells et al., "Injection-site Reactions in Adalimumab Rheumatoid Arthritis (RA) Pivotal Clinical Trials." 2003 Ann. Rheum. Dis., vol. 62(Suppl. 1):411.
Winter, "Humanized antibodies." 1993 Immunology Today, vol. 14(6):243-246.
Winter et al. "Making Antibodies by Phage Display Technology." 1994 Annu. Rev. Immunol., vol. 12:433-455.
Zou, J.X. et al., "Immunological basis for the use of TNF-α-blocking agents in ankylosing spondylitis and immunological changes during treatment." 2002 Clin. Exp. Rheumatol., vol. 20(Suppl. 28):S34-S37.
Bombardieri S, Ruiz AA, Fardellone P, et al. Effectiveness of adalimumab for rheumatoid arthritis in patients with a history of TNF-antagonist therapy in clinical practice. Rheumatology 2007;46;1191-1199.
Burmester GR, Matucci Cerinic M, Mariette X, et al. Safety and effectiveness of adalimumab (Humira®) Is maintained in patients with rheumatoid arthritis—three-year results of ReAlise, a post-marketing observational study Presented at: 2008 EULAR Annual European Congress of Rheumatology; Jun. 11-14, 2008; Paris, France.
Emery P, Genovese M, Van Vollenhoven R, Patra K, Sasso E. Different relationships exist between radiographic progression and clinical status for adalimumab (ADA) plus methotrexate (MTX) versus ADA or MTX monotherapy: subanalysis of PREMIER. Presented at the American College of Rheumatology Annual Scientific meeting; Nov. 6-11, 2007; Boston, MA.
Burmester GR, Mariette X, Montecucco C, et al. Adalimumab alone and in combination with disease-modifying antirheumatic drugs for the treatment of rheumatoid arthritis in clinical practice: the Research in Active Rheumatoid Arthritis (ReAct) trial. Ann Rheum Dis 2007;66:732-739.
Keystone EC, Kavanaugh AF, Sharp JT, et al. Radiographic, clinical and functional outcomes with adalimumab (a human anti-TNF monoclonal antibody) in the treatment of patients with active rheumatoid arthritis on concomitant methotrexate therapy: A randomized, placebo-controlled, 52-week trial. Arthritis Rheum 2004;50(5):1400-1411.
Felson DT et al. "American College of Rheumatology preliminary definition of improvement in rheumatoid arthritis." Arthritis Rheum 1995;38(6):727-735.
U.S. Appl. No. 13/019,810, Kupper et al.
U.S. Appl. No. 14/175,993, Fischkoff et al.
U.S. Appl. No. 14/256,886, Fischkoff et al.
U.S. Appl. No. 14/173,780, Hoffman et al.
U.S. Appl. No. 14/010,172, Hoffman et al.
U.S. Appl. No. 14/170,045, Julian et al.
U.S. Appl. No. 14/183,845, Kaymakcalan et al.
U.S. Appl. No. 14/195,588, Pla et al.
U.S. Appl. No. 14/226,333, Pla et al.
U.S. Appl. No. 14/226,579, Pla et al.
van der Bilj AW, Breedveld FC, Antoni C, et al. Infliximab Failures in Rheumatoid Arthritis can be Successfully Treated with Adalimumab (Humira®). Ann Rheum Dis 2004;63(Suppl 1):264 (Poster FRI0055).
Breedveld et al., Arthritis and Rheumatism, 54:26-27 (2006).
Bennett, A.N. et al., "Adalimumab in Clinical Practice: Outcome in 70 Rheumatoid Arthritis Patients, Includiing Comparison of Patients with and without Previous Anti-TNF Exposure," Rheumatology, vol. 44:1026-1031 (2005).
Vollenhoven, Clin and Experimental Rheum, 22(Suppl.35):S115-S121 (2004).
Breedveld et al., Ann Rheum Dis, 63:149-155 (2004).
Brandt et al., "Successful short term treatment of severe undifferentiated spondyloarthropathy with the anti-tumor necrosis factor-alpha monoclonal antibody infliximab," J Rheumatol, 29(1):118-122 (2002).
Bathon et al., "Safety and efficacy of etanercept treatment in elderly subjects with rheumatoid arthritis," J. Rheum. 33:234-243 (2006).
Breedvald et al., "The efficacy and safety of Adalimunab (Humira((R))) plus Methotrexate vs. Adalimumab alone or methotrexate alone in the early treatment of rheumatoid arthritis (RA): 1- and 2-year results of the premier study," Annals of the Rheumatic Diseases, 64(3): 60 (2005).
Chevillotte-Maillard et al., "Survival and safety of treatment with infliximab in the elderly population," J. Rheum. 30:691-696 (2003).
Cox et al., "Influenza Virus: Immunity and Vaccination Strategies. Comparison of the Immune Response to Inactivated and Live, Attenuated Influenza Vaccines," Scand. J. Immunol. 59:1-15 (2004).
Cvetkovic et al., "Adalimumab A Review of its Use in Adulted Patients with Rheumatorid Arthritis," Biodrugs 20:293-311 (2006).
Elkayam et al., "The Effect of Tumor Necrosis Factor Blockade on the Response to Pneumococcal Vaccination in Patients with Rheumatoid Arthritis and Ankylosing Spondylitis," Sem. Arth. Rheum. 33:283-288 (2004).
Fleischmann et al., "Response to etanercept (Enbrel) in elderly patients with rheumatorid arthritis: a retrospective analysis of clinical trial results," J. Rheum. 30:691-696 (2003).
Fomin et al., "Vaccination against influenza in rheumatoid arthritis: the effect of disease modifying drugs, including TNF-alpha blockers," Ann. Rheum. Dis. 65:191-194 (2006).
Fransen et al., "The Disease Activity Score and the EULAR response criteria," Clin. Exp. Rheum. 23:S93-S99 (2005).
Genevay et al., "Tolerance and Effectiveness of Anti-Tumor Necrosis Factor α Therapies in Elderly Patients With Rheumatoid Arthritis: A Population-Based Cohort Study," 57:679-685 (2007).
Kaine et al., "Abilities to Develop Protective Antibodies to Pneumococcal and Influenza Vaccine are Maintained in Rheumatoid Arthritis (RA) Patients Treated with Adalimumab (Humira®)," 2006 Annu. Sci. Meeting, Amer. Coll. Rheumatol. (Presentation #1235) (2006).
Key Facts About Flu Vaccine, 2004; https://web.archive.org/web/20041216091152/http://www.cdc.gov/flu/protect/keyfacts.htm, downloaded Apr. 9, 2015.
Keystone et al., "Developing an effective treatment algorithm for rheumatoid arthritis," Rheumatol. 51:v48-v54 (2012).
Navarro-Sarabia et al., "Adalimumab for treating rheumatoid arthritis," J. Rheumatol. 33:1075-1081 (2006).
Office Action cited during prosecution of U.S. Appl. No. 10/163,657, dated Jun. 18, 2007.
Office Action cited during prosecution of U.S. Appl. No. 10/163,657, dated Sep. 21, 2006.
Olivieri et al., "Management Issues with Elderly-Onset Rheumatoid Arthritis" Drugs Aging 22:809-822 (2005).

(56) References Cited

OTHER PUBLICATIONS

Pinals et al., "Preliminary criteria for clinical remission in rheumatoid arthritis," Arth. Rheum. 24:1308-1315 (1981).

Ranganathan et al., "Will pharmacogenetics allow better prediction of methotrexate toxicity and efficacy in patients with rheumatoid arthritis," Ann. Rheum. Dis. 62:4-9 (2003).

Schiff et al., "Long-term Experience with Etanercept in the Treatment of Rheumatoid Arthritis in Elderly and Younger Patients," Drugs Aging 23:167-178 (2006).

Sesin et al., "Remission in Rheumatoid Arthritis: Wishful Thinking or Clinical Reality," Semin. Arthr. Rheum. 35:185-196 (2005).

Smolen et al., "A Simplified disease activity index for rheumatoid arthritis for use in clinical practice," Rheumatology 42(2):244-57 (2003).

Subvirion definition; http://www.definition-of.com/Subvirion+vaccine, downloaded Dec. 22, 2014.

Tutuncu et al., "Do patients with older-onset rheumatoid arthritis receive less aggressive treatment?" Ann. Rheum. Dis. 65:1226-1229 (2006).

Wolfe et al., "A composite disease activity scale for clinical practice observational studies and Clinical trials: the patient activity scale (PAS/PAS-11)," Journal of Rheumatology 32(12):2410-2415, 2005.

* cited by examiner

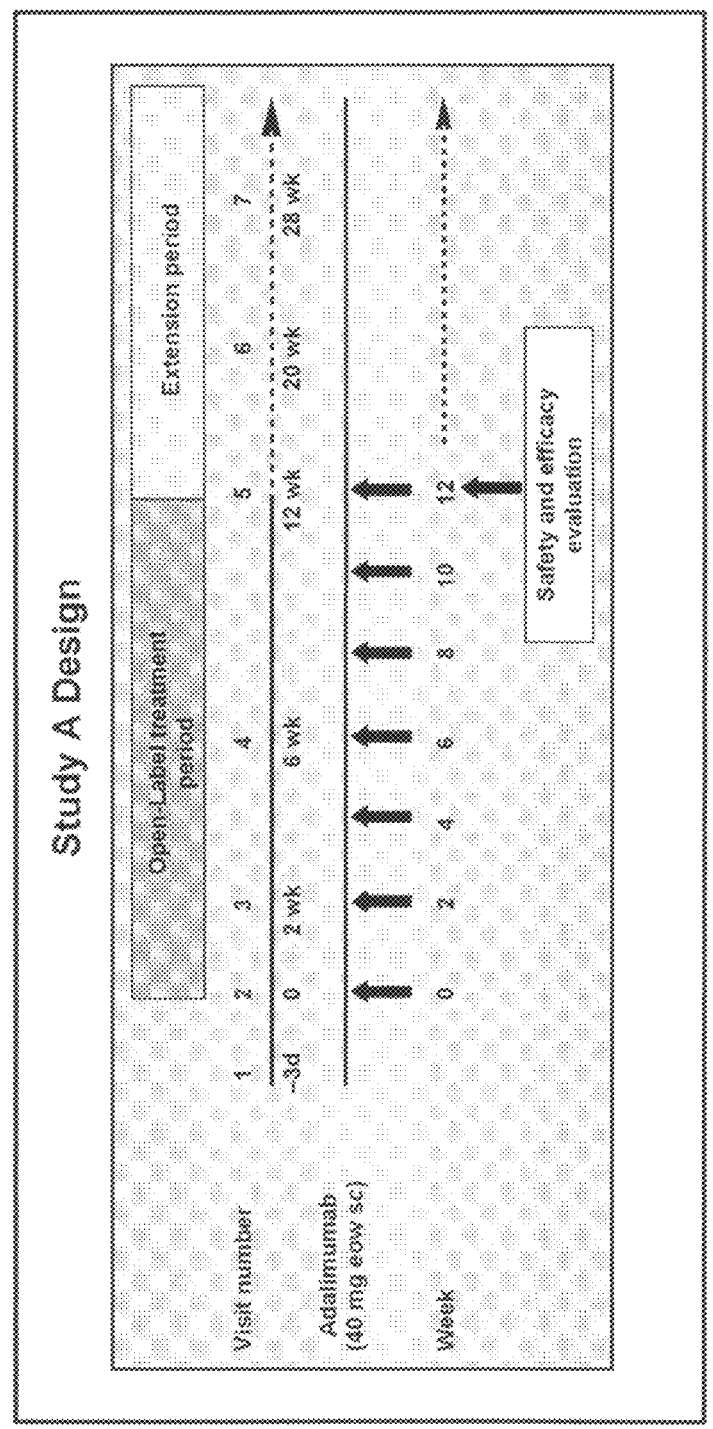
Figure 1. Study A Design

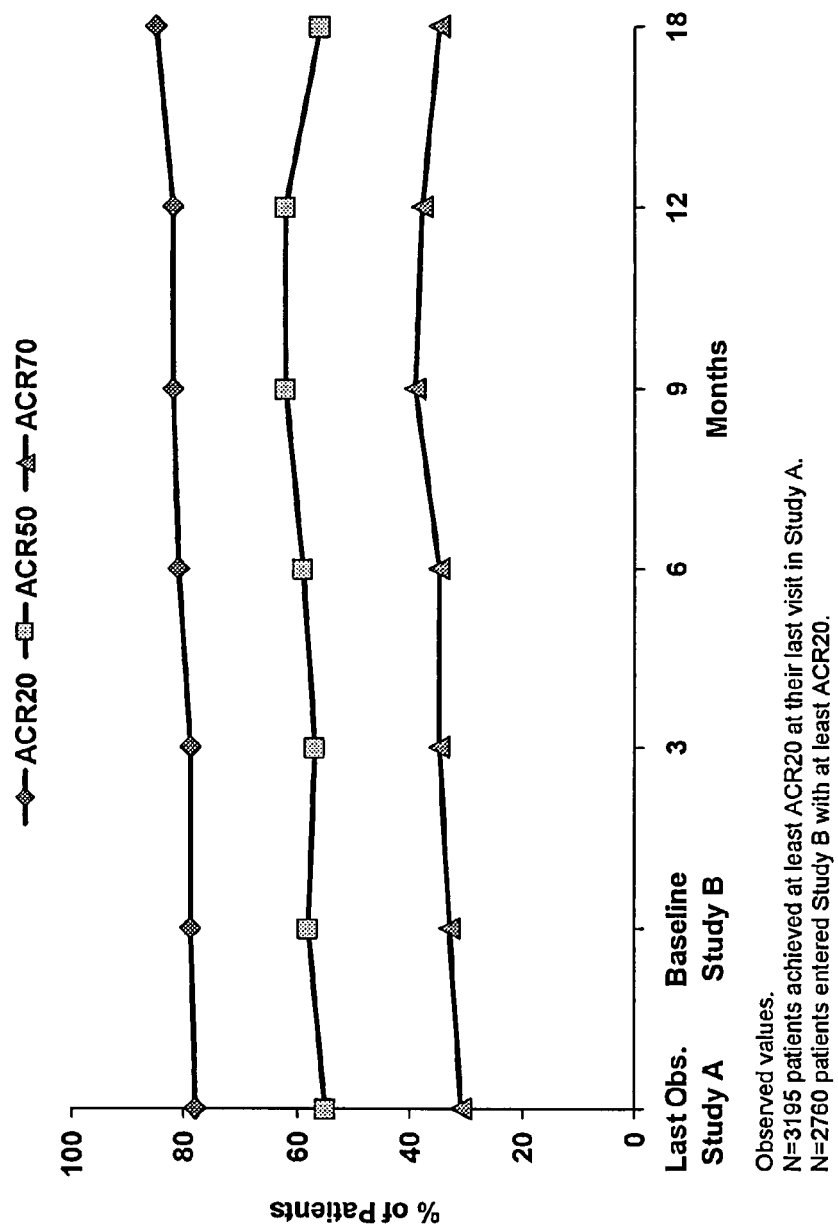

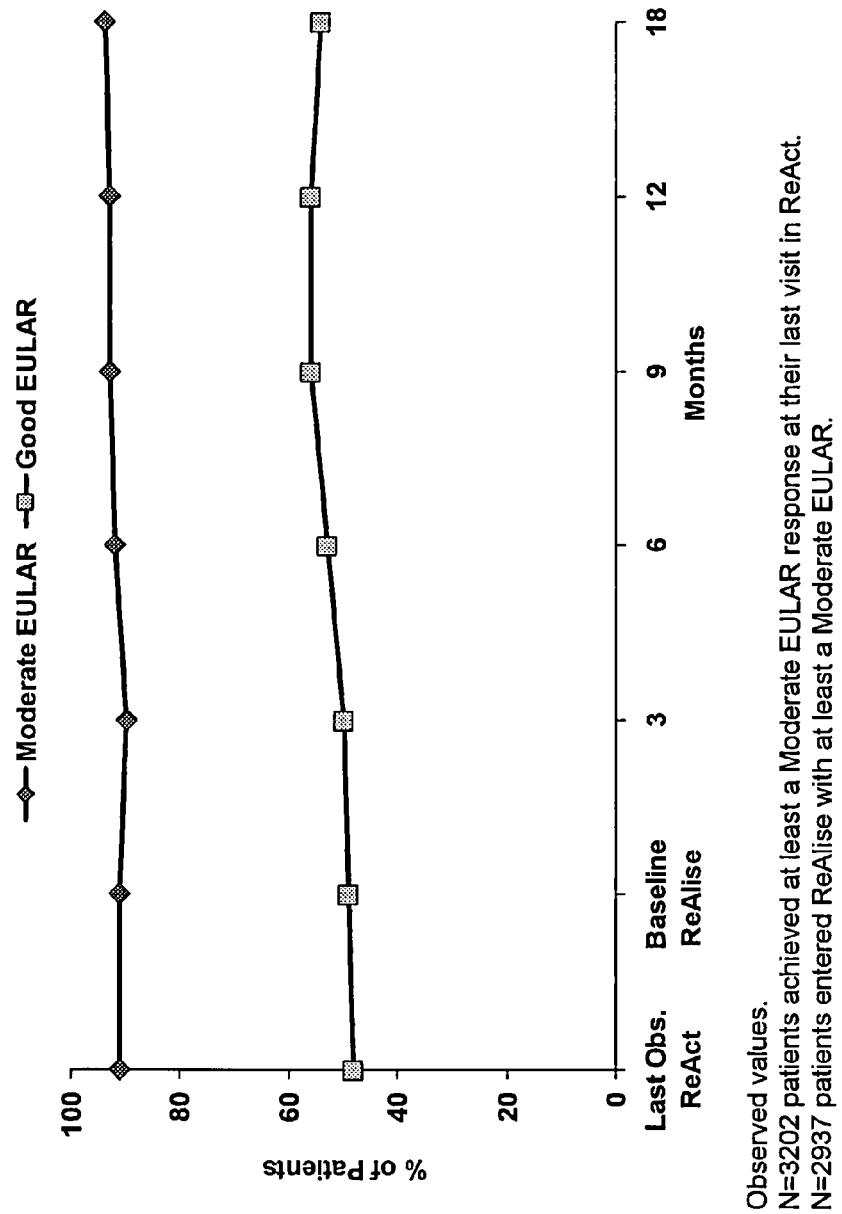

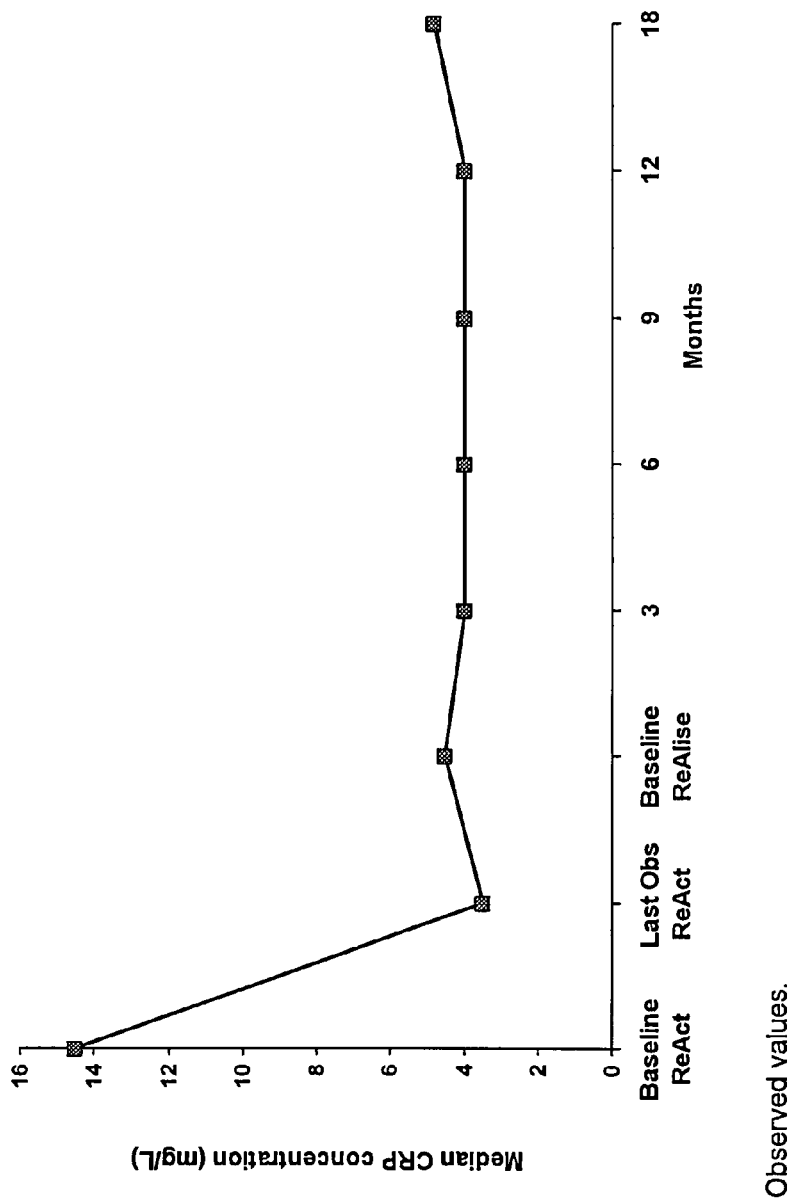
Figure 4. Median C-Reactive Protein Concentrations (mg/L) Over Time

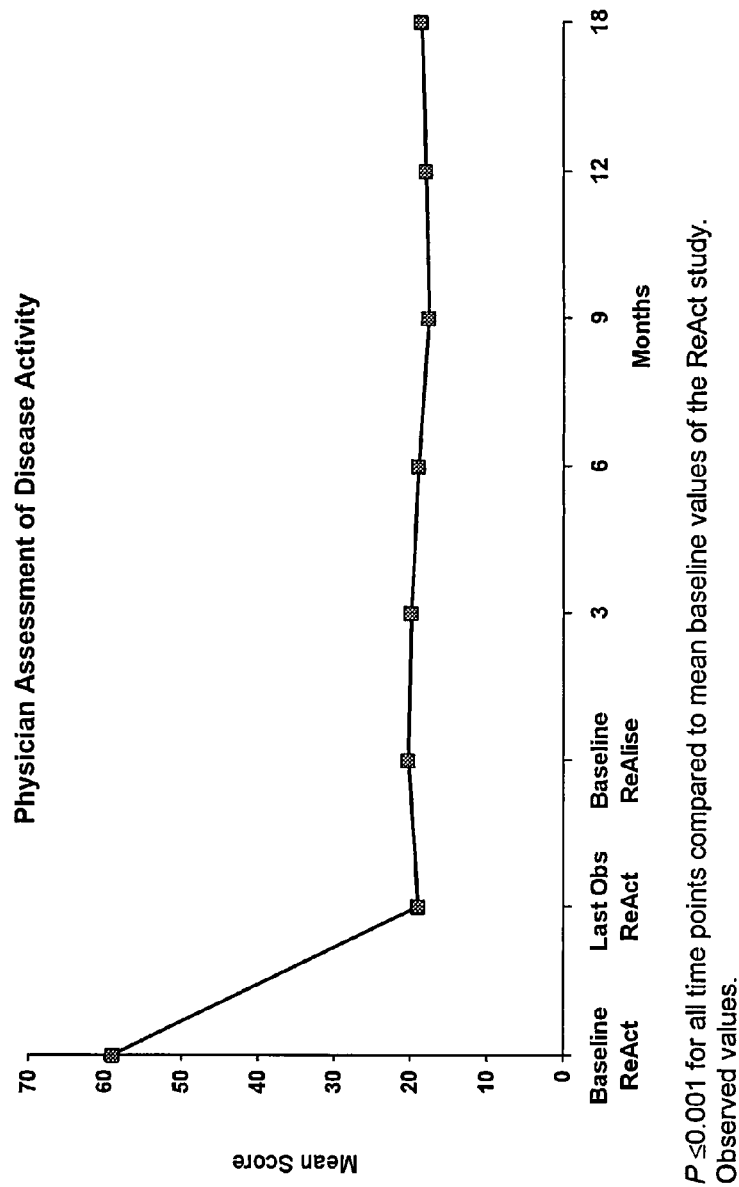
Figure 5. Physician and Patient Assessments of Disease Activity and Pain Over Time Through 18 Months

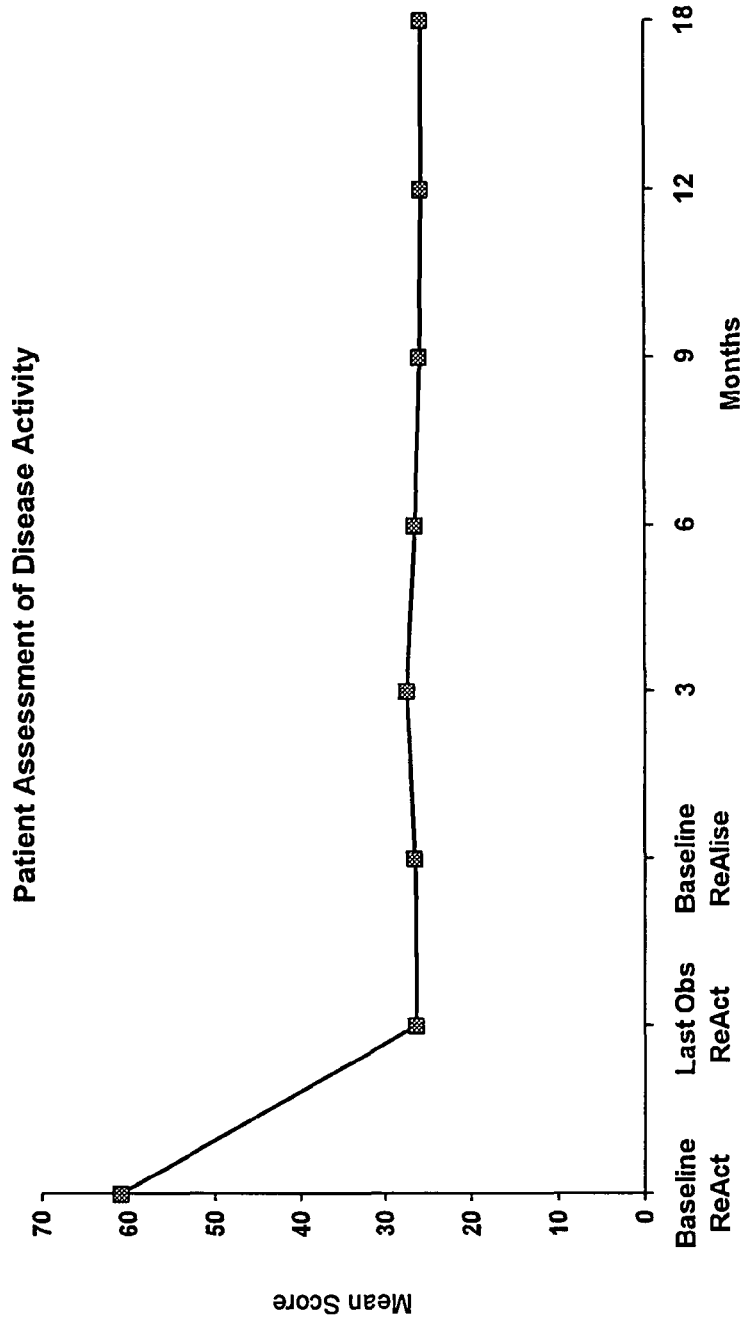

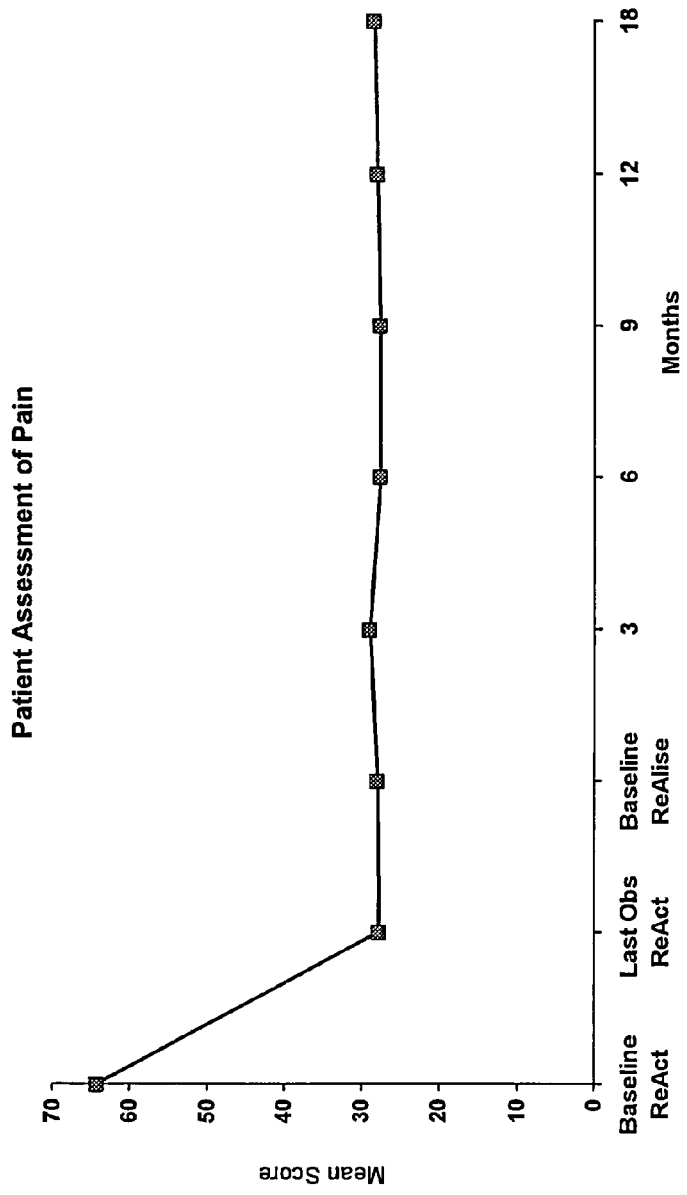
Figure 7. Physician and Patient Assessments of Disease Activity and Pain Over Time Through 18 Months
$P \leq 0.001$ for all time points compared to mean baseline values of the ReAct study. Observed values.

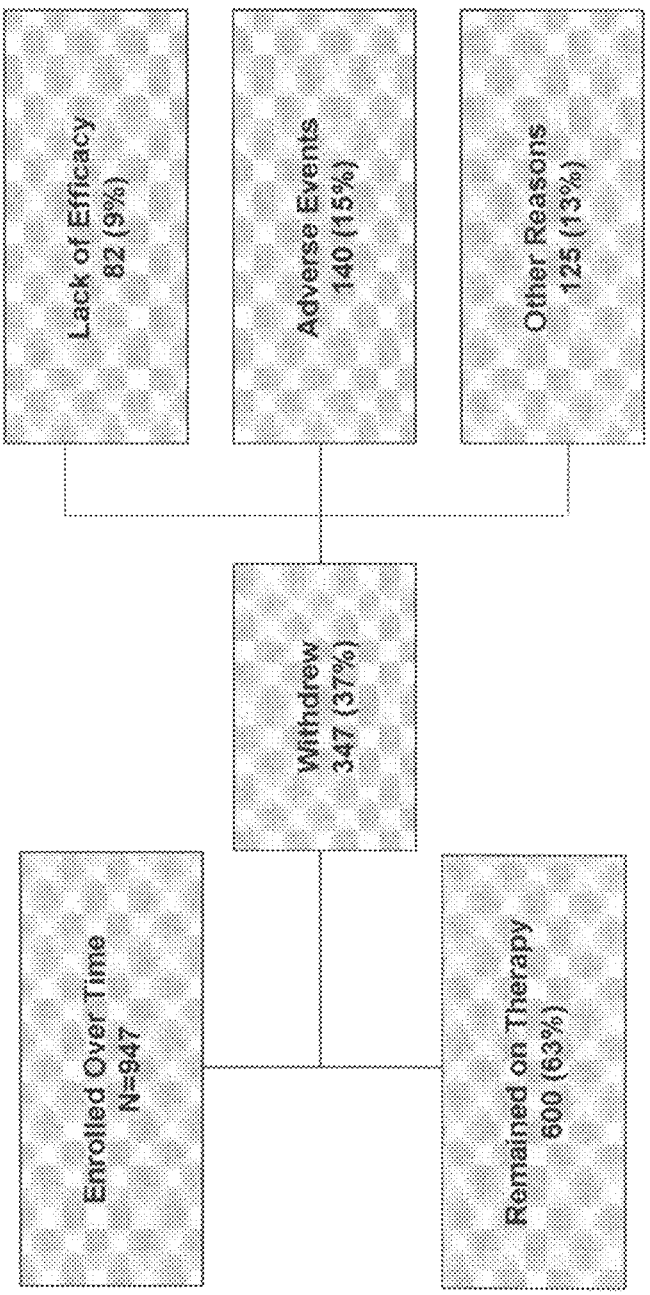

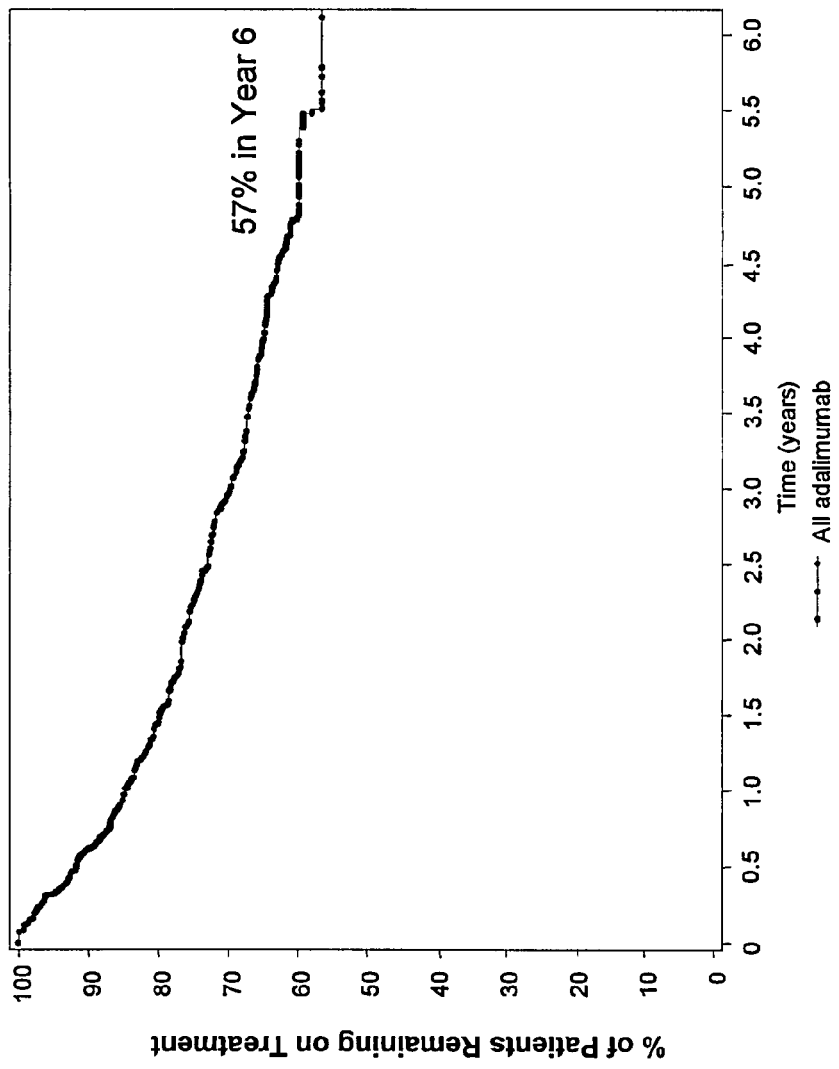
Figure 9. Percent of Patients Continuing on Adalimumab Treatment from First Dose Figure 10. Disease Activity and Functional Disability Scores by ACR20 Response
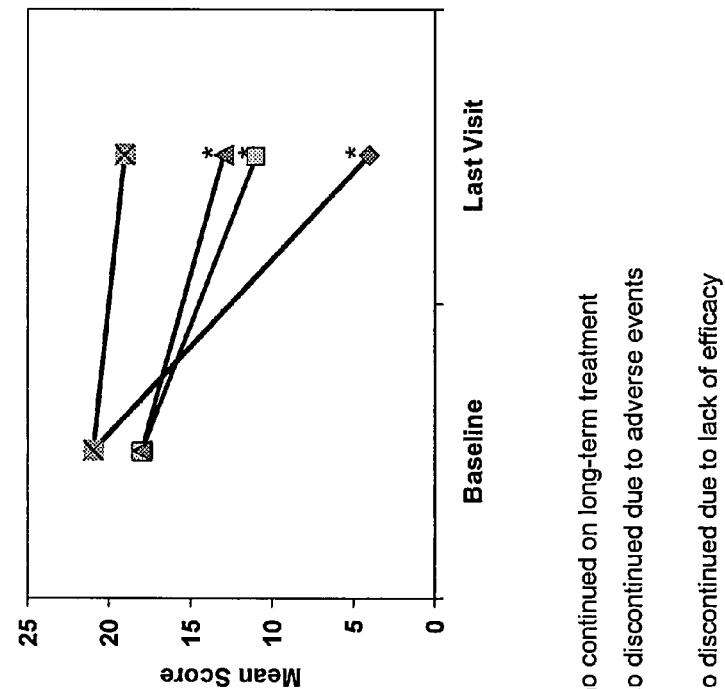
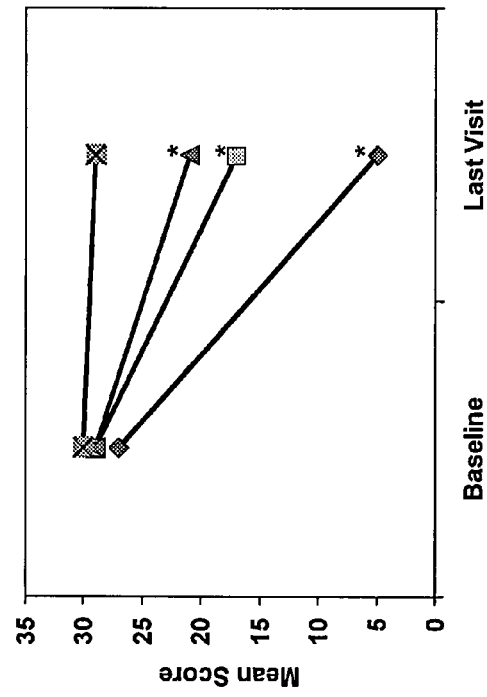

Figure 11. Disease Activity and Functional Disability Scores by ACR20 Response

DAS28

HAQ Disability Index

♦ ACR20 responders
■ ACR20 non-responders who continued on long-term treatment
▲ ACR20 non-responders who discontinued due to adverse events or other reasons
— ACR20 non-responders who discontinued due to lack of efficacy

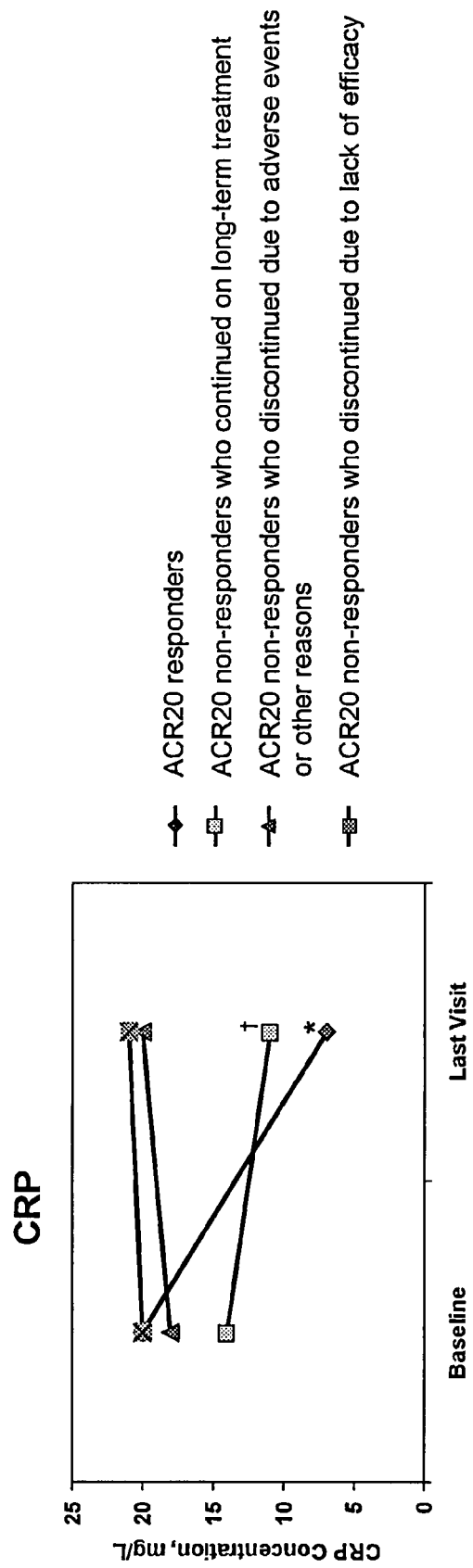
Figure 12. Disease Activity and Functional Disability Scores by ACR20 Response

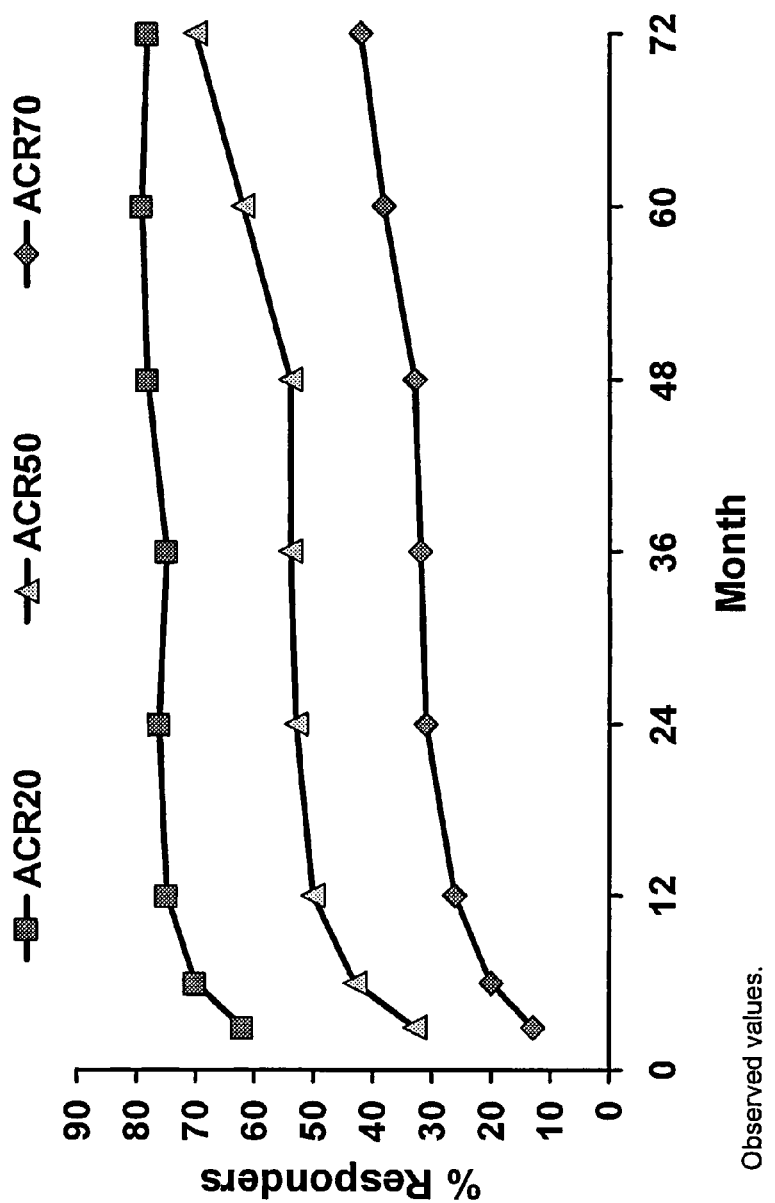
Figure 13. ACR Response Rates

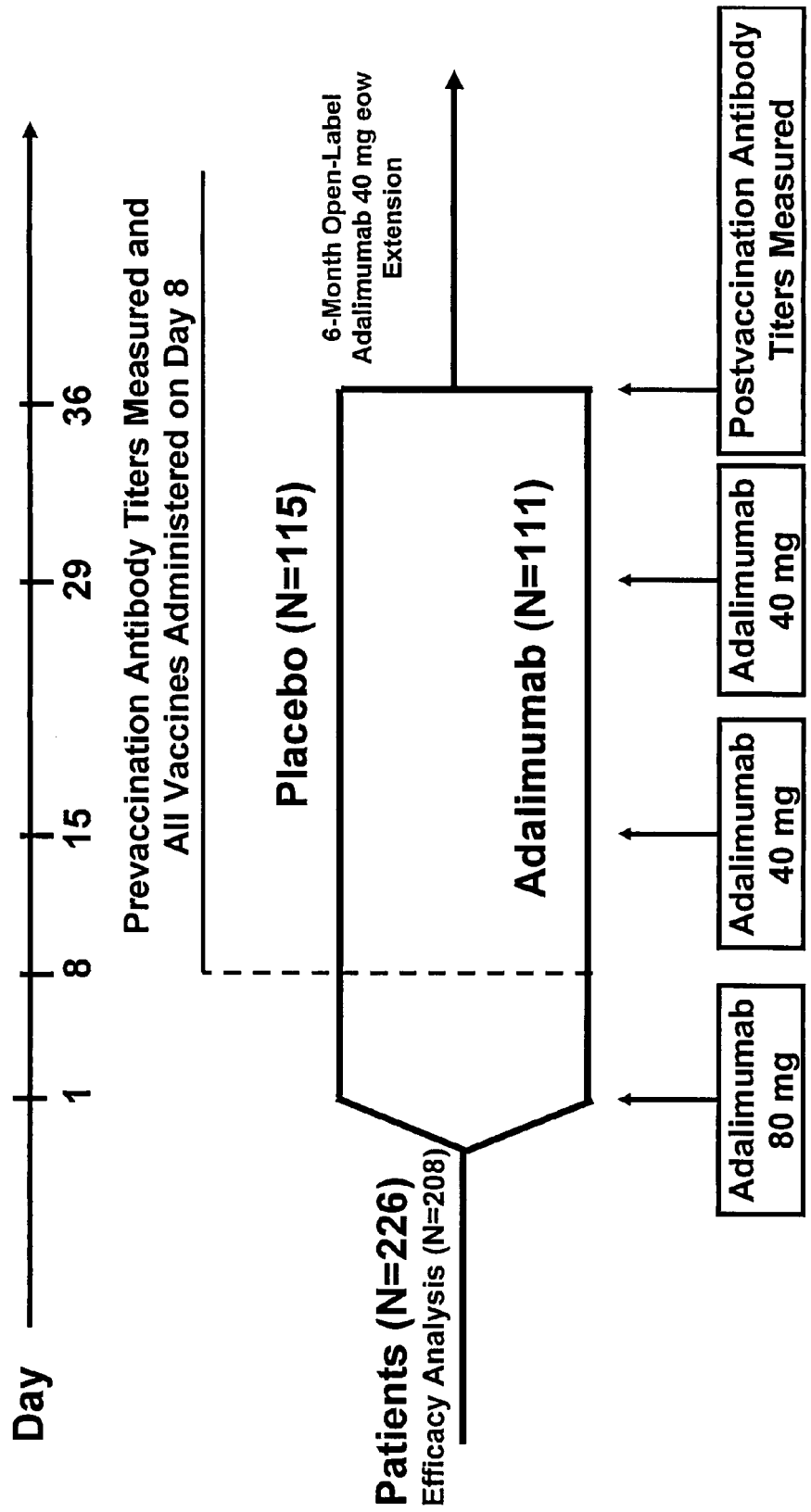
Figure 14. Study Design

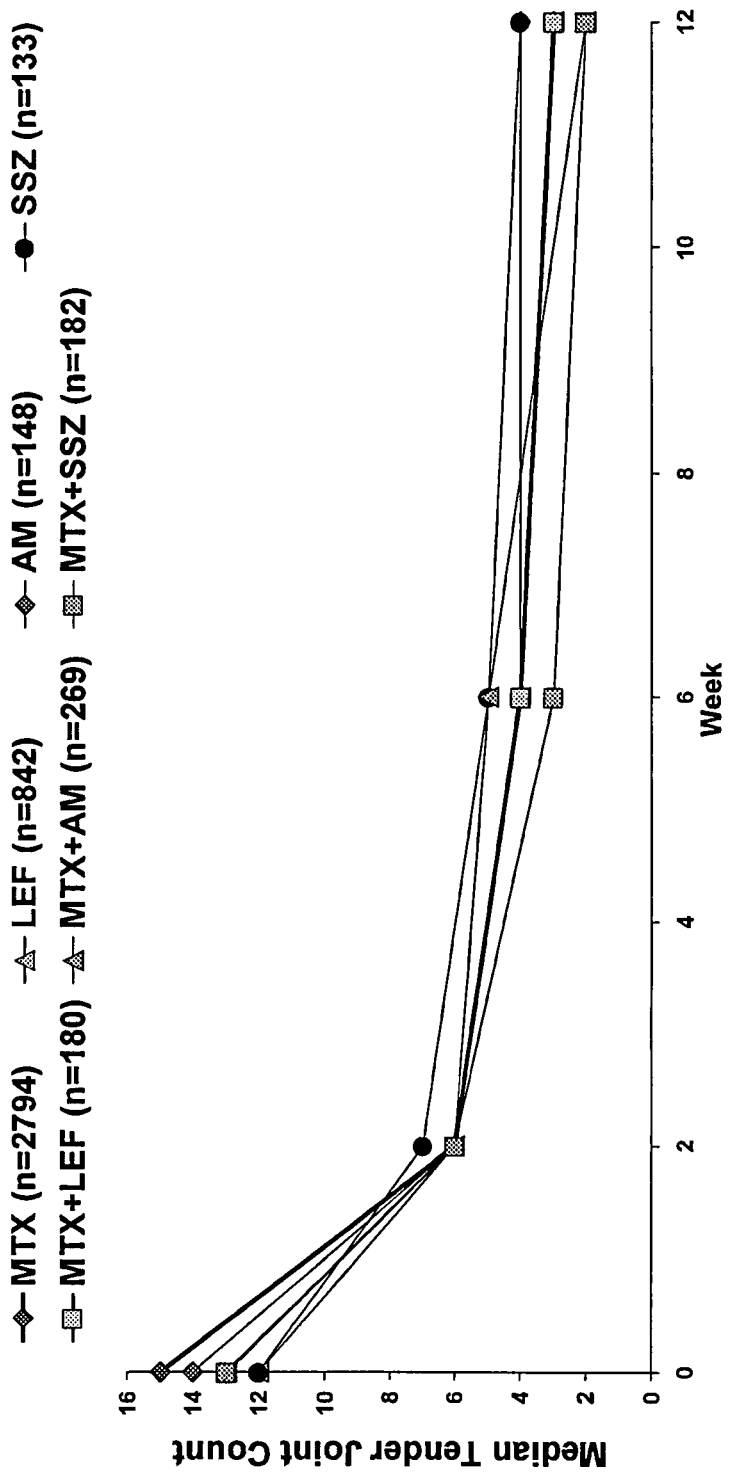
Figure 15. Median Tender Joint Count (TJC28) Through Week 12 by DMARD Combinations with Adalimumab

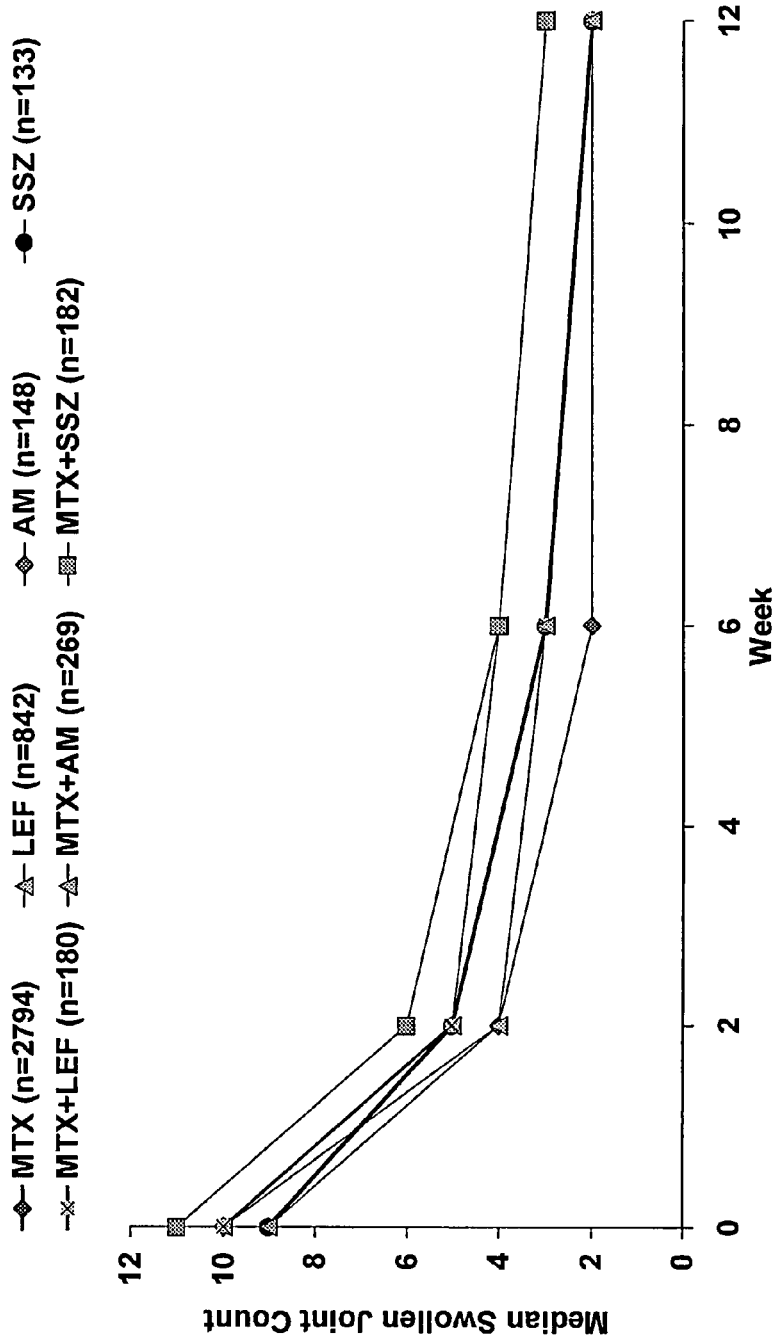
Figure 16. Median Swollen Joint Count (SJC28) at Week 12 by DMARD Combinations with Adalimumab

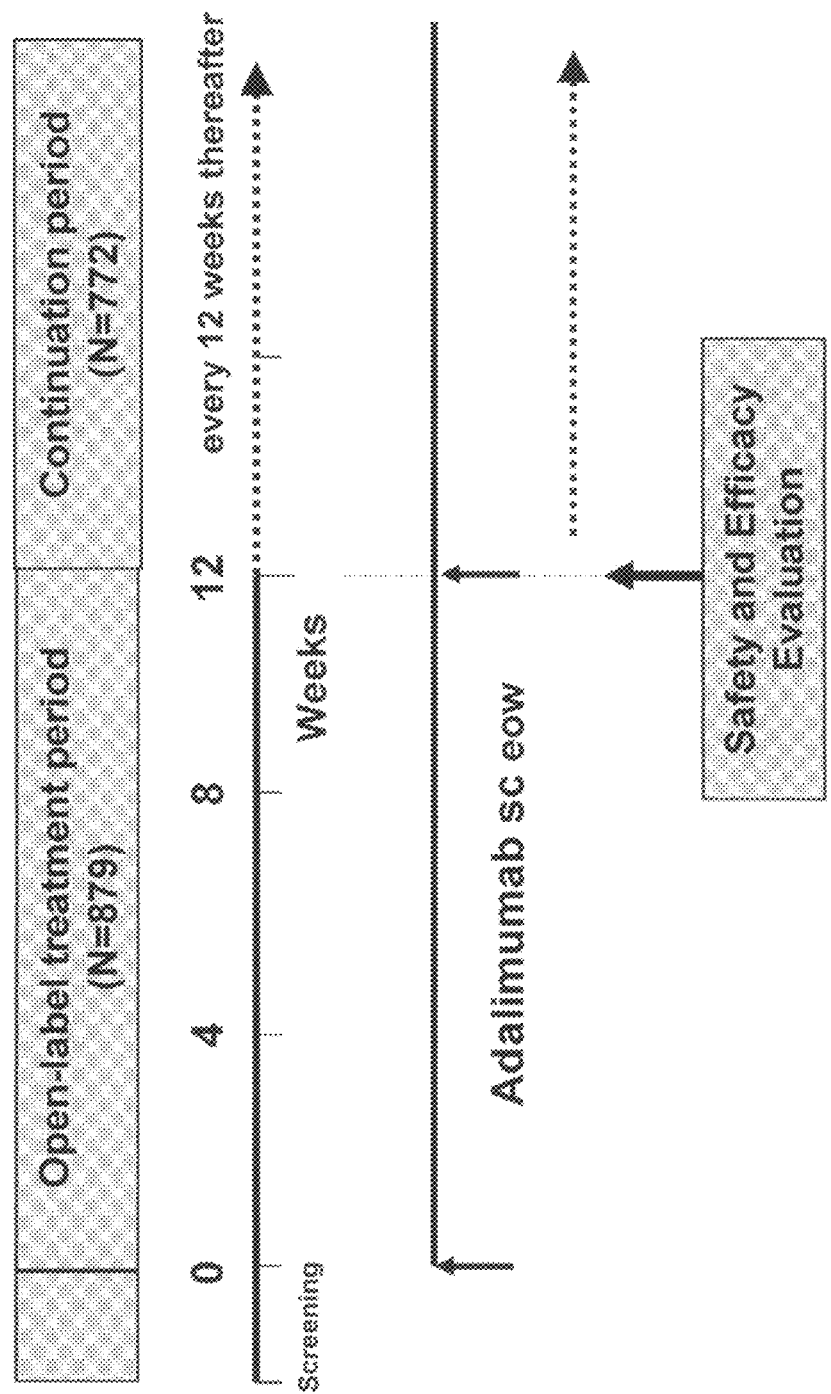
Figure 17. Study C Design

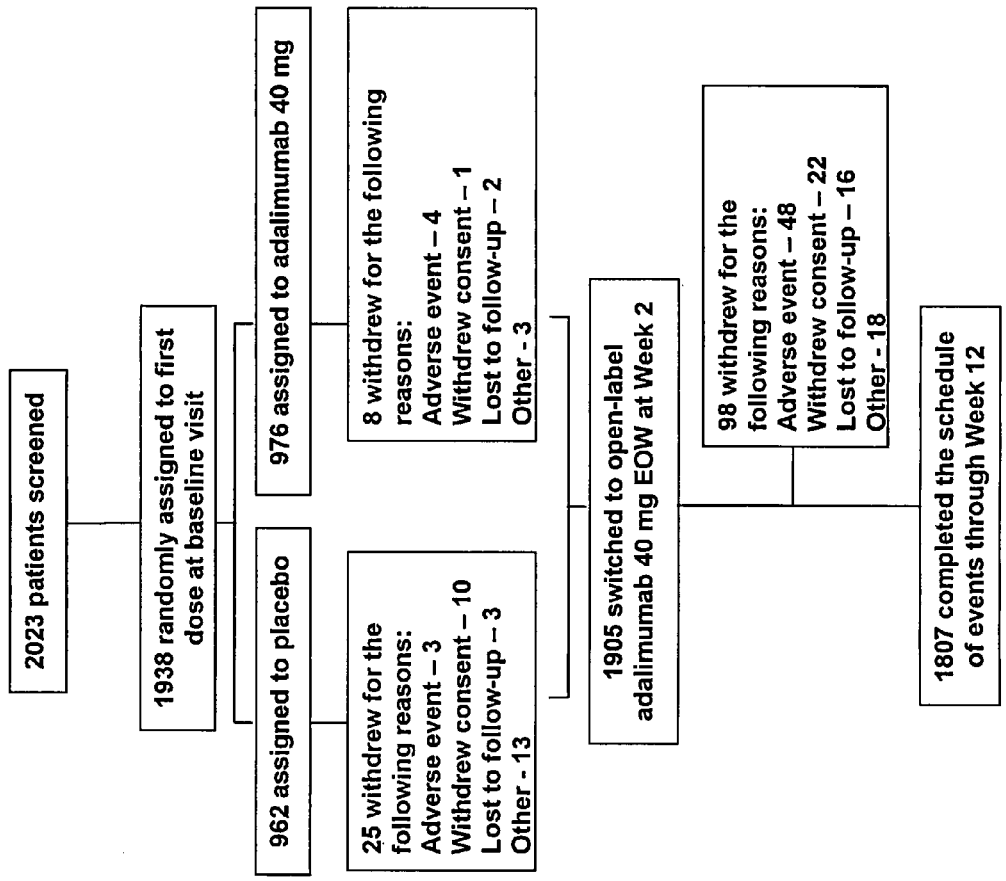
Figure 18. Disposition of Patients

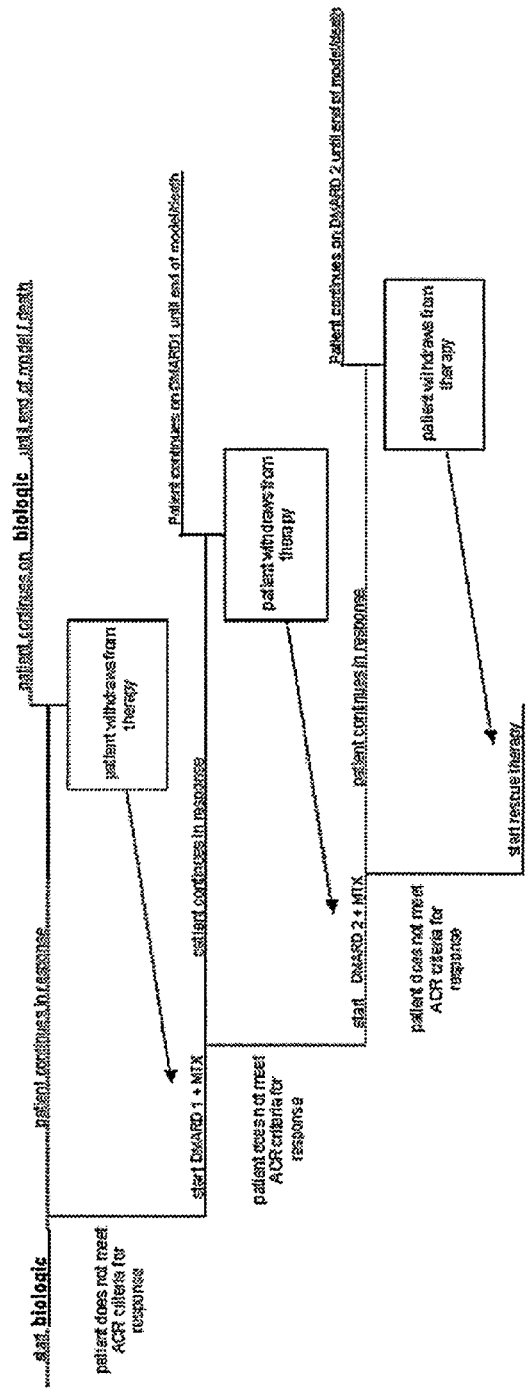
Figure 19. Illustration of Model Pathway
Model uses a 6-month cycle.
ACR response is determined 6 months after treatment, and subsequent withdrawal at 6-month intervals.
Following withdrawal, patients were switched to non-biologic DMARDs or rescue therapy.

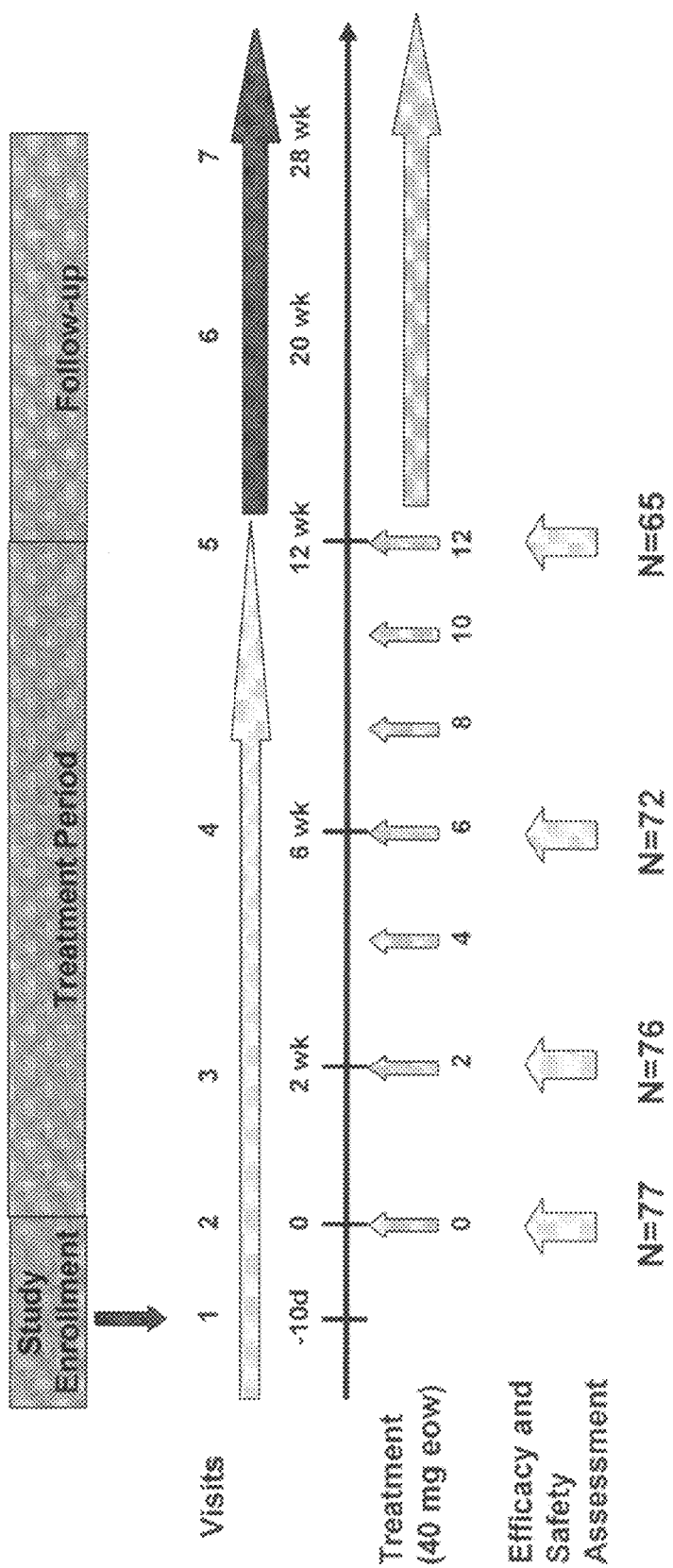
Figure 20. Study Design

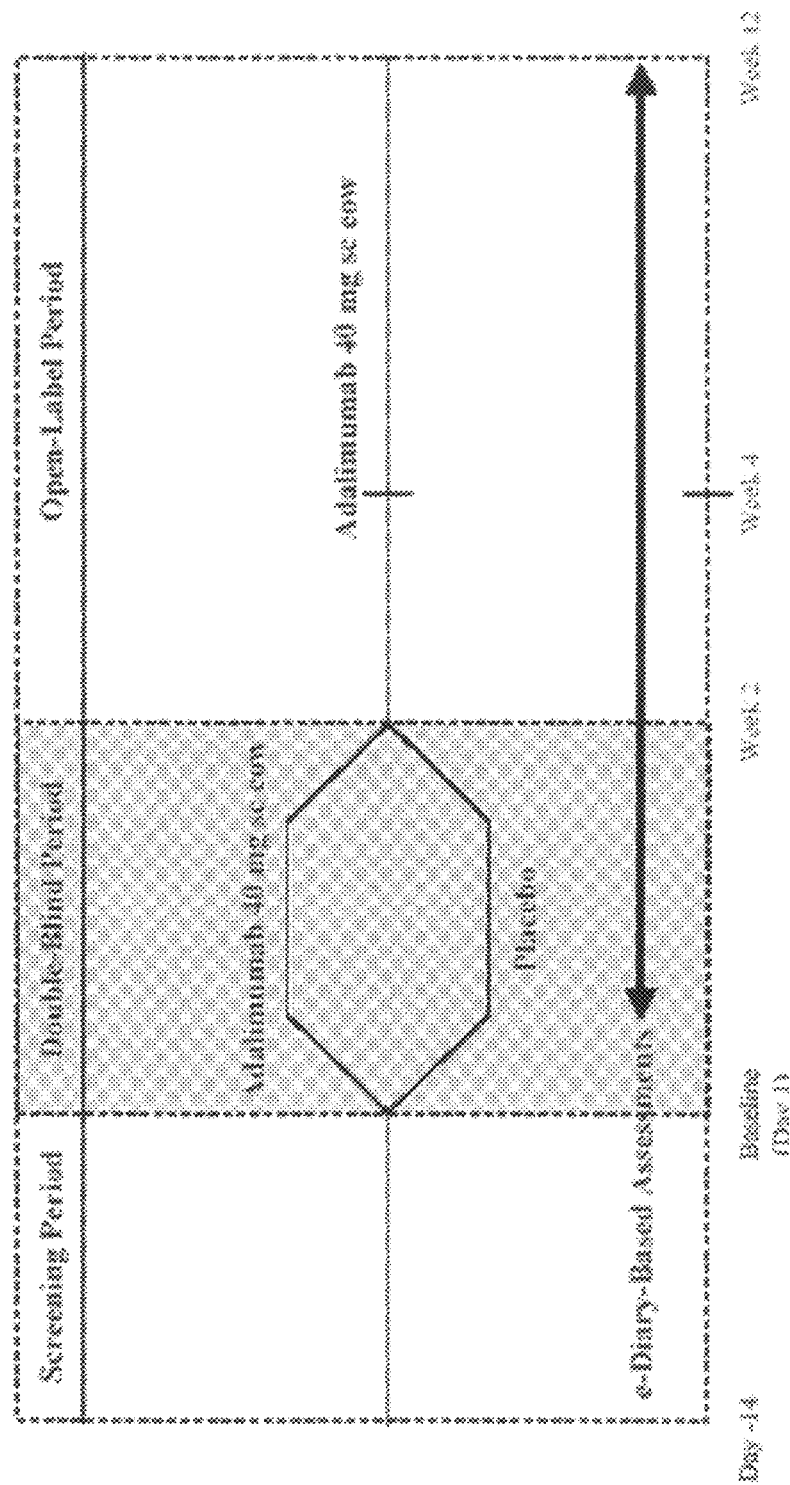
Figure 21. Study D Design

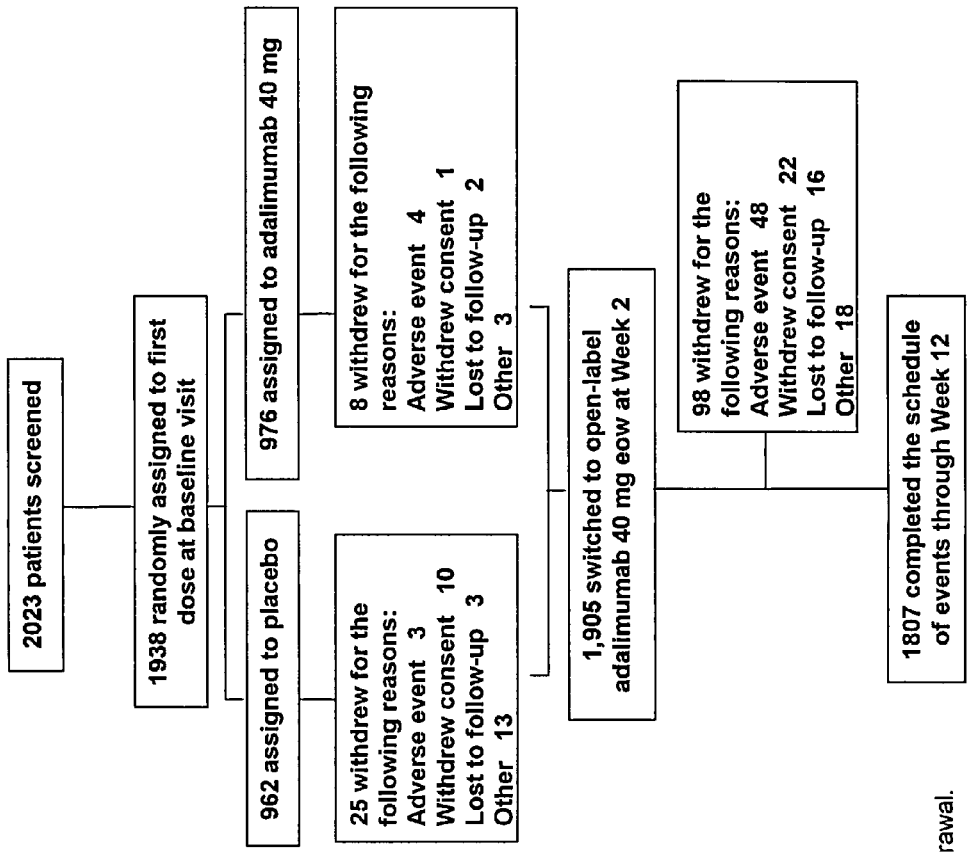
Figure 22. Study Disposition

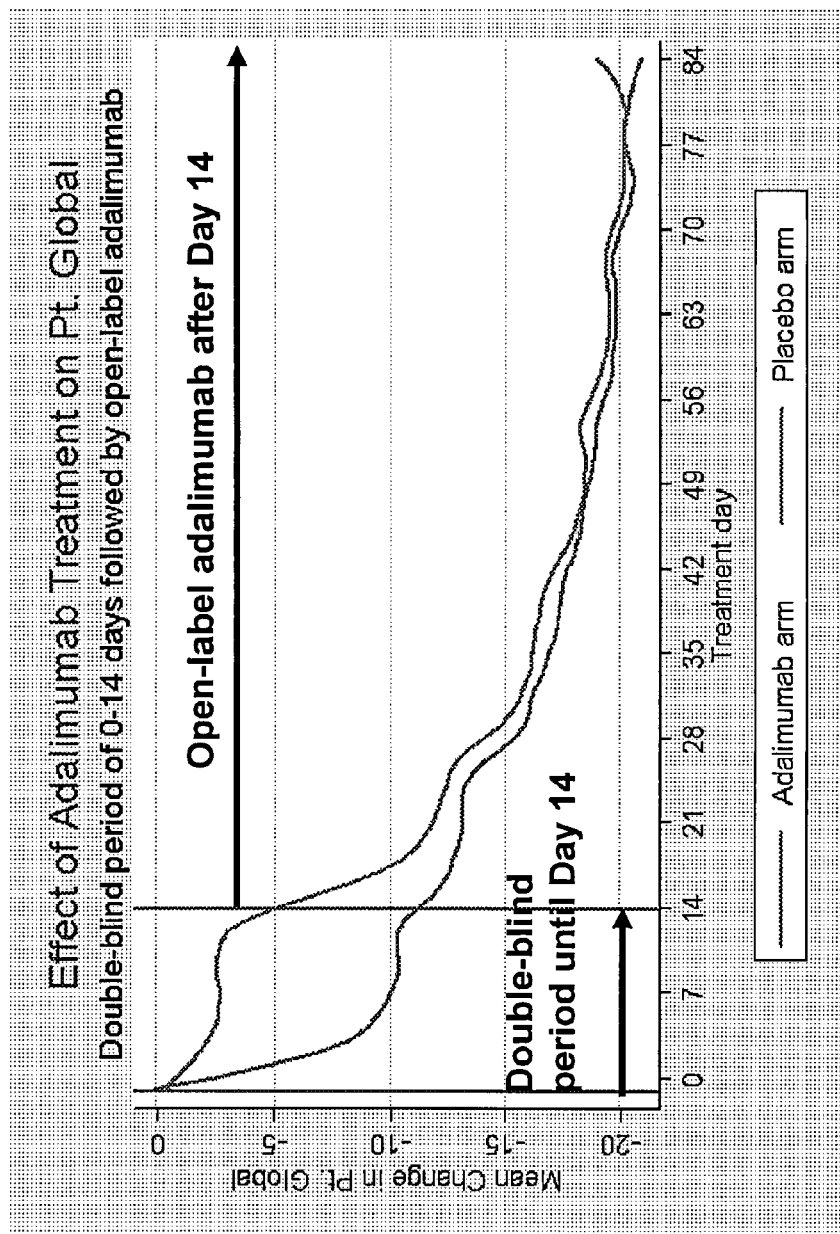
Figure 23. Time Course of Mean Change in E-diary Assessments to Week 12

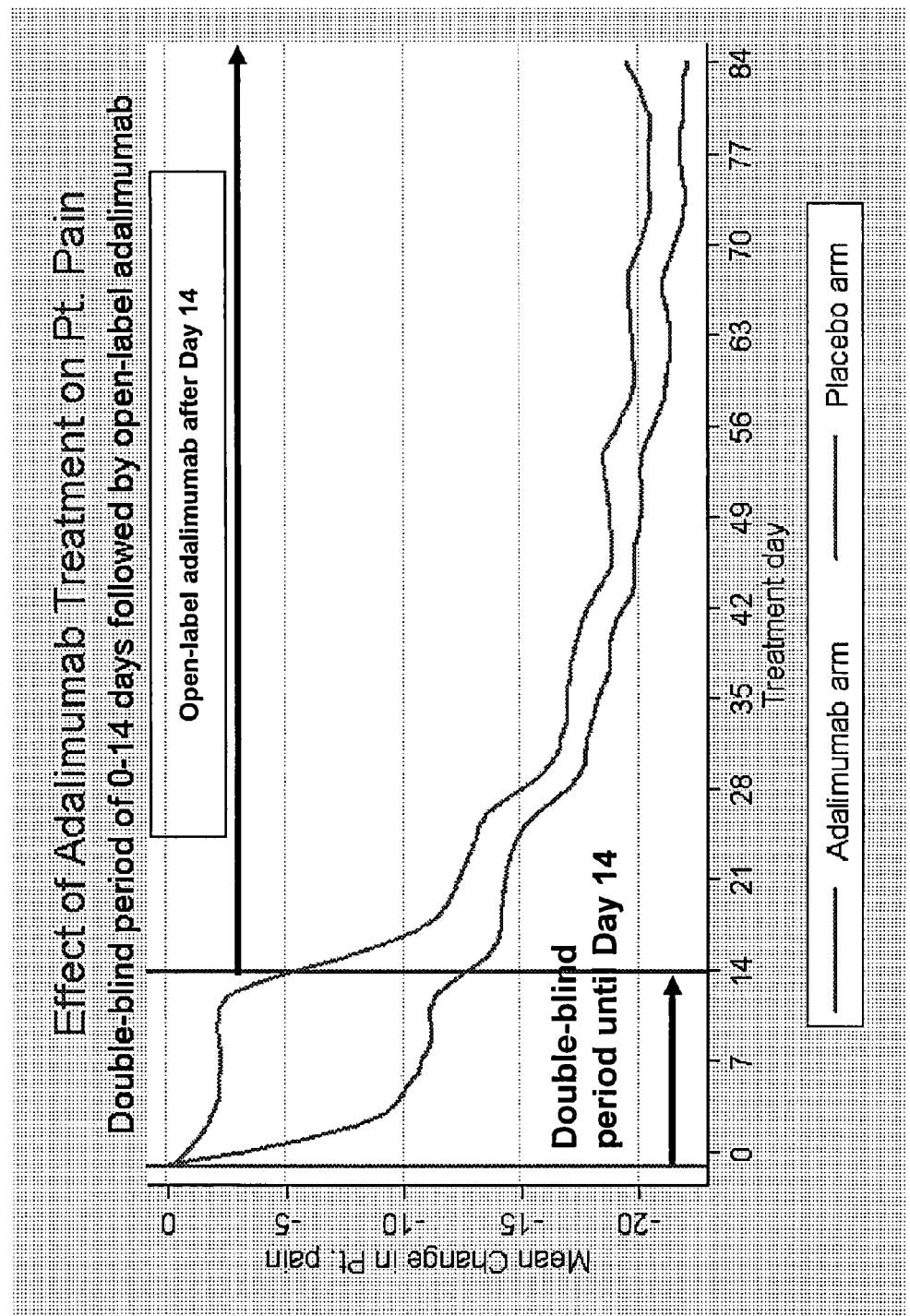
Figure 24. Effect of Adalimumab Treatment on Patient Pain

Figure 25. Effect of Adalimumab Treatment on Functional Disability
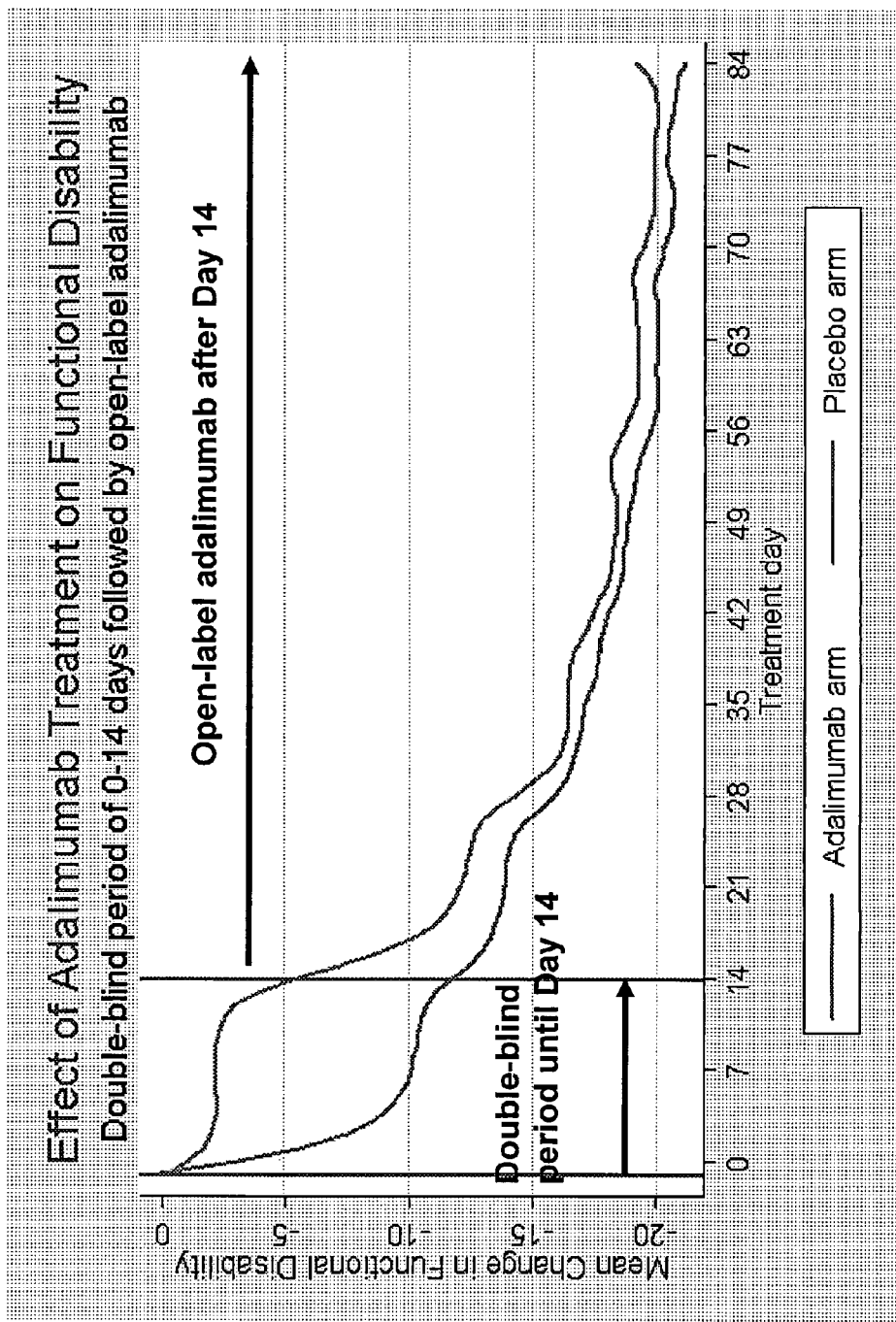

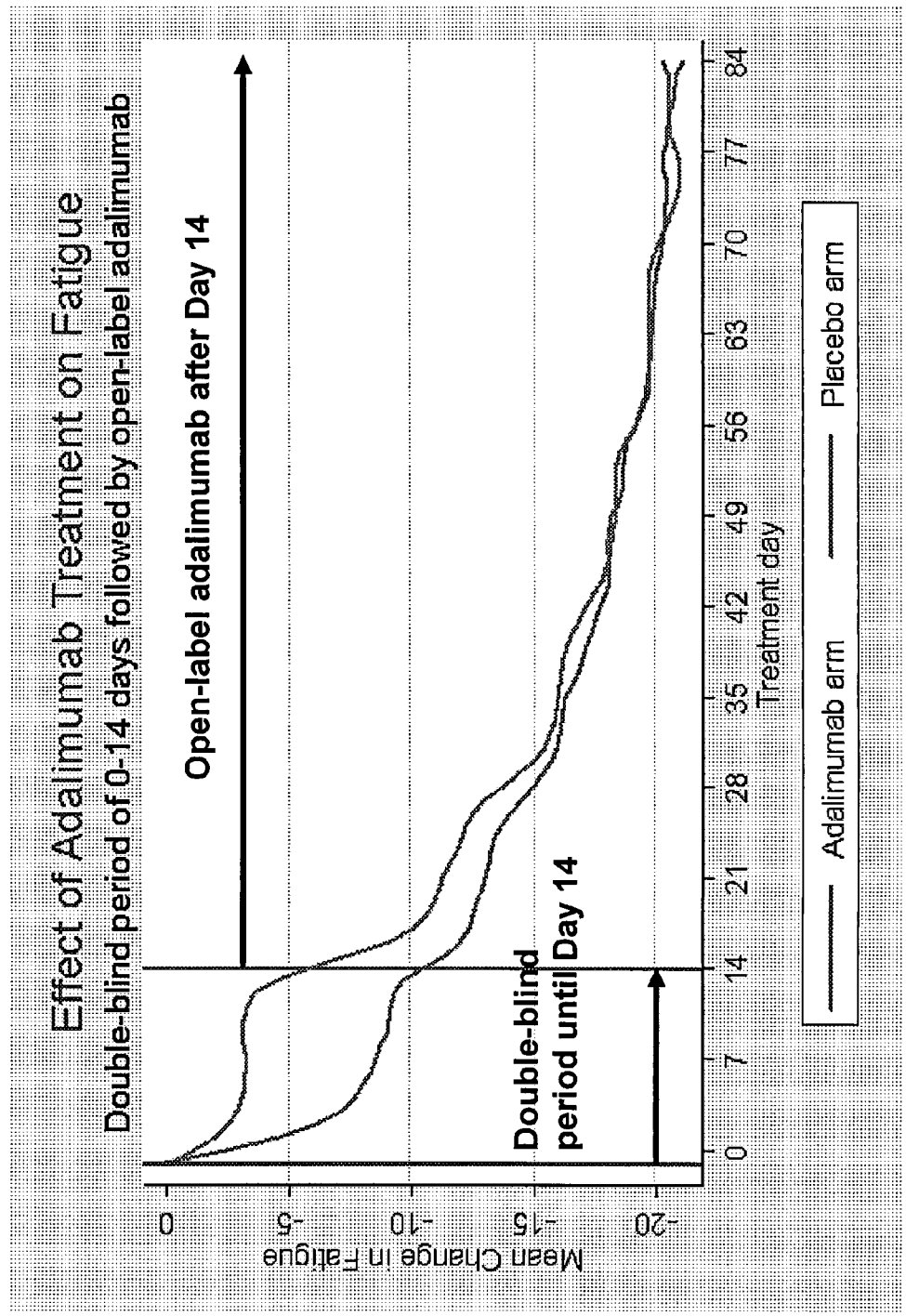
Figure 26. Effect of Adalimumab Treatment on Fatigue

Figure 27. Effect of Adalimumab Treatment on AM Stiffness Severity
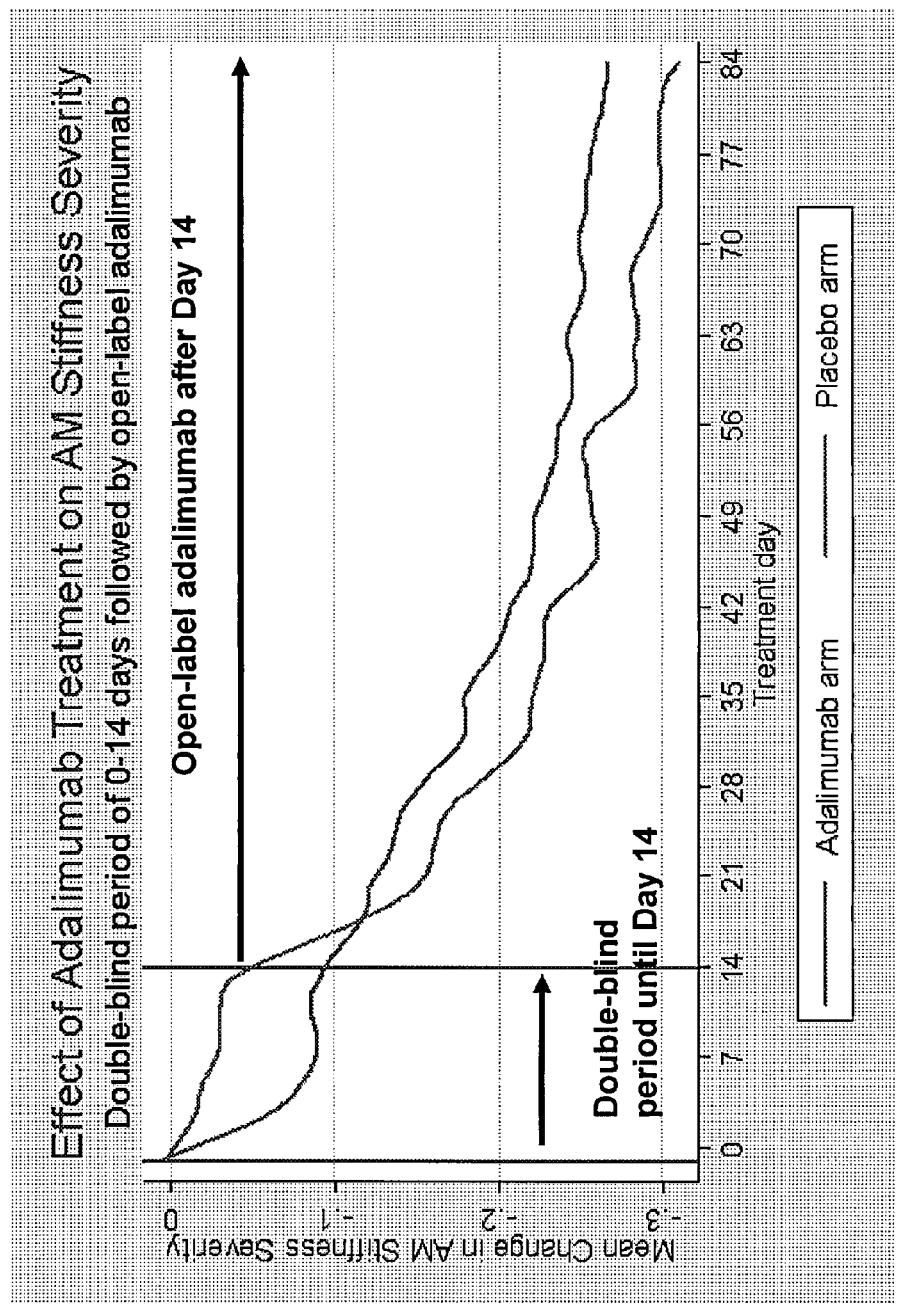

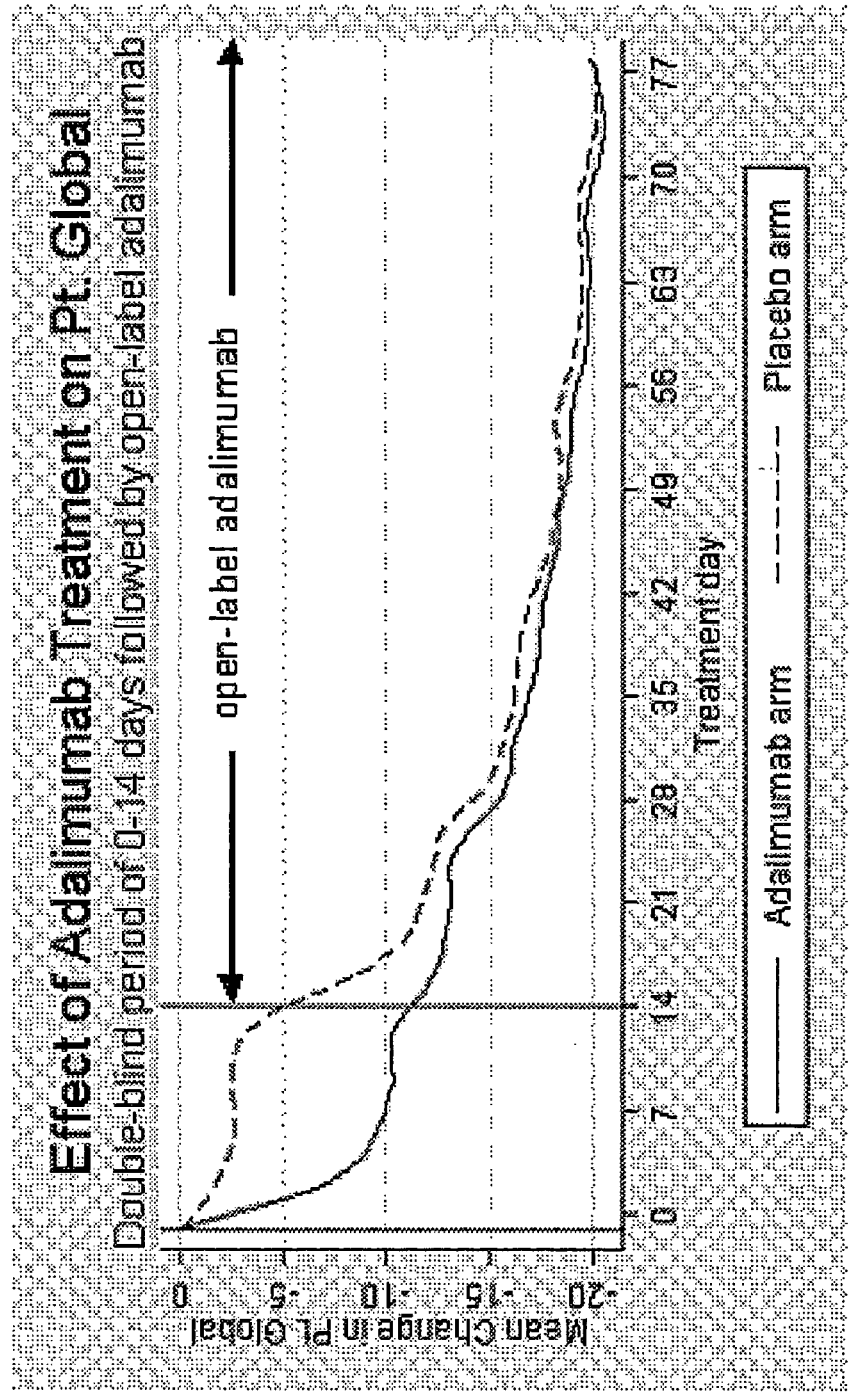
Figure 28. Effect of Adalimumab Treatment on Patient Global

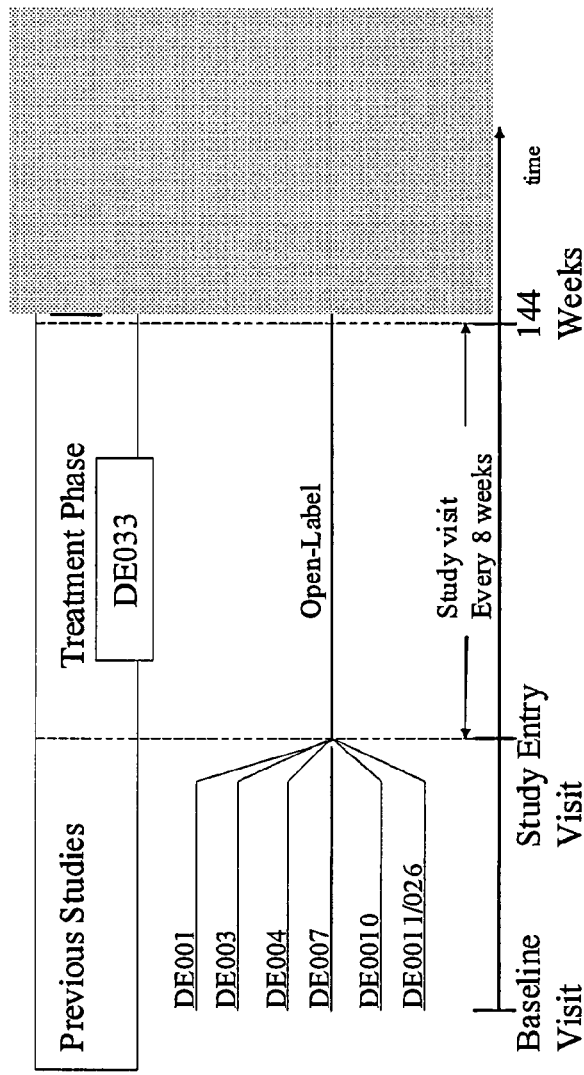
Figure 29. Enrollment of Study Participants
All dose-finding studies had different time durations.
Resource utilization data for the Health Outcomes study DE033 were collected at baseline retrospectively for 6 months and at various time points during the study for all patients.

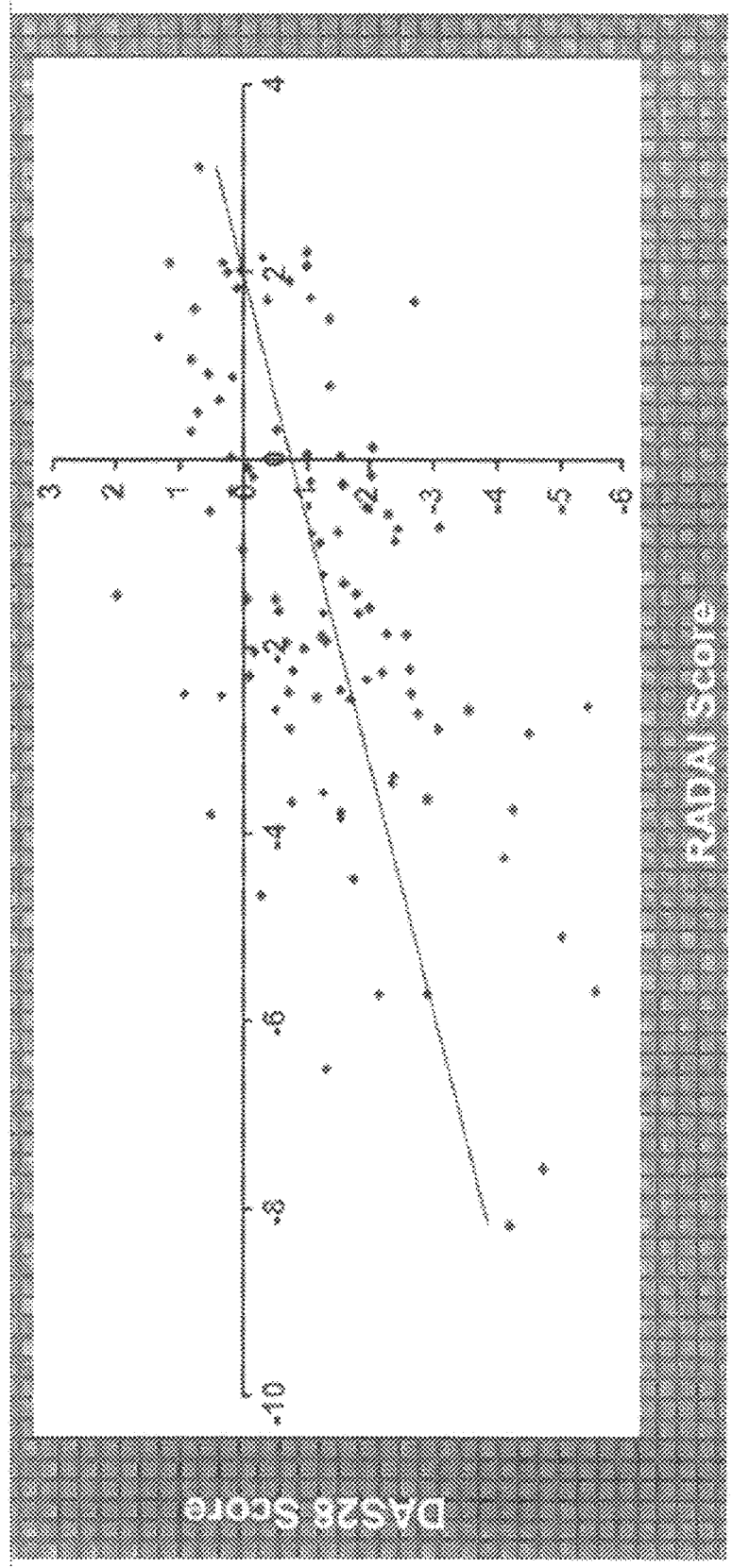
Figure 30. Correlation of RADAI and DAS28 Scores after 6 Months of Adalimumab Therapy (N=100)

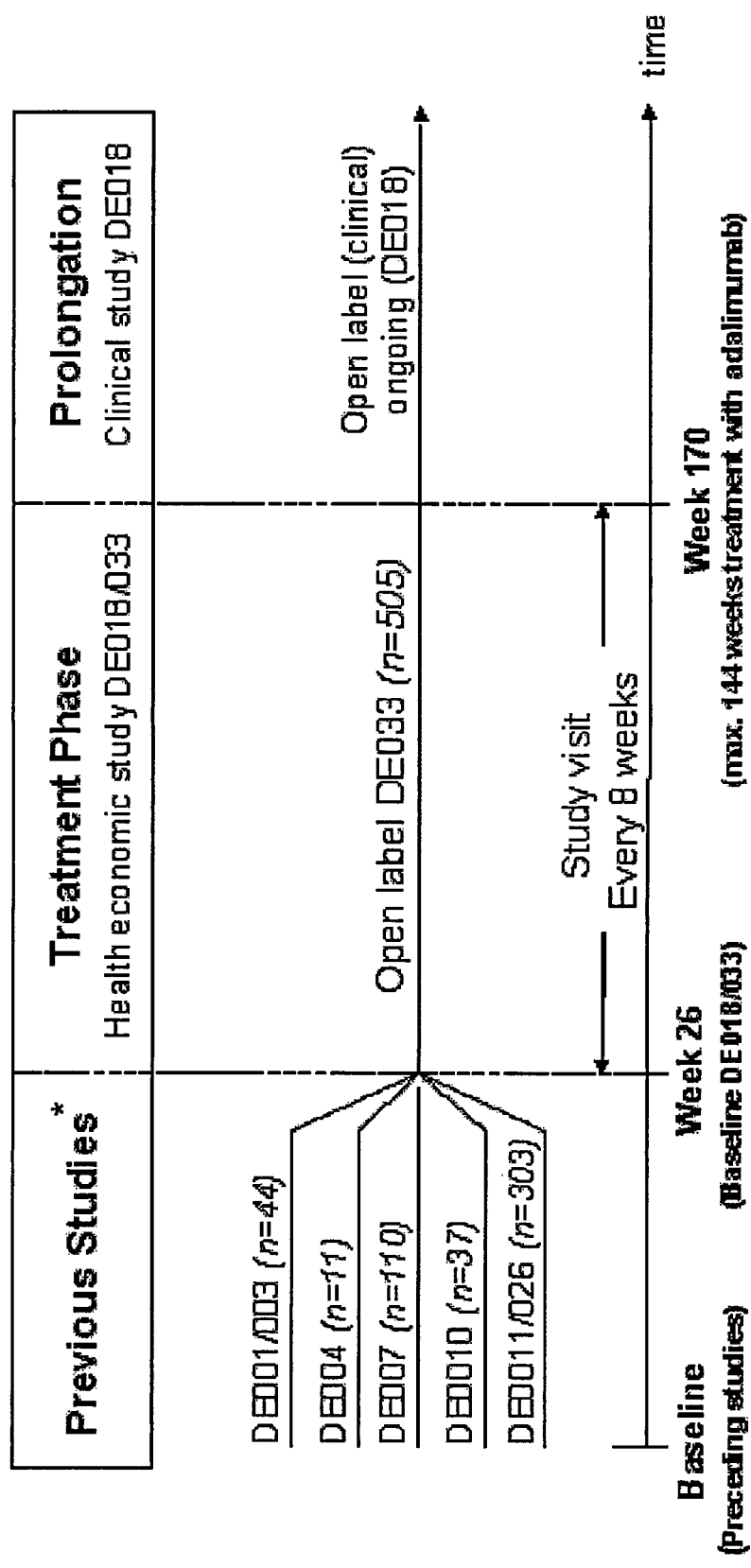
Figure 31. Composition of the study population with regard to preceding dose-finding studies

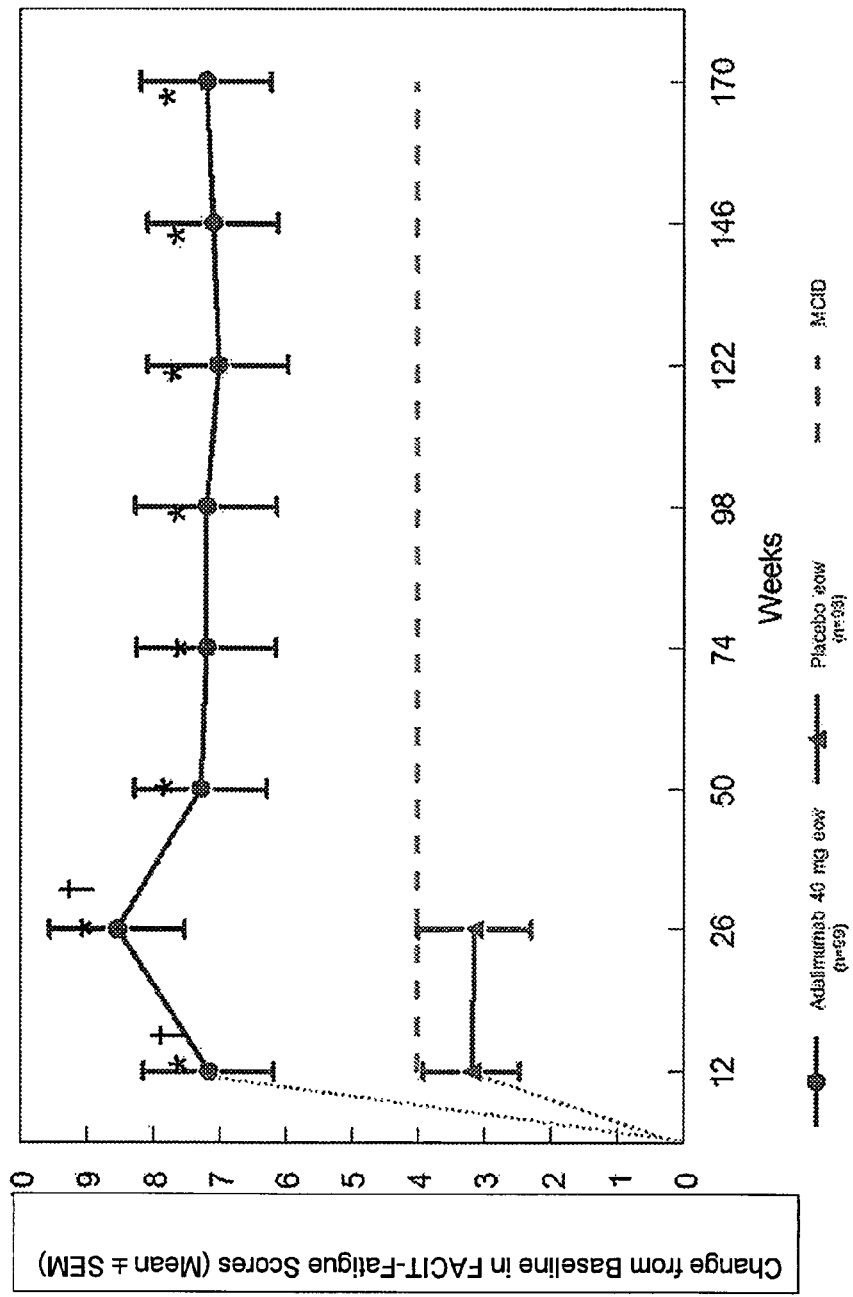
Figure 32. Change from baseline in Functional Assessment of Chronic Illness Therapy-Fatigue (FACIT-Fatigue) scores in the DE026 subgroup over 3 years (n=99)

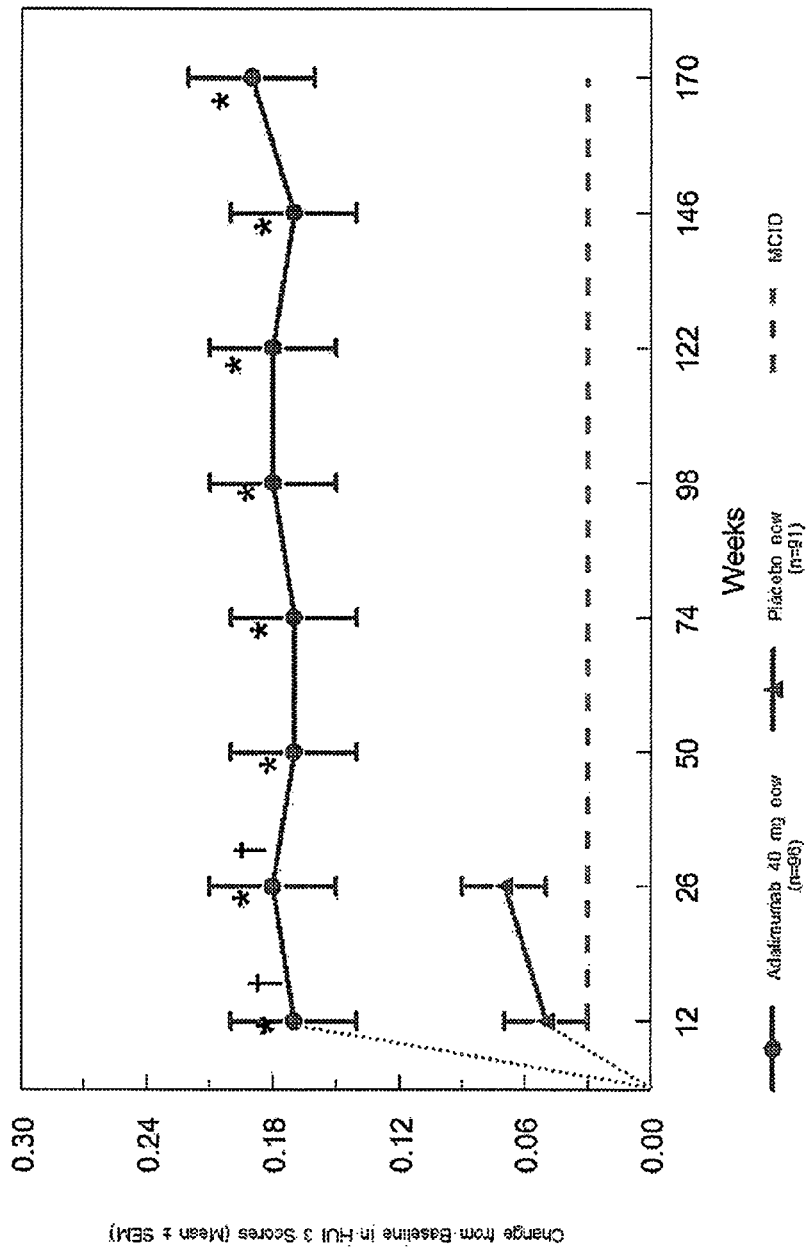
Figure 33. Change from baseline in health utility index (HUI3) scores in the DE026 subgroup over 3 years (n=99)

US 9,399,061 B2

METHODS FOR DETERMINING EFFICACY OF TNF-α INHIBITORS FOR TREATMENT OF RHEUMATOID ARTHRITIS

RELATED APPLICATIONS

This application claims the benefit of priority to U.S. provisional patent application No. 60/790,909 filed on Apr. 10, 2006; U.S. provisional patent application No. 60/809,770 filed on May 30, 2006; U.S. provisional patent application No. 60/815,489 filed on Jun. 20, 2006; U.S. provisional patent application No. 60/858,376, filed on Nov. 10, 2006; U.S. provisional patent application No. 60/902,427 filed on Feb. 21, 2007; U.S. provisional patent application No. 60/899,262 filed on Feb. 2, 2007; and U.S. provisional patent application No. 60/909,683 filed on Apr. 2, 2007. The contents of all the above-mentioned priority applications are hereby incorporated by reference in their entirety.

BACKGROUND OF THE INVENTION

Rheumatoid arthritis (RA) is considered a chronic, inflammatory autoimmune disorder. RA is a disabling and painful inflammatory condition which can lead to the substantial loss of mobility due to pain and joint destruction. RA leads to the soft-tissue swelling of joints.

SUMMARY OF THE INVENTION

In one aspect, the invention provides a method of preventing Pneumococcal disease and treating rheumatoid arthritis (RA) in a subject comprising administering a pneumococcal vaccine and a human TNFα antibody, or antigen-binding portion thereof, to the subject, such that Pneumococcal disease is prevented and rheumatoid arthritis is treated.

In one aspect, the invention provides the use of a human TNFα antibody, or antigen-binding portion thereof, in the manufacture of a medicament for the treatment of RA in a subject, wherein the medicament is designed to be administered in combination with a pneumococcal vaccine for the prevention of Pneumococcal disease.

In another aspect, the invention provides a method of treating late-onset RA comprising administering a human TNFα antibody, or antigen-binding portion thereof, to a patient having late-onset RA.

In another aspect, the invention provides the use of a human TNFα antibody, or antigen-binding portion thereof, in the manufacture of a medicament for the treatment of late-onset RA in a subject.

In one embodiment, the subject is over 60 years old.

In another embodiment, the human TNFα antibody, or antigen-binding portion thereof, is administered to the subject in a biweekly dosing regimen. In another embodiment, the human TNFα antibody, or antigen-binding portion thereof, is administered to the subject in a dose of 40 mg. In one embodiment, the human TNFα antibody, or antigen-binding portion thereof, is administered to the subject subcutaneously.

In one aspect, the invention provides a method of determining the efficacy of a TNFα inhibitor for treating RA in a subject comprising determining an ACR20 response of a patient population having RA and who was administered the TNFα inhibitor, wherein an ACR20 response in at least about 80% of the patient population indicates that the TNFα inhibitor is an effective TNFα inhibitor for the treatment of RA in a subject.

In one embodiment, an ACR20 response in at least about 85% of the patient population indicates that the TNFα inhibitor is an effective TNFα inhibitor for the treatment of RA in a subject.

In another aspect, the invention provides a method of determining the efficacy of a TNFα inhibitor for treating RA in a subject comprising determining an ACR50 response of a patient population having RA and who was administered the TNFα inhibitor, wherein an ACR50 response in at least about 62% of the patient population indicates that the TNFα inhibitor is an effective TNFα inhibitor for the treatment of RA in a subject.

In one embodiment, an ACR50 response in at least about 65% of the patient population indicates that the TNFα inhibitor is an effective TNFα inhibitor for the treatment of RA in a subject. In another embodiment, the method further comprises administering the effective TNFα inhibitor to a subject for the treatment of RA.

In one aspect, the invention provides a method of treating RA in a subject comprising administering an effective TNFα inhibitor, wherein the effective TNFα inhibitor was identified as providing an ACR20 response in at least about 80% of a patient population who received the effective TNFα inhibitor for the treatment of RA.

In one aspect, the invention provides the use of an effective TNFα inhibitor in the manufacture of a medicament for the treatment of RA in a subject, wherein the TNFα inhibitor was identified as providing an ACR20 response in at least about 80% of a patient population who received the effective TNFα inhibitor for the treatment of RA.

In one aspect, the invention provides a method of treating RA in a subject comprising administering an effective TNFα inhibitor, wherein the effective TNFα inhibitor was identified as providing an ACR50 response in at least about 62% of a patient population who received the effective TNFα inhibitor for the treatment of RA.

In one aspect, the invention provides the use of an effective TNFα inhibitor in the manufacture of a medicament for the treatment of RA in a subject, wherein the effective TNFα inhibitor was identified as providing an ACR50 response in at least about 62% of a patient population who received the effective TNFα inhibitor for the treatment of RA.

In one aspect, the invention provides a method for predicting the efficacy of a TNFα inhibitor for the treatment of rheumatoid arthritis (RA) in a subject comprising using the combination of a C-reactive protein (CRP) level of the subject and a Patient Activity Score (PAS) of the subject, wherein an improvement in the CRP level and the PAS score early in the treatment of the patient with the TNFα inhibitor indicates that the TNFα inhibitor is an effective TNFα inhibitor for the treatment of RA in the subject.

In one embodiment, the improvement in the CRP level and the PAS score early in the treatment of the subject occurs at about two weeks following initiation of the treatment in the subject. In another embodiment, the PAS score is determined using the Health Assessment Questionnaire (HAQ) of the subject. In another embodiment, the improvement in the CRP level is at least as described in the Examples below. In another embodiment, the improvement in the HAQ score is at least about 0.4.

In another aspect, the invention provides a method for determining the efficacy of a TNFα inhibitor for the treatment of rheumatoid arthritis (RA) in a subject comprising determining a Simplified Disease Activity Score (SDAI) of a patient population having RA and who was administered the TNFα inhibitor, wherein a mean SDAI of no greater than about 3.3 in at least about 11% of the patient population indicates that the TNFα inhibitor is an effective TNFα inhibitor for treating RA.

In one embodiment, the TNFα inhibitor is a TNFα antibody, or antigen-binding portion thereof, or a TNFα fusion protein. In one embodiment, the TNFα fusion protein is etanercept. In one embodiment, the TNFα antibody, or antigen-binding portion thereof, is an antibody selected from the group consisting of a humanized antibody, a chimeric antibody, a human antibody, and a multivalent antibody. In one embodiment, the TNFα antibody, or antigen-binding portion thereof, is infliximab or golimumab.

In another aspect, the invention provides a method for determining the efficacy of a human TNFα antibody, or antigen-binding portion thereof, for treating RA in a subject comprising determining an ACR70 response of a patient population having RA and who was administered the human TNFα antibody, or antigen-binding portion thereof, wherein an ACR70 response in at least about 20% of the patient population indicates that the human TNFα antibody, or antigen-binding portion thereof, is an effective human TNFα antibody, or antigen-binding portion thereof, for the treatment of RA in a subject.

In one embodiment, an ACR70 response in at least about 25% of the patient population indicates that the human TNFα antibody, or antigen-binding portion thereof, is an effective human TNFα antibody, or antigen-binding portion thereof, for the treatment of RA in a subject. In one embodiment, an ACR70 response in at least about 30% of the patient population indicates that the human TNFα antibody, or antigen-binding portion thereof, is an effective human TNFα antibody, or antigen-binding portion thereof, for the treatment of RA in a subject. In another embodiment, an ACR70 response in at least about 35% of the patient population indicates that the human TNFα antibody, or antigen-binding portion thereof, is an effective human TNFα antibody, or antigen-binding portion thereof, for the treatment of RA in a subject. In yet another embodiment, an ACR70 response in at least about 40% of the patient population indicates that the human TNFα antibody, or antigen-binding portion thereof, is an effective human TNFα antibody, or antigen-binding portion thereof, for the treatment of RA in a subject.

In one embodiment the method further comprises administering the effective human TNFα antibody, or antigen-binding portion thereof, to a subject for the treatment of RA.

In one aspect, the invention provides a method of treating RA in a subject comprising administering an effective human TNFα antibody, or antigen-binding portion thereof, for the treatment of RA in a subject, wherein the effective human TNFα antibody, or antigen-binding portion thereof, was identified as achieving an ACR70 response in at least about 20% of a patient population who was administered the human TNFα antibody, or antigen-binding portion thereof.

In another aspect, the invention provides the use of an effective human TNFα antibody, or antigen-binding portion thereof, in the manufacture of a medicament for treating RA in a subject, wherein the effective human TNFα antibody, or antigen-binding portion thereof, was identified as achieving an ACR70 response in at least about 20% of a patient population who was administered the human TNFα antibody, or antigen-binding portion thereof.

In one aspect, the invention provides a method for determining the efficacy of a human TNFα antibody, or antigen-binding portion thereof, for treating RA in a subject comprising determining a moderate EULAR response of a patient population having RA and who was administered the human TNFα antibody, or antigen-binding portion thereof, wherein a moderate EULAR response in at least about 83% of the patient population indicates that the human TNFα antibody, or antigen-binding portion thereof, is an effective human TNFα antibody, or antigen-binding portion thereof, for the treatment of RA.

In one embodiment, a moderate EULAR response in at least about 85% of the patient population indicates that the human TNFα antibody, or antigen-binding portion thereof, is an effective human TNFα antibody, or antigen-binding portion thereof, for the treatment of RA. In another embodiment, a moderate EULAR response in at least about 90% of the patient population indicates that the human TNFα antibody, or antigen-binding portion thereof, is an effective human TNFα antibody, or antigen-binding portion thereof, for the treatment of RA. In another embodiment, a moderate EULAR response in at least about 92% of the patient population indicates that the human TNFα antibody, or antigen-binding portion thereof, is an effective human TNFα antibody, or antigen-binding portion thereof, for the treatment of RA.

In one embodiment the method further comprises administering the effective human TNFα antibody, or antigen-binding portion thereof, to a subject for the treatment of RA.

In one aspect, the invention provides a method of treating RA in a subject comprising administering an effective human TNFα antibody, or antigen-binding portion thereof, for the treatment of RA in a subject, wherein the effective human TNFα antibody, or antigen-binding portion thereof, was identified as achieving a moderate EULAR response in at least about 83% of a patient population who was administered the human TNFα antibody, or antigen-binding portion thereof.

In another aspect, the invention provides the use of an effective human TNFα antibody, or antigen-binding portion thereof, in the manufacture of a medicament for treating RA in a subject, wherein the effective human TNFα antibody, or antigen-binding portion thereof, was identified as achieving a moderate EULAR response in at least about 83% of a patient population who was administered the human TNFα antibody, or antigen-binding portion thereof.

In one aspect, the invention provides a method for determining the efficacy of a human TNFα antibody, or antigen-binding portion thereof, for treating RA in a subject comprising determining a good EULAR response of a patient population having RA and who was administered the human TNFα antibody, or antigen-binding portion thereof, wherein a good EULAR response response in at least about 35% of the patient population indicates that the human TNFα antibody, or antigen-binding portion thereof, is an effective human TNFα antibody, or antigen-binding portion thereof, for the treatment of RA in a subject.

In one embodiment, a good EULAR response response in at least about 40% of the patient population indicates that the human TNFα antibody, or antigen-binding portion thereof, is an effective human TNFα antibody, or antigen-binding portion thereof, for the treatment of RA in a subject.

In one aspect, the invention provides a method for determining the efficacy of a human TNFα antibody, or antigen-binding portion thereof, for treating RA in a subject who has failed prior infliximab treatment comprising determining an ACR20 response of a patient population having RA who has failed previous infliximab treatment and who was administered the human TNFα antibody, or antigen-binding portion thereof, wherein an ACR20 response in at least about 50% of the patient population indicates that the human TNFα antibody, or antigen-binding portion thereof, is an effective human TNFα antibody, or antigen-binding portion thereof, for the treatment of RA in a subject who has failed prior infliximab treatment.

In one embodiment, an ACR20 response in at least about 50% of the patient population indicates that the human TNFα antibody, or antigen-binding portion thereof, is an effective human TNFα antibody, or antigen-binding portion thereof, for the treatment of RA in a subject who has failed prior infliximab treatment. In another embodiment, an ACR20 response in at least about 55% of the patient population indicates that the human TNFα antibody, or antigen-binding portion thereof, is an effective human TNFα antibody, or antigen-binding portion thereof, for the treatment of RA in a subject who has failed prior infliximab treatment. In another embodiment, an ACR20 response in at least about 60% of the patient population indicates that the human TNFα antibody, or antigen-binding portion thereof, is an effective human TNFα antibody, or antigen-binding portion thereof, for the treatment of RA in a subject who has failed prior infliximab treatment. In yet another embodiment, an ACR20 response in at least about 65% of the patient population indicates that the human TNFα antibody, or antigen-binding portion thereof, is an effective human TNFα antibody, or antigen-binding portion thereof, for the treatment of RA in a subject who has failed prior infliximab treatment. In one embodiment, an ACR20 response in at least about 69% of the patient population indicates that the human TNFα antibody, or antigen-binding portion thereof, is an effective human TNFα antibody, or antigen-binding portion thereof, for the treatment of RA in a subject who has failed prior infliximab treatment.

In one embodiment, the method further comprises administering the effective human TNFα antibody, or antigen-binding portion thereof, to a subject to maintain treat RA.

In another embodiment, the human TNFα antibody, or an antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less.

In one embodiment, the human TNFα antibody, or an antigen-binding portion thereof, has the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In another embodiment, the human TNFα antibody, or an antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In another embodiment, the human TNFα antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2.

In one embodiment, the human TNFα antibody, or an antigen-binding portion thereof, is adalimumab.

In another aspect, the invention provides an article of manufacture comprising
  a) a packaging material;
  b) a TNFα antibody, or antigen-binding portion thereof; and
  c) a label or package insert indicating that patients with RA receiving treatment with the TNFα antibody, or antigen-binding portion thereof, can be administered a pneumonococcal vaccine concurrently with the TNFα antibody, or antigen-binding portion thereof.

In one embodiment, the pneumonococcal vaccine is a pneumonococcal polysaccharide vaccine.

In another aspect, the invention provides an article of manufacture comprising
  a) a packaging material;
  b) pneumonococcal or influenza virus vaccine; and
  c) a label or package insert contained within the packaging material indicating that patients receiving the pneumonococcal or influenza virus vaccine can be safely administered a TNFα inhibitor.

In another aspect, the invention provides an article of manufacture comprising
  a) a packaging material;
  b) a TNFα antibody, or antigen-binding portion thereof; and
  c) a label or package insert contained within the packaging material indicating that in studies of the TNFα antibody, or antigen-binding portion thereof, observed malignancies included melanoma and/or granulose cell tumor of the ovary.

In one embodiment, the TNFα antibody, or antigen-binding portion thereof, is a human TNFα antibody, or antigen-binding portion thereof, and dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less.

In another embodiment, the TNFα antibody, or an antigen-binding portion thereof, has the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In another embodiment, the TNFα antibody, or an antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In yet another embodiment, the TNFα antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2.

In one embodiment, the human TNFα antibody, or an antigen-binding portion thereof, is adalimumab.

In one embodiment of the invention, the subject having RA is an adult patient (or subject) with moderately to severely active disease.

The invention provides an article of manufacture comprising a packaging material; a TNFα inhibitor; and a label or package insert contained within the packaging material indicating that the standardized mortality rate for the TNFα inhibitor was calculated at about 0.67.

The invention also provides a method of treating a human subject having rheumatoid arthritis (RA) comprising administering a TNFα inhibitor to the subject, wherein the subject has previously failed an anti-TNFα therapy comprising administration of an alternate TNFα antagonist. In one embodiment, the alternate TNFα antagonist is a biologic agent. In one embodiment, the biologic agent comprises etanercept or infliximab. In another embodiment, the alternate TNFα antagonist was discontinued for a reason selected from the group consisting of no response, lost efficacy, and intolerance.

The invention includes a method for monitoring the effectiveness of a TNFα inhibitor for the treatment of rheumatoid arthritis (RA) in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR20 achieved in about 58-85% of the patient population indicates that the TNFα inhibitor is effective at treating RA.

The invention also provides a method for monitoring the effectiveness of a TNFα inhibitor for the treatment of RA in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR50 achieved in about 30-62% of the patient population indicates that the TNFα inhibitor is effective at treating RA.

The invention also provides a method for monitoring the effectiveness of a TNFα inhibitor for the treatment of RA in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR70 achieved in about 12-38% of the patient population indicates that the TNFα inhibitor is effective at treating RA. In one embodiment, preselected patient population has already been administered the TNFα inhibitor.

The invention includes a method for monitoring the effectiveness of a TNFα inhibitor for the treatment of RA in a human subject comprising administering the TNFα inhibitor to a preselected patient population having rheumatoid arthritis; determining the effectiveness of the TNFα inhibitor using a baseline Disease Activity Score $(DAS)_{28}$ score of the patient population and a DAS28 score of the patient population following administration of the TNFα inhibitor, wherein a mean change in the DAS28 score of between about −1.9 and −2.8 of the patient population indicates that the TNFα inhibitor is effective at treating RA. In one embodiment, the TNFα inhibitor has already been administered to the pre-selected patient population.

The invention includes an article of manufacture comprising a packaging material; a TNFα inhibitor; and a label or package insert contained within the packaging material indicating that patients receiving treatment with the TNFα inhibitor can be safely administered a pneumonococcal or influenza virus vaccine.

The invention also includes an article of manufacture comprising a packaging material; pneumonococcal or influenza virus vaccine; and a label or package insert contained within the packaging material indicating that patients receiving the pneumonococcal or influenza virus vaccine can be safely administered a TNFα inhibitor.

The invention provides a method for treating RA and immunizing against a pneumonococcal or influenza virus antigen in a human subject comprising administering a TNFα inhibitor to the subject; and administering a pneumonococcal or influenza viral vaccine to the subject.

The invention further provides an article of manufacture comprising a packaging material; a TNFα inhibitor; and a label or package insert contained within the packaging material indicating that in studies of the TNFα inhibitor, observed malignancies included melanoma and granulose cell tumor of the ovary.

The invention includes a method of achieving an early clinical response in a Hispanic human subject having RA comprising administering a TNFα inhibitor such that an early clinical response in the Hispanic human subject is achieved. In one embodiment, the Hispanic human subject is Venezuelan. In one embodiment, the early clinical response is determined using an assessment test selected from the group consisting of DAS28, TJC28, SJC28, HAQ, pain on VAS, ESR, and CRP. In another embodiment, the invention includes the early clinical response occurs at about 2 weeks following administration of the TNFα inhibitor.

The invention provides a method of testing the efficacy of a TNFα inhibitor for the rapid improvement of moderate to severe RA in a Hispanic patient population comprising administering the TNFα inhibitor to a preselected Hispanic patient population having moderate to severe RA; determining the efficacy of the TNFα inhibitor using a baseline Health Assessment Questionnaire (HAQ) score of the patient population and an HAQ score of the patient population following administration of the TNFα inhibitor, wherein a decrease in the mean HAQ score of at least about −0.5 indicates that the TNFα inhibitor is efficacious for the rapid improvement of moderate to severe RA in a Hispanic patient population. In one embodiment, the rapid improvement occurs at about 2 weeks following administration of the TNFα inhibitor. In one embodiment, the TNFα inhibitor has already been administered to the pre-selected patient population.

The invention provides an article of manufacture comprising a packaging material; a TNFα inhibitor; and a label or package insert contained within the packaging material indicating that in studies of the TNFα inhibitor for the treatment of rheumatoid arthritis (RA) the most common adverse events (AEs) were infections. In one embodiment, the infections include mild upper respiratory infections.

In one embodiment, the TNFα inhibitor is administered weekly. In another embodiment, the TNFα inhibitor is administered every other week.

The invention further provides a package comprising a TNFα inhibitor and a label, in a position which is visible to prospective purchasers, comprising a printed statement which informs prospective purchasers that the median apparent clearance (CL/F) of the TNFα inhibitor ranges from about 13.2 to about 15.0 mL/hr. In one embodiment of the invention, the package further informs prospective purchasers that concomitant therapy with either immunosuppressant 6 mercaptopurine or azathioprine has slightly lower or no impact on TNFα inhibitor CL/F. In one embodiment, the anti-TNFα antibody, or antigen-binding portion thereof, is a 40 mg dose.

The invention describes a package comprising a TNFα inhibitor and a label, in a position which is visible to prospective purchasers, comprising a printed statement which informs prospective purchasers that TNFα inhibitor mean steady-state trough concentrations of approximately 6-7 μg/mL and 7-9 μg/mL were observed without and with methotrexate, respectively.

The invention also includes a package comprising a TNFα inhibitor, wherein the package contains, on the label and in a position which is visible to prospective purchasers, a printed statement which informs prospective purchasers that available data suggest that the clinical response is usually achieved within 12 weeks of treatment; and continued therapy should be carefully reconsidered in a patient not responding within this time period.

The invention provides a package comprising adalimumab, wherein the package contains, on the label and in a position which is visible to prospective purchasers, a printed statement which informs prospective purchasers that the proportion of patients who discontinued treatment due to adverse events during the double-blind, controlled portion of Studies 1-IX was 5.1% for patients taking the adalimumab and 3.2% for control treated patients.

The invention also provides a package comprising a TNFα inhibitor, wherein the package contains, on the label and in a position which is visible to prospective purchasers, a printed statement which informs prospective purchasers that the TNFα inhibitor has been shown to have an uncommon undesirable effect in clinical studies selected from the group consisting of vaginal infection (including fungal), hyperglycaemia, dysphonia, pharyngeal erythema, wheezing, skin reaction, skin exfoliation, spasm, rheumatoid nodule, shoulder pain, and feeling hot.

The invention further provides a package comprising adalimumab, wherein the package contains, on the label and in a position which is visible to prospective purchasers, a printed statement which informs prospective purchasers of at least one of the following notifications: in the nine controlled trials, 17% of patients treated with adalimumab developed injection site reactions (erythema and/or itching, hemorrhage, pain or swelling), compared to 10% of patients receiving placebo or active control; in the nine controlled trials, the rate of infection was 1.52 per patient year in the adalimumab treated patients and 1.40 per patient year in the placebo and active control-treated patients; in the nine controlled trials, 29 malignancies were reported in 2370 adalimumab treated patients with 1779 patient-years of exposure (16.3 per 1000 patient years), and 6 malignancies were reported in 1309 control treated patients observed with 872 patient-years of exposure (6.9 per 1000 patient years); this included 2 lymphomas in the adalimumab treated patients (1.1 per 1000 patient years) and 1 lymphoma in the control treated patients (1.1 per 1000 patient years); and two patients out of 3834 treated with adalimumab in all rheumatoid arthritis, psoriatic arthritis and ankylosing spondylitis studies developed clinical signs suggestive of new-onset lupus-like syndrome.

In one embodiment of the invention, the TNFα inhibitor is selected from the group consisting of an anti-TNFα antibody, or an antigen-binding portion thereof, a TNF fusion protein, or a recombinant TNF binding protein. In one embodiment, the TNF fusion protein is etanercept. In another embodiment of the invention, the anti-TNFα antibody, or antigen-binding portion thereof, is selected from the group consisting of a chimeric antibody, a humanized antibody, and a multivalent antibody.

In one embodiment of the invention, the anti-TNFα antibody, or antigen-binding portion thereof, is a human antibody.

In another embodiment, the anti-TNFα antibody, or antigen-binding portion thereof, is an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less.

In one embodiment of the invention, the anti-TNFα antibody is an isolated human antibody, or antigen-binding portion thereof, with the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment of the invention, the anti-TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2. In one embodiment, the anti-TNFα antibody, or antigen-binding portion thereof, is adalimumab.

In one embodiment, the anti-TNFα antibody, or antigen-binding portion thereof, is a 40 mg dose.

In another embodiment, the anti-TNFα antibody, or antigen-binding portion thereof, is administered subcutaneously.

The another embodiment of the invention, the anti-TNFα antibody, or antigen-binding portion thereof, is infliximab or golimumab.

The invention provides a package comprising a TNFα inhibitor and a label, in a position which is visible to prospective purchasers, comprising a printed statement which informs prospective purchasers that the median apparent clearance (CL/F) of the TNFα inhibitor ranges from about 13.2 to about 15.0 mL/hr.

In one embodiment, the printed statement further informs prospective purchasers that concomitant therapy with either immunosuppressant 6 mercaptopurine or azathioprine has slightly lower or no impact on TNFα inhibitor CL/F.

In one embodiment the TNFα inhibitor is a human anti-TNFα antibody, or antigen-binding portion thereof. In one embodiment of the invention, the anti-TNFα antibody, or antigen-binding portion thereof, is an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less.

In another embodiment the anti-TNFα antibody is an isolated human antibody, or antigen-binding portion thereof, with the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment, the anti-TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2

In one embodiment, the anti-TNFα antibody, or antigen-binding portion thereof, is adalimumab.

In one embodiment, the anti-TNFα antibody, or antigen-binding portion thereof, is a 40 mg dose.

The invention also includes a label which indicates warnings and precautions regarding the use of the TNFα inhibitor. In one embodiment, the information provided in the label describes malignancies. In another embodiment, the label of the invention may indicate during the controlled portions of TNFα inhibitor trials in patients with rheumatoid arthritis, psoriatic arthritis, ankylosing spondylitis, and Crohn's disease, malignancies, other than lymphoma and non-melanoma skin cancer, were observed at a rate (95% confidence interval) of 0.6 (0.3, 1.0)/100 patient-years among 2887 adalimumab-treated patients versus a rate of 0.4 (0.2, 1.1)/100 patient-years among 1570 control patients (median duration of treatment of 5.7 months for adalimumab-treated patients and 5.5 months for control-treated patients). In another embodiment, the label of the invention indicates that the size of the control group and limited duration of the controlled portions of studies precludes the ability to draw firm conclusions. In one embodiment, the label indicates that in the controlled and uncontrolled open-label portions of the clinical trials of the TNFα inhibitor, the more frequently observed malignancies, other than lymphoma and non-melanoma skin cancer, were breast, colon, prostate, lung and melanoma. In one embodiment, the label indicates that these malignancies in TNFα inhibitor treated and control-treated patients were similar in type and number to what would be expected in the general population. In a further embodiment, the label indicates that during the controlled portions of the TNFα inhibitor rheumatoid arthritis, psoriatic arthritis, ankylosing spondylitis, and Crohn's disease trials, the rate (95% confidence interval) of non-melanoma skin cancers was 0.8 (0.47, 1.24)/100 patient-years among adalimumab-treated patients 0.2 (0.05, 0.82)/100 patient-years among control patients. In one embodiment, the label indicates that the potential role of TNF blocking therapy in the development of malignancies is not known. In one embodiment, the label indicates that in the controlled portions of clinical trials of all the TNF-blocking agents, more cases of lymphoma have been observed among patients receiving TNF blockers compared to control patients. In one embodiment, the label indicates that in controlled trials in patients with rheumatoid arthritis, psoriatic arthritis, ankylosing spondylitis, and Crohn's disease, 2 lymphomas were observed among 2887 HUMIRA-treated patients versus 1 among 1570 control patients. In another embodiment, the label of the invention indicates that in combining the controlled and uncontrolled open-label portions of these clinical trials with a median duration of approximately 2 years, including 4843 patients and over 13,000 patient-years of therapy, the observed rate of lymphomas is approximately 0.12/100 patient-years, and that this is approximately 3.5-fold higher than expected in the general population.

The label of the invention may also contain information regarding the drug interactions of the TNFα inhibitor, with other drugs. In one embodiment, the label indicates that methotrexate (MTX) reduced adalimumab apparent clearance after single and multiple dosing by 29% and 44% respectively, in patients with rheumatoid arthritis.

In one embodiment, the invention provides a method of treating a human subject having rheumatoid arthritis (RA) comprising administering a TNFα inhibitor to the subject, wherein the subject has previously failed an anti-TNFα therapy comprising administration of an alternate TNFα antagonist, e.g. a biologic agent, such as the etanercept or infliximab. In one embodiment, the alternate TNFα antagonist was discontinued for a reason selected from the group consisting of no response, lost efficacy, and intolerance.

The invention also provides a method for monitoring the effectiveness of a TNFα inhibitor for the treatment of rheumatoid arthritis (RA) in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR20 achieved in about 58-85% of the patient population indicates that the TNFα inhibitor is effective at treating RA.

The invention also provides a method for monitoring the effectiveness of a TNFα inhibitor for the treatment of RA in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR50 achieved in about 30-62% of the patient population indicates that the TNFα inhibitor is effective at treating RA.

The invention also provides a method for monitoring the effectiveness of a TNFα inhibitor for the treatment of RA in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR70 achieved in about 12-38% of the patient population indicates that the TNFα inhibitor is effective at treating RA.

The invention further provides a method for monitoring the effectiveness of a TNFα inhibitor for the treatment of RA in a human subject comprising administering the TNFα inhibitor to a preselected patient population having rheumatoid arthritis; determining the effectiveness of the TNFα inhibitor using a baseline Disease Activity Score (DAS)28 score of the patient population and a DAS28 score of the patient population following administration of the TNFα inhibitor, wherein a mean change in the DAS28 score of between about −1.9 and −2.8 of the patient population indicates that the TNFα inhibitor is effective at treating RA.

The invention also provides a method of achieving an early clinical response in a Hispanic human subject having RA comprising administering a TNFα inhibitor such that an early clinical response in the Hispanic human subject is achieved. In one embodiment, the Hispanic human subject is Venezuelan. In another embodiment, the early clinical response is determined using an assessment test selected from the group consisting of DAS28, TJC28, SJC28, HAQ, pain on VAS, ESR, and CRP. In another embodiment, the early clinical response occurs at about 2 weeks following administration of the TNFα inhibitor.

The invention also provides a method of testing the efficacy of a TNFα inhibitor for the rapid improvement of moderate to severe RA in a Hispanic patient population comprising administering the TNFα inhibitor to a preselected Hispanic patient population having moderate to severe RA; determining the efficacy of the TNFα inhibitor using a baseline Health Assessment Questionnaire (HAQ) score of the patient population and an HAQ score of the patient population following administration of the TNFα inhibitor, wherein a decrease in the mean HAQ score of at least about −0.5 indicates that the TNFα inhibitor is efficacious for the rapid improvement of moderate to severe RA in a Hispanic patient population.

The invention further provides a method of testing the efficacy of a in a Hispanic patient population comprising administering the TNFα inhibitor to a preselected Hispanic patient population having moderate to severe RA; determining the efficacy of the TNFα inhibitor using a baseline Health Assessment Questionnaire (HAQ) score of the patient population and an HAQ score of the patient population following administration of the TNFα inhibitor, wherein a decrease in the mean HAQ score of at least about −0.5 indicates that the TNFα inhibitor is efficacious for the rapid improvement of moderate to severe RA in a Hispanic patient population.

The invention includes a method for predicting the efficacy of a TNFα inhibitor for improving the quality of life of a patient having rheumatoid arthritis (RA) in a patient comprising comparing the baseline DAS28 score of the patient with a DAS28 score of the patient following treatment with the TNFα inhibitor, wherein an improvement in the DAS28 indicates that the TNFα inhibitor will be effective for improving the quality of life in the patient. In one embodiment, the patient has severe RA.

The invention also includes a method for predicting the efficacy of a TNFα inhibitor for the treatment of rheumatoid arthritis in a subject comprising using a mean baseline score selected from the group consisting of a global assessment of the patient's disease activity, pain, function, fatigue, and stiffness, wherein an improvement selected from the group consisting of an improvement of at least about 2.4 in the patient global score, an improvement of at least about 2.8 in the pain score, an improvement of at least about 2.7 in the function score, an improvement of at least about 0.8 in the fatigue score, and an improvement of at least about 1.2 in the stiffness score, at day 1 from baseline, indicates that the TNFα inhibitor will be effective for treating RA in the patient The invention further provides an article of manufacture comprising a packaging material; a TNFα inhibitor; and a label or package insert contained within the packaging material indicating that the standardized mortality rate for the TNFα inhibitor was calculated at about 0.67.

In one embodiment, the invention provides methods, uses, and compositions for reducing signs and symptoms of rheumatoid arthritis in a subject. In another embodiment, the invention provides methods, uses, and compositions for inducing major clinical response of rheumatoid arthritis in a subject. In another embodiment, the invention provides methods, uses, and compositions for inhibiting the progression of structural damage associated with RA in a subject. In one embodiment, the invention provides methods, uses, and compositions for improving physical function in adult patients with moderately to severely active disease.

BRIEF DESCRIPTION OF THE FIGURES

FIG. 1 graphically depicts Study A's design.

FIG. 2 shows ACR responses through 18 months in Study B.

FIG. 3 shows EULAR responses through 18 months in Study B.

FIG. 4 shows median C-Reactive Protein Concentrations (mg/L) over time for patients in the study of example 4.

FIG. 5 graphically depicts physician and patient assessments of disease activity and pain over time through 18 months for patients in the study of example 4.

FIG. 6 graphically depicts physician and patient assessments of disease activity and pain over time through 18 months for patients in the study of example 4.

FIG. 7 graphically depicts physician and patient assessments of disease activity and pain over time through 18 months for patients in the study of example 4.

FIG. 8 graphically depicts the disposition of patients treated with adalimumab 40 mg eow for patients in the study of example 5.

FIG. 9 graphically depicts the percent of patients continuing on adalimumab treatment from first dose for patients in the study of example 5.

FIG. 10 shows disease activity and functional disability scores (TJC68 and SJC66) by ACR20 response for patients in the study of example 5.

FIG. 12 shows disease activity and functional disability scores (CRP) by ACR20 response for patients in the study of example 5.

FIG. 13 shows ACR response rates for patients in the study of example 5.

FIG. 14 shows the study design of the study in example 6.

FIG. 15 shows Median Tender Joint Count (TJC28) through week 12 by DMARD combinations with adalimumab for patients in the study of example 9.

FIG. 16 shows Median Swollen Joint Count (SJC28) at week 12 by DMARD combinations with adalimumab for patients in the study of example 9.

FIG. 17 shows Study C's Design.

FIG. 18 shows the disposition of the study for patients in the study of example 11.

FIG. 19 depicts the Model Pathway.

FIG. 20 graphically depicts the study design of the study described in example 12.

FIG. 21 describes an overview of the Study D design study.

FIG. 22 describes the study disposition.

FIG. 23 shows the time course of mean change in e-diary assessments to week 12.

FIG. 24 shows the effect of adalimumab treatment on patient pain.

FIG. 25 shows the effect of adalimumab treatment on functional disability.

FIG. 26 shows the effect of adalimumab treatment on fatigue.

FIG. 27 shows the effect of adalimumab treatment on morning stiffness severity.

FIG. 28 shows the effect of adalimumab treatment on patient global.

FIG. 29 shows the enrollment of study participants.

FIG. 30 shows the correlation of RADAI and DAS28 Scores after 6 Months of Adalimumab Therapy (N=100).

FIG. 31 depicts the composition of the study population with regard to preceding dose-finding studies. *Only study DE011/DE026 comprised 26 weeks; other studies had different durations before enrollment in DE033.

FIG. 32 depicts the change from baseline in Functional Assessment of Chronic Illness Therapy-Fatigue (FACIT-Fatigue) scores in the DE026 subgroup over 3 years (n=99). *$P<0.001$ vs. baseline. †$P<0.01$ vs. placebo. Last observation carried forward. eow=every other week; MCID=minimum clinically important difference; SEM=standard error of the mean.

FIG. 33 depicts the change from baseline in health utility index (HUI3) scores in the DE026 subgroup over 3 years (n=99). *$P<0.001$ vs. baseline. †$P<0.05$ vs. placebo. Last observation carried forward. eow=every other week; MCID=minimum clinically important difference; SEM=standard error of the mean.

DETAILED DESCRIPTION OF THE INVENTION

I. Definitions

Figure 11A:
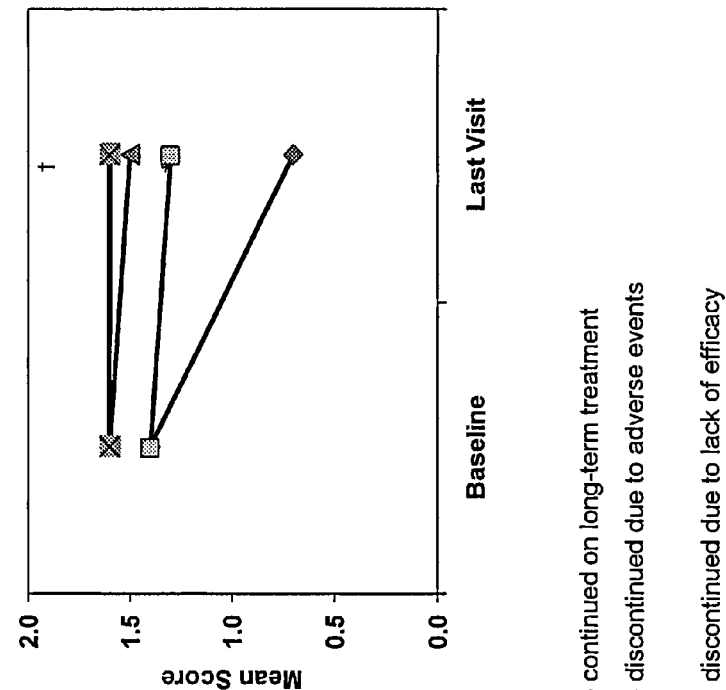
FIG. 11 shows disease activity and functional disability scores (DAS28 and HAQ Disability Index) by ACR20 response for patients in the study of example 5.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" includes agents which interfere with TNFα activity. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406,476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" or "antigen-binding fragment" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Binding fragments include Fab, Fab', F(ab')$_2$, Fabc, Fv, single chains, and single-chain antibodies. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al.

(1994) *Mol. Immunol.* 31:1047-1058). Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173, 494; PCT International Publication No. WO 86/01533; U.S. Pat. No. 4,816,567; European Patent Application No. 125, 023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314: 446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141: 4053-4060, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693, 762, Selick et al., WO 90/07861, and Winter, U.S. Pat. No. 5,225,539.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "dose," as used herein, refers to an amount of TNFα inhibitor which is administered to a subject.

The term "dosing", as used herein, refers to the administration of a substance (e.g., an anti-TNFα antibody) to achieve a therapeutic objective (e.g., treatment of rheumatoid arthritis).

A "dosing regimen" describes a treatment schedule for a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The terms "biweekly dosing regimen", "biweekly dosing", and "biweekly administration", as used herein, refer to the time course of administering a substance (e.g., an anti-TNFα antibody) to a subject to achieve a therapeutic objective, i, throughout the course of treatment. The biweekly dosing regimen is not intended to include a weekly dosing regimen. Preferably, the substance is administered every 9-19 days, more preferably, every 11-17 days, even more preferably, every 13-15 days, and most preferably, every 14 days. In one embodiment, the biweekly dosing regimen is initiated in a subject at week 0 of treatment. In another embodiment, a maintenance dose is administered on a biweekly dosing regimen. In one embodiment, both the loading and maintenance doses are administered according to a biweekly dosing regimen. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in US 20030235585, incorporated by reference herein.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "treatment," as used within the context of the present invention, is meant to include therapeutic treatment, as well as prophylactic or suppressive measures, for the treatment of rheumatoid arthritis. For example, the term treatment may include administration of a TNFα inhibitor prior to or following the onset of rheumatoid arthritis thereby preventing or removing signs of the disease or disorder. As another example, administration of a TNFα inhibitor after clinical manifestation of rheumatoid arthritis to combat the symptoms and/or complications and disorders associated with rheumatoid arthritis comprises "treatment" of the disease. Further, administration of the agent after onset and after clinical symptoms and/or complications have developed where administration affects clinical parameters of the disease or disorder and perhaps amelioration of the disease, comprises "treatment" of rheumatoid arthritis. In one embodiment, treatment of rheumatoid arthritis in a subject comprises reducing signs and symptoms. In another embodiment, treatment of rheumatoid arthritis in a subject comprises inducing major clinical response of rheumatoid arthritis. In another embodiment, treatment of rheumatoid arthritis in a subject comprises inhibiting the progression of structural damage. In one embodiment, treatment of rheumatoid arthritis comprises improving physical function in adult patients with moderately to severely active disease.

Those "in need of treatment" include mammals, such as humans, already having rheumatoid arthritis, including those in which the disease or disorder is to be prevented.

Various aspects of the invention are described in further detail herein.

The invention provides improved uses and compositions for treating rheumatoid arthritis with a TNFα inhibitor, e.g., a human TNFα antibody, or an antigen-binding portion thereof. Compositions and articles of manufacture, including kits, relating to the methods and uses for treating rheumatoid arthritis are also contemplated as part of the invention.

II. TNF Inhibitors

A TNFα inhibitor which is used in the methods and compositions of the invention includes any agent which interferes with TNFα activity. In a preferred embodiment, the TNFα inhibitor can neutralize TNFα activity, particularly detrimental TNFα activity which is associated with rheumatoid arthritis, and related complications and symptoms.

In one embodiment, the TNFα inhibitor used in the invention is an TNFα antibody (also referred to herein as a TNFα antibody), or an antigen-binding fragment thereof, including chimeric, humanized, and human antibodies. Examples of TNFα antibodies which may be used in the invention include, but not limited to, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein.

Other examples of TNFα inhibitors which may be used in the methods and compositions of the invention include etanercept (Enbrel, described in WO 91/03553 and WO 09/406,476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features uses and composition for treating or determining the efficacy of a TNFα inhibitor for the treatment of rheumatoid arthritis, wherein the TNFα antibody is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα antibodies. The most preferred recombinant, neutralizing antibody of the invention is referred to herein as D2E7, also referred to as HUMIRA® or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in Salfeld et al., U.S. Pat. Nos. 6,090,382, 6,258,562, and 6,509,015, which are each incorporated by reference herein. The methods of the invention may also be performed using chimeric and humanized murine anti-hTNFα antibodies which have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

In one embodiment, the method of the invention includes determining the efficacy of D2E7 antibodies and antibody portions, D2E7-related antibodies and antibody portions, or other human antibodies and antibody portions with equivalent properties to D2E7, such as high affinity binding to hTNFα with low dissociation kinetics and high neutralizing capacity, for the treatment of rheumatoid arthritis. In one embodiment, the invention provides treatment with an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an $IC_{50}$ of $1 \times 10^{-8}$ M or less, even more preferably with an $IC_{50}$ of $1 \times 10^{-9}$ M or less and still more preferably with an $IC_{50}$ of $1 \times 10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to treating rheumatoid arthritis by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5\times10^{-4}$ s$^{-1}$ or less. Even more preferably, the antibody, or antigen-binding portion thereof, dissociates from human TNFα with a $K_{off}$ of $1\times10^{-4}$ s$^{-1}$ or less.

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_\kappa I$ human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H3$ human germline family, more preferably from the DP-31 human germline VH gene and most preferably from the D2E7 VH framework sequences shown in FIGS. 2A and 2B of U.S. Pat. No. 6,090,382.

Accordingly, in another embodiment, the antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention includes uses of an isolated human antibody, or an antigen-binding portions thereof, containing D2E7-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the methods and compositions of the invention may be modified for improved treatment of rheumatoid arthritis. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (Cl—ClO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat rheumatoid arthritis by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion used in the methods of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of proteins of immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schafflier et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNFα antibody adalimumab (D2E7). The nucleotide sequence encoding the D2E7 light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989) *Science* 246:1275-1281; McCafferty et al., *Nature* (1990) 348:552-554; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J.* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions.

These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human neutralizing antibodies with high affinity and a low off rate constant for hTNFα are described in U.S. Pat. Nos. 6,090,382, 6,258,562, and 6,509,015, each of which is incorporated by reference herein.

Antibodies, antibody-portions, and other TNFα inhibitors for use in the methods of the invention, can be incorporated into pharmaceutical compositions suitable for administration to a subject. Typically, the pharmaceutical composition comprises an antibody, antibody portion, or other TNFα inhibitor, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody or other TNFα inhibitor is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the invention includes pharmaceutical compositions comprising an effective TNFα inhibitor and a pharmaceutically acceptable carrier, wherein the effective TNFα inhibitor may be used to treat rheumatoid arthritis.

In one embodiment, the antibody or antibody portion for use in the methods of the invention is incorporated into a pharmaceutical formulation as described in PCT/IB03/04502 and U.S. Appln. No. 20040033228, incorporated by reference herein. This formulation includes a concentration 50 mg/ml of the antibody D2E7 (adalimumab), wherein one pre-filled syringe contains 40 mg of antibody for subcutaneous injection.

The antibodies, antibody-portions, and other TNFα inhibitors of the present invention can be administered by a variety of methods known in the art, although for many therapeutic applications, the preferred route/mode of administration is parenteral, e.g., subcutaneous injection. In another embodiment, administration is via intravenous injection or infusion.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

In one embodiment, the TNFα antibodies and inhibitors used in the invention are delivered to a subject subcutaneously. In one embodiment, the subject administers the TNFα inhibitor, including, but not limited to, TNFα antibody, or antigen-binding portion thereof, to himself/herself.

The TNFα antibodies and inhibitors used in the invention may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Appln. No. 20040033228, incorporated by reference herein, are used to treat rheumatoid arthritis using the treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion for use in the methods of the invention is coformulated with and/or coadministered with one or more additional therapeutic agents, including a rheumatoid arthritis inhibitor or antagonist. For example, an anti-hTNFα antibody or antibody portion of the invention may be coformulated and/or coadministered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Additional description regarding methods and uses of the invention comprising administration of a TNFα inhibitor are described in Part III of this specification.

The invention also pertains to packaged pharmaceutical compositions or kits for administering the anti-TNF antibodies of the invention for the treatment of rheumatoid arthritis. In one embodiment of the invention, the kit comprises a TNFα inhibitor, such as an antibody and instructions for administration of the TNFα inhibitor for treatment of rheumatoid arthritis. The instructions may describe how, e.g., subcutaneously, and when, e.g., at week 0, week 2, week 4, etc., the different doses of TNFα inhibitor shall be administered to a subject for treatment.

Another aspect of the invention pertains to kits containing a pharmaceutical composition comprising a TNFα inhibitor, such as an antibody, and a pharmaceutically acceptable carrier and one or more pharmaceutical compositions each comprising an additional therapeutic agent useful for treating rheumatoid arthritis, and a pharmaceutically acceptable carrier. Alternatively, the kit comprises a single pharmaceutical composition comprising an anti-TNFα antibody, one or more drugs useful for treating rheumatoid arthritis, and a pharmaceutically acceptable carrier. The instructions may describe how, e.g., subcutaneously, and when, e.g., at week 0, week 2, week 4, etc., the different doses of TNFα inhibitor and/or the additional therapeutic agent shall be administered to a subject for treatment.

The kit may contain instructions for dosing of the pharmaceutical compositions for the treatment of rheumatoid arthritis. Additional description regarding articles of manufacture of the invention are described in subsection III.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

III. Uses and Compositions for Treating Rheumatoid Arthritis

Tumor necrosis factor has been implicated in playing a role in the pathophysiology of a variety of autoimmune diseases, including rheumatoid arthritis. TNFα is an important cytokine in the pathogenesis of rheumatoid arthritis, with elevated concentrations of TNFα playing a role in pathologic inflammation. TNFα has been implicated in activating tissue inflammation and causing joint destruction in rheumatoid arthritis (see e.g., Moeller, A., et al. (1990) *Cytokine* 2:162-169; U.S. Pat. No. 5,231,024 to Moeller et al.; European Patent Publication No. 260 610 B1 by Moeller, A.; Tracey and Cerami, supra; Arend, W. P. and Dayer, J-M. (1995) *Arth. Rheum.* 38:151-160; Fava, R. A., et al. (1993) *Clin. Exp. Immunol.* 94:261-266).

Tumor necrosis factor (TNF) is a pivotal cytokine in the pathogenesis of rheumatoid arthritis (RA). In recent years biologic response modifiers that inhibit TNF activity have become established therapies for RA. Adalimumab, etanercept, and infliximab have demonstrated marked improvements in both disease control and delay and prevention of radiographic damage among RA patients, particularly when used in combination with methotrexate (Breedveld et al, Arthritis Rheum 2006; 54:26-37; Genovese et al J Rheumatol 2005; 32:1232-42; Keystone et al, Arthritis Rheum 2004; 50:1400-11; Navarro-Sarabia et al, Cochrane Database Syst Rev 2005 Jul. 20; (3):CD005113; Smolen et al, Arthritis Rheum 2006; 54:702-10; St. Clair et al Arthritis Rheum 2004; 50:3432-43; van der Heijde et al, Arthritis Rheum 2006; 54:1063-74).

In one aspect, the invention discloses that adalimumab is safe in global clinical trials and has reduced mortality in RA. The invention further discloses the efficacy and safety of adalimumab in patients with RA who previously failed etanercept and/or infliximab in clinical practice and that efficacy and safety is maintained during long-term treatment of RA within a large cohort of patients (various age groups, including late-onset RA) in normal clinical practice across multiple countries. The invention also discloses that adalimumab is effective and safe with different traditional concomitant DMARDs in treating RA. Finally, the invention discloses that disease activity and physical function improve significantly in most patients with RA receiving adalimumab.

In one embodiment, the invention provides a method for treating rheumatoid arthritis in a subject such that signs and symptoms are reduced. In one embodiment, the methods of the invention includes inducing a major clinical response of a subject having RA. The TNFα antibody, or an antigen-binding portion thereof, may be administered to the subject on a biweekly dosing regimen. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc.

In one embodiment, treatment of rheumatoid arthritis is achieved by administering a TNFα inhibitor to a subject in accordance with a biweekly dosing regimen. Biweekly dosing regimens can be used to treat disorders in which TNFα activity is detrimental, and are further described in U.S. application Ser. No. 10/163,657 (US 20030235585), incorporated by reference herein.

In one embodiment, the invention provides a method of treating rheumatoid arthritis in a subject comprising administering a human TNFα antibody, or antigen-binding portion thereof, e.g., adalimumab, to the subject at week 0 on a biweekly dosing regimen. In one embodiment, the human TNFα antibody, or antigen-binding portion thereof, is administered subcutaneously. In one embodiment, rheumatoid arthritis is treated by administering a human TNFα antibody, or antigen-binding portion thereof, on biweekly dosing regimen for at least about 2 weeks, at least about 6 weeks, at least about 12 weeks, at least about 16 weeks, at least about 18 weeks, at least about 20 weeks, at least about 22 weeks, at least about 24 weeks, at least about 30 weeks, at least about 36 weeks, at least about 52 weeks at least about 72 weeks, at least about 96 weeks. Ranges of values between any of the above recited values are also intended to be included in the scope of the invention, e.g. 23 weeks, 60 week, 64 weeks, etc.

In one embodiment, rheumatoid arthritis is treated by administering a human TNFα antibody, or antigen-binding portion thereof, for at least about 2 weeks, at least about 6 weeks, at least about 12 weeks, at least about 16 weeks, at least about 18 weeks, at least about 20 weeks, at least about 22 weeks, at least about 24 weeks, at least about 30 weeks, at least about 36 weeks, at least about 52 weeks at least about 72 weeks, at least about 96 weeks. Ranges of values between any of the above recited values are also intended to be included in the scope of the invention, e.g, 23 weeks, 60 week, 64 weeks, etc.

In one embodiment, the TNFα inhibitor, e,g, antibody, or an antigen-binding portion thereof, may also be administered to a subject for the treatment of RA for a period defined in months, e.g., 3 months, 6 months, 12 months, 18 months, 24 months, 30 months, 36 months, 42 months, 48 months, 54 months, 60 months, etc. Ranges of values between any of the above recited values are also intended to be included in the scope of the invention, e.g., 38 months, 50 months, 52 months.

In one embodiment, the TNFα inhibitor, e,g, antibody, or an antigen-binding portion thereof, may also be administered to a subject for the treatment of RA for a period defined in years, e.g., 1 year, 2 years, 3 years, 4 years, 5 years, 6 years, 7 years, 8 years, etc. Ranges of values between any of the above recited values are also intended to be included in the scope of the invention, e.g., 1.5 years, 2.2 years, 3.5 years.

In one embodiment, treatment of rheumatoid arthritis is achieved by administering a human TNFα antibody, or an antigen-binding portion thereof, to a subject having rheumatoid arthritis, wherein the human TNFα antibody, or an antigen-binding portion thereof, is administered on a biweekly dosing regimen. In one embodiment, the human TNFα antibody, or an antigen-binding portion thereof, is administered in a dose of about 40 mg. In one embodiment, the human TNFα antibody, or an antigen-binding portion thereof, is adalimumab.

Methods of treatment described herein may include administration of a TNFα inhibitor to a subject to achieve a therapeutic goal, e.g., achieving a certain ACR response, e.g., ACR20, ACR50, ACR70, improving an MRI score, improving EULAR response, DAS28 score, RAPID score, CRP level, FACIT-F score, HAQ score, HUI3 score, TJC, SJC, change in TSS, SF-36 score, and AIMS2 score. Also included in the scope of the invention are uses of a TNFα inhibitor in the manufacture of a medicament to achieve a therapeutic goal, e.g., achieving a certain ACR response, e.g., ACR20, ACR50, ACR70, improving an MRI score, improving EULAR response, DAS28 score, RAPID score, CRP level, FACIT-F score, HAQ score, HUI3 score, TJC, SJC, change in TSS, SF-36 score, and AIMS2 score. Thus, where methods are described herein, it is also intended to be part of this invention that the use of the TNFα inhibitor in the manufacture of a medicament for the purpose of the method is also considered within the scope of the invention. Likewise, where a use of a TNFα inhibitor in the manufacture of a medicament for the purpose of achieving a therapeutic goal is described, methods of treatment resulting in the therapeutic goal are also intended to be part of the invention.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Dosage regimens described herein may be adjusted to provide the optimum desired response, e.g., treatment of rheumatoid arthritis, in consideration of the teachings herein. It is to be noted that dosage values may vary with the type and severity of rheumatoid arthritis. It is to be further understood that for any particular subject, specific dosage regimens may be adjusted over time according to the teachings of the specification and the individual need and the professional judgment of the person administering or supervising the administration of the compositions, and that dosage amounts and ranges set forth herein are exemplary only and are not intended to limit the scope or practice of the claimed invention.

Examples of other methods and uses of TNFα inhibitors for the treatment of rheumatoid arthritis are also described in 60/793,737, 60/812,705, 60/798,149, 60/801,584, 60/858,328, 60/872,753, 60/857,352, incorporated herein.

Subpopulations

The invention provides uses and methods for treating certain subpopulations of rheumatoid arthritis patients with a TNFα inhibitor.

In one embodiment, the invention provides methods and uses for treating subjects of a certain age range having rheumatoid arthritis. In one embodiment, the methods and uses of the invention are directed to treating subjects having late-onset RA. As such, the invention provides a method of treating late-onset RA comprising administering a human TNFα antibody, or antigen-binding portion thereof, to a patient having late-onset RA. The invention also provides a use of a human TNFα antibody, or antigen-binding portion thereof, in the manufacture of a medicament for the treatment of late-onset RA in a subject. In one embodiment, late-onset RA is defined as RA in a subject who is over 60 years old.

Although TNF antagonists are highly effective, a subset of patients with RA may be intolerant to one of these agents or may experience an inadequate response or a loss of response over time (Nurmohamed and Dijkmans, 2005). A relevant clinical question, therefore, is whether switching to a different TNF antagonist would be effective when the first has failed or resulted in intolerance. Clinical reports to date in mostly small numbers of patients suggest that a switch from one TNF antagonist to another is safe and effective, resulting in few withdrawals due to intolerance or lack of effectiveness (Brocq et al, Joint Bone Spine 2004; 71:601-3; Gomez-Reino et al, Arthritis Res Ther 2006; 8:R29; Hansen et al, J Rheumatol 2004; 31:1098-102; Haraoui et al, J Rheumatol 2004; 31:2356-9; Nikas et al, Ann Rheum Dis 2006; 65:257-60; van Vollenhoven et al, Ann Rheum Dis 2003; 62:1195-8). Most of these studies addressed switching between infliximab and etanercept. Data are very limited, however, regarding switching to adalimumab from one of these other TNF antagonists (Nikas et al, Ann Rheum Dis 2006; 65:257-60).

In one embodiment, the invention provides a method for treating a subpopulation of RA patients who are intolerant to or have lost response to a first TNFα inhibitor, e.g., infliximab, for the treatment of RA.

In one embodiment, the invention also provides methods and compositions for use in a subject who has not previously been administered infliximab. Thus, in one embodiment, the methods and compositions of the invention are directed to a subpopulation of RA patients who have not previously received infliximab.

In one embodiment, the invention provides an article of manufacture comprising adalimumab and a package insert, wherein the package insert indicates that adalimumab may be used to treat RA in patients who have had an inadequate response to conventional therapy and/or who have lost response to or are intolerant to infliximab.

Articles of Manufacture

The invention also provides a packaged pharmaceutical composition wherein the TNFα inhibitor, e.g., TNFα antibody, is packaged within a kit or an article of manufacture. The kit or article of manufacture of the invention contains materials useful for the treatment, including induction and/or remission, prevention and/or diagnosis of RA. The kit or article of manufacture comprises a container and a label or package insert or printed material on or associated with the container which provides information regarding use of the TNFα inhibitor, e.g., a TNFα antibody, for the treatment of RA.

A kit or an article of manufacture refers to a packaged product comprising components with which to administer a TNFα inhibitor for treatment of a RA. The kit preferably comprises a box or container that holds the components of the kit. The box or container is affixed with a label or a Food and Drug Administration approved label, including a protocol for administering the TNFα inhibitor. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody adalimumab (or D2E7), as described in PCT/IB03/04502 and U.S. application Ser. No. 10/222,140, incorporated by reference herein.

The term "package insert" is used to refer to instructions customarily included in commercial packages of therapeutic products, that contain information about the indications, usage, dosage, administration, contraindications and/or warnings concerning the use of such therapeutic products.

In one embodiment, the article of manufacture of the invention comprises (a) a first container with a composition contained therein, wherein the composition comprises a TNFα antibody; and (b) a package insert indicating that the TNFα antibody may be used for reducing signs and symptoms of RA.

Suitable containers for the TNFα inhibitor, e.g., a TNFα antibody, include, for example, bottles, vials, syringes, pens, etc. The containers may be formed from a variety of materials such as glass or plastic. The container holds a composition which is by itself or when combined with another composition effective for treating, preventing and/or diagnosing the condition and may have a sterile access port.

In one embodiment, the article of manufacture comprises a TNFα inhibitor, e.g., a TNFα antibody, and a label which indicates to a subject who will be administering the TNFα inhibitor about using the TNFα inhibitor for the treatment of RA. The label may be anywhere within or on the article of manufacture. In one embodiment, the article of manufacture comprises a container, such as a box, which comprises the TNFα inhibitor and a package insert or label providing information pertaining to use of the TNFα inhibitor for the treatment of RA. In another embodiment, the information is printed on a label which is on the outside of the article of manufacture, in a position which is visible to prospective purchasers.

In one embodiment, the package insert of the invention informs a reader, including a subject, e.g., a purchaser, who will be administering the TNFα inhibitor for treatment, that the TNFα inhibitor, e.g., a TNFα antibody such as adalimumab, is an indicated treatment of RA, including of moderately to severely active disease in adult patients.

In one embodiment, the package insert describes certain patient populations who may respond favorably to the TNFα inhibitor within the article of manufacture. For example, the package insert may indicate that the TNFα antibody, e.g., adalimumab, may be used to treat RA in patients who have had an inadequate response to conventional therapy and/or who have lost response to or are intolerant to infliximab.

In another embodiment, the label of the invention indicates that adalimumab is indicated for treatment of moderately to severely active RA in adult patients who have had an inadequate response to conventional therapy. In another embodiment, the label of the invention indicates that the TNFα inhibitor, e.g., a TNFα antibody such as adalimumab, is also indicated for treatment in adult patients with moderately to severely active RA who have lost response to or are intolerant to infliximab.

In one embodiment, the package insert of the invention describes certain therapeutic benefits of the TNFα antibody, e.g., adalimumab, including specific symptoms of RA which may be reduced by using the TNFα antibody, e.g., adalimumab. It should be noted that the package insert may also contain information pertaining to other disorders which are treatable using the TNFα antibody, e.g., adalimumab. Information described herein which is provided in a package insert and pertains to other disorders, i.e., diseases other than RA, is also included within the scope of the invention. The package insert of the invention may indicate that extra TNFα in your body can attack normal healthy body tissues and cause inflammation especially in the tissues in your bones, cartilage, joints and digestive tract. The package insert of the invention may also indicate that adalimumab helps reduce the signs and symptoms of immune diseases, including rheumatoid and psoriatic arthritis (pain and swollen joints), ankylosing spondylitis (morning stiffness and back pain), and Crohn's disease (abdominal pain and diarrhea).

The package insert of the invention may also provide information to subjects who will be receiving adalimumab regarding combination uses for both safety and efficacy purposes. The package insert of the invention may contain warnings and precautions regarding the use of the TNFα inhibitor, e.g., a TNFα antibody such as adalimumab. In one embodiment, the invention provides an article of manufacture comprising a packaging material; a TNFα antibody, or antigen-binding portion thereof; and a label or package insert contained within the packaging material indicating that in studies of the TNFα antibody, or antigen-binding portion thereof, observed malignancies included melanoma and/or granulose cell tumor of the ovary.

In one embodiment, the information provided in the label describes safety regarding use of the TNFα inhibitor and vaccines. In one embodiment, the invention provides an article of manufacture comprising a packaging material; a TNFα antibody, or antigen-binding portion thereof; and a label or package insert indicating that patients with RA receiving treatment with the TNFα antibody, or antigen-binding portion thereof, can be administered a pneumonococcal vaccine concurrently with the TNFα antibody, or antigen-binding portion thereof. The invention also provides an article of manufacture comprising a packaging material; pneumonococcal or influenza virus vaccine; and a label or package insert contained within the packaging material indicating that patients receiving the pneumonococcal or influenza virus vaccine can be safely administered a TNFα inhibitor. In one embodiment, the pneumonococcal vaccine is a pneumonococcal polysaccharide vaccine.

The label of the invention may contain information regarding the use of the TNFα inhibitor, e.g., a TNFα antibody such as adalimumab, in clinical studies for RA. In one embodiment, the label of the invention describes the studies described herein as the Examples, either as a whole or in portion.

In one embodiment of the invention, the kit comprises a TNFα inhibitor, such as an antibody, an second pharmaceutical composition comprising an additional therapeutic agent, and instructions for administration of both agents for the treatment of RA. The instructions may describe how, e.g., subcutaneously, and when, e.g., at week 0, week 2, and biweekly thereafter, doses of TNFα antibody and/or the additional therapeutic agent shall be administered to a subject for treatment.

Another aspect of the invention pertains to kits containing a pharmaceutical composition comprising an anti-TNFα antibody and a pharmaceutically acceptable carrier and one or more additional pharmaceutical compositions each comprising a drug useful for treating a TNFα related disorder and a pharmaceutically acceptable carrier. Alternatively, the kit comprises a single pharmaceutical composition comprising an anti-TNFα antibody, one or more drugs useful for treating a TNFα related disorder and a pharmaceutically acceptable carrier. The kits further contain instructions for dosing of the pharmaceutical compositions for the treatment of a TNFα related disorder.

The package or kit alternatively may contain the TNFα inhibitor and it may be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

Additional Therapeutic Agents

Methods, uses, and compositions of the invention also include combinations of TNFα inhibitors, including antibodies, and other therapeutic agents. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Binding proteins described herein may be used in combination with additional therapeutic agents such as a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine. Preferred examples of nonsteroidal anti-inflammatory drug(s) also referred to as NSAIDS include drugs like ibuprofen. Other preferred combinations are corticosteroids including prednisolone; the well known side effects of steroid use can be reduced or even eliminated by tapering the steroid dose required when treating patients in combination with the anti-TNFα antibodies of this invention. Non-limiting examples of therapeutic agents for rheumatoid arthritis with which an antibody, or antibody portion, of the invention can be combined include the following: cytokine suppressive anti-inflammatory drug(s)

(CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists such as soluble p55 or p75 TNF receptors, derivatives, thereof, (p75TNFR1gG (Enbrel™) or p55TNFR1gG (Lenercept), chimeric, humanized or human TNF antibodies, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein. Other combinations including TNFα converting enzyme (TACE) inhibitors; IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with TNFα function; especially preferred are IL-18 antagonists including IL-18 antibodies or soluble IL-18 receptors, or IL-18 binding proteins. It has been shown that TNFα and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFR1gG (Enbrel™ and p55TNFR1gG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine.

Nonlimiting additional agents which can also be used in combination with an TNFα antibody, or antigen-binding portion thereof, to treat rheumatoid arthritis include, but are not limited to, the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., *Arthritis & Rheumatism* (1994) Vol. 37, S295; *J. Invest. Med.* (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., *Arthritis & Rheumatism* (1996) Vol. 39, No. 9 (supplement), S284; *Amer. J. Physiol.-Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-

1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-11 converting enzyme); zap-70 and/or 1ck inhibitor (inhibitor of the tyrosine kinase zap-70 or 1ck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents.

In one embodiment, the TNFα antibody, or antigen-binding portion thereof, is administered in combination with one of the following agents for the treatment of rheumatoid arthritis: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hcl; sulfadiazine; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram. In another embodiment, a TNF antibody, or antigen-binding portion thereof, is administered for the treatment of an TNF-related disorder in combination with one of the above mentioned agents for the treatment of rheumatoid arthritis.

The antibodies of the invention, or antigen binding portions thereof, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

IV. Efficacy of TNFα Inhibitor for Rheumatoid Arthritis

The invention also provides methods for determining whether a TNFα inhibitor is effective at treating rheumatoid arthritis (RA) in a subject. Such methods may be used to determine the efficacy of a TNFα inhibitor, including those which are unknown or unconfirmed to have such efficacy. Using the methods described herein, effective TNFα inhibitors may be determined or confirmed, and, subsequently, used in the method of treating RA.

In one embodiment, the invention provides a method for determining the efficacy of a TNFα inhibitor, including a human TNFα antibody, for treating RA in a subject, using the ACR response. The American College of Rheumatology preliminary criteria for improvement in Rheumatoid Arthritis (ACR20, 50, 70 responses) was developed to provide a efficacy measures for rheumatoid arthritis (RA) treatments. ACR20, ACR50 and ACR70 requires a greater than 20%, 50% and 70% improvement respectively. Response criteria are detailed in Felson D T, Anderson J J, Boers M, Bombardier C, Furst D, Goldsmith C, et al. American College of Rheumatology preliminary definition of improvement in rheumatoid arthritis. Arthritis Rheum 1995; 38:727-35, incorporated by reference herein. Generally, patients are examined clinically at screening, baseline, and frequently during treatment. The primary efficacy for signs and symptoms is measured via American College of Rheumatology preliminary criteria for improvement (ACR20) at 12 weeks. An additional primary endpoint includes evaluation of radiologic changes over 6 to 12 months to assess changes in structural damage. The efficacy of a TNFα inhibitor for treating RA may be determined by the ACR response of a patient population who may be evaluated by determining the percentage of the patient population in whom an ACR response occurs following administration of the TNFα inhibitor.

The ACR response may be used as an index for measuring efficacy of a TNFα inhibitor in a patient population having RA, where attaining a certain percentage of patients within a population who were administered the TNFα inhibitor and who achieve an ACR response, i.e. ACR20, ACR50, ACR70, indicates that the TNFα inhibitor is effective for treating RA. In one embodiment, the invention provides a method for determining whether a human TNFα antibody is effective for treating RA.

In one embodiment, the invention provides a method of determining the efficacy of a TNFα inhibitor for treating RA in a subject comprising determining an ACR20 response of a patient population having RA and who was administered the TNFα inhibitor, wherein an ACR20 response in at least about 80% of the patient population indicates that the TNFα inhibitor is an effective TNFα inhibitor for the treatment of RA in a subject. In one embodiment, an ACR20 response in at least about 85% of the patient population indicates that the TNFα inhibitor is an effective TNFα inhibitor for the treatment of RA in a subject. In one embodiment, an ACR20 response in at least about 43%, at least about 56%, at least about 60%, at least about 65%, at least about 66%, at least about 67%, at least about 69%, at least about 70%, at least about 73%, at least about 75%, at least about 78%, at least about 81%, at least about 82%, or at least about 85%, of the patient population indicates that the TNFα inhibitor is an effective TNFα inhibitor for the treatment of RA in a subject. Numbers intermediate to the above recited percentages, e.g., 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, as well as all other numbers recited herein, are also intended to be part of this invention. Ranges of values using a combination of any of the above recited values as upper and/or lower limits are intended to be included in the scope of the invention.

In one embodiment, the invention provides a method for determining the efficacy of a human TNFα antibody, or antigen-binding portion thereof, for treating RA in a subject who has failed prior infliximab treatment comprising determining an ACR20 response of a patient population having RA who has failed previous infliximab treatment and who was administered the human TNFα antibody, or antigen-binding portion thereof, wherein an ACR20 response in at least about 50% of the patient population indicates that the human TNFα antibody, or antigen-binding portion thereof, is an effective human TNFα antibody, or antigen-binding portion thereof, for the treatment of RA in a subject who has failed prior infliximab treatment. In one embodiment, an ACR20 response in at least about 50% of the patient population indicates that the human TNFα antibody, or antigen-binding portion thereof, is an effective human TNFα antibody, or antigen-binding portion thereof, for the treatment of RA in a subject who has failed prior infliximab treatment. In one embodiment, an ACR20 response in at least about 55% of the patient population indicates that the human TNFα antibody, or antigen-binding portion thereof, is an effective human TNFα antibody, or antigen-binding portion thereof, for the treatment of RA in a subject who has failed prior infliximab treatment. In one embodiment, an ACR20 response in at least about 60% of the patient population indicates that the human TNFα antibody, or antigen-binding portion thereof, is an effective human TNFα antibody, or antigen-binding portion thereof, for the treatment of RA in a subject who has failed prior infliximab treatment. In one embodiment, an ACR20 response in at least about 65% of the patient population indicates that the human TNFα antibody, or antigen-binding portion thereof, is an effective human TNFα antibody, or antigen-binding portion thereof, for the treatment of RA in a subject who has failed prior infliximab treatment. In one embodiment, an ACR20 response in at least about 69% of the patient population indicates that the human TNFα antibody, or antigen-binding portion thereof, is an effective human TNFα antibody, or antigen-binding portion thereof, for the treatment of RA in a subject who has failed prior infliximab treatment.

Numbers intermediate to the above recited percentages, e.g., 60%, 63%, 64%, as well as all other numbers recited herein, are also intended to be part of this invention. Ranges of values using a combination of any of the above recited values as upper and/or lower limits are intended to be included in the scope of the invention.

In one embodiment, the invention provides a method of determining the efficacy of a TNFα inhibitor for treating RA in a subject comprising determining an ACR50 response of a patient population having RA and who was administered the TNFα inhibitor, wherein an ACR50 response in at least about 62% of the patient population indicates that the TNFα inhibitor is an effective TNFα inhibitor for the treatment of RA in a subject. In one embodiment, an ACR50 response in at least about 65% of the patient population indicates that the TNFα inhibitor is an effective TNFα inhibitor for the treatment of RA in a subject. In one embodiment, an ACR50 response in at least about 21%, at least about 28%, at least about 35%, at least about 37%, at least about 40%, at least about 41%, at least about 43%, at least about 45%, at least about 55%, at least about 57%, at least about 59%, at least about 60%, at least about 62%, at least about 65% of the patient population indicates that the TNFα inhibitor is an effective TNFα inhibitor for the treatment of RA in a subject. Numbers intermediate to the above recited percentages, e.g., 21%, 22%, 23%, 24%, 25%, 26%, 27%, 28%, 29%, 30%, 31%, 32%, 33%, 34%. 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, as well as all other numbers recited herein, are also intended to be part of this invention. Ranges of values using a combination of any of the above recited values as upper and/or lower limits are intended to be included in the scope of the invention.

In one embodiment, the invention provides a method for determining the efficacy of a human TNFα antibody, or antigen-binding portion thereof, for treating RA in a subject comprising determining an ACR70 response of a patient population having RA and who was administered the human TNFα antibody, or antigen-binding portion thereof, wherein an ACR70 response in at least about 20% of the patient population indicates that the human TNFα antibody, or antigen-binding portion thereof, is an effective human TNFα antibody, or antigen-binding portion thereof, for the treatment of RA in a subject. In one embodiment, an ACR70 response in at least about 25% of the patient population indicates that the human TNFα antibody, or antigen-binding portion thereof, is an effective human TNFα antibody, or antigen-binding portion thereof, for the treatment of RA in a subject. In one embodiment, an ACR70 response in at least about 30% of the patient population indicates that the human TNFα antibody, or antigen-binding portion thereof, is an effective human TNFα antibody, or antigen-binding portion thereof, for the treatment of RA in a subject. In one embodiment, an ACR70 response in at least about 35% of the patient population indicates that the human TNFα antibody, or antigen-binding portion thereof, is an effective human TNFα antibody, or antigen-binding portion thereof, for the treatment of RA in a subject. In one embodiment, an ACR70 response in at least about 40% of the patient population indicates that the human TNFα antibody, or antigen-binding portion thereof, is an effective human TNFα antibody, or antigen-binding portion thereof, for the treatment of RA in a subject. In one embodiment, an ACR70 response in at least about 14%, at least about 16%, at least about 17%, at least about 18%, at least about 19%, at least about 20%, at least about 21%, at least about 25%, at least about 26%, at least about 30%, at least about 35%, at least about 36%, at least about 38%, at least about 40% of the patient population indicates that the human TNFα antibody, or antigen-binding portion thereof, is an effective human TNFα antibody, or antigen-binding portion thereof, for the treatment of RA in a subject. Numbers intermediate to the above recited percentages, e.g., 15%, 16%, 17%, 18%, 19%, 20%, 21%, 22%, 23%, 24%, 25%, 26%, 27%, 28%, 29%, 30%, 31%, 32%, 33%, 34%. 35%, 36%, 37%, 38%, 39%, 40%, as well as all other numbers recited herein, are also intended to be part of this invention. Ranges of values using a combination of any of the above recited values as upper and/or lower limits are intended to be included in the scope of the invention.

In one embodiment, the invention provides a method for determining the efficacy of a TNFα inhibitor, including a human TNFα antibody, for treating RA in a subject, using the EULAR response of a subject or patient population. European League Against Rheumatism (EULAR) Response Criteria is based on the Disease Activity Score (DAS) index. To be classified as responders, patients should have a significant change in DAS and also low current disease activity. Three categories are defined: good, moderate, and non-responders. For details of EULAR criteria see: Van Gestel A M, Prevoo M L, van 't Hof M A, van Rijswijk M H, van de Putte L B, van Riel P L. Development and validation of the European League Against, incorporated by reference herein.

In one embodiment, the invention provides a method for determining the efficacy of a human TNFα antibody, or antigen-binding portion thereof, for treating RA in a subject comprising determining a good EULAR response of a patient population having RA and who was administered the human TNFα antibody, or antigen-binding portion thereof, wherein a good EULAR response response in at least about 35% of the patient population indicates that the human TNFα antibody, or antigen-binding portion thereof, is an effective human TNFα antibody, or antigen-binding portion thereof, for the treatment of RA in a subject. In one embodiment, a good EULAR response response in at least about 40% of the patient population indicates that the human TNFα antibody, or antigen-binding portion thereof, is an effective human TNFα antibody, or antigen-binding portion thereof, for the treatment of RA in a subject. In one embodiment, a good EULAR response response in at least about 13%, at least about 20%, at least about 24%, at least about 25%, at least about 28%, at least about 30%, at least about 32%, at least about 33%, at least about 35%, at least about 36%, at least about 38%, or at least about 40% of the patient population indicates that the human TNFα antibody, or antigen-binding portion thereof, is an effective human TNFα antibody, or antigen-binding portion thereof, for the treatment of RA in a subject. Numbers intermediate to the above recited percentages, e.g., 13%, 14%, 15%, 16%, 17%, 18%, 19%, 20%, 21%, 22%, 23%, 24%, 25%, 26%, 27%, 28%, 29%, 30%, 31%, 32%, 33%, 34%. 35%, 36%, 37%, 38%, 39%, 40%, as well as all other numbers recited herein, are also intended to be part of this invention. Ranges of values using a combination of any of the above recited values as upper and/or lower limits are intended to be included in the scope of the invention.

In one embodiment, the invention provides a method for determining the efficacy of a human TNFα antibody, or antigen-binding portion thereof, for treating RA in a subject comprising determining a moderate EULAR response of a patient population having RA and who was administered the human TNFα antibody, or antigen-binding portion thereof, wherein a moderate EULAR response in at least about 83% of the patient population indicates that the human TNFα antibody, or antigen-binding portion thereof, is an effective human TNFα antibody, or antigen-binding portion thereof, for the treatment of RA. In one embodiment, a moderate EULAR response in at least about 85% of the patient population indicates that the human TNFα antibody, or antigen-binding portion thereof, is an effective human TNFα antibody, or antigen-binding portion thereof, for the treatment of RA. In one embodiment, a moderate EULAR response in at least about 90% of the patient population indicates that the human TNFα antibody, or antigen-binding portion thereof, is an effective human TNFα antibody, or antigen-binding portion thereof, for the treatment of RA. In one embodiment, a moderate EULAR response in at least about 92% of the patient population indicates that the human TNFα antibody, or antigen-binding portion thereof, is an effective human TNFα antibody, or antigen-binding portion thereof, for the treatment of RA. In one embodiment, a moderate EULAR response in at least about 60%, at least about 61%, at least about 62%, at least about 78%, at least about 80%, at least about 82%, at least about 83%, at least about 85%, at least about 88%, or at least about 90%, or at least about 92% of the patient population indicates that the human TNFα antibody, or antigen-binding portion thereof, is an effective human TNFα antibody, or antigen-binding portion thereof, for the treatment of RA. Numbers intermediate to the above recited percentages, e.g., 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, as well as all other numbers recited herein, are also intended to be part of this invention. Ranges of values using a combination of any of the above recited values as upper and/or lower limits are intended to be included in the scope of the invention.

The invention also provides a method for determining the efficacy of a TNFα inhibitor, including a human TNFα antibody, for treating RA in a subject, using the Simplified Disease Activity Index Score (SDAI). The SDAI is a valid and sensitive assessment of disease activity and treatment response that is comparable with the DAS 28 and ACR response criteria; it is easy to calculate and therefore a viable tool for day-to-day clinical assessment of RA treatment (see Smolen et al. Rheumatology (Oxford). 2003 February;42(2): 244-57).

In one embodiment, the invention provides a method for determining the efficacy of a TNFα inhibitor for the treatment of rheumatoid arthritis (RA) in a subject comprising determining a Simplified Disease Activity Score (SDAI) of a patient population having RA and who was administered the TNFα inhibitor, wherein a mean SDAI of no greater than about 3.3 in at least about 11% of the patient population indicates that the TNFα inhibitor is an effective TNFα inhibitor for treating RA.

Other indices described in the art, including those referenced in the Examples, may also be used to determine the efficacy of a TNFα inhibitor in accordance with the methods of the invention. For example, TJC and/or SJC counts may be used, HAQ scores may be used, and DAS scores may be used to determine whether a TNFα inhibitor is efficacious for treating RA in a subject. Tender joint count (TJC) is an assessment of 28 or more joints where several different aspects of tenderness are assessed by pressure and joint manipulation on physical examination. Swollen joint count (SJC): an assessment of 28 or more joints where joints are classified as either swollen or not swollen. For TJC and SJC scoring see Fuchs and Pincus, Arthritis Rheum 37:470-475, 1994; American College of Rheumatology Committee on Outcome Measures in Rheumatoid Arthritis Clinical Trials: Reduced joint counts in rheumatoid arthritis clinical trials. Arthritis Rheum 37:463-464, 1994).

Health Assessment Questionnaire (HAQ) is a standardized disability questionnaire that was initially developed for use in rheumatoid arthritis (RA). A high HAQ score has been shown to be a strong predictor of morbidity and mortality in RA, and low HAQ scores are predictive of better outcomes (see Fries et al. Arthritis Rheum 1980; 23:137-45.

DAS28 (disease activity score) is also an accepted measure of the activity of rheumatoid arthritis in an affected subject. The following parameters are included in the calculation: Number of joints tender to the touch (TEN); Number of swollen joints (SW); Erythrocyte sedimentation rate (ESR); Patient assessment of disease activity (VAS; mm) (see Van der Heijde et al. Ann Rheum Dis 1990; 49:916-20). In modified DAS (DAS28) 28 joints are assessed (see Prevoo M L L, et al. Arthritis Rheum 1995; 38:44-8).

In one embodiment, the invention provides a method for determining the efficacy of a TNFα inhibitor, including a human TNFα antibody, for treating RA in a subject, using the CRP level in correlation with a Patient Activity Score (PAS). The invention. The invention provides a method for predicting the efficacy of a TNFα inhibitor for the treatment of rheumatoid arthritis (RA) in a subject comprising using the combination of a C-reactive protein (CRP) level of the subject and a Patient Activity Score (PAS) of the subject, wherein an improvement in the CRP level and the PAS score early in the treatment of the patient with the TNFα inhibitor indicates that the TNFα inhibitor is an effective TNFα inhibitor for the treatment of RA in the subject. In one embodiment, the improvement in the CRP level and the PAS score early in the treatment of the subject occurs at about two weeks following initiation of the treatment in the subject. In one embodiment, the PAS score is determined using the Health Assessment Questionnaire (HAQ) of the subject. In one embodiment, the improvement in the CRP level is at least as described in the Examples below. In one embodiment, the improvement in the HAQ score is at least about 0.4.

Also encompassed in the scope of the invention is administering the effective TNF inhibitor, e.g., human TNFα antibody, or antigen-binding portion thereof, to a subject for the treatment of RA, wherein the TNF inhibitor is identified as an effective TNF inhibitor using any of the methods and uses described herein, as well as those methods described in the Examples.

The invention further provides a method of treating RA in a subject comprising administering an effective human TNFα antibody, or antigen-binding portion thereof, for the treatment of RA in a subject, wherein the effective human TNFα antibody, or antigen-binding portion thereof, was identified as achieving a moderate EULAR response in at least about 83% of a patient population who was administered the human TNFα antibody, or antigen-binding portion thereof. In one embodiment, the invention provides a use of an effective human TNFα antibody, or antigen-binding portion thereof, in the manufacture of a medicament for treating RA in a subject, wherein the effective human TNFα antibody, or antigen-binding portion thereof, was identified as achieving a moderate EULAR response in at least about 83% of a patient population who was administered the human TNFα antibody, or antigen-binding portion thereof.

The invention also provides a method of treating RA based on the determination of a TNFα inhibitor as an effective TNFα inhibitor for achieving a certain ACR response in a patient population having taken the TNFα inhibitor. Thus, in one embodiment, the invention provides a method of treating in a subject comprising administering an effective TNFα inhibitor, wherein the effective TNFα inhibitor was identified as providing an ACR20 response in at least about 80% of a patient population who received the effective TNFα inhibitor for the treatment of RA. The invention also provides, in another embodiment, use of an effective TNFα inhibitor in the manufacture of a medicament for the treatment of RA in a subject, wherein the TNFα inhibitor was identified as providing an ACR20 response in at least about 80% of a patient population who received the effective TNFα inhibitor for the treatment of RA.

In one embodiment, the invention provides a method of treating RA in a subject comprising administering an effective human TNFα antibody, or antigen-binding portion thereof, for the treatment of RA in a subject, wherein the effective human TNFα antibody, or antigen-binding portion thereof, was identified as achieving an ACR70 response in at least about 20% of a patient population who was administered the human TNFα antibody, or antigen-binding portion thereof. In one embodiment, the invention provides a use of an effective human TNFα antibody, or antigen-binding portion thereof, in the manufacture of a medicament for treating RA in a subject, wherein the effective human TNFα antibody, or antigen-binding portion thereof, was identified as achieving an ACR70 response in at least about 20% of a patient population who was administered the human TNFα antibody, or antigen-binding portion thereof.

It should be noted that the Examples provided herein represent different methods of determining the efficacy of a TNFα inhibitor, such as a human TNFα antibody, or antigen-binding portion thereof. As such, data and results described in the Examples section which shows efficacy of a TNFα inhibitor, e.g., ability to treat RA, are included in the methods of determining efficacy of the invention.

Time points for determining efficacy will be understood by those of skill in the art to depend on the type of efficacy being determined, e.g., treatment of RA. In one embodiment, measurements in scores, e.g., an improvement in the ACR or EULAR response of a subject, may be measured against a subject's baseline score. Generally, a baseline refers to a measurement or score of a patient before treatment, i.e. week 0. Other time points may also be included as a starting point in determining efficacy, however. For example, in determining the efficacy of a TNFα inhibitor for treating RA in a patient population, a determination of the percentage of the patient population who is treated, e.g., improvement in ACR response, may be determined based on a time point from when treatment was initiated.

Patient populations described in the methods of the invention are generally selected based on common characteristics, such as, but not limited to, subjects diagnosed with RA who on a dosing regimen comprising a TNFα inhibitor. Such a patient population would be appropriate for determining the efficacy of the TNFα inhibitor for treating RA in the given patient population. In one embodiment, the patient population is an adult population. In another embodiment, members of a patient population have all been diagnosed with moderate to severe Ra, including moderate to severe active RA.

In one embodiment, the methods of the invention for determining whether a TNFα inhibitor is an effective TNFα inhibitor, include determining changes, improvements, measurements, etc., in RA using appropriate indices known in the art, e.g., ACR, EULAR, DAS, HAQ, from a patient population who has already been administered the TNFα inhibitor. Such a patient population may be pre-selected according to common characteristics, e.g., RA, loss of response to infliximab, and may have already been given the TNFα inhibitor. Administration of the TNFα inhibitor may or may not be performed by the same person of ordinary skill who is determining the efficacy of the TNFα inhibitor in accordance with the teachings of the specification.

In one embodiment, the methods of the invention comprise administering the TNFα inhibitor to the subjects of a patient population and determining the efficacy of the TNFα inhibitor by determining changes, improvements, measurements, etc., using RA indices known in the art, in the patient population in comparison to the Examples set forth below. For example, in one embodiment the invention includes a method for determining efficacy of a TNFα inhibitor for the treatment of RA comprising administering the TNFα inhibitor to a preselected patient population having RA; and determining the effectiveness of the TNFα inhibitor by using a mean baseline TJC or SJC score of the patient population and a mean TJC or SJC score following administration of the TNFα inhibitor.

Methods of the invention relating to determining efficacy, i.e., determining whether a TNFα inhibitor is an effective TNFα inhibitor, may also be applied to specific patient populations within the overall patient population who together have specific, common characteristics, i.e., a subpopulation. For example, the patient population may comprise patients who have failed prior infliximab treatment.

In addition, while the above methods are described in terms of patient populations, methods of efficacy described herein may also be applied to individual subjects. For example, a method for determining efficacy may comprise determining whether a subject having RA and who is on a dosage regimen, e.g., a biweekly dosing regimen, comprising a human TNFα antibody, is able to achieve an ACR50 response, wherein an ACR50 response would indicate that the human TNFα antibody is an effective human TNFα antibody.

The Examples and discoveries described herein are representative of a TNFα inhibitor, i.e., adalimumab, which is effective for treating RA, including reducing signs and symptoms of RA, inducing major clinical response in RA, inhibiting the radiographic progression of RA, and improving physical function in patients having RA. As such, the studies and results described in the Examples section herein may be used as a guideline for determining the efficacy of a TNFα inhibitor, i.e., whether a TNFα inhibitor is an effective TNFα inhibitor for the treatment of RA. In one embodiment, methods of determining efficacy described herein may be used to determine whether a TNFα inhibitor is bioequivalent to another TNFα inhibitor.

In one embodiment, the article of manufacture of the invention comprises instructions regarding how to determine the efficacy of the TNF inhibitor for the treatment of RA.

The present invention is further illustrated by the following examples which should not be construed as limiting in any way.

EXAMPLE 1

Adalimumab (HUMIRA®) is Safe in Global Clinical Trials in Multiple Indications and Reduced Mortality in Rheumatoid Arthritis A study was performed to assess the safety of adalimumab (ADA) in treating patients (pts) with rheumatoid arthritis (RA), psoriatic arthritis (PsA), ankylosing spondylitis (AS), psoriasis (Ps), or juvenile idiopathic arthritis (JIA) in global clinical trials.

Patients treated with ADA in global clinical trials were routinely assessed for safety. Serious adverse events (SAE) of interest to physicians prescribing anti-tumor necrosis factor (TNF) therapy were assessed per 100 pt years (E/100PY). SAEs were coded using the Medical Dictionary for Regulatory Activities (MedDRA).

Adverse events (AEs) were routinely collected in global clinical trials for all indications and labeled as a serious adverse event (SAE) based on regulatory criteria/definition: 1) Fatal, 2) Life-threatening, 3) Requires inpatient hospitalization, 4) Prolongs hospitalization, 5) Results in congenital anomaly/birth defect, 6) Causes persistent or significant disability/incapacity, 7) Important medical event that jeopardizes the patient and requires medical/surgical intervention to prevent another serious outcome.

The Standardized Mortality Ratio (SMR) was calculated using the expected number of deaths from an age and sex matched general population as published in the World Health Organization (WHO) website. The WHO 2000 mortality data for the US was used in determining the expected number of deaths per age category.

Randomized clinical trials and open-label studies were conducted to determine the safety of ADA across several indications. The patient demographic data is listed in Table 1. The randomized clinical trials (RCT) and open-label (OL) studies included as follows, by indication:

RA—All clinical trials (except for the early RA trial), including Phase II and III RCTs, OL extensions, and OL Phase IIIb trials.

PsA—A 24-week (wk) Phase III RCT in NSAID non-responders; a 12-wk Phase III study in DMARD non-responders; and an ongoing OL extension for completers of the 2 studies.

AS—Two ongoing Phase III multicenter studies in US, EU, and Canada, each with a 24-wk RCT phase followed by an 80-wk OL extension.

Ps—A 12-wk Phase II RCT with a 48-wk OL extension.

JIA—The 16-week OL lead-in and 32-wk RCT phases of a multicenter Phase III randomized, double-blind stratified parallel-group study in children with polyarticular JIA.

TABLE 1

Baseline Demographics

| | RA N = 10,049+ | PsA N = 395 | AS N = 393 | Ps N = 142 | JIA N = 171 |
|---|---|---|---|---|---|
| Age, mean (yrs) | 53.9 | 49 | 42 | 44.6 | 11.3 |
| % Female | 79.5 | 44.6 | 24.2 | 31 | 78.9 |
| Disease duration, mean (yrs) | 11.0‡ | 9.1 | 11.4 | 19.2 | 3.8 |
| % on concomitant immunosuppressive/DMARD therapy | 85.5 | 54.2 | 20.4 | 0* | 49.7 |
| % on concomitant corticosteroid therapy | 64.8 | 12.4 | 9.4 | 0* | 11.1 |

*Per protocol, patients were required to discontinue all systemic therapies for psoriasis prior to study entry
+1 patient out of the 10,050 had missing demographic information
‡Based on data from 9,955 patients As of Apr. 15, 2005, the ADA RA clinical trial safety database included data for 10,050 patients, representing 12,506 patient years (PY) of exposure to ADA. The rate of serious infections, 5.05/100PY, was comparable to that reported on Aug. 31, 2002 (4.9/100PY), and to published reports of RA populations naïve to anti-TNF therapy. (Singh et al. (1999) *Arthritis Rheum* 42(Suppl):S242 and Doran et al. (2002) *Arthritis Rheum* 46:2287) The number of patients, PY of exposure, and rates of SAEs of interest for ADA-treated patients in multiple indications are given below in Table 2. In addition, rates of serious infection separated by indications are given in Table 3 and rates of lymphomas by indication are given in Table 4.

TABLE 2

Rates of SAEs of Interest (E/100PY)

| Indication | RA | PsA | AS | Ps | JIA |
|---|---|---|---|---|---|
| Exposure (PY) | 12,506 | 484 | 423 | 135 | 99 |
| Patients | 10,050 | 395 | 393 | 142 | 171 |
| Serious Infections | 5.05 | 2.07 | 1.18 | 0.74 | 4.04 |
| Tuberculosis | 0.27 | 0 | 0 | 0 | 0 |
| Lymphomas | 0.12 | 0.41 | 0.24 | 0 | 0 |
| Demyelinating Disease | 0.08 | 0 | 0 | 0 | 0 |
| SLE/Lupus-like Syndrome | 0.10 | 0 | 0 | 0 | 0 |
| CHF | 0.28 | 0 | 0 | 0 | 0 |

TABLE 3

Rates of Serious Infection by Indication

|  | RA[1] | PSA | AS | Ps | JIA |
|---|---|---|---|---|---|
| N | 10,050 | 395 | 393 | 142 | 171 |
| Exposure (PY) | 12,506 | 484 | 423 | 135 | 99 |
| Events per 100 PY | 5.05 | 2.07 | 1.18 | 0.74 | 4.04 |

[1]Schiff M. H., et al. *Ann Rheum Dis* 2006; doi: 10.1136/ard.2005.043166.

TABLE 4

Rates of Lymphomas by Indication

|  | RA[1] | PSA | AS | Ps | JIA |
|---|---|---|---|---|---|
| No. of lymphomas | 15 | 2 | 1 | 0 | 0 |
| N | 10,050 | 395 | 393 | 142 | 171 |
| Exposure (PY) | 12,506 | 484 | 423 | 135 | 99 |
| Events per 100 PY | 0.12 | 0.41 | 0.24 | 0 | 0 |

[1]Schiff M. H., et al. *Ann Rheum Dis* 2006; doi: 10.1136/ard.2005.043166.

In the RA clinical trials, which have the largest number of ADA-treated patients, the standardized mortality ratio was calculated at 0.67 (95% CI 0.53-0.83), a much lower value than previously reported for the RA population prior to the availability of anti-TNF agents. (Gabriel et al. *Arthritis Rheum* 2003; 48(1):54 and Wolfe et al. *Arthritis Rheum* 1994; 37(4):481). The observed deaths, and standard mortality ratios, listed by gender and age matched populations are given below in Table 5.

TABLE 5

Standardized Mortality Ratios: All Adalimumab-Treated Patients with RA Compared to a Gender and Age Matched General Population

| Gender | Age | N | Expected Deaths | Observed Deaths | SMR (95% CI) |
|---|---|---|---|---|---|
| Female | 15-24 | 137 | 0.1 | 0 | |
| | 25-34 | 534 | 0.4 | 0 | |
| | 35-44 | 1319 | 2.7 | 3 | |
| | 45-54 | 2046 | 9.2 | 8 | |
| | 55-64 | 2147 | 25.2 | 19 | |
| | 65-74 | 1465 | 35.8 | 22 | |
| | >/=75 | 343 | 31.6 | 12 | |
| Subtotal | | 7991 | 104.9 | 64 | 0.61 (0.47-0.78) |
| Male | 15-24 | 19 | 0 | 0 | |
| | 25-34 | 99 | 0.2 | 0 | |
| | 35-44 | 286 | 1.1 | 1 | |
| | 45-54 | 549 | 5.0 | 3 | |
| | 55-64 | 664 | 12.3 | 10 | |
| | 65-74 | 370 | 15.0 | 12 | |
| | >/=75 | 71 | 6.3 | 3 | |
| Subtotal | | 2058 | 40 | 29 | 0.73 (0.49-1.04) |
| Total | | 10,049 | 144.9 | 93 | 0.64 (0.52-0.79) |

In conclusion, adalimumab treatment demonstrated a consistent safety profile in global clinical trials for various TNF-mediated diseases. SAE rates of interest did not differ significantly across the clinical trials evaluated. In RA clinical trials, evidence suggests a decrease in mortality in adalimumab-treated patients compared to a sex and age matched non-RA population.

EXAMPLE 2

Adalimumab is Effective in Treating in Patients with Rheumatoid Arthritis (RA) Who Previously Failed Infliximab Treatment A proportion of patients with RA do not respond optimally, or may be intolerant, to an initial anti-TNF therapy. Limited data availability prohibited the examination of important questions about the safety and efficacy of treating such patients with an alternate TNF antagonist. The objective of this study was to compare the efficacy and safety of adalimumab (Ada) in a large cohort of patients with RA who previously failed infliximab (I) therapy due to lack or loss of response or to intolerance.

Patients with long-standing, moderate to severe RA were enrolled in Study A (ReACT) and received adalimumab 40 mg subcutaneously (sc) every other week (eow). The core study period was 16 weeks followed by maintenance therapy up to week 56.

Inclusion criteria included patients over the age of 18, with RA (American College of Rheumatology criteria) for =6 months. Patients had active RA (DAS28=3.2) and had an unsatisfactory response, loss of response, or intolerance (e.g., infusion reactions) prior to infliximab treatment. Previous use of infliximab was defined as administration of at least four infusions. In addition, treatment with another TNF antagonist, if any, had to have been discontinued=2 months before study entry.

Table 6 summarizes the RA disease severity characteristics and history of prior infliximab and DMARD administration for the study population. Of the patients enrolled in the study, 90.2% completed 16 weeks of treatment, and 30 patients (73.2%) were still receiving the study drug at the week 56 visit. Of the 11 patients who withdrew from the study prior to week 56, 6 (14.4%) withdrew due to the occurrence of one or more adverse effects and 7 (17.1%) withdrew due to a lack of effectiveness.

TABLE 6

Disease Severity Characteristics and Prior Infliximab/DMARD Administration by Reason for Discontinuation of Prior Infliximab

| | | Reason for Discontinuation of Prior Infliximab | | |
|---|---|---|---|---|
| Parameter* | All Patients N = 41 | No Response n = 15 | Loss of Response n = 21 | Intolerance n = 5 |
| Mean duration of RA (years) | 11.6 ± 7.4 | 12.2 ± 9.2 | 11.8 ± 7.0 | 9.2 ± 2.5 |
| Number of prior DMARDs (includes infliximab) | 5.3 | 5.5 | 5.5 | 4.2 |
| Mean duration of infliximab treatment (months) | 17.3 ± 15.1 | 9.3 ± 5.3 | 23.4 ± 17.6 | 15.6 ± 14.0 |
| Mean dose per infliximab infusion (mg) | 262.4 ± 87.6 | 263.7 ± 81.9 | 267.5 ± 100.0 | 237.2 ± 47.8 |
| DAS28 | 6.09 ± 0.91 | 5.85 ± 0.70 | 6.18 ± 1.03 | 6.48 ± 0.86 |
| Tender joint count (28 joints) | 14.81 ± 6.57 | 13.73 ± 6.89 | 14.67 ± 6.64 | 18.60 ± 4.72 |
| Swollen joint count (28 joints) | 8.22 ± 4.75 | 5.93 ± 4.10 | 8.95 ± 4.62 | 12.00 ± 4.42 |
| Physician's global assessment of disease activity (100 mm VAS) | 49.81 ± 20.01 | 41.93 ± 17.36 | 53.00 ± 21.28 | 60.00 ± 16.43 |
| Patient's global assessment of disease activity (100 mm VAS) | 63.02 ± 19.76 | 58.87 ± 21.02 | 68.43 ± 16.43 | 52.80 ± 25.67 |
| Patient's global assessment of pain (100 mm VAS) | 65.78 ± 21.00 | 57.60 ± 24.59 | 73.38 ± 14.13 | 58.40 ± 25.97 |
| HAQ DI | 1.85 ± 0.49 | 1.92 ± 0.52 | 1.80 ± 0.43 | 1.85 ± 0.71 |
| Erythrocyte sedimentation rate (mm/h) | 37.34 ± 23.24 | 33.87 ± 12.94 | 39.48 ± 27.96 | 38.80 ± 28.86 |
| CRP (mg/L) | 25.13 ± 32.00 | 23.27 ± 26.84 | 26.26 ± 38.06 | 26.00 ± 21.43 |

*Mean ± SD except where otherwise specified.
CRP = C-reactive protein;
DAS28 = Disease Activity Score 28;
DMARD = disease-modifying antirheumatic drug;
HAQ DI = Health Assessment Questionnaire Disability Index;
RA = rheumatoid arthritis;
VAS = visual analog scale.

A total of 27 patients were receiving DMARDs at baseline, with methotrexate being the most common (25/27 patients). A total of 17/41 (41.5%) patients had measurable serum HACA concentrations at baseline. Nine patients were not assessable for HACA status owing to remaining infliximab serum concentrations. The mean interval between the last infliximab infusion and the first adalimumab injection in HACA-negative and HACA-positive patients was 12 and 15 weeks, respectively, and in patients without and with remaining infliximab serum concentrations, the mean interval was 14 and 11 weeks, respectively. HACA status and presence of infliximab serum concentration at study entry stratified by reason for discontinuation of infliximab treatment are presented in Table 7. A total of 6 (14.4%) patients received isoniazid prophylaxis for TB based on baseline chest radiograph indicative of latent TB, positive PPD skin test, or other risk factors.

TABLE 7

Baseline HACA Status and Infliximab Serum Concentration Status by Reason for Discontinuation of Prior Infliximab

| Reason for Discontinuation of Prior Infliximab | HACA Status* | | Measurable Infliximab Serum Concentration at Study Entry | |
|---|---|---|---|---|
| | Positive, n = 17 | Negative, n = 15 | Yes, n = 9 | No, n = 32 |
| No response | 4 | 6 | 4 | 10 |
| Loss of response | 10 | 7 | 5 | 17 |
| Intolerance | 3 | 2 | 0 | 5 |

*In nine patients, HACA could not be determined because of measurable infliximab serum concentrations (see second column from right).
HACA = human anti-chimeric antibody Clinically meaningful improvements occurred in all measures of RA activity in the overall patient population after 16 weeks of adalimumab treatment, and improvements were maintained through 56 weeks. Patients experienced steady increases in ACR response over time, with 46.2%, 28.2%, and 12.8% of patients achieving ACR20, 50, and 70, respectively, at Week 16, and 56.4%, 28.2%, and 17.9% achieving ACR20, 50, and 70, respectively, at Week 56 (Table 9). A total of 61.0% of patients achieved at least a moderate EULAR response, and 17.1% of patients achieved a good EULAR response at Week 16, with clinically important improvements being maintained through Week 56 (Table 8). Similarly, the DAS28 improved from baseline, with a mean change of −1.45 at Week 16 (mean −23.0% change) and of −1.63 at Week 56 (mean −25.8% change) (Table 10). Patients also experienced decreased TJC and SJC at all measured time points, with statistically significant ($p<0.001$) improvements from baseline of −6.8 (−38.4%) and −7.1 (−41.7%) at Weeks 16 and 56, respectively, for TJC, and of −4.6 (−52.8%) and −4.8 (−54.4%) at Weeks 16 and 56, respectively, for SJC.

Patient assessment of pain and both physician and patient global assessments of disease activity were similarly clinically improved (Table 8). HAQ DI scores also improved from baseline at all measurement time points during adalimumab treatment, with a mean change from baseline of −0.21 at Week 16 and of −0.19 at Week 56 (>10% decrease from baseline, $p<0.037$). The mean reduction in C-reactive protein concentration from baseline was −3.83 mg/L at Week 16 and −3.46 mg/L (78.5% decrease from baseline, $p<0.244$) at Week 56. The erythrocyte sedimentation rate also declined at all measured time points, with a mean change from baseline of −6.6 mm/h at Week 16 and of −6.5 mm/h at Week 56 (−6.3% decrease from baseline, $p=0.571$).

TABLE 8

Adalimumab Efficacy at Week 56 (LOCF Data)

|  | All Patients* (N = 41) | Reason for Discontinuation of Prior Infliximab* | | | HACA Status*‡ | |
|---|---|---|---|---|---|---|
|  |  | No Response (n = 15) | Loss of Response (n = 21) | Intolerance† (n = 5) | Positive (n = 17) | Negative (n = 15) |
| ACR20 response (%) | 56 | 43 | 65 | 60 | 47 | 64 |
| ACR50 response (%) | 28 | 21 | 35 | 20 | 29 | 36 |
| ACR70 response (%) | 18 | 14 | 25 | 0 | 18 | 29 |
| Moderate EULAR response (%) | 61 | 60 | 62 | 60 | 47 | 67 |
| Good EULAR response (%) | 24 | 13 | 33 | 20 | 29 | 27 |
| DAS28, mean change from baseline | | | | | | |
| Absolute change ± SD | −1.63 ± 1.72 | −1.25 ± 1.33 | −1.97 ± 2.08 | −1.38 ± 0.65 | −1.72 ± 2.02 | −1.79 ± 1.70 |
| Percent change | −26 | −21 | −30 | −22 | −26 | −28 |
| HAQ DI score (0-3), mean change from baseline | | | | | | |
| Absolute change ± SD | −0.19 ± 0.48 | −0.14 ± 0.48 | −0.25 ± 0.54 | −0.07 ± 0.19 | −0.32 ± 0.55 | −0.03 ± 0.43 |
| Percent change | −11 | −9 | −14 | −3 | −16 | −4 |
| Tender joint count (0-28 joints), mean change from baseline | | | | | | |
| Absolute change ± SD | −7.1 ± 8.4 | −6.0 ± 6.5 | −7.4 ± 10.2 | −9.0 ± 5.0 | −6.4 ± 9.5 | −8.4 ± 8.7 |
| Percent change | −42 | −40 | −42 | −47 | −32 | −53 |
| Swollen joint count (0-28 joints), mean change from baseline | | | | | | |
| Absolute change ± SD | −4.8 ± 6.4 | −3.1 ± 5.1 | −5.2 ± 7.3 | −7.6 ± 4.7 | −5.6 ± 5.9 | −5.3 ± 7.2 |
| Percent change | −54 | −51 | −55 | −61 | −53 | −64 |
| Patient's global assessment of disease (0-100 mm VAS), mean change from baseline | | | | | | |
| Absolute change ± SD | −22 ± 29 | −9 ± 27 | −32 ± 25 | −14 ± 38 | −20 ± 35 | −24 ± 27 |
| Percent change | −31 | −10 | −48 | −21 | −26 | −38 |
| Physician's global assessment of disease (0-100 mm VAS), mean change from baseline | | | | | | |
| Absolute change ± SD | −21 ± 27 | −17 ± 22 | −24 ± 32 | −22 ± 19 | −19 ± 33 | −25 ± 25 |
| Percent change | −37 | −40 | −34 | −39 | −18 | −55 |
| Patient's assessment of pain (0-100 mm VAS), mean change from baseline | | | | | | |
| Absolute change ± SD | −24 ± 32 | −9 ± 30 | −36 ± 29 | −18 ± 31 | −24 ± 38 | −24 ± 31 |
| Percent change | −27 | −7 | −49 | −37 | −30 | −25 |

*Total number of patients enrolled; last observation carried forward (LOCF).
†Those patients who had discontinued prior infliximab treatment for both an efficacy and safety reason were assigned to the corresponding efficacy subgroup. The intolerance subgroup consists of patients who had discontinued prior infliximab treatment strictly because of intolerance.
‡Nine patients were not assessable for HACA due to measurable infliximab concentrations.
ACR = American College of Rheumatology;
DAS28 = Disease Activity Score 28;
EULAR = European League Against Rheumatism;
HACA = human anti-chimeric antibody;
HAQ DI = Health Assessment Questionnaire Disability Index;
VAS = visual analog scale.

Adalimumab treatment led to clinically relevant improvement in disease activity irrespective of the reason for stopping prior infliximab therapy. At Week 16, ACR20 was 28.6% among those patients who had no response to infliximab, 60.0% among patients who had experienced a loss of response to infliximab, and 40.0% among patients who were intolerant to infliximab. By Week 56, 42.9% (no response subgroup) to 65.0% (loss of response subgroup) of patients achieved an ACR20 response (Table 9). A similar trend was observed for ACR50 and ACR70 response rates (Table 9).

TABLE 9

American College of Rheumatology (ACR) 20, 50, 70 improvement response rates with adalimumab treatment at Week 56 (LOCF) by reason for discontinuation of prior infliximab

|  | PatientType | Patients (%) |
|---|---|---|
| ACR 20 | All (N = 41) | 56 |
|  | No response (N = 15) | 43 |
|  | Loss of Response (N = 21) | 65 |
|  | Intolerance (N = 5) | 60 |

TABLE 9-continued

American College of Rheumatology (ACR) 20, 50, 70 improvement response rates with adalimumab treatment at Week 56 (LOCF) by reason for discontinuation of prior infliximab

|  | PatientType | Patients (%) |
|---|---|---|
| ACR 50 | All (N = 41) | 28 |
|  | No response (N = 15) | 21 |
|  | Loss of Response (N = 21) | 35 |
|  | Intolerance (N = 5) | 20 |
| ACR 70 | All (N = 41) | 18 |
|  | No response (N = 15) | 14 |
|  | Loss of Response (N = 21) | 25 |
|  | Intolerance (N = 5) | 0 |

At Week 16, a moderate EULAR response was achieved by 46.7% of patients who had no response to infliximab, 66.7% of patients who had a loss of response to infliximab, and 80% of patients who were intolerant to infliximab. At Week 56, at least 50% of patients in each subgroup achieved a moderate EULAR response, with those patients who had experienced loss of response or no response to infliximab achieving moderate EULAR response rates of 61.9% and 60.0%, respectively (Table 11). A good EULAR response was achieved at Week 16 by 6.7%, 23.8%, and 20.0% of patients with no response, loss of response, and intolerance, respectively. The respective data among patients with no response, loss of response, and intolerance at Week 56 were 13.3%, 33.3% and 20.0%. The DAS28 improved from baseline in all three subgroups at all time points evaluated, with the greatest response occurring in those patients who had stopped infliximab due to loss of response (Table 10).

TABLE 10

Change in Disease Activity Score 28 (DAS28) at Week 16 and Week 56 by reason for discontinuation of prior infliximab (LOCF).

| | PatientType | Mean Change from Baseline in DAS28 |
|---|---|---|
| Week 16 | All (N = 41) | −1.45* |
| | No response (N = 15) | −.95* |
| | Loss of Response (N = 21) | −1.81* |
| | Intolerance (N = 5) | −1.44* |
| Week 56 | All (N = 41) | −1.63* |
| | No response (N = 15) | −1.25* |
| | Loss of Response (N = 21) | −1.97* |
| | Intolerance (N = 5) | −1.38* |

*$p < 0.01$

TABLE 11

European League Against Rheumatism (EULAR) response to adalimumab treatment at Week 56 (LOCF) by reason for discontinuation of prior infliximab.

| | PatientType | Patients (%) |
|---|---|---|
| Moderate EULAR | All (N = 41) | 61 |
| | No response (N = 15) | 60 |
| | Loss of Response (N = 21) | 62 |
| | Intolerance (N = 5) | 60 |
| GOOD EULAR | All (N = 41) | 24 |
| | No response (N = 15) | 13 |
| | Loss of Response (N = 21) | 33 |
| | Intolerance (N = 5) | 20 |

All three subgroups experienced improvements from baseline in both TJC and SJC at all time points measured, with those who reported intolerance to infliximab achieving a slightly greater benefit compared with those who had an unsatisfactory response or loss of effectiveness with infliximab (Table 8).

After 56 weeks of adalimumab treatment, clinically important mean changes in other measures of disease activity, including physician's global assessment of disease, patient's global assessments of disease and pain, and HAQ DI, were achieved in all three subgroups, including those who had no response to prior infliximab therapy (Table 8).

Patients experienced clinically meaningful improvements in disease activity measures with adalimumab treatment irrespective of baseline HACA status. At 56 weeks, a total of 47% of HACA-positive patients and 64% of HACA-negative patients achieved an ACR20 response, while 29% and 36% of these patient subgroups, respectively, achieved an ACR50 response (Table 8). Similarly, 47% of HACA-positive patients and 67% of HACA-negative patients achieved a moderate EULAR response at 56 weeks. Both HACA-positive and HACA-negative patients achieved clinically important mean changes in other measures of disease activity, including TJC and SJC, DAS28, physician's global assessment of disease, patient's global assessments of disease and pain, and HAQ DI (Table 8).

From Weeks 17 to 45 of the study, 8 of 41 patients (19.5%) switched to 40 mg weekly administration of adalimumab based on disease severity and investigator's request. Twelve of 16 patients receiving adalimumab 40 mg eow monotherapy without methotrexate and 21 of 25 patients receiving adalimumab 40 mg eow with methotrexate remained on the original dose regimen for the duration of the study. The summary statistics of serum adalimumab concentrations for these patients are provided in Table 12. Mean serum trough adalimumab concentrations in these patients were within or slightly above the 4- to 8-μg/mL range, which is the typical trough concentration for the recommended regimen of 40 mg eow.

TABLE 12

Summary Statistics of Serum Adalimumab Concentrations (μg/mL) for Patients Remaining on the Original Dose Regimen (40 mg every other week) (N = 33)

| | Week | | | | | |
|---|---|---|---|---|---|---|
| | Without Methotrexate | | | With Methotrexate | | |
| | Baseline* | Week 16 | Week 56 | Baseline* | Week 16 | Week 56 |
| n | 12 | 10 | 5 | 21 | 19 | 17 |
| Mean | — | 4.4 | 7.2 | — | 6.3 | 7.1 |
| SD | — | 4.0 | 5.9 | — | 3.6 | 3.9 |
| Min | — | 0.0 | 0.0 | — | 0.4 | 0.0 |
| Median | — | 3.1 | 5.0 | — | 5.8 | 7.6 |
| Max | — | 10.6 | 13.6 | — | 14.6 | 12.6 |
| CV % | — | 93.6 | 81.1 | — | 56.7 | 54.4 |

*For nine patients who had measurable infliximab results at baseline, baseline adalimumab concentrations were not included in the summary statistics because there is potential for infliximab to interfere with the adalimumab assay.
CV = coefficient of variation.

For patients with measurable HACA at baseline, mean serum adalimumab trough concentrations ranged from 1 to 4 μg/mL, which is lower than those achieved in patients without measurable HACA levels and below the typical trough concentration for 40 mg eow (data not shown). As noted earlier (see Effectiveness by HACA status), baseline HACA status did not appear to have a major impact on effectiveness outcome parameters. Two patients (4.9%, both of whom had measurable HACA concentrations at baseline) developed AAA, and both responded well to adalimumab, with a DAS28 change from baseline to Week 56 of −1.5 in one patient (AAA present at Week 16 only, despite weekly adalimumab injections beyond Week 16) and of −5.4 in the other patient (AAA present at Week 40 and Week 56, with no dose increase of adalimumab).

The mean duration of exposure to adalimumab for all patients was 46.7 weeks, with total exposure equal to 36.7 patient-years. Almost all patients (40/41) reported one or more treatment-emergent adverse events during adalimumab treatment, the most frequent being RA (14/41, 34.1%; this represents exacerbation of patient's current condition), nasopharyngitis (13/41, 31.7%), and influenza or diarrhea (both 6/41, 14.6%). All other adverse events were reported by ≤5 patients each.

Of the 43 events reported by 34 patients that were considered at least possibly related to study drug administration, the most common clinical AEs were nasopharyngitis (6/43, 14%), influenza (4/43, 9.3%), RA (4/43, 9.3%), and pruritus (4/43, 9.3%). Neither former infliximab intolerance status nor baseline HACA status appeared to have a clinically meaningful impact on the frequency or severity of adverse events.

Five patients experienced six adverse events that led to withdrawal from the study. Four of these were considered either possibly or probably related to study drug (common cold, cough with sputum, adalimumab allergy, and painful injection). Of note, the medical history of the patient with suspected adalimumab allergy was significant for drug allergy due to leflunomide and rash. No demyelinating disorders or other autoimmune disorders, including lupus-like reactions, were reported. One patient with a history of hypertension died during the study as a result of intracerebral bleeding; the death was considered to have been probably unrelated to study drug administration.

Two serious infections were reported. One patient developed pulmonary TB during the study period that was considered probably related to adalimumab by the investigator. Approximately six months after study entry, the patient developed dry cough and five additional months later TB was diagnosed based on a positive polymerase chain reaction of the sputum. The culture for *mycobacterium* TB was negative. At screening, the patient, who had contact with a person with active TB ten years before, had no abnormalities in the chest X-ray and a negative PPD test result. Though night sweats and cough had occurred during the former infliximab treatment as well, no TB was diagnosed at that time. The event resolved after nine months of anti-TB therapy. One case of cellulitis was reported, which the investigator considered probably related to study drug.

Two patients reported the development of lymphomas during the study. Both events were considered either unrelated or probably unrelated to study drug administration due to the short exposure to adalimumab and history of previous exposure to other immunosuppressive agents. A large B-cell lymphoma diagnosed in a patient two weeks after the initiation of adalimumab treatment was considered probably not related to study drug due to the short exposure to adalimumab (three injections), increased risk of lymphoma in patients with RA, and previous longstanding therapy with methotrexate (eight years) and infliximab (five years). A T-cell lymphoma was diagnosed one year after initiation of adalimumab treatment in a patient with RA and Sjögren's syndrome who had previously received methotrexate, cyclosporine, and infliximab. It was considered probably not related to study drug, given the increased lymphoma risk in patients with RA and Sjögren's syndrome and the patient's prior immunosuppressive history.

The results of this study indicate that patients with RA who had previously discontinued treatment with infliximab, regardless of the reason for discontinuation, experienced clinically meaningful improvements in all effectiveness endpoints with adalimumab treatment. By Week 16 (the primary effectiveness evaluation period), the mean changes from baseline in TJC and SJC were −38.4% and −52.8%, respectively, and −23.0% (−1.45) for DAS28. A total of 61.0% of patients achieved a moderate EULAR response, and 17.1% achieved a good EULAR response by Week 16. ACR response rates at Week 16 were 46.2% for ACR20, 28.2% for ACR50, and 12.8% for ACR70. Decreases in the physician's and patient's global assessment of disease activity, patient's assessment of pain, and the HAQ DI through Week 16 also were indicative of clinically significant improvements in disease activity with adalimumab treatment.

Of the 41 enrolled patients, 30 continued adalimumab treatment for 56 weeks. Effectiveness results through 56 weeks of adalimumab treatment correlated well with improvements observed through Week 16.

Subgroup analyses by reason for infliximab discontinuation indicated that all three subgroups demonstrated clinically relevant improvements in all disease severity and response measures. The patients who reported a loss of response under infliximab treatment appeared to experience the greatest effectiveness with adalimumab by several disease response measures in this study. At Week 56, 60% of patients who had no response and 61.9% of patients who had loss of response to infliximab treatment achieved at least a moderate EULAR response with adalimumab. In addition, 60% of patients who were intolerant to infliximab treatment achieved a moderate EULAR response with adalimumab.

Results of the pharmacokinetic analysis indicate that, for the majority of patients, the mean steady-state serum adalimumab trough concentrations achieved with the recommended regimen of 40 mg eow were near or above 4 to 8 µg/mL, which is consistent with what has been observed in other pharmacokinetic trials of adalimumab in patients with RA (Awni et al, 2003; Granneman et al, 2003).

Adalimumab was generally well-tolerated in this selected population, and safety results did not suggest any new signals in regard to the safety of the drug. Five of 41 patients experiencing six adverse events were withdrawn from the study due to adverse events, with four of the six events considered possibly or probably related to study drug administration. The one patient diagnosed with TB had a history of previous TB contact and had developed fatigue, night sweats, weight loss, and intermittent cough prior to study entry.

In the two patients diagnosed with malignancies (cutaneous T-cell lymphoma in one and a B-cell lymphoma in the other), exposure to adalimumab was ≤1 year, and the patients had previously undergone extensive immunosuppressive treatment. The fact that the lymphoma risk is higher in patients with RA also mitigates any potential relationship to adalimumab administration. No other significant adverse events of special interest were noted, such as events associated with congestive heart failure, demyelinating diseases, or other autoimmune disorders. Coincidentally, one of the two lymphoma cases occurred in the same patient that was diagnosed with TB.

The results of this pilot study indicate that adalimumab is effective and well-tolerated for the treatment of RA in patients who have failed infliximab therapy (including those who have developed HACA for infliximab) and those who are intolerant to infliximab.

EXAMPLE 3

Efficacy and Safety of Adalimumab (Humira®) in Patients with Rheumatoid Arthritis (RA) Who Previously Failed Etanercept and/or Infliximab in Clinical Practice A proportion of patients with RA do not respond optimally, or may be intolerant, to an initial anti-TNF therapy. Limited data availability prohibited the examination of important questions about the safety and efficacy of treating such patients with an alternate TNF antagonist. The objective of this study was to compare the efficacy and safety of adalimumab (Ada) in a large cohort of patients with RA who previously failed etanercept (E) and/or infliximab (I) therapies.

Patients with long-standing, moderate to severe RA were enrolled in Study A (ReACT) and received adalimumab 40 mg subcutaneously (sc) every other week (eow). The core study period was 12 weeks followed by an optional extension phase until adalimumab was commercially available.

Inclusion criteria included patients over the age of 18, with RA (American College of Rheumatology criteria) for =3 months. Patients had active RA (DAS28=3.2) and unsatisfactory response or intolerance to at least one prior disease modifying anti-rheumatic drug (DMARD). In addition, treatment with another TNF antagonist, if any, had to have been discontinued=2 months before study entry.

As shown in Table 13, Of the patients enrolled in the study 5711 patients had not experienced anti-TNF treatment before, 899 patients had previously discontinued a treatment with another TNF antagonist (etanercept and/or infliximab), 591 patients had received as TNF antagonist infliximab only, 188 patients had received as TNF antagonist etanercept only, and 120 patients had been treated with both TNF antagonists.

TABLE 13

Baseline Characteristics by Prior TNF Antagonist

|  | No prior TNF antagonist (n = 5711) | Prior TNF antagonist (n = 899) | Prior IFX Only (n = 591) | Prior ETN Only (n = 188) | Prior ETN and IFX (n = 120) |
|---|---|---|---|---|---|
| Age (mean, years) | 54 | 53 | 53 | 54 | 52 |
| Female, % | 81 | 81 | 80 | 80 | 86 |
| Rheumatoid factor+, % | 73 | 72 | 72 | 71 | 75 |
| RA Duration (mean, years)† | 11 | 12 | 12 | 13 | 12 |
| # Prior DMARDs (mean) | 2.7 | 5.0 | 4.6 | 5.2 | 7.1 |
| DAS28 (mean) | 6.0 | 6.3 | 6.2 | 6.5 | 6.6 |
| HAQ DI score (0-3), (mean) | 1.60 | 1.85 | 1.83 | 1.89 | 1.93 |
| DMARD use, % | 75 | 69 | 75 | 50 | 68 |
| Steroid use, % | 70 | 77 | 75 | 78 | 83 |
| Time from last prior TNF antagonist dose to first dose adalimumab (median, weeks) | NA | 17 | 17 | 22 | 31 |

Patients entering Study A received Ada 40 mg sc eow for 12 weeks in addition to their current anti-rheumatic therapy—other than anti-TNF agents, which had been discontinued—and optionally continued therapy until Ada was commercially available. Efficacy and safety were assessed at Wks 2, 6, 12, and every 8 wks thereafter as shown in FIG. 1. Outcomes were compared by history of prior anti-TNF therapy, and subgroup analyses were conducted by reported reason for discontinuation (d/c) of prior anti-TNF therapy as shown in Table 14.

TABLE 14

Withdrawal Rates by Prior TNF Antagonist Therapy and by Reason for Its Discontinuation

|  | N | All withdrawals, complete treatment period, (%) | Withdrew for adverse event, (%) | Withdrew for lack of efficacy (%) |
|---|---|---|---|---|
| No ETN or IFX | 5711 | 20 | 10 | 6 |
| ETN and/or IFX | 899 | 26 | 13 | 11 |
| ETN no response | 63 | 24 | 10 | 13 |
| IFX no response | 110 | 30 | 16 | 10 |
| ETN loss response | 48 | 31 | 8 | 13 |
| IFX loss response | 258 | 19 | 11 | 9 |
| ETN intolerance | 40 | 30 | 13 | 10 |
| IFX intolerance | 139 | 29 | 17 | 9 |

As shown in Table 15-Table 21, of 6610 enrolled patients, 899 had received prior E and/or I therapy (median treatment of 9.5 months). Patients with a history of anti-TNF therapy had a higher baseline disease activity and more prior DMARDs compared to those without. Mean exposure in the study was 30 weeks for patients with prior anti-TNF treatment and 34 weeks for those without. Ada treatment lead to robust responses in both groups, with somewhat higher responses seen in patients without prior anti-TNF therapy. Marked responses to Ada therapy were seen in all subgroups, with responses in patients who had discontinued prior anti-TNF therapy because of loss of efficacy or intolerance similar to those in patients naïve to anti-TNF. Results were maintained in patients who continued beyond Wk 12, as demonstrated by last observed values (Table 13). Up to Week 12, reasons for withdrawal for patients with/without anti-TNF history included (%): lack of efficacy 2.9/1.2, and adverse events (AE) 5.6/4.1, respectively; for the entire study duration, reasons included (%): lack of efficacy, 10.6/6.2; and AE, 12.6/10.0, respectively. No new safety signals were observed. The frequency of patients experiencing serious infections was 4.3% for those with anti-TNF history and 2.9% for those without.

TABLE 15

Ada efficacy overall and by reasons for d/c prior etanercept and/or infliximab

| Prior anti-TNF | Reason for d/c | N | ACR20 12 wks | ACR50 12 wks | ACR70 12 wks | ΔDAS28* 12 wks | ΔDAS28* last obs. |
|---|---|---|---|---|---|---|---|
| No E or I |  | 5711 | 70% | 41% | 19% | −2.2 | −2.3 |
| E and/or I |  | 899 | 60% | 33% | 13% | −1.9 | −1.9 |
| Etanercept | No response | 63 | 41% | 26% | 11% | −2.0 | −2.1 |
| Infliximab | No response | 110 | 59% | 25% | 7% | −1.8 | −2.0 |
| Etanercept | Lost effic. | 48 | 67% | 34% | 14% | −2.2 | −2.0 |
| Infliximab | Lost effic. | 258 | 67% | 37% | 13% | −2.0 | −1.9 |
| Etanercept | Intolerance | 40 | 67% | 42% | 19% | −2.3 | −2.2 |
| Infliximab | Intolerance | 139 | 67% | 37% | 16% | −2.3 | −2.3 |

Observed values *Means

TABLE 16

ACR Response at Week 12 by Prior (p) TNF Antagonist Therapy

| | % of Patients | | |
|---|---|---|---|
| | ACR20 | ACR50 | ACR70 |
| No pTNF (n = 5711) | 70 | 41 | 19 |
| pTNF (n = 899) | 60 | 33 | 13 |
| pETN only (n = 188) | 57 | 34 | 19 |
| pIFX only (n = 591) | 64 | 34 | 13 |
| pETN + pIFX (n = 120) | 46 | 29 | 11 |

TABLE 17

ACR Response at Week 12 by Reason for Discontinuing Prior (p) TNF Antagonist Therapy

| | % of Patients | | |
|---|---|---|---|
| | ACR20 | ACR50 | ACR70 |
| pIFX no response (n = 110) | 59 | 25 | 7 |
| pETN no response (n = 63) | 41 | 26 | 11 |
| pIFX loss of response (n = 258) | 67 | 37 | 13 |
| pETN loss of response (n = 48) | 67 | 34 | 14 |
| pIFX intolerance (n = 139) | 67 | 37 | 16 |
| pETN intolerance (n = 40) | 67 | 42 | 19 |

TABLE 18

EULAR Response at Week 12 by Prior (p) TNF Antagonist Therapy

| | % of Patients | |
|---|---|---|
| | Moderate EULAR | Good EULAR |
| No pTNF (n = 5711) | 84 | 35 |
| pTNF (n = 899) | 76 | 23 |
| pETN only (n = 188) | 79 | 21 |
| pIFX only (n = 591) | 78 | 26 |
| pETN + pIFX (n = 120) | 62 | 11 |

TABLE 19

EULAR Response at Week 12 by Reason for Discontinuing Prior (p) TNF Antagonist Therapy

| | % of Patients | |
|---|---|---|
| | Moderate EULAR | Good EULAR |
| pIFX no response (n = 110) | 73 | 18 |
| pETN no response (n = 63) | 75 | 20 |
| pIFX loss of response (n = 258) | 79 | 23 |
| pETN loss of response (n = 48) | 81 | 19 |
| pIFX intolerance (n = 139) | 83 | 31 |
| pETN intolerance (n = 40) | 89 | 20 |

TABLE 20

ACR50, ACR70, and Good EULAR Response Rates (%) at Last Observation* by Reason for Discontinuing Prior (p) TNF Antagonist Therapy

| | % of Patients | | |
|---|---|---|---|
| | ACR50 | ACR70 | Good EULAR |
| pIFX no response (n = 110) | 30 | 14 | 23 |
| pETN no response (n = 63) | 27 | 15 | 26 |
| pIFX loss of response (n = 258) | 36 | 16 | 29 |
| pETN loss of response (n = 48) | 38 | 21 | 29 |
| pIFX intolerance (n = 139) | 38 | 17 | 35 |
| pETN intolerance (n = 40) | 26 | 16 | 18 |

*Mean/median treatment duration for all patients with prior TNF-antagonist therapy = 30/28 weeks

TABLE 21

Mean Change in HAQ from Baseline to Last Observation*

| | Mean Change from Baseline[†] |
|---|---|
| No pETN or pIFX (n = 5711) | −0.58 |
| pETN and/or IFX (n = 899) | −0.48 |
| pIFX only (n = 591) | −0.52 |
| pETN only (n = 188) | −0.45 |
| pETN + IFX (n = 120) | −0.31 |

*Mean/median treatment duration was 30/28 weeks for patients with prior anti-TNF therapy; and 34/32 weeks for patients naive to TNF antagonist therapy.
[†]MCID = Minimum Clinically Important Difference = −0.22; Goldsmith C, et al. *J Rheumatol* 1993; 20: 561-5.

The results shown in Table 16 show that Adalimumab treatment was effective as assessed by ACR response rates at Week 12 in patients with a history of treatment with 1 or 2 prior TNF antagonists. In addition Table 17 shows that Adalimumab treatment was effective as assessed by ACR response rates at Week 12, irrespective of reason for discontinuing prior therapy.

Adalimumab treatment was also effective as assessed by EULAR response rates at Week 12 in patients with a history of treatment with 1 or 2 prior TNF antagonists, as shown in Table 18, and irrespective of reason for discontinuing prior therapy, as shown in Table 19.

Additionally, results shown in Table 20 indicate a good clinical response beyond week 12. The proportion of patients with good clinical response increased when measured by ACR50, ACR70, and good EULAR rates at last observation.

Treatment with adalimumab also led to clinically important improvements in physical functioning—including in difficult-to-treat patients who had previously received 2 TNF antagonists—as measured by the mean change in HAQ scores from baseline to the last observation as indicated in Table 21.

In conclusion, in patients with RA treated in real-life clinical practice, adalimumab was safe, well-tolerated and effective in patients with a history of anti-TNF therapy, irrespective of reason for discontinuation of that therapy.

EXAMPLE 4

Adalimumab (Humira®) is Effective and Safe in Treating Rheumatoid Arthritis (RA) in Real-Life Clinical Practice The completed Study A trial (ReAct) offers the largest database available for a prospective evaluation of the efficacy and safety of adalimumab (Ada) in patients with active, insufficiently treated RA, various co-morbidities, a broad range of antirheumatic co-medications, and varied social care systems. The objective of this study was to assess and summarize the efficacy and safety of adalimumab in the final analysis of the Study A trial.

mumab treatment. Table 22 shows withdrawal rates because of lack of efficacy or intolerance to adalimumab (all types side effects), which were low overall.

TABLE 22

Withdrawals Up to Week 12 and During the Complete Study Period, by Concomitant Therapy and Reason for Withdrawal, N (%)

| Reason for Withdrawal | All (N = 6610) | No Concomitant DMARDs (N = 1731) | Concomitant DMARDs (N = 4879) | No Prior TNF Antagonist (N = 5711) | Prior TNF Antagonist (N = 899) |
|---|---|---|---|---|---|
| All Week 12 withdrawals | 470 (7) | 174 (10) | 296 (6) | 381 (7) | 89 (10) |
| Adverse event | 284 (4) | 100 (6) | 184 (34) | 234 (4) | 50 (6) |
| Lack of efficacy | 94 (1) | 39 (2) | 55 (1) | 68 (1) | 26 (3) |
| Total withdrawals* | 1377 (21) | 468 (27) | 909 (19) | 1147 (20) | 230 (26) |
| Adverse event | 682 (10) | 226 (13) | 456 (9) | 569 (10) | 113 (13) |
| Lack of efficacy | 450 (7) | 166 (10) | 284 (6) | 355 (6) | 95 (11) |

*Withdrawals during complete study period, up to week 96

Patients with active RA and prior DMARD therapy enrolled in the Study A trial at 448 sites in 11 European countries and Australia. Selected patients were at least 18 years of age, had RA (defined by American College of Rheumatology criteria) for at least 3 months, had prior unsatisfactory response or intolerance to at least one prior DMARD and active RA (DAS28=3.2). Patients entering Study A received Ada 40 mg sc eow for 12 weeks in addition to their pre-existing but insufficient antirheumatic standard therapies, and optionally continued therapy until Ada was commercially available. Efficacy and safety evaluations were conducted at Wks 2, 6, 12, and every 8 wks thereafter. Adverse events (AE) were collected throughout the treatment period.

In all, 6610 patients enrolled in the Study A trial. Adalimumab was used alone (26%) or in combination with existing DMARD(s), leading to 43 Ada-DMARD combinations. After 12 wks, 93% of patients remained and retention in the study was 79% overall. The mean exposure to Ada was 33 wks (96 wks, maximum). Mean baseline characteristics included: age, 54 yrs; female, 71%; disease duration, 11 yrs; DAS28, 6.0; HAQ, 1.64; TJC28, 14; SJC28, 10; prior DMARDs, 3; $RF^+$, 73%; concomitant DMARD treatment, 74%; concomitant steroid treatment, 71%; and 13.6% had failed prior anti-TNF therapy.

Of those patients on concomitant DMARD treatment, 4004 (61%) patients received adalimumab in combination with exactly 1 DMARD; 769 (12%) patients, with 2 concomitant DMARDs; and 106 (2%) patients, with ≥3 concomitant DMARDs. Of patients on non-exclusive concomitant DMARD treatment combinations, 3567 (54%) patients on Methotrexate; 1109 (17%) patients taking Leflunomide; 450 (7%) patients taking Sulfazalazine; 576 (9%) patients taking Antimalarials; 63 (<1%) patients taking Azathioprine; 52 (<1%) patients taking Parenteral gold; 7 (<1%) patients taking Penicillamine; and 3 (<1%) patients taking Oral gold.

Of those 899 patients whom failed prior anti-TNF therapy (etanercept and/or infliximab) 591 patients had received as TNF antagonist infliximab only; 188 patients had received as TNF antagonist etanercept only; and 120 patients had been treated with both TNF antagonists.

The mean treatment duration with adalimumab was 233 days (33 weeks) with a maximum of 669 days (96 weeks) and at Week 12, 93% of the patients remained in Study A. Overall, of the 6610 patients who enrolled, 79% completed the trial, which provided data from 4210 patient-years (PY) of adali- Adalimumab was well-tolerated, and no new safety signals were observed. Overall, reasons for withdrawals included lack of efficacy in 6.8% and AE in 10.3% of patients. Serious adverse events of lupus or demyelinating disease were rarely seen, with only 2 and 4 events reported, respectively. The incidence of malignancies, including lymphomas, was similar to the general population. The rate of malignancies (1.1/100PY) gave a Standard Incidence Ratio (SIR) of 0.71 vs. an age and sex matched population. Two lymphomas (0.05/100PY; SIR 1.09) were reported. The rate of serious infections (5.5/100PY) was within the range previously reported in RA.

Efficacy was similar across subpopulations using different Ada-DMARD combinations, and responses were seen irrespective of RF status or previous failure of anti-TNF therapy. Table 23 presents key efficacy outcomes to Wk 12 and at last observation.

TABLE 23

|  | Week 2 | Week 6 | Week 12 | Last visit** |
|---|---|---|---|---|
| ACR20 (%) | 42 | 59 | 69 | 67 |
| ACR50 (%) | 12 | 28 | 40 | 45 |
| ACR70 (%) | 3 | 10 | 18 | 25 |
| ΔDAS28** | −1.4 | −1.8 | −2.1 | −2.3 |
| ΔDAS28 < 2.6 (%) | n.a. | n.a | 20 | 26 |
| ΔHAQ* | −0.32 | −0.45 | −0.54 | −0.57 |

Observed values;
*Mean exposure 33 wks;
**Means

Table 24-Table 29 show other key efficacy outcomes. Table 24 shows that adalimumab treatment was efficacious as assessed by ACR response rates at Week 12 and last observation and Table 25 shows Moderate and Good EULAR Response (%) at Week 12 (WI 2) and at Last Visit (LV) by Concomitant DMARD (cDMARD) and by Prior TNF-Antagonist (pTNF) Therapy. In addition, Table 26 shows that Adalimumab significantly decreased the number of tender joints and Table 27 shows that Adalimumab significantly decreased the number of swollen joints. Table 28 reports that Adalimumab relevantly reduced the disease activity measured by mean change from baseline DAS28 to the last observation (mean of each individual last observation) and Table 29 demonstrates that treatment with adalimumab led to clinically important improvement of physical function, as measured by the mean change from baseline HAQ score to the last observation (mean of each individual last observation).

TABLE 24

ACR Response (%) at Week 12 (W12) and at Last Visit (LV) by Concomitant DMARD (cDMARD) and by Prior TNF-Antagonist (pTNF) Therapy

| | % of Patients | | | | | |
|---|---|---|---|---|---|---|
| | ACR20 W12 | ACR20 LV | ACR50 W12 | ACR50 LV | ACR70 W12 | ACR70 LV |
| All (n = 6110) | 69 | 67 | 40 | 45 | 18 | 25 |
| No cDMARD (n = 1731) | 60 | 60 | 32 | 37 | 15 | 20 |
| cDMARD (n = 4879) | 72 | 70 | 43 | 48 | 19 | 26 |
| No pTNF (n = 5711) | 70 | 69 | 41 | 47 | 19 | 26 |
| pTNF (n = 899) | 60 | 56 | 33 | 33 | 13 | 15 |

TABLE 25

EULAR Response (%) at Week 12 (W12) and at Last Visit (LV) by Concomitant DMARD (cDMARD) and by Prior TNF-Antagonist (pTNF) Therapy

| | % of Patients | | | |
|---|---|---|---|---|
| | Mod. EULAR W12 | Mod. EULAR LV | Good EULAR W12 | Good EULAR LV |
| All (n = 6110) | 83 | 82 | 33 | 39 |
| No cDMARD (n = 1731) | 74 | 74 | 23 | 30 |
| cDMARD (n = 4879) | 86 | 84 | 37 | 42 |
| No pTNF (n = 5711) | 84 | 83 | 35 | 41 |
| pTNF (n = 899) | 76 | 73 | 23 | 26 |

TABLE 26

Median Tender Joint Count (TJC28) to Week 12 and to Last Visit (Mean of Individual Last Visits) by Concomitant DMARD (cDMARD) and Prior TNF-Antagonist (pTNF) Therapy

| | Median Tender Joint Count | | | | |
|---|---|---|---|---|---|
| | Week 0 | Week 2 | Week 6 | Week 12 | Last Visit |
| All (n = 6610) | 13 | 6 | 4 | 3 | 2 |
| No cDMARD (n = 1731) | 14 | 7 | 5 | 4 | 3 |
| cDMARD (n = 4879) | 13 | 6 | 4 | 3 | 2 |
| No pTNF (n = 5711) | 12 | 6 | 4 | 3 | 2 |
| pTNF (n = 899) | 15 | 8 | 5 | 4 | 4 |

TABLE 27

Median Swollen Joint Count (SJC28) to Week 12 and to Last Visit (Mean of Individual Last Visits) by Concomitant DMARD (cDMARD) and Prior TNF-Antagonist (pTNF) Therapy

| | Median Swollen Joint Count | | | | |
|---|---|---|---|---|---|
| | Week 0 | Week 2 | Week 6 | Week 12 | Last Visit |
| All (n = 6610) | 10 | 5 | 3 | 2 | 2 |
| No cDMARD (n = 1731) | 10 | 6 | 4 | 3 | 3 |
| cDMARD (n = 4879) | 10 | 5 | 3 | 2 | 2 |
| No pTNF (n = 5711) | 10 | 5 | 3 | 2 | 2 |
| pTNF (n = 899) | 11 | 6 | 4 | 3 | 3 |

TABLE 28

Mean Change in DAS28 from Baseline to Last Observation

| | Mean Change from Baseline |
|---|---|
| All (n = 6610) | −2.3 |
| No cDMARD (n = 1731) | −2.0 |
| cDMARD (n = 4879) | −2.4 |
| No pTNF (n = 5711) | −2.3 |
| pTNF (n = 899) | −1.9 |

TABLE 29

Mean Change in HAQ from Baseline to Last Observation

| | Mean Change from Baseline* |
|---|---|
| All (n = 6610) | −0.57 |
| No cDMARD (n = 1731) | −0.49 |
| cDMARD (n = 4879) | −0.59 |
| No pTNF (n = 5711) | −0.58 |
| pTNF (n = 899) | −0.48 |

*MCID = Minimum Clinically Important Difference = −0.22; Goldsmith C, et al. *J Rheumatol* 1993; 20: 561-5.

In addition, the criteria of clinical remission were fulfilled. Within 2 consecutive visits of at least a 6-week interval: 21% of patients had DAS<2.6.16% of patients had no tender or swollen joints.

The efficacy of adalimumab was higher when used in combination with standard DMARDs than with monotherapy. Patients with a history of treatment with TNF antagonists experienced relevant reductions in the signs and symptoms of RA during treatment with adalimumab.

In conclusion, adalimumab therapy led to clinically significant and sustained improvements in all key efficacy parameters. During the entire treatment period with adalimumab, a DAS28<2.6 was achieved at one or more visits by 38% of all patients and 30% of all patients were reported to have TJC=0 and SJC=0 at least at one visit during the study period. Study A data confirmed observations from adalimumab pivotal trials, and demonstrated a positive benefit/risk ratio for the treatment of severe RA when adalimumab is combined with standards of care in real-life settings. Overall, Adalimumab was well-tolerated and withdrawal rates because of lack of efficacy or adverse events were low.

EXAMPLE 5

Efficacy and Safety of Adalimumab (Humira®) is Maintained During Long-Term Treatment of Rheumatoid Arthritis within a Large Cohort of Patients in Normal Clinical Practice Study B (ReAlise) was established to evaluate the long-term safety and efficacy of adalimumab (Ada) for up to 5 years in patients with rheumatoid arthritis (RA) who had completed a previous study, i.e., Study A (ReAct), a Phase IIIb study. In Study A, Ada 40 mg every other week was added to pre-existing, inadequate, standard antirheumatic therapies in patients with long-standing, severely active RA, including patients who had failed previous biologics. An interim analysis of the efficacy and safety of Ada therapy in Study B.

Patients were eligible to enroll in Study B within 12 months of the conclusion of their participation in Study A (Active RA defined by Disease Activity Score 28 (DAS28)=3.2 at baseline and unsatisfactory response or intolerance to at least one prior DMARD was required for enrollment in Study A). Patients were treated according to the European Summary of Product Characteristics (SPC) for HUMIRA®, which recommended Ada 40 mg every other week given by subcutaneous injections either in addition to or as replacement of their pre-existing antirheumatic therapy in the Study A trial. Patients underwent a 12-week study period that was followed by an optional extension phase with efficacy assessments performed at Weeks 2, 6, 12, and every eight weeks thereafter. Patients discontinued the study when they stopped receiving adalimumab or received commercial HUMIRA®. During the study period, parameters of efficacy—including ACR20/50/70 response, moderate and good EULAR response, DAS28 score, tender joint count (TJC), swollen joint count (SJC), C-reactive protein (CRP), and health assessment questionnaire-disability index (HAQ), Physician and patient assessments of disease activity and patient assessment of pain on a visual analog scale (VAS)— were assessed every 3 months. Semi-annual assessments were conducted thereafter. All reports of adverse events (AE) were tabulated per 100 patient years (E/100PY).

3452 patients enrolled in Study B at 432 sites in 11 countries. Data for 3228 patients is presented here for this analysis (Gender: 79% female, Mean Age: 53 years)(See Table 30). The mean overall treatment duration for all patients was 502 days, from the first exposure to Ada in Study A (with a mean treatment duration of 250 days in Study B). At entry to Study A the mean disease severity baseline values were: DAS28, 6.0; HAQ, 1.61; SJC, 10.4; and TJC, 13.3. Most patients (72%) received Ada in combination with DMARDs in Study B, the majority with methotrexate. Key efficacy parameters were stable over time as compared to baseline values in Study A (Table 31, N's over time reflect differing enrolment time points). No new safety signals were observed in the analysis of AE reported. The rate of serious infections was low, 3.0/100PY. The rate of malignancies was 1.0/100PY. No serious immunologic reactions were observed.

TABLE 30

Study B Baseline Clinical Characteristics

| Characteristics* | N = 3228 |
|---|---|
| Age (years) | 55 |
| Duration of RA (years) | 12 |
| # previous DMARDs | 3.4 |
| DAS28 | 3.5 |
| HAQ DI | 0.89 |
| CRP (mg/L) | 9.5 |

*Mean values.

TABLE 31

Efficacy of adalimumab observed over time in Study B

| Parameter | Study B baseline | 6 months | 12 months | 18 months |
|---|---|---|---|---|
| N available | 3228 | 2042 | 1026 | 265 |
| ACR20 (%) | 79 | 81 | 82 | 85 |
| ACR50 (%) | 58 | 59 | 62 | 57 |
| ACR70 (%) | 33 | 36 | 38 | 35 |
| Moderate EULAR (%) | 91 | 91 | 93 | 94 |
| Good EULAR (%) | 49 | 53 | 56 | 54 |
| ΔDAS28* | −2.4 | −2.7 | −2.8 | −2.8 |
| ΔHAQ* | −0.70 | −0.69 | −0.66 | −0.57 |

*Mean values

Substantial percentages of patients (78%) had achieved ACR20 responses by the end of Study A, prior to entering Study B. These high ACR20 response rates were maintained through Month 18 of Study B as reported in Table 32 and FIG. 2. The same figure also reports that ACR50 and ACR70 responses observed at the end of 18 months in Study B were also similar to those observed at the end of Study A.

Substantial percentages of patients had also achieved at least moderate EULAR and good EULAR responses by the end of Study A, prior to entering Study B. These high EULAR response rates were maintained through Month 18 of Study B (Table 33, FIG. 3).

Referring to Table 34, at the start of Study A, patients had a mean DAS28 of 6.0, and Table 34 indicates DAS28 improvements and that the DAS28 improvements were sustained through Month 18.

Similarly in Table 35, at the start of Study A, patients had a mean HAQ score of 1.61, and Table 35 indicates HAQ improvements and shows that HAQ improvements were maintained through Month 18.

In addition, median improvements in TJC and SJC were sustained through Month 18 as shown in Table 36. Also median CRP concentrations were low and sustained through Month 18 as shown in Table 37 and FIG. 4, and significant improvements in disease activity and pain assessments were maintained through Month 18, as shown in Table 38 and FIGS. 5-7.

The safety of adalimumab in Study B was consistent with reports of the adalimumab safety profile overall. The rate of 3 serious infections per 100-patient-years was lower than rates previously reported in adalimumab clinical trials and no demyelinating disease was observed. Data showing the number of patients recorded with serious averse events is displayed in Table 39.

TABLE 32

ACR Responses Through 18 Months in Study B

| | % of Patients | | |
|---|---|---|---|
| | ACR20 | ACR50 | ACR70 |
| Last Obs. Study A | 78 | 55 | 30 |
| Baseline Study B | 78 | 60 | 33 |
| 3 Months | 78 | 56 | 35 |
| 6 Months | 80 | 60 | 35 |
| 9 Months | 80 | 62 | 40 |
| 12 Months | 80 | 62 | 38 |
| 18 Months | 85 | 55 | 35 |

Observed values.
N = 3195 patients achieved at least ACR20 at their last visit in Study A.
N = 2760 patients entered Study B with at least ACR20.

TABLE 33

EULAR Responses Through 18 Months in Study B

| | % of Patients | |
|---|---|---|
| | Moderate EULAR | Good EULAR |
| Last Obs. ReAct | 90 | 48 |
| Baseline ReAlise | 90 | 48 |
| 3 Months | 85 | 50 |
| 6 Months | 90 | 52 |
| 9 Months | 90 | 55 |
| 12 Months | 90 | 55 |
| 18 Months | 92 | 52 |

Observed values.
N = 3202 patients achieved at least a Moderate EULAR response at their last visit in ReAct.
N = 2937 patients entered ReAlise with at least a Moderate EULAR.

TABLE 34

Mean Change in DAS28 Over Time

| | Mean ΔDAS28 |
|---|---|
| Last Obs. in ReAct (n = 3203) | −2.6 |
| Baseline ReAlise (n = 2582) | −2.7 |
| 3 Months (n = 2197) | −2.7 |
| 6 Months (n = 1842) | −2.7 |
| 9 Months (n = 1380) | −2.8 |
| 12 Months (n = 972) | −2.8 |
| 18 Months (n = 253) | −2.8 |

P = 0.001 for all time points compared with baseline of ReAct study. Observed values.

TABLE 35

Mean Change in HAQ Over Time

| | Mean ΔHAQ* |
|---|---|
| Last Obs. In ReAct (n = 3206) | −0.69 |
| Baseline ReAlise (n = 2805) | −0.70 |
| 3 Months (n = 2334) | −0.71 |
| 6 Months (n = 1949) | −0.69 |
| 9 Months (n = 1434) | −0.68 |
| 12 Months (n = 1009) | −0.66 |
| 18 Months (n = 261) | −0.57 |

P = 0.001 for all time points compared with baseline of ReAct study. Observed values.
*MCID = Minimum Clinically Important Difference = −0.22.

TABLE 36

Median TJC and SJC Responses Over Time

| | Median Tender Joint Count | Median Swollen Joint Count |
|---|---|---|
| Baseline ReAct | 13 | 10 |
| Last Obs. ReAct | 2 | 1 |
| Baseline ReAlise | 2 | 1 |
| 3 Months | 1 | 1 |
| 6 Months | 1 | 1 |
| 9 Months | 1 | 1 |
| 12 Months | 1 | 1 |
| 18 Months | 1 | 1 |

Observed Values

TABLE 37

Median C-Reactive Protein Concentrations (mg/L) Over Time

| | Median CRP Concentration (mg/L) |
|---|---|
| Baseline ReAct | 14.5 |
| Last Obs. ReAct | 3.5 |
| Baseline ReAlise | 4.5 |
| 3 Months | 4 |
| 6 Months | 4 |
| 9 Months | 4 |
| 12 Months | 4 |
| 18 Months | 5 |

Observed Values

TABLE 38

Physician and Patient Assessments of Disease Activity and Pain Over Time Through 18 Months

| | Mean Score | | |
|---|---|---|---|
| | Physician Assessment of Disease Activity | Patient Assessment of Disease Activity | Patient Assessment of Pain |
| Baseline Study A | 60 | 60 | 65 |
| Last Obs. Study A | 20 | 25 | 28 |
| Baseline Study B | 22 | 25 | 28 |
| 3 Months | 20 | 25 | 30 |
| 6 Months | 20 | 22 | 28 |
| 9 Months | 18 | 22 | 28 |
| 12 Months | 20 | 22 | 28 |
| 18 Months | 20 | 22 | 28 |

P = 0.001 for all time points compared to mean baseline values of the ReAct study.
Observed Values

TABLE 39

Serious Adverse Events - Interim Analysis of 3228 Patients (N, %) Representing 2195 Patient-Years

| | N (%) |
|---|---|
| All Serious Adverse Events (SAE) | 245 (7.6) |
| Serious infections | 61 (1.9) |
| Congestive heart failure (CHF) | 4 (0.1) |
| Gastrointestinal Disorders | 11 (0.3) |
| General Disorders | 20 (0.6) |
| Musculoskeletal/Connective Tissue Disorders | 50 (1.5) |
| Systemic lupus erythematosus (SLE) | 3 (0.1) |
| Respiratory, Thoracic, Mediastinal Disorders | 26 (0.8) |
| Malignancies | 20 (0.6) |
| Lymphoma | 3 (0.1) |

In conclusion, in patients with long-standing, severely active RA who participated in the post-marketing observational study, Study B, the efficacy of adalimumab was maintained up to 18 months in all key efficacy parameters and no new safety signals were identified.

EXAMPLE 6

Clinical Characteristics of Patients Who Continued Long-Term Treatment in a 6-Year Extension Study of Adalimumab Therapy in RA Open-label extension studies following adalimumab randomized clinical trials (RCTs) have demonstrated that a majority of patients receiving continued adalimumab treatment maintain robust improvements in RA disease activity and physical function. Although the ACR response rate is a key measure of therapeutic efficacy in RCTs, its value in therapeutic decision-making has not been demonstrated in long-term studies of RA.

The objectives of this study were to determine clinically relevant characteristics supporting continuation on therapy in an open-label extension study of adalimumab and methotrexate (MTX); to determine levels of disease activity and functional measurements in patients not fulfiling the ACR20 response criteria over time; to assess sustained efficacy and remission parameters for up to 6 years; and to confirm long-term safety and tolerability over time.

Patients enrolled in other studies were eligible to enter an extension study of adalimumab 40 mg every other week (eow) subcutaneous (sc) and MTX. Efficacy and safety were evaluated in all patients' last visits for up to 6 years, including withdrawals for any reason. The clinical characteristics of patients were studied in the following 4 categories: (a) ACR20 responders; (b) ACR20 non-responders who continued on long-term treatment; (c) ACR20 non-responders who discontinued due to adverse events or other reasons; and (d) ACR20 non-responders who discontinued due to lack of efficacy.

The demographics and baseline disease characteristics of RA patients were consistent with moderate to severe RA (N=947), as shown in Table 40.

TABLE 40

Baseline Demographics and Disease Characteristics

| Characteristic | Value |
| --- | --- |
| Age, years* | 55 ± 12 |
| Gender, % female | 78 |
| Disease duration, years | 11 ± 9 |
| TJC (0-68)* | 28 ± 13 |
| SJC (0-66)* | 20 ± 10 |
| HAQ disability index (0-3)* | 1.4 ± 0.6 |
| Disease Activity Score 28 (DAS28)* | 5.7 ± 0.9 |
| CRP, mg/dL* | 1.9 ± 2.3 |
| Rheumatoid factor, % positive | 77 |
| Number of previous DMARDs* | 2.4 ± 1.5 |

*Mean ± standard deviation.

Treatment time was calculated beginning with the first subcutaneous injection of adalimumab at any dose for: ACR20, ACR50, ACR70 criteria and indices of remission (DAS28<2.6, TJC68=0, SJC66=0, HAQ=0). Patients were monitored for adverse events (AEs) during the entire length of the study. Data collected until Aug. 31, 2005 are reported.

Of 947 patients entering the 4 RCTs (Mean±SD exposure of 41±22 months), 600 (63%) remained on adalimumab plus MTX for up to 6 years. FIG. 8 shows reasons for withdrawals included lack of efficacy (82, 9%), adverse events (140, 15%), and others, such as protocol violation and loss to follow-up (125, 13%). Table 41 and Table 42 show that the number of patients withdrawing from the study decreased over time. Table 41 displays the percentage of patient withdrawals, which demonstrated a steady decline over time, especially with patients that withdrew because of lack of efficacy. Table 42 and FIG. 9 display the results of a Kaplan-Meier curve providing the probability that patients receiving adalimumab will remain on therapy at Year 6.

Figure 11B:
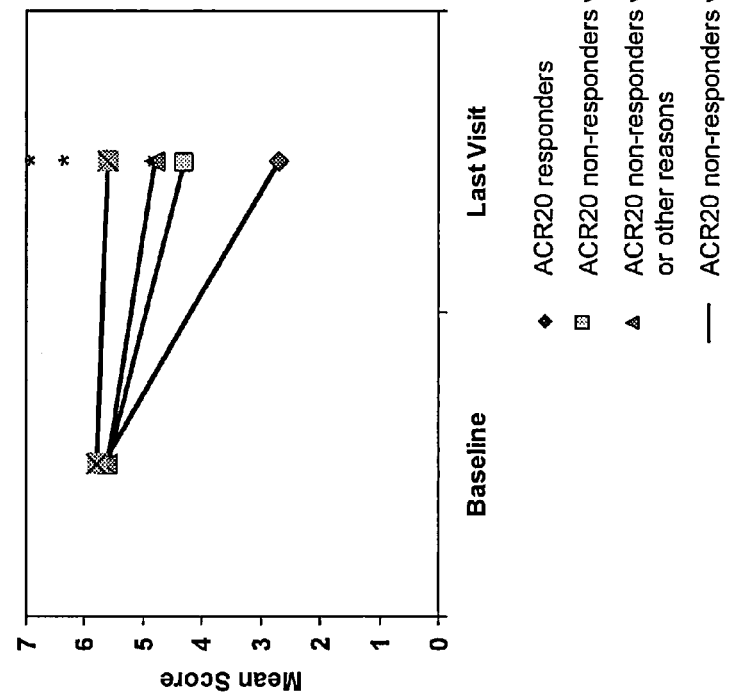

Table 43 and FIGS. 10-12 show that patients achieving ACR20 response had significant reductions in disease activity (TJC, SJC, CRP, DAS28) as well as improvements in functional disability (HAQ) at last visit. While patients who did not achieve ACR20 response, but who either continued on therapy or discontinued treatment for adverse events or other reasons, had significant but less pronounced improvements in TJC, SJC, DAS28, and HAQ. CRP was only marginally reduced. Those patients who discontinued because of lack of efficacy had no improvements.

Referring to Table 44 and FIG. 13, those patients demonstrating ACR responses showed sustained ACR responses into Year 6. And over 55% of patients achieved remission (DAS28<2.6) after 6 years of adalimumab therapy as shown in Table 45. Of all patients, the proportions achieving clinical response and remission measures at last visit were ACR20, 50, 70: 66%, 42%, 26%; DAS28<2.6: 35%; TJC68=0: 24%; SJC66=0: 20%; and HAQ=0: 19%. Table 46 presents baseline and last visit outcomes of ACR20 responders and 3 categories of ACR20 non-responders: 1) patients who continued in the study (Mean±SD exposure of 51±18 months) and demonstrated statistically significant improvements; 2) patients who discontinued due to AEs or other reasons and who also showed significant improvement levels; and 3) patients who discontinued due to lack of efficacy (LOE) and had no improvements. Rates and types of adverse events (3,203 patient-years) were consistent with reports from other adalimumab trials. Table 47 shows that rates and types of serious adverse events over the long term demonstrated a consistent safety profile in relation to the randomized and controlled pivotal trials.

TABLE 41

Percentages of Withdrawals by Year and Reason

| | % of Withdrawals | | | |
| --- | --- | --- | --- | --- |
| | Total % Withdrawals | Lack of Efficacy | AE | Other* |
| Year 1 (n = 947**) | 14.7 | 4.2 | 4.6 | 5.9 |
| Year 2 (n = 761) | 9.9 | 2.0 | 4.0 | 3.9 |
| Year 3 (n = 679) | 9.0 | 2.0 | 3.5 | 3.5 |
| Year 4 (n = 618) | 6.8 | 1.0 | 3.5 | 2.3 |
| Year 5 (n = 573) | 4.7 | 0.5 | 2.2 | 2 |
| Year 6 (n = 163) | 1.8 | 0 | 1.8 | 0 |

*Includes withdrawals for other reasons: protocol violation, lost to follow-up, consent withdrawal, administrative reasons.
**n = patients entering the corresponding year.

TABLE 42

Percent of Patients Continuing on Adalimumab Treatment from First Dose

| | Time (years) | | | | | | | | | | | | |
| --- | --- | --- | --- | --- | --- | --- | --- | --- | --- | --- | --- | --- | --- |
| | 0 | 0.5 | 1.0 | 1.5 | 2.0 | 2.5 | 3.0 | 3.5 | 4.0 | 4.5 | 5.0 | 5.5 | 6.0 |
| % of Patients Remaining on Treatment | 100 | 90 | 85 | 80 | 75 | 72 | 70 | 65 | 60 | 60 | 58 | 57 | 57 |

TABLE 43

Disease Activity and Functional Disability Scores by ACR20 Response

| | ACR20 Responders | ACR20 Non-Responders who continued long-term treatment | ACR20 Non-Responders who discontinued due to adverse events or other reasons | ACR20 Non-Responders who discontinued due to lack of efficacy |
|---|---|---|---|---|
| | Mean Score | | | |
| TJC68 | | | | |
| Baseline | 26 | 28 | 28 | 30 |
| Last Visit | 5* | 18* | 22* | 28 |
| SJC66 | | | | |
| Baseline | 22 | 18 | 18 | 22 |
| Last Visit | 5* | 11* | 13* | 20 |
| DAS28 | | | | |
| Baseline | 5.8 | 5.8 | 5.8 | 6 |
| Last Visit | 2.8* | 4.5* | 5* | 5.8 |
| HAQ disability index | | | | |
| Baseline | 1.4 | 1.4 | 1.7 | 1.7 |
| Last Visit | 0.7 | 1.3 | 1.5 | 1.7 |
| | CRP Concentration, mg/L | | | |
| CRP | | | | |
| Baseline | 20 | 14 | 18 | 20 |
| Last Visit | 7* | 11† | 20 | 21 |

*$p < 0.001$, †$p < 0.05$, both vs. baseline

TABLE 44

ACR Response Rates

| | % Responders | | | | | | |
|---|---|---|---|---|---|---|---|
| | 6 Month | 12 Month | 24 Month | 36 Month | 48 Month | 60 Month | 72 Month |
| ACR20 | 70 | 75 | 75 | 70 | 75 | 75 | 70 |
| ACR50 | 42 | 50 | 50 | 50 | 50 | 60 | 65 |
| ACR70 | 20 | 25 | 30 | 30 | 30 | 35 | 40 |

Approximate Observed Values

TABLE 45

Long-term Indicators of Clinical Remission

| | % of Patients | | | |
|---|---|---|---|---|
| | DAS28 < 2.6 | TJC = 0 | SJC = 0 | HAQ = 0 |
| 3 Months | 18 | 10 | 9 | 12 |
| 6 Months | 30 | 16 | 14 | 18 |
| 12 Months | 35 | 20 | 22 | 20 |
| 24 Months | 40 | 22 | 25 | 20 |
| 36 Months | 40 | 27 | 25 | 22 |
| 48 Months | 42 | 30 | 22 | 22 |
| 60 Months | 52 | 32 | 22 | 27 |
| 72 Months | 60 | 37 | 32 | 32 |

Observed Values.

TABLE 46

Baseline (BL) and Last Visit (LV) Outcomes of ACR20 Responders and
Non-Responders (NR) By Status Of Continuation and Reasons for Discontinuation

| ACR20 category | Patients N = 947 | ACR50, 70 response | DAS28* BL | DAS28* LV | HAQ* BL | HAQ* LV | TJC68* BL | TJC68* LV | SJC66* BL | SJC66* LV | CRP* BL | CRP* LV |
|---|---|---|---|---|---|---|---|---|---|---|---|---|
| Responders | 621, 66% | 64%, 38% | 5.7 | 2.7† | 1.4 | 0.7† | 27 | 5† | 21 | 4† | 20 | 7† |
| NR Continued | 143, 15% | — | 5.6 | 4.3† | 1.4 | 1.3‡ | 29 | 17† | 18 | 11† | 14 | 11‡ |
| NR Disc. AE, Other | 119, 13% | — | 5.6 | 4.8† | 1.6 | 1.5 | 29 | 21† | 18 | 13† | 18 | 20 |
| NR Disc. LOE | 64, 7% | — | 5.8 | 5.6 | 1.6 | 1.6 | 30 | 29 | 21 | 19 | 20 | 21 |

*Mean values;
†p < 0.001, ‡p < 0.05, both last visit vs. baseline

TABLE 47

| Serious Adverse Events (MEDRA Coding) | | |
|---|---|---|
| Serious Adverse Event (E) E/100 PY | Pivotal Trials 793 PYs | Extension Study 3203 PYs As of Aug. 31, 2005 |
| Serious Infections | 4.16 | 3.15 |
| Pneumonia | 1.13 | 0.62 |
| Urinary Tract Infections | 0.50 | 0.34 |
| Septic Arthritis | 0.38 | 0.12 |
| Tuberculosis | 0.13 | 0.06 |
| Histoplasmosis | 0.13 | 0 |
| Demyelinating Diseases | 0.13 | 0.03 |
| Lymphoma | 0.25 | 0.16 |
| SLE/Lupus-like Syndrome | 0.13 | 0.03 |
| Pancytopenia | 0.25 | 0 |

In conclusion, adalimumab plus MTX induced a sustained ACR20 response in 66% and clinical remission in more than 20% of all patients, including patients who withdrew. Clinical improvements above 20% in individual ACR components observed in ACR20 non-responders may justify their continuation on therapy. In addition, patients maintained clinical improvements and significant reductions in disease activity for up to 6 years of continuous treatment with adalimumab. Remission (DAS28<2.6) was observed in over 55% of patients after 6 years on therapy, and adalimumab was safe and well-tolerated for up to 6 years.

EXAMPLE 7

Effect of Adalimumab (HUMIRA®) on Response to Influenza Virus and Pneumococcal Vaccines in Patients with Rheumatoid Arthritis (RA)

The following study evaluated the effects of adalimumab on antibody response to pneumococcal and influenza virus vaccines in adult RA patients.

In this randomized, double-blind, placebo-controlled, multi-center, 36-day study, patients with active RA were enrolled during the 2003-04 US influenza season and received adalimumab or placebo. Patients were considered eligible for the study if they were 20 years of age or older and had a documented history of RA as defined by ACR diagnosis criteria. Patients were required to discontinue administration of any TNF antagonists including ADA, at least two months prior to Day 1. Exclusion criteria included: a recent (3-month) history of any influenza or pneumococcal infection; receipt of any vaccine within 3 months prior to initial study drug administration; or receipt of an influenza vaccine within 6 months or a pneumococcal vaccine within 5 years. All patients underwent purified protein derivative (PPD) testing for latent tuberculosis infection and chest radiographs at screening.

Patients were allowed to continue their pre-study doses of non-biologic anti-rheumatic therapy, including non-steroidal anti-inflammatory drugs, corticosteroids (prednisone equivalent of =10 mg/day), and conventional (non-biologic) disease-modifying anti-rheumatic drugs (DMARDs); however dosage changes were not permitted during the blinded phase of the study.

Patients were stratified by concomitant MTX use (yes/no). Patients randomized to adalimumab received 80 mg on Day 1 followed by 40 mg on Days 15 and 29. Commercially available 2003-2004 trivalent subvirion influenza virus vaccine (0.5 mL) and standard 23-valent pneumococcal vaccine (0.5 mL) were administered intramuscularly to all patients on Day 8 (vaccination baseline). Antibody titers for both vaccines were measured on Day 8 (pre-vaccination) and Day 36. For pneumococcal vaccine, antibody titers for 9V, 14, 18C, 19F, and 23F were measured. Protective antibody concentration was defined as =1.6 µg/mL in =3 of 5 antigens and response to vaccination was defined as =2-fold increase from baseline in antibody titer in =3 of 5 antigens. For influenza A and B vaccines, antibody titers for H1N1, H3N2, and Hong Kong were measured. Protective antibody concentration was defined as =1:40 titer in =2 of 3 antigens, and response to vaccination was defined as =4-fold increase from baseline in antibody titer in =2 of 3 antigens. After Day 36, patients had the option to continue adalimumab treatment (40 mg every other week) in a 6-month open-label extension. Safety evaluations, including physical examinations, laboratory assessments, vital signs, and adverse event (AE) reports, were assessed throughout the study. FIG. 14 shows the study design.

Serum pneumococcal antibody titers were determined using the enzyme-linked immunosorbent assay (ELISA), and serum influenza A and B antibody titers were determined using the hemagglutination inhibition antibody assay. All antibody titer analyses were conducted by ViroMed Laboratories, Minnetonka, Minn.

The primary measure of response was the percentage of patients achieving a satisfactory humoral response as defined by a=2-fold titer increase from vaccination baseline (Day 8) in =3 of 5 pneumococcal antigens (9V, 14, 18C, 19F, and 23F) (Go and Ballas, 1996) and a=4-fold titer increase from vaccination baseline (Day 8) in =2 of 3 influenza antigens (H1N1, H3N2, and Hong Kong) (Gross et al, 1985; Hermogenes et al, 1992).

Secondary measures of response included 1) the percentage of patients with protective antibody titers 4 weeks post-vaccination (defined as antibody titer≥1.6 µg/mL for ≥3 of 5 antigens for the pneumococcal vaccine (Hodges-Savola et al, 2005; Schmid et al, 1981) and antibody titer≥21:40 for ≥2 of 3 antigens for the influenza vaccine (Gross et al, 1985; Hermogenes et al, 1992); 2) the percentage of patients achieving a=2-fold increase in pneumococcal antibody titers and =4-fold increase in influenza titers from baseline by antigen; and 3) the mean changes in antibody titers from baseline by antigen. Results are presented as the means of variables expressed in a $\log_2$ scale, transformed into GMTs. Differences between means of variables expressed in a $\log_2$ scale were transformed into geometric mean ratios (GMRs).

The primary analysis was performed in a "per-protocol" population (Hwang and Morikawa, 1999). The Per-protocol Analysis Set for the pneumococcal/influenza vaccine was defined as all patients who were randomized; who received the pneumococcal/influenza vaccine on Day 8 (vaccination baseline); who received adalimumab or placebo on Day 1 and Day 15; and for whom a complete set of blood samples for pneumococcal/influenza antibody assay (from both Day 8 and Day 36) was collected and available for analysis. Patients who had missing data were classified as nonresponders. The treatment differences in the percentages were assessed using chi-square tests.

Covariates that might influence immunogenicity such as age, sex, co-morbid conditions (diabetes and pulmonary disease), and concomitant RA medications (DMARDs, corticosteroids, and MTX) were examined using logistic regression models.

226 patients were randomized. Of the 226 patients randomized to receive treatment, 15 were assigned to the placebo group and 111 to the adalimumab group. A total of 220 patients completed the double-blind period of the study and participated in the open label extension. Of the 226 patients enrolled in the study, 208 met the per-protocol definition and were included in the efficacy analysis. Table 48 shows the disposition of all patients.

TABLE 48

Disposition of Patients

| | Placebo N =115 n (%) | Adalimumab 40 mg N =111 | Total N =226 |
|---|---|---|---|
| Full Analysis Set | 115 (100.0) | 111 (100.0) | 226 (100.0) |
| Completed Day 36 visit | 112 (97.4) | 108 (97.3) | 220 (97.3) |
| Death | 0 | 0 | 0 |
| Early Discontinuation[a] | 3 (2.6) | 3 (2.7) | 6 (2.7) |
| Adverse event | 3 (2.6) | 1 (0.9) | 4 (1.8) |
| Other | 0 | 2 (1.8) | 2 (0.9) |
| Withdrew consent | 1 (0.9) | 0 | 1 (0.4) |
| Lost to follow-up | 0 | 0 | 0 |

The 208 patients received at least the first 2 doses of blinded study drug (on Days 1 and 15) and had both pre- and post-vaccine blood samples for antibody analysis. There was no significant difference in baseline demographics or in protective antibody concentrations between groups. The baseline characteristics for the 208 patients were comparable between treatment groups and are presented below in Table 49.

TABLE 49

Baseline Characteristics

| | Placebo (n =109) n (%) | Adalimumab 40 mg eow (n =99) n (%) | Total (N =208) n (%) | P value* |
|---|---|---|---|---|
| Age (years), mean ± SD | 51.1 ± 11.46 | 52.2 ± 11.90 | 51.7 ± 11.66 | 0.504 |
| Age category (years), n (%) | | | | 0.664 |
| ≤40 | 22 (20.2) | 20 (20.2) | 42 (20.2) | |
| >40-65 | 78 (71.6) | 67 (67.7) | 145 (69.7) | |
| >65 | 9 (8.3) | 12 (12.1) | 21 (10.1) | |
| Sex, n (%) | | | | 0.084 |
| Male | 27 (24.8) | 15 (15.2) | 42 (20.2) | |
| Female | 82 (75.2) | 84 (84.8) | 166 (79.8) | |
| Disease | | | | |
| Diabetes mellitus | 4 (3.7) | 6 (6.1) | 10 (4.9) | 0.421 |
| Pulmonary disease | 38 (34.9) | 30 (30.3) | 68 (32.6) | 0.484 |
| Concomitant medication | | | | |
| MTX, n (%) | 59 (54.1) | 55 (55.6) | 114 (54.9) | 0.836 |
| DMARDs (no MTX), n (%) | 32 (29.4) | 17 (17.2) | 49 (46.6) | 0.039 |
| Corticosteroids, n (%) | 50 (45.9) | 45 (45.5) | 95 (45.7) | 0.952 |
| CRP status | | | | |
| Normal | 57 (52.3) | 52 (52.5) | 109 (52.4) | 0.973 |
| Elevated (>0.8 mg/dL) | 52 (47.7) | 47 (47.5) | 99 (47.6) | |

*Continuous comparisons from one-way analysis of variance model; discrete variables compared using the chi-square test. If 25% of cells had expected count of <5, Fisher's exact test was used.
CRP =C-reactive protein;
DMARDs =disease-modifying anti-rheumatic drugs;
eow =every other week;
MTX =methotrexate.

As can be seen in Table 49, patients had a mean age of 51.7 years. Fifty-two percent (57/109) of placebo-treated patients and 53% (52/99) of adalimumab-treated patients had normal C-reactive protein (CRP) concentration status (<0.8 mg/dL). No statistically significant differences were observed between treatment groups in the percentages of patients using MTX or corticosteroids; however, there was a significantly higher percentage of patients in the placebo group using concomitant DMARDs other than MTX compared with the adalimumab group (29.4% vs. 17.2%, respectively). All patients had negative PPD skin tests.

There was no significant difference between treatment groups in baseline antibody titer for the individual pneumococcal and influenza antigens, with the exception of antibody for pneumococcal antigen 14 ((1.45 µg/mL in the placebo group; 2.22 µg/mL in the adalimumab group) (Table 50). Both treatment groups had similar percentages of patients with baseline protective antibody titers. Table 51 shows the similarity in immune response to pneumococcal vaccine between groups.

TABLE 51

Similar Immune Response* to Pneumococcal Vaccine Between Groups

| | % of Patients | |
|---|---|---|
| | Placebo | Adalimumab |
| +Protective Antibody at Baseline | 27.4 | 28.1 |
| −Protective Antibody at Baseline | 54.7 | 50.0 |
| Overall | 40.4[†] | 37.4[†] |

*Response to vaccination was defined as =2-fold increase from baseline in antibody titer in =3 of 5 antigens.
[†]CI 95% (−16.2, 10.3) for difference between placebo and adalimumab groups.

TABLE 50

Mean pneumococcal and influenza antibody titers by antigen at prevaccination and postvaccination and change in pneumococcal and influenza antibody titers by antigen.

| | n | Prevaccination GMT | Postvaccination GMT | Within-group comparison (postvaccination:prevaccination) GMR (95% CI)* | Between-group comparison (adalimumab:placebo) GMR (95% CI)* |
|---|---|---|---|---|---|
| Pneumococcal antigen treatment 9V | | | | | |
| Placebo | 109 | 2.65 | 6.23 | 2.34 (1.97, 2.79) | 1.00 (0.77, 1.28) |
| Adalimumab | 99 | 2.60 | 6.10 | 2.36 (1.96, 2.83) | |
| 14 | | | | | |
| Placebo | 109 | 1.45 | 4.40 | 3.03 (2.47, 3.73) | 1.32 (0.98, 1.78) |
| Adalimumab | 99 | 2.22 | 5.09 | 2.30 (1.85, 2.86) | |
| 18C | | | | | |
| Placebo | 109 | 2.84 | 7.49 | 2.63 (2.18, 3.17) | 1.08 (0.82, 1.41) |
| Adalimumab | 99 | 2.90 | 7.05 | 2.44 (2.01, 2.97) | |
| 19F | | | | | |
| Placebo | 109 | 2.16 | 4.16 | 1.92 (1.61, 2.28) | 0.95 (0.74, 1.22) |
| Adalimumab | 99 | 1.96 | 3.96 | 2.03 (1.69, 2.43) | |
| 23F | | | | | |
| Placebo | 109 | 2.26 | 4.22 | 1.86 (1.57, 2.19) | 0.85 (0.67, 1.08) |
| Adalimumab | 99 | 1.84 | 4.01 | 2.19 (1.84, 2.60) | |
| Influenza antigen treatment H1N1 | | | | | |
| Placebo | 109 | 51.89 | 188.68 | 3.63 (2.92, 4.51) | 1.05 (0.77, 1.44) |
| Adalimumab | 99 | 47.16 | 162.64 | 3.46 (2.75, 4.34) | |
| H3N2 | | | | | |
| Placebo | 109 | 89.13 | 602.81 | 6.74 (5.04, 9.02) | 1.51 (0.99, 2.30) |
| Adalimumab | 99 | 105.86 | 472.25 | 4.48 (3.30, 6.08) | |
| B (HongKong) | | | | | |
| Placebo | 109 | 22.71 | 92.94 | 4.08 (3.28, 5.08) | 1.25 (0.91, 1.71) |
| Adalimumab | 99 | 22.62 | 73.86 | 3.27 (2.60, 4.12) | |

*Adjusted GMRs are from analysis of covariance (ANCOVA) model: model response = therapy methotrexate use, where response = [$\log_2$ (Day 36 titer) − $\log_2$ (Day 8 titer)]. In the ANCOVA model, titers are expressed in a $\log_2$ scale. $\log_2$ (titer) are analyzed and transformed back to the original scale (ie, least square means were transformed to GMRs of endpoint titers and differences of least square means were transformed into GMRs of titers in adalimumab group to titers in placebo group.
Note:
Any pneumococcal antibody titer <1.3 µg/mL (undetectable) is expressed as 0.65 µg/mL.
Note:
For prevaccination and postvaccination, the GMT was used. For change from prevaccination, the GMR of postvaccination titer to prevaccination titer was used.
CI = confidence interval;
GMT = geometric mean titer;
GMR = geometric mean ratio.

TABLE 52

Similar Percentage of Patients With a Protective Pneumococcal Antibody Titer* Between Groups at 4 Weeks Postvaccination

| | % of Patients | |
|---|---|---|
| | Placebo | Adalimumab |
| +Protective Antibody at Baseline and Continued to have Protective Antibody Post-vaccination | 100.0 (n =62) | 100.0 (n =57) |
| −Protective Antibody at Baseline and Developed Protective Antibody Post-vaccination | 57.4 (n =27) | 66.7 (n =28) |
| Overall | 81.7 (n =89) | 85.9 (n =85) |

*Protective antibody titer was defined as =1.6 µg/mL in =3 of 5 antigens.

For pneumococcal vaccine, the percentage of patients with protective antibody concentrations at Day 36 were similar in both arms, as were the percentages of patients in both groups who developed antibody response. Table 52 depicts the similarity in the percentages of patients with protective pneumococcal antibody titer between groups at 4 weeks postvaccination. The percentage of patients who received adalimumab and achieved a=2-fold increase in =3 of 5 pneumococcal antibody titers was similar to the placebo group (37.4% vs. 40.4%, respectively; 95% confidence interval [CI] of difference between treatment groups [−16.2, 10.3]) (Table 53). Across both treatment groups, the percentage of patients who achieved a=2-fold increase in =3 of 5 pneumococcal antibody titers was higher in the group without protective antibody titers at baseline (Table 53). Table 53 shows the primary efficacy results for each co-primary endpoint; sensitivity analyses of the number (%) of patients with a=2-fold increase from baseline in =3 of 5 pneumococcal titers and a=4-fold increase from baseline at Day 36 in =2 of 3 influenza antibody titers.

TABLE 53

| Pneumococcal vaccine Per-protocol Analysis Set | Placebo n =109 | Adalimumab 40 mg eow n =99 |
|---|---|---|
| Responders, n (%) | 44 (40.4) | 37 (37.4) |
| Difference between treatment groups, % (95% CI) | −3.0 (−16.2, 10.3) | |

TABLE 53-continued

| Presence of protective antibody concentration at baseline* | Placebo n =62 | Adalimumab 40 mg eow n =57 |
|---|---|---|
| Responders, n (%) | 17 (27.4) | 16 (28.1) |
| Difference between treatment groups, % (95% CI) | 0.7 (−15.5, 16.8) | |

| Absence of protective antibody concentration at baseline* | Placebo n =47 | Adalimumab 40 mg eow n =42 |
|---|---|---|
| Responders, n (%) | 27 (57.4) | 21 (50.0) |
| Difference between treatment groups, % (95% CI) | −7.4 (−28.1, 13.3) | |

| Influenza vaccine Per-protocol Analysis Set | Placebo n =109 | Adalimumab 40 mg eow n =99 |
|---|---|---|
| Responders, n (%) | 69 (63.3) | 51 (51.5) |
| Difference between treatment groups, % (95% CI) | −11.8 (−25.2, 1.6) | |

| Presence of protective antibody concentration at baseline† | Placebo n =63 | Adalimumab 40 mg eow n =58 |
|---|---|---|
| Responders, n (%) | 35 (55.6) | 21 (36.2) |
| Difference between treatment groups, % (95% CI) | −19.3 (−36.8, −1.9) | |

| Absence of protective antibody concentration at baseline† | Placebo n =46 | Adalimumab 40 mg eow n =41 |
|---|---|---|
| Responders, n (%) | 34 (73.9) | 30 (73.2) |
| Difference between treatment groups, % (95% CI) | −0.7 (−19.3, 17.8) | |

*Protective antibody concentration in =3 of 5 pneumococcal titers at baseline.
Note:
Any pneumococcal antibody titer <1.3 µg/mL (undetectable) was expressed as 0.65 µg/mL; any influenza antibody titer <1:20 (undetectable) was expressed as 1:10.
†Protective antibody concentration in =2 of 3 influenza titers at baseline.
CI =confidence interval;
eow =every other week.

Univariate analyses of the primary measure of response demonstrated that concomitant MTX use (p<0.0001), concomitant DMARD use (p<0.044), and protective antibody titers at baseline (p<0.0001) significantly reduced the response rate to pneumococcal vaccine, whereas elevated baseline CRP concentration significantly increased the response rate (p<0.035) (Table 54). Sex, age, race, weight, concomitant corticosteroid use, diabetes, and pulmonary disease did not affect the response rate.

TABLE 54

| | Pneumococcal vaccine | | | | Influenza Vaccine | | | |
|---|---|---|---|---|---|---|---|---|
| Correlate | Placebo n/N (%) | Adalimumab n/N (%) | Odds Ratio* (95% CI) | P-value* | Placebo n/N (%) | Adalimumab n/N (%) | Odds Ratio* (95% CI) | P-value* |
| Sex | | | | 0.820 | | | | 0.436 |
| Male | 9/27 (33.3) | 8/15 (53.3) | 1.08 (0.54, 2.15) | | 15/27 (55.6) | 7/15 (46.7) | 0.76 (0.39, 1.51) | |
| Female | 35/82 (42.7) | 29/84 (34.5) | | | 54/82 (65.9) | 44/84 (52.4) | | |
| Age (years) | | | | 0.292 | | | | 0.316 |
| ≤40 | 6/22 (27.3) | 6/20 (30.0) | 1.82 (0.88, 3.95) | | 16/22 (72.7) | 12/20 (60.0) | 0.65 (0.31, 1.32) | |
| >40-65 | 35/78 (44.9) | 26/67 (38.8) | 1.54 (0.50, 4.66) | | 35/78 (44.9) | 26/67 (38.8) | 0.45 (0.15, 1.32) | |
| >65 | 3/9 (33.3) | 5/12 (41.7) | | | 5/9 (55.6) | 5/12 (41.7) | | |

TABLE 54-continued

| | Pneumococcal vaccine | | | | Influenza Vaccine | | | |
|---|---|---|---|---|---|---|---|---|
| Correlate | Placebo n/N (%) | Adalimumab n/N (%) | Odds Ratio* (95% CI) | P-value* | Placebo n/N (%) | Adalimumab n/N (%) | Odds Ratio* (95% CI) | P-value* |
| MTX use† | | | | <0.001 | | | | 0.288 |
| Yes | 17/59 (28.8) | 10/55 (18.2) | 0.23 (0.13, 0.41) | | 33/59 (55.9) | 29/55 (52.7) | 0.74 (0.42, 1.29) | |
| No | 27/50 (54.0) | 27/44 (61.4) | | | 36/50 (72.0) | 22/44 (50.0) | | |
| MTX dose(mg/week) | | | | 0.321 | | | | 0.052 |
| >0-10 | 3/16 (18.8) | 3/17 (17.6) | 1.12 (0.35, 3.80) | | 6/16 (37.5) | 6/17 (35.3) | 2.92 (1.14, 7.78) | |
| >10-15 | 5/21 (23.8) | 3/19 (15.8) | 2.09 (0.72, 6.68) | | 5/21 (23.8) | 3/19 (15.8) | 2.73 (1.08, 7.22) | |
| >15 | 9/22 (40.9) | 4/19 (21.1) | | | 14/22 (63.6) | 11/19 (57.9) | | |
| DMARD use(except MTX) | | | | 0.044 | | | | 0.810 |
| Yes | 11/32 (34.4) | 2/17 (11.8) | 0.48 (0.23, 0.96) | | 18/32 (56.3) | 11/17 (64.7) | 1.08 (0.57, 2.10) | |
| No | 33/77 (42.9) | 35/82 (42.7) | | | 51/77 (66.2) | 40/82 (48.8) | | |
| Corticosteroid use | | | | 0.776 | | | | 0.369 |
| Yes | 19/50 (38.0) | 17/45 (37.8) | 0.92 (0.53, 1.61) | | 33/50 (66.0) | 25/45 (55.6) | 1.29 (0.74, 2.25) | |
| No | 25/59 (42.4) | 20/54 (37.0) | | | 36/59 (61.0) | 26/54 (48.1) | | |
| Diabetes | | | | 0.944 | | | | 0.944 |
| Yes | 2/4 (50.0) | 2/6 (33.3) | 1.05 (0.26, 3.79) | | 1/4 (25.0) | 3/6 (50.0) | 0.47 (0.12, 1.70) | |
| No | 42/105 (40.0) | 35/93 (37.6) | | | 68/105 (64.8) | 48/93 (51.6) | | |
| Pulmonary disease‡ | | | | 0.645 | | | | 0.155 |
| Yes | 17/38 (44.7) | 11/30 (36.7) | 1.15 (0.63, 2.07) | | 27/38 (71.1) | 17/30 (56.7) | 1.54 (0.85, 2.84) | |
| No | 27/71 (38.0) | 26/69 (37.7) | | | 42/71 (59.2) | 34/69 (49.3) | | |
| CRP status | | | | 0.035 | | | | 0.596 |
| Normal | 18/57 (31.6) | 17/52 (32.7) | 1.84 (1.05, 3.24) | | 35/57 (61.4) | 26/52 (50.0) | 1.16 (0.67, 2.02) | |
| Elevated(>0.8 mg/dL) | 26/52 (50.0) | 20/47 (42.6) | | | 34/52 (65.4) | 25/47 (53.2) | | |
| Protective antibody concentration | | | | <0.001 | | | | <0.001 |
| Yes | 17/62 (27.4) | 16/57 (28.1) | 0.33 (0.18, 0.58) | | 35/63 (55.6) | 21/58 (36.2) | 0.31 (0.17, 0.56) | |
| No | 27/47 (57.4) | 21/42 (50.0) | | | 34/46 (73.9) | 30/41 (73.2) | | |

Similarly high percentages of patients in both the placebo (81.7%) and adalimumab (85.9%) treatment groups achieved protective antibody titers (antibody titer=1.6 µg/mL in =3 of 5 antigens) 4 weeks postvaccination (Table 55). Table 55 shows a shift of protective pneumococcal antibody concentration in =3 of 5 titers and protective influenza antibody concentration in =2 of 3 titers from baseline to final value including by MTX use (Per-protocol Analysis Set). A higher percentage of adalimumab-treated patients (66.7%) converted from unprotected to protected status in =3 of 5 antigens versus placebo-treated patients (57.4%). When shifts from unprotected to protected status were examined by MTX use, a greater percentage of patients converted from unprotected status to protected status in the absence of MTX use (Table 55).

TABLE 55

| Therapy | Irrespective of MTX use Final value | | MTX use Final value | | No MTX use Final value | |
|---|---|---|---|---|---|---|
| Baseline Value | Unprotected | Protected | Unprotected | Protected | Unprotected | Protected |
| | | | n (%) | | | |
| Pneumococcal vaccine | | | | | | |
| Placebo | | | | | | |
| Unprotected | 20 (42.6) | 27 (57.4) | 14 (56.0) | 11 (44.0) | 6 (27.3) | 16 (72.7) |
| Protected | 0 | 62 (100.0) | 0 | 34 (100.0) | 0 | 28 (100.0) |
| Total | 20 (18.3) | 89 (81.7) | 14 (23.7) | 45 (76.3) | 6 (12.0) | 44 (88.0) |
| Adalimumab | | | | | | |
| Unprotected | 14 (33.3) | 28 (66.7) | 10 (40.0) | 15 (60.0) | 4 (23.5) | 13 (76.5) |
| Protected | 0 | 57 (100.0) | 0 | 30 (100.0) | 0 | 27 (100.0) |
| Total | 14 (14.1) | 85 (85.9) | 10 (18.2) | 45 (81.8) | 4 (9.1) | 40 (90.9) |
| Influenza vaccine | | | | | | |
| Placebo | | | | | | |
| Unprotected | 6 (13.0) | 40 (87.0) | 4 (20.0) | 16 (80.0) | 2 (7.7) | 24 (92.3) |
| Protected | 0 | 63 (100.0) | 0 | 39 (100.0) | 0 | 24 (100.0) |
| Total | 6 (5.5) | 103 (94.5) | 4 (6.8) | 55 (93.2) | 2 (4.0) | 48 (96.0) |
| Adalimumab | | | | | | |
| Unprotected | 1 (2.4) | 40 (97.6) | 1 (4.2) | 23 (95.8) | 0 | 17 (100.0) |
| Protected | 1 (1.7) | 57 (98.3) | 1 (3.2) | 30 (96.8) | 0 | 27 (100.0) |
| Total | 2 (2.0) | 97 (98.0) | 2 (3.6) | 53 (96.4) | 0 | 44 (100.0) |

Note:
Any pneumococcal antibody titer <1.3 μg/mL (undetectable) is expressed as 0.65 μg/mL.
Any influenza antibody titer <1:20 (undetectable) was expressed as 1:10.
The protective antibody concentration is defined as an antibody titer =1:40.
MTX = methotrexate.

Overall, the percentages of patients with a=2-fold increase in pneumococcal antibody titers from baseline at 4 weeks postvaccination were similar between treatment groups (Table 56). Antibody response was fairly uniform among antigens, with a similar range of response observed between the placebo and adalimumab treatment groups (36%-50% and 36%-47%, respectively). Table 56 shows the number (%) of patients with a=2-fold increase in pneumococcal antibody titers or a=4-fold increase in influenza antibody titers from baseline at Day 36 by antigen (Per-protocol Analysis Set).

TABLE 56

| | Placebo N =109 | Adalimumab N =99 | |
|---|---|---|---|
| | n (%) | | Odds ratio (95% CI)* |
| Pneumococcal antigen | | | |
| 9V | 46 (42.2) | 45 (45.5) | 1.17 (0.66, 2.08) |
| 14 | 54 (49.5) | 41 (41.4) | 0.72 (0.41, 1.26) |
| 18C | 53 (48.6) | 46 (46.5) | 0.92 (0.53, 1.61) |
| 19F | 39 (35.8) | 36 (36.4) | 1.04 (0.58, 1.87) |
| 23F | 41 (37.6) | 44 (44.4) | 1.40 (0.78, 2.54) |
| Influenza antigen | | | |
| H1N1 | 61 (56.0) | 50 (50.5) | 0.81 (0.46, 1.40) |
| H3N2 | 74 (67.9) | 58 (58.6) | 0.67 (0.38, 1.18) |
| B (Hong Kong) | 66 (60.6) | 48 (48.5) | 0.61 (0.35, 1.07) |

Table 57 shows the percentages of patients who overall developed protective antibody concentrations, or had antibody responses.

TABLE 57

| | Adalimumab | Placebo |
|---|---|---|
| Pneumococcal - Protective antibody concentration | 85/99 (85.9%) | 89/109 (81.7%) |
| Pneumococcal - Developed antibody response | 37/99 (37.4%) | 44/109 (40.4%) |
| Response in patients with protective pneumococcal antibody concentration at baseline | 16/57 (28.1%) | 17/62 (27.4%) |
| Response in patients without protective pneumococcal antibody concentration at baseline | 21/42 (50.0%) | 27/47 (54.7%) |
| Influenza - Protective antibody concentration | 97/99 (98%) | 103/109 (94.5%) |
| Influenza - Developed antibody response | 51/99 (51.5%) | 69/109 (63.3%) |
| Response in patients with protective influenza antibody concentration at baseline | 21/58 (36.2%) | 35/63 (55.6%) |
| Response in patients without protective influenza antibody concentration at baseline | 30/41 (73.3%) | 34/46 (73.9%) |

Changes from baseline in antibody titers 4 weeks after pneumococcal vaccination were statistically significant for all 5 antigens tested and were similar between treatment groups, as demonstrated by lack of statistical significance between group comparisons of GMR (Table 50). Similar trends were observed when the change from baseline at 4 weeks postvaccination was examined by MTX use; however, markedly larger increases in GMTs were observed for both treatment groups in the absence of MTX use (data not shown).

With respect to the immune response to influenza vaccine, a smaller, though not statistically significant percentage of patients who received adalimumab achieved a=4-fold increase in =2 of 3 influenza antibody titers compared with patients who received placebo (51.5% vs. 63.3%, 95% CI of difference between treatment groups [−25.2, 1.6]) (Table 53). Table 58 shows the similar immune response to influenza vaccine between groups. The lower percentage of response in the adalimumab group is driven by the subgroup of patients with pre-existing protective antibody titers (≥1:40 antibody titer to ≥2 of 3 antigens) at baseline. In this subgroup, the percentage of patients who achieved a=4-fold increase in =2 of 3 influenza antibody titers was 36.2% in the adalimumab group and 55.6% in the placebo group. In the subgroup of patients without protective antibody titers at baseline, the percentage of patients who achieved=4-fold increase in =2 of 3 influenza antibody titers was similar in the adalimumab and placebo treatment groups (73.3% and 73.9%, respectively) (Table 53).

Univariate analyses of the primary measure of response demonstrated that protective antibody titers at baseline significantly reduced response rates to influenza vaccine (p<0.001). Although concomitant MTX use also reduced the response rate, the reduction was not statistically significant. Concomitant DMARD use, baseline CRP concentration, sex, age, concomitant corticosteroid use, diabetes, and pulmonary disease did not affect the response rate (Table 54).

Similarly high percentages of patients in the placebo and adalimumab treatment groups (94.5% and 98.0%, respectively) achieved protective antibody titers (=1:40 antibody titer in =2 out of 3 antigens) at 4 weeks postvaccination (Table 55). Table 59 depicts the similarity in the percentages of patients with protective influenza antibody titer between groups at 4 weeks postvaccination. In addition, a greater percentage of adalimumab-treated vs. placebo-treated patients experienced conversion to protected status in =2 of 3 antigens (97.6% vs. 87.0%, respectively). When shifts from unprotected to protected status were examined by MTX use, a slightly greater percentage of patients converted from unprotected status to protected status in the absence of MTX use (Table 55).

TABLE 58

Similar Immune Response* to Influenza Vaccine Between Groups

| | % of Patients | |
| --- | --- | --- |
| | Placebo | Adalimumab |
| +Protective Antibody at Baseline | 55.6 | 36.2 |
| −Protective Antibody at Baseline | 73.9 | 73.3 |
| Overall | 63.3* | 51.5* |

*Response to vaccination was defined as =4-fold increase from baseline in antibody titer in =2 of 3 antigens.
CI 95% (−25.2, 1.6) for difference between placebo and adalimumab groups.

TABLE 59

Similar Percentage of Patients With Protective Influenza Antibody Titer* Between Groups at 4 Weeks Post-Vaccination

| | % of Patients | |
| --- | --- | --- |
| | Placebo | Adalimumab |
| +Protective Antibody at Baseline and Continued to have Protective Antibody Post-vaccination | 100.0 (n =63) | 98.3 (n =57) |
| −Protective Antibody at Baseline and Developed Protective Antibody Post-vaccination | 87 (n =40) | 97.6 (n =40) |
| Overall | 94.5 (n =103) | 98.0 (n =97) |

*Protective antibody concentration was defined as =1:40 titer in =2 of 3 antigens.

Overall, at Day 36, the percentage of patients with a=4-fold increase in influenza antibody titers from baseline by antigen was lower in the adalimumab treatment group versus the placebo treatment group, although the differences were not statistically significant (Table 56). Within each treatment group, the immunogenicity of the 3 antigens was similar (56%-68% in the placebo group and 49%-59% in the adalimumab group).

Changes from baseline in antibody titers 4 weeks after influenza vaccination were statistically significant for all 3 antigens tested in both treatment groups (GMR range from 3.3-6.7). The increase from baseline was higher in the placebo treatment group compared with the adalimumab group, though the difference was not statistically significant (Table 50). Significant increases in titers 4 weeks post-vaccination were observed in groups with and without MTX use. However, larger increases in titers, although not significant, were observed for both treatment groups in the absence of MTX.

Adalimumab was generally well-tolerated. During the blinded period of the study no deaths were reported, and 1 patient receiving placebo reported a serious AE. A slightly greater percentage of patients in the placebo group reported an AE than did patients in the adalimumab group (54.8% [63/115] vs. 45.9% [51/111], respectively). The most frequently reported treatment-emergent AEs occurring during the blinded period of the study were upper respiratory tract infection and injection site reaction, both were reported more frequently by placebo-treated patients. There were no serious infectious AEs, malignancies, or opportunistic infections, including tuberculosis, reported during the double-blind period. The rate of infectious AEs was statistically significantly higher in the placebo treatment group (23.5% [27/115]) vs the adalimumab group (12.6% [14/111]) (p=0.039). The percentages of patients reporting AEs leading to discontinuation of study drug were similar between the 2 groups.

In conclusion, in this study, adalimumab does not diminish humoral response to commercially available 23-valent pneumococcal polysaccharide and trivalent subvirion influenza virus vaccines in RA patients, and that 4 weeks after vaccination, the majority of patients have protective antibody titers. Similarly high percentage of patients in both the placebo and adalimumab treatment groups achieved protective pneumococcal antibody titers (81.7% and 85.9%, respectively) as well as influenza antibody titers (94.5% and 98.0%, respectively) 4 weeks postvaccination, as defined by antibody titers≥1.6 µg/mL in ≥3 of 5 antigens and ≥1:40 antibody titer in ≥2 of 3 antigens, respectively.

The data described herein shows that RA patients were able to develop an effective antibody response to pneumococcal vaccine, and that concomitant adalimumab use did not appear to affect the response; a=2-fold increase in =3 of 5 pneumococcal antibody titers was achieved by 37.4% of patients treated with adalimumab compared with 40.4% of placebo-treated patients. Patients receiving concomitant MTX, concomitant DMARDs, or with protective antibody titers at baseline were significantly less likely to respond to pneumococcal vaccination. It should be noted that 89 of 208 (43%) subjects entering the study had protective pneumococcal antibody titer levels at baseline and this led to the appearance of a lower response rate than other studies. In the patients without protective antibody titer levels at baseline, the response rates in the adalimumab and placebo groups were 50.0% and 57.4%, respectively.

In the subgroup of RA patients without protective antibody titers at baseline, antibody response to influenza vaccination (=4-fold increase in =2 of 3 influenza antibody titers) was similar in the adalimumab and placebo treatment groups (73.3% and 73.9%, respectively). Protective antibody titers at baseline (found in 58% of subjects) significantly reduced response rates to influenza vaccine as did concomitant MTX use; however, the latter reduction was not statistically significant. Concomitant DMARD use did not affect the response rate to influenza vaccination. These findings demonstrate that adalimumab-treated patients can be safely immunized with these antigens.

EXAMPLE 8

Adalimumab (HUMIRA®) is Effective and Safe in the Treatment of Rheumatoid Arthritis Across all Participating Countries in the Study a Trial The Study A trial (ReAct) was designed to assess the efficacy and safety of adalimumab (ADA) in real-life clinical practice in a large cohort of patients across multiple countries with active, insufficiently treated RA, various co-morbidities, a broad range of anti-rheumatic co-medications, and varied social care systems. The objective of this study was to compare the efficacy and safety results of ADA treatment in different countries at Week 12 in the Study A trial.

Patients with active RA despite previous or current DMARD treatment enrolled at 448 sites in 11 European countries and Australia in the Study A trial. Patient inclusion criteria required active RA defined by Disease Activity Score 28 (DAS28)=3.2 at baseline and patients had demonstrated unsatisfactory response or intolerance to at least 1 prior DMARD. Upon enrollment patients received ADA 40 mg subcutaneous (sc) every other week (eow) in addition to their current anti-rheumatic therapy. Routine safety and efficacy evaluations were conducted at Weeks 2, 6, and 12. Key baseline (BL) characteristics and Week 12 country-specific efficacy and safety data were summarized and compared. The efficacy outcomes measured included: ACR20, ACR50, ACR70, EULAR response, Changes in DAS28, TJC, SJC, CRP, and HAQ. Adverse events (AE) were also collected.

Of 6610 patients enrolled in the Study A trial, nearly 92% of all patients were enrolled in Italy (I), Spain (E), Germany (D), France (F), Belgium (B), Greece (GR), and The Netherlands (NL). Across all countries, patients enrolled had long-standing, severely active RA with a mean disease duration of 10-11 years, DAS28 scores ranging from 5.9 to 6.2, and HAQ scores that indicated marked disability (1.48-2.00). The number of DMARDs used prior to enrolment (1.6-3.8) and percentage of patients taking concomitant DMARDs with ADA during the study (66%-84%) varied somewhat between countries. Only small differences were seen in efficacy outcomes between countries, and the safety profiles were similar across countries. Key efficacy and safety results at Week 12 for these countries are summarized in Table 60, while Table 61 demonstrates that patient baseline characteristics were similar across countries. Table 62 shows that the pattern of concomitant DMARDs used in the participating countries was similar overall; methotrexate was the most frequently used DMARD, followed (in varied order) by leflunomide, antimalarials, or sulfasalazine.

TABLE 60

Efficacy and safety of adalimumab by country at Week 12 in Study A

| | Country | | | | | | |
|---|---|---|---|---|---|---|---|
| | I | E | D | F | B | GR | NL |
| N | 1527 | 1169 | 1143 | 1002 | 455 | 399 | 378 |
| Baseline DAS28 | 6.2 | 5.9 | 6.0 | 5.9 | 6.1 | 6.1 | 6.0 |
| ACR20 (%) | 73 | 70 | 66 | 66 | 70 | 58 | 68 |
| ACR50 (%) | 43 | 41 | 37 | 37 | 41 | 35 | 37 |
| ACR70 (%) | 21 | 19 | 16 | 16 | 20 | 18 | 17 |
| ΔDAS28* | −2.2 | −2.2 | −2.0 | −2.0 | −2.3 | −1.9 | −2.0 |
| ΔHAQ* | −0.61 | −0.52 | −0.42 | −0.52 | −0.69 | −0.60 | −0.50 |
| Serious infections (%) | 0.8 | 1.5 | 2.2 | 1.4 | 1.5 | 1.5 | 0.8 |

*Mean change (Δ) from Baseline

TABLE 61

Patient Baseline Characteristics by Country

| | Australia | Austria | Belgium | France | Germany | Greece | Italy | Netherlands | Portugal | Spain | Switzerland | UK |
|---|---|---|---|---|---|---|---|---|---|---|---|---|
| Patients, n | 74 | 150 | 455 | 1002 | 1143 | 399 | 1527 | 378 | 125 | 1169 | 71 | 117 |
| Age* (yrs) | 55 | 52 | 55 | 54 | 53 | 54 | 54 | 54 | 49 | 54 | 54 | 55 |
| Female (%) | 74 | 85 | 76 | 78 | 81 | 83 | 84 | 74 | 87 | 82 | 75 | 73 |
| Duration RA* (yrs) | 12 | 10 | 11 | 11 | 11 | 11 | 10 | 10 | 10 | 10 | 10 | 12 |
| Prior DMARDs* | 4.7 | 1 | 3 | 3.4 | 3.6 | 1.6 | 2.4 | 3.8 | 1.3 | 3.2 | 3.4 | 3.4 |
| DAS28* | 6.9 | 5.7 | 6.1 | 5.9 | 6.0 | 6.1 | 6.2 | 6.0 | 6.4 | 5.9 | 5.7 | 6.6 |

TABLE 61-continued

Patient Baseline Characteristics by Country

|  | Australia | Austria | Belgium | France | Germany | Greece | Italy | Netherlands | Portugal | Spain | Switzerland | UK |
|---|---|---|---|---|---|---|---|---|---|---|---|---|
| HAQ* | 1.83 | 1.46 | 2.00 | 1.65 | 1.59 | 1.48 | 1.61 | 1.67 | 1.69 | 1.61 | 1.51 | 1.91 |
| Steroid use (%) | 68 | 81 | 52 | 74 | 78 | 70 | 76 | 64 | 94 | 75 | 56 | 56 |
| DMARD use (%) | 78 | 69 | 66 | 69 | 72 | 80 | 69 | 78 | 92 | 84 | 66 | 80 |

*Means

TABLE 62

Patient Baseline Concomitant DMARD Use by Country

|  | Australia | Austria | Belgium | France | Germany | Greece | Italy | Netherlands | Portugal | Spain | Switzerland | UK |
|---|---|---|---|---|---|---|---|---|---|---|---|---|
| Patients, n | 74 | 150 | 455 | 1002 | 1143 | 399 | 1527 | 378 | 125 | 1169 | 71 | 117 |
| Concomitant DMARD use, % | 78 | 69 | 66 | 69 | 72 | 80 | 69 | 78 | 92 | 84 | 66 | 80 |
| DMARD (non-exclusive) |  |  |  |  |  |  |  |  |  |  |  |  |
| Methotrexate, % | 74 | 47 | 57 | 49 | 50 | 60 | 55 | 66 | 86 | 61 | 34 | 54 |
| Leflunomide, % | 38 | 20 | 7 | 18 | 22 | 20 | 10 | 5 | 3 | 28 | 27 | 15 |
| Antimalarials, % | 26 | 5 | 2 | 4 | 7 | 8 | 13 | 12 | 15 | 9 | 10 | 13 |
| Sulfazalazine, % | 3 | 7 | 6 | 5 | 9 | 2 | 4 | 19 | 16 | 6 | 20 | 19 |
| Azathioprine, % | none | 3 | 1 | 0.2 | 2 | 1 | 1 | 2 | 2 | 1 | none | 2 |
| Parenteral gold, % | 3 | none | 0.2 | 0.4 | 1 | 1 | 1 | 1 | 1 | 2 | none | 3 |

DMARDs used in less than half of all countries not shown

Table 63 and Table 64 demonstrate that the ACR20 and ACR50 (Table 63) and EULAR (Table 64) response rates were similar in all countries.

Withdrawal rates were also similar across the studied countries. Withdrawals due to lack of efficacy or to intolerance to adalimumab (all types of side-effects) were overall low. Table 65 displays recorded data regarding patients who withdrew from the study due to an adverse event, broken down by country.

TABLE 63

ACR20 and ACR50 Response by Country

| | % of Patients ||
|---|---|---|
| | ACR20 | ACR50 |
| Australia | 82 | 48 |
| Austria | 65 | 45 |
| Belgium | 70 | 40 |
| France | 68 | 38 |
| Germany | 68 | 38 |
| Greece | 60 | 35 |
| Italy | 72 | 40 |
| Netherlands | 70 | 38 |
| Portugal | 72 | 45 |
| Spain | 70 | 40 |
| Switzerland | 68 | 38 |
| UK | 80 | 55 |

TABLE 64

Moderate and Good EULAR Response by Country

| | % of Patients ||
|---|---|---|
| | Moderate EULAR Response | Good EULAR Response |
| Australia | 92 | 20 |
| Austria | 82 | 40 |
| Belgium | 85 | 35 |
| France | 80 | 35 |
| Germany | 80 | 35 |
| Greece | 78 | 25 |
| Italy | 85 | 28 |
| Netherlands | 82 | 30 |
| Portugal | 88 | 28 |
| Spain | 85 | 38 |
| Switzerland | 80 | 32 |
| UK | 90 | 30 |

TABLE 65

Percentage of Patients Who Withdrew Because of an Adverse Event (AE) or Lack of Efficacy at Week 12 by Country

| Reason for Withdrawal | Australia | Austria | Belgium | France | Germany | Greece | Italy | Netherlands | Portugal | Spain | Switzer-land | UK |
|---|---|---|---|---|---|---|---|---|---|---|---|---|
| Total, % | 7 | 7 | 7 | 6 | 10 | 6 | 8 | 6 | 5 | 6 | 13 | 5 |
| AE, % | 7 | 4 | 3 | 3 | 6 | 4 | 5 | 3 | 3 | 4 | 9 | 3 |
| Lack of Efficacy, % | 0 | 3 | 1 | 2 | 2 | 1 | 1 | 2 | 0 | 1 | 3 | 0 |
| Other, % | 0 | 0 | 3 | 1 | 2 | 1 | 2 | 1 | 2 | 1 | 1 | 2 |

In addition to being safe and consistent across all countries, Adalimumab was effective in decreasing the number of tender and swollen joints, as shown in Table 66 and Table 67. The effect of adalimumab measured by the mean change from baseline DAS28 was comparable across all countries as shown in Table 68. Adalimumab treatment led to clinically important improvement of physical function in patients from all countries, as measured by the mean change from baseline HAQ score at Week 12, shown in Table 69.

Adalimumab was overall well-tolerated during 12 weeks of exposure in patients from all participating European countries (Table 70).

TABLE 66

Median Tender Joint Count (TJC28) Through Week 12 by Country

| | Australia | Austria | Belgium | France | Germany | Greece | Italy | Netherlands | Portugal | Spain | Switzer-land | UK |
|---|---|---|---|---|---|---|---|---|---|---|---|---|
| | | | | | Median Tender Joint Count | | | | | | | |
| Week 0 | 18 | 16 | 14 | 12 | 13 | 12 | 14 | 11 | 15 | 12 | 11 | 15 |
| Week 2 | 10.5 | 8 | 7 | 7 | 7 | 6 | 7 | 6 | 7 | 5 | 5 | 7 |
| Week 6 | 7 | 6 | 4 | 5 | 4 | 5 | 5 | 4 | 4 | 3 | 3 | 4 |
| Week 12 | 3 | 5 | 3 | 3 | 3 | 3 | 3 | 3 | 2 | 2 | 2 | 4 |

TABLE 67

Median Swollen Joint Count (SJC28) Through Week 12 by Country

| | Australia | Austria | Belgium | France | Germany | Greece | Italy | Netherlands | Portugal | Spain | Switzer-land | UK |
|---|---|---|---|---|---|---|---|---|---|---|---|---|
| | | | | | Median Swollen Joint Count | | | | | | | |
| Week 0 | 17 | 8 | 12 | 9 | 10 | 9 | 9 | 12 | 11 | 9 | 11 | 12 |
| Week 2 | 10.5 | 4 | 6 | 5 | 6 | 4 | 5 | 7 | 5 | 4 | 6.5 | 6 |
| Week 6 | 8 | 3 | 4 | 4 | 4 | 3 | 3 | 5 | 4 | 3 | 4.5 | 5 |
| Week 12 | 5 | 2 | 3 | 3 | 3 | 2 | 2 | 4 | 3 | 2 | 3 | 3 |

TABLE 68

Mean Change from Baseline in DAS28 at Week 12 by Country

| | Mean Change from Baseline |
|---|---|
| Australia (n =74) | -2.7 |
| Austria (n =150) | -2.1 |
| Belgium (n =455) | -2.3 |
| France (n =1002) | -2.0 |
| Germany (n =1143) | -2.0 |
| Greece (n =399) | -1.9 |
| Italy (n =1527) | -2.2 |
| Netherlands (n =378) | -2.0 |
| Portugal (n =125) | -2.4 |
| Spain (n =1169) | -2.2 |
| Switzerland (n =71) | -1.8 |
| UK (n =117) | -2.7 |

TABLE 69

Mean Change from Baseline in HAQ at Week 12 by Country*

| | Mean Change from Baseline |
|---|---|
| Australia (n =74) | -0.63 |
| Austria (n =150) | -0.37 |
| Belgium (n =455) | -0.69 |
| France (n =1002) | -0.52 |
| Germany (n =1143) | -0.42 |
| Greece (n =399) | -0.47 |
| Italy (n =1527) | -0.61 |
| Netherlands (n =378) | -0.47 |
| Portugal (n =125) | -0.64 |
| Spain (n =1169) | -0.63 |
| Switzerland (n =71) | -0.45 |
| UK (n =117) | -0.53 |

*MCID =Minimum Clinically Important Difference =-0.22; Goldsmith C, et al. *J Rheumatol* 1993; 20: 561-5.

TABLE 70

Serious Adverse Events (SAE) by Country

|  | Australia | Austria | Belgium | France | Germany | Greece | Italy | Netherlands | Portugal | Spain | Switzerland | UK |
|---|---|---|---|---|---|---|---|---|---|---|---|---|
| Patients per Country, n (%) | 74 | 150 | 455 | 1002 | 1143 | 399 | 1527 | 378 | 125 | 1169 | 71 | 117 |
| SAE, n (%) | 5 (6.8) | 9 (6.0) | 24 (5.3) | 78 (7.8) | 115 (10.1) | 20 (5.0) | 50 (3.3) | 19 (5.0) | 7 (5.6) | 47 (4.0) | 6 (8.5) | 6 (5.1) |
| Serious Infections, n (%) | 3 (4.1) | 2 (1.3) | 7 (1.5) | 14 (1.4) | 25 (2.2) | 6 (1.5) | 12 (0.8) | 3 (0.8) | 2 (1.6) | 18 (1.5) | 2 (2.8) | 0 (0.0) |
| Musculoskeletal/ connective tissue disorders, n (%) | 1 (1.4) | 3 (2.0) | 4 (0.9) | 26 (2.6) | 42 (3.7) | 3 (0.8) | 4 (0.3) | 5 (1.3) | 1 (0.8) | 10 (0.9) | 3 (4.2) | 1 (0.9) |

In conclusion, adalimumab therapy led to clinically important improvements at 12 weeks in all major efficacy parameters irrespective of the country where patients were treated. In Australia and the 11 European countries participating in Study A, patients with long-standing RA and an insufficient response to previous DMARD therapy achieved substantial improvements with adalimumab treatment in all key efficacy parameters within 12 weeks. Safety profiles were not markedly different between countries in real-life clinical practice. In addition, Adalimumab was well-tolerated. Withdrawal rates because of lack of efficacy or adverse events within 12 weeks were low and similar across participating countries. The frequency and pattern of serious adverse events were similar overall in all countries.

EXAMPLE 9

Adalimumab (Humira®) is Effective and Safe with Different Traditional Concomitant DMARDs in Treating Rheumatoid Arthritis in Real-Life Clinical Practice TNF-antagonist and concomitant methotrexate (MTX) therapy has been shown to be effective in treating patients with rheumatoid arthritis (RA). However, some patients are intolerant to MTX treatment and other factors may limit the use of MTX. Evaluations of concomitant DMARDs are few and limited. The completed Study A trial offers the largest database available for the analysis of the efficacy and safety of TNF-antagonists in combination with other DMARDs.

The object of the study is to investigate the efficacy and the safety of adalimumab when added to various standard DMARDs in a large patient population with active RA after a 12-week treatment period in real-life clinical practice. In particular the object of the study was to assess the efficacy and safety profiles resulting from adalimumab (ADA) treatment in combination with MTX, leflunomide (LEF), sulfasalazine (SSZ), or the antimalarials chloroquine/hydroxychloroquine (AM), in a large cohort of patients with active RA.

Patients with active RA enrolled at 448 sites in 11 European countries and Australia in the Study A trial. All patients had Active RA as defined by Disease Activity Score 28 (DAS28)=3.2 at baseline and demonstrated an unsatisfactory response or intolerance to at least 1 prior DMARD. All patients received ADA 40 mg subcutaneously (sc) every other week (eow) in addition to their existing but insufficient antirheumatic therapies in the Study A trial.

The efficacy outcomes measured were: ACR20, 50, 70, EULAR response, change in DAS28, TJC, SJC, HAQ, and CRP. Safety, efficacy data and adverse events were collected at Weeks 2, 6, and 12.

In all, 6610 patients enrolled in the Study A trial. Mean baseline (BL) characteristics included age, 54 yrs; disease duration, 11 yrs; DAS28, 6.0; and HAQ, 1.64. Of those enrolled, 75% received ADA-DMARD combination therapy: 61% with 1, 12% with 2, and 2% with 3 or more DMARDs; 43 distinct ADA-DMARD combinations were reported. See Table 71 for baseline statistics across subgroups.

TABLE 71

Baseline Characteristics by Concomitant DMARD (Exclusively)

| Characteristics* | MTX | LEF | AM | SSZ | MTX + LEF | MTX + AM | MTX + SSZ |
|---|---|---|---|---|---|---|---|
| N | 2794 | 842 | 148 | 133 | 180 | 269 | 182 |
| Duration of RA (yrs) | 10 | 11 | 8 | 11 | 10 | 8 | 9 |
| # Prior DMARDs | 2.7 | 3.3 | 2.8 | 3.1 | 3.5 | 2.9 | 3.0 |
| % Steroid use | 70 | 73 | 78 | 63 | 81 | 74 | 69 |
| HAQ | 1.61 | 1.58 | 1.62 | 1.70 | 1.55 | 1.52 | 1.57 |
| DAS28 | 6.0 | 6.0 | 6.2 | 6.1 | 6.1 | 6.0 | 5.9 |
| TJC28 | 13 | 13 | 15 | 14 | 13 | 14 | 13 |
| SJC28 | 10 | 11 | 10 | 11 | 11 | 10 | 11 |

*Mean values 4,879 (74%) patients received adalimumab with one or more concomitant DMARDs, accounting for 43 different combinations. Adalimumab was added to 1 DMARD in 4004 (61%) patients, to 2 DMARDs in 769 (12%) patients, and to 3 or more DMARDs in 106 (2%) patients. In patients treated with adalimumab and only 1 concomitant DMARD, 2794 (42% of 6,610) were exclusively treated with MTX; 842 (13%) with leflunomide (LEF); 148 (0.2%) with antimalarials (AM); and 133 (0.2%) with sulfasalazine (SSZ)

Comparisons of BL characteristics for groups receiving ADA only, ADA+MTX, ADA+LEF, ADA+AM, and ADA+SSZ revealed no marked differences in BL disease severity—BL DAS28 and HAQ score ranges measured (6.0-6.2) and (1.58-1.73), respectively. Week 12 ACR responses and mean changes in DAS28 and HAQ scores in the combination therapy groups revealed similar responses independent of the concomitant DMARD used, but superior to responses with monotherapy. The safety profile was similar across groups. Key efficacy outcomes and the safety parameter of serious infection rates are shown in Table 72 for these groups (observed values).

TABLE 72

Baseline Characteristics and Clinical Response to ADA Therapy at Week 12

|  | ADA only n = 1731 | ADA + MTX n = 2794 | ADA + LEF n = 842 | ADA + AM n = 148 | ADA + SSZ n = 133 |
| --- | --- | --- | --- | --- | --- |
| Prior DMARDS* | 3.1 | 2.7 | 3.3 | 2.8 | 3.1 |
| Previous MTX (%) | 80 | 100 | 76 | 59 | 71 |
| ACR20 (%) | 60 | 74 | 66 | 72 | 63 |
| ACR50 (%) | 32 | 45 | 37 | 49 | 37 |
| ACR70 (%) | 15 | 21 | 14 | 23 | 15 |
| ΔDAS28* | −1.9 | −2.3 | −2.0 | −2.4 | −2.1 |
| ΔHAQ* | −0.47 | −0.58 | −0.49 | −0.72 | −0.52 |
| Serious infect. (%) | 1.5 | 1.0 | 1.8 | 2.0 | 2.3 |

*Means

The effect of adding adalimumab to LEF, AM, SSZ, or to combinations of MTX+LEF, MTX+AM, MTX+SSZ, was similar to the effect of adalimumab and concomitant MTX, as measured by ACR response (Table 73), EULAR response (Table 74), as measured by the median change from baseline TJC28 (FIG. 15) and baseline SJC28 (FIG. 16), and as measured by the mean change from baseline DAS28 (Table 75) and baseline HAQ score (Table 76).

Withdrawal rates, as shown in Table 77, because of lack of efficacy or intolerance to adalimumab (multiple types of side effects) were low overall. The lowest withdrawal rate through Week 12 was seen for adalimumab and the combination of MTX plus SSZ.

TABLE 73

ACR Response (%) at Week 12 by DMARD Combinations with Adalimumab

|  | % of Patients | | |
| --- | --- | --- | --- |
|  | ACR20 | ACR50 | ACR70 |
| MTX (n =2794) | 74 | 45 | 21 |
| LEF (n =842) | 66 | 37 | 14 |
| AM (n =148) | 72 | 49 | 23 |
| SSZ (n =133) | 63 | 37 | 15 |
| MTX + LEF (n =180) | 67 | 38 | 17 |
| MTX + AM (n =269) | 75 | 45 | 20 |
| MTX + SSZ (n =182) | 75 | 46 | 21 |

TABLE 74

EULAR Response (%) at Week 12 by DMARD Combinations with Adalimumab

|  | % of Patients | |
| --- | --- | --- |
|  | Good EULAR | Moderate EULAR |
| MTX (n =2794) | 39 | 87 |
| LEF (n =842) | 32 | 81 |
| AM (n =148) | 34 | 84 |
| SSZ (n =133) | 35 | 82 |
| MTX + LEF (n =180) | 31 | 86 |

TABLE 74-continued

EULAR Response (%) at Week 12 by DMARD Combinations with Adalimumab

|  | % of Patients | |
| --- | --- | --- |
|  | Good EULAR | Moderate EULAR |
| MTX + AM (n =269) | 39 | 90 |
| MTX + SSZ (n =182) | 38 | 90 |

TABLE 75

Mean Change from Baseline DAS28 Score at Week 12 by DMARD Combinations with Adalimumab

|  | Mean Change from Baseline |
| --- | --- |
| MTX (n = 2794) | −2.3 |
| LEF (n = 842) | −2.0 |
| AM (n = 148) | −2.4 |
| SSZ (n = 133) | −2.1 |
| MTX + LEF (n = 180) | −2.2 |
| MTX + AM (n = 269) | −2.4 |
| MTX + SSZ (n = 182) | −2.4 |

TABLE 76

Mean Change from Baseline HAQ Score* at Week 12 by DMARD Combinations with Adalimumab

|  | Mean Change from Baseline |
| --- | --- |
| MTX (n = 2794) | −0.58 |
| LEF (n = 842) | −0.49 |
| AM (n = 148) | −0.72 |
| SSZ (n = 133) | −0.52 |
| MTX + LEF (n = 180) | −0.54 |

TABLE 76-continued

Mean Change from Baseline HAQ Score* at Week 12 by DMARD Combinations with Adalimumab

| | Mean Change from Baseline |
|---|---|
| MTX + AM (n = 269) | −0.63 |
| MTX + SSZ (n = 182) | −0.55 |

*Minimum Clinically Important Difference = −0.22; Goldsmith C, et al. *J Rheumatol* 1993; 20: 561-5.

TABLE 77

Withdrawal Rates Because of Intolerance or Lack of Efficacy by Concomitant DMARD at Week 12 (%)

| Reason for Withdrawal | MTX | LEF | AM | SSZ | MTX + LEF | MTX + AM | MTX + SSZ |
|---|---|---|---|---|---|---|---|
| N | 2794 | 842 | 148 | 133 | 180 | 269 | 182 |
| Total* | 5.8 | 8.0 | 6.1 | 6.8 | 3.9 | 6.7 | 2.7 |
| Intolerance | 3.6 | 5.0 | 3.4 | 3.8 | 2.8 | 3.3 | 0.5 |
| Lack of Efficacy | 1.3 | 1.0 | 1.4 | 0.8 | none | 1.1 | 0.5 |

*Not all reasons are shown.

In conclusion, concomitant adalimumab and DMARD therapies led to clinically important improvements at Week 12 in all major efficacy parameters—irrespective of the type of concomitant DMARD used—and were well-tolerated in the treatment of patients with RA in real-life clinical practice. Clinical outcomes tended to be superior to those achieved with monotherapy.

EXAMPLE 10

Efficacy and Safety of Adalimumab (HUMIRA®) in Clinical Practice

The objective of this study was to evaluate the efficacy and safety of adalimumab. The Study C (CanAct) was an open-label, multi-center, Phase IIIb study conducted in Canada. The study design is shown in FIG. 17. Patients with moderate to severe rheumatoid arthritis (RA) who had an inadequate response to standard antirheumatic therapy, including methotrexate (MTX), were treated with adalimumab 40 mg every other week in addition to their pre-existing therapies. Criteria Age for inclusion in study C required the patient be ≥18 years of age, have RA defined by ACR criteria for ≥3 months, with Active RA (>5 swollen joints and one of positive RF, 1 or more joint erosions, a HAQ score>1), and an unsatisfactory response or intolerance to therapy as per provincial guidelines required for biologic therapy. Finally, concomitant prednisone had to be <10 mg/day.

Each patient underwent a minimum 12-week treatment period. Patients who completed the 12-week treatment period before adalimumab was commercially available could have entered into an extension phase, which ended when adalimumab became commercially available. The extension phase, therefore, had variable durations for different patients. The maximum duration of follow-up for this analysis was 24 weeks. Efficacy assessments included tender joint count (TJC, 0-28), swollen joint count (SJC, 0-28), Disease Activity Score 28 (DAS28), EULAR response, ACR 20/50/70, and the disability index of the Health Assessment Questionnaire (HAQ). Safety assessments included collection of adverse events (AEs), serious AEs, and severe AEs. FIG. 55 shows the study design of study C.

A total of 879 patients enrolled in Study C. Baseline characteristics were: mean age=54.4 years; % female=78.7; mean RA duration=12.5 years; % with 1, 2, 3 and =3 DMARD failures at study entry=5.6%, 6.3%, 17.0% and 69.1%, respectively; and the % with prior exposure to 1 biologic DMARD (BDMARD)=27.5%, all shown in Table 78. Other baseline characteristics and the data on the efficacy of adalimumab at 12, and 24 weeks are presented below in Table 79.

TABLE 78

Baseline Demographics and Disease Severity

| Characteristics* | All Randomized Patients N = 879 | Patients who completed 12 Weeks n = 772 | Patients who completed 24 Weeks n = 238 |
|---|---|---|---|
| Age (years) | 54.4 ± 11.5 | 54.1 ± 11.4 | 52.8 ± 11.0 |
| Female (%) | 79 | 78 | 76 |
| Disease duration (years) | 12.5 ± 9.7 | 12.3 ± 9.5 | 12.5 ± 9.3 |
| TJC (0-28) | 14.9 ± 7.1 | 14.9 ± 7.1 | 16.5 ± 7.2 |
| SJC (0-28) | 13.2 ± 5.2 | 13.2 ± 5.2 | 14.6 ± 5.6 |
| DAS28 | 6.1 ± 1.2 | 6.1 ± 1.2 | 6.3 ± 1.2 |
| HAQ (0-3) | 1.5 ± 0.6 | 1.5 ± 0.6 | 1.5 ± 0.7 |
| Failed 1 DMARD (%) | 6 | 5 | 6 |
| Failed 2 DMARDs (%) | 6 | 7 | 4 |
| Failed 3 DMARDs (%) | 17 | 18 | 16 |
| Failed >3 DMARDs (%) | 69 | 69 | 73 |
| Prior biologics (%) | 28 | 28 | 27 |

*Mean values ± SD except percentages.

TABLE 79

Baseline and Efficacy Results from Study C

| Efficacy Measures | Baseline (n = 879) | 12 week (n = 879) | 24 week (n = 238) |
|---|---|---|---|
| TJC (0-28) (mean) | 14.9 | 6.8 | 6.0 |
| SJC (0-28) (mean) | 13.2 | 6.4 | 5.9 |
| DAS28 (mean) | 6.1 | 4.2 | 3.9 |
| DAS28 (mean) | | | |
| One prior BDMARD | 6.3 | 4.6 | 4.2 |
| No prior BDMARD | 6.1 | 4.0 | 3.8 |
| % with DAS28: | | | |
| <3.2 | 1.3 | 26.2 | 31.5 |
| <2.6 | 0.5 | 15.3 | 13.5 |
| <2.4 | 0.5 | 11.0 | 10.9 |
| EULAR | | | |
| % moderate | | 51.4 | 51.7 |
| % good | | 27.0 | 32.5 |
| % ACR 20/50/70 | | 58.4/30.6/12.7 | 71.9/41.2/17.7 |
| HAQ (mean) | 1.55 | 1.04 | 0.89 |
| % with HAQ<0.5 | 5.0% | 25.5% | 33.2% |
| ESR (mm/hr) | 30.3 | 20.1 | 16.9 |
| CRP (mm/L) | 21.2 | 11.8 | NA |

NA = not available.

The adverse events profile is comparable to that of other randomized, controlled clinical trials. Only 2 AEs occurred in more than 5% of patients. These were injection site reaction (10.0%) and headache (5.5%). In addition, 2.4% of patients experienced an infection, and 1.1% of patients experienced an infection judged to be serious. No cases of lymphoma or TB reactivation were reported, and no new safety signals were observed during this clinical trial. Table 80 displays the incidents of adverse advents occurring in greater that 2% of the patients. Table 81 displays the medically relevant adverse advents.

TABLE 80

Adverse Events ≥2%

| Adverse events observed in ≥2% of the patients (Probably or Possibly Related to adalimumab) | Events (n) | Patients n (%) |
|---|---|---|
| Injection site reaction* NOS† | 268 | 91 (10.4) |
| Headache | 74 | 56 (6.4) |
| Injection site erythema | 66 | 35 (4.0) |
| Nausea | 42 | 30 (3.4) |
| Rash NOS† | 37 | 30 (3.4) |

Injection site reaction (defined as localized bruising, burning, dermatitis, erythema, induration, inflammation, irritation, mass, oedema, pain, pruritus, rash, stinging, swelling and warmth).
†Not otherwise specified.

TABLE 81

Medically Relevant Adverse Events

| Medically relevant adverse events | Events (n) | Patients (n) % | Events/100 pt-yrs |
|---|---|---|---|
| Serious infections | 29 | 11 (1.3) | 7.166 |
| Death* | 2 | 2 (0.2) | 0.005 |
| Congestive Heart Failure† | 9 | 4 (0.5) | 0.022 |
| Malignancies‡ | 4 | 3 (0.3) | 0.009 |

*One subject presented aggravated pneumonia and was diagnosed with metastatic lung cancer (see below). Both events were classified as probably not related, and not related to adalimumab, respectively. One subject was diagnosed has having Staphylococcal sepsis and developed and acute MI. The sepsis was considered to be possibly related to adalimumab. The acute MI was considered probably not related to adalimumab.
†Two subjects had events considered probably or possibly related to adalimumab.
‡One subject was diagnosed with basal cell carcinoma. The event was probably not related to adalimumab. One subject was diagnosed with adenocarcinoma of the cervix/the event was considered possibly related to adalimumab. One subject was diagnosed with a metastatic lung cancer. The event was not related to adalimumab.

The study revealed a reduction in tender and swollen joints, a reduction in DAS28 scores, increasing beneficial ACR response rates over the term of the study, and reduced HAQ scores. At Week 24, mean tender and swollen joint counts reduced by 40% and 45% from baseline, respectively as shown in Table 82. Table 83 demonstrates that at Weeks 12 and 24, mean DAS28 scores were reduced by 31% and 36% from baseline, respectively.

At Week 12, patients with and without previous biologic experience demonstrated substantial improvement in DAS28 scores from baseline as shown in Table 84. Table 85 shows that at Week 24, overall ACR20 and ACR50 response rates were significantly higher than at Week 12, and ACR70 response rates were maintained from Week 12-59. Additionally, by Week 24, HAQ scores of adalimumab-treated patients reduced by 42.6% from baseline as shown in Table 86.

TABLE 82

Mean Tender and Swollen 28 Joint Count Through Week 24

| | Mean Joint Count | | |
|---|---|---|---|
| | Week 0 (n = 879) | Week 12 (n = 767) | Week 24 (n = 236) |
| Tender Joint Count | 15 | 8 | 6 |
| Swollen Joint Count | 13 | 8 | 6 |

Observed data.
p < 0.001 vs. baseline at all time points.

TABLE 83

DAS28 Scores Through Week 24

| | Week 0 (n = 876) | Week 12 (n = 742) | Week 24 (n = 234) |
|---|---|---|---|
| Mean DAS28 Scores | 6.1 | 4.2 | 3.9 |
| 95% CI | (6.0, 6.2) | (4.1, 4.3) | (3.7, 4.1) |

Observed data.
p < 0.001 vs. baseline at all time points.

TABLE 84

DAS28 Scores With or Without Prior Biologic Use

| | Mean DAS28 Score | |
|---|---|---|
| | Baseline | Week 12 |
| No Previous Biologics | 6.1 (n = 637) | 4.0* (n = 559) |
| 1 Previous Biologic | 6.3 (n = 242) | 4.6†‡ (n = 213) |

Mean values.
Biologics: Infliximab, Etanercept, Anakinra, Investigational Drugs.
*p < 0.001 vs. baseline (no previous biologics);
†p = 0.0019 vs. baseline (1 previous biologic);
‡p = 0.001 vs. Week 12 (no previous biologics).

TABLE 85

ACR Responses at Weeks 12 and 24

| | % of Patients | | |
|---|---|---|---|
| | ACR20 | ACR50 | ACR70 |
| Week 12 | 58.4 (n = 451) | 30.6 (n = 236) | 12.7 (n = 98) |
| Week 24 | 71.8* (n = 171) | 41.2† (n = 98) | 17.6‡ (n = 42) |

Mean values.
Observed data.
p < 0.001 for all changes from baseline to Week 12.
*p = 0.0003,
†p = 0.003,
‡p = 0.068,
Week 24 vs. Week 12.

TABLE 86

HAQ Scores Through Week 24

| | Week 0 (n = 878) | Week 12 (n = 758) | Week 24 (n = 238) |
|---|---|---|---|
| Mean HAQ Score | 1.5494 | 1.0393 | 0.8889 |
| 95% CI | (1.5, 1.6) | (1.0, 1.1) | (0.8, 1.0) |

Observed data.
p < 0.001 vs. baseline at all time point.
MCID = 0.22 - Goldsmith C, et al. *J Rheum* 1993; 20: 561-5.

In conclusion, RA patients in the study who received adalimumab consistently experienced substantial reductions in the signs and symptoms of their disease. Efficacy of open-label adalimumab was demonstrated in Canadian clinical practice setting and was consistent with findings of other published clinical studies, such as Study A. Similarly, Adalimumab safety in routine clinical setting was consistent with other studies and no new safety concerns were identified. Study C provided confidence in treatment with adalimumab when used in routine clinical practice and Adalimumab was generally safe and well-tolerated.

EXAMPLE 11

Safety of Humira in Patients with Active Rheumatoid Arthritis who Participated in Clinical Study D Study D was initiated to demonstrate the early efficacy, safety and tolerability of adalimumab in patients with active rheumatoid arthritis (RA), with particular emphasis on patient-reported outcomes and early response.

The objective of Study D was to determine the rates of serious adverse events (SAEs) of interest with adalimumab therapy observed during Study D.

Study D is an ongoing, randomized, double-blind (first dose), placebo-controlled, multi-center, Phase IV study in the United States, designed to demonstrate the efficacy of adalimumab 40 mg subcutaneously (sc) every other week (eow) in patients with active RA. After a screening period, all eligible patients receive a single, blinded dose of study medication, followed by 10 weeks of open-label adalimumab 40 mg sc eow, beginning at week 2.

Patients were trained to use a Palm OS-based electronic diary to report on their pain, function, fatigue, morning stiffness, and disease activity using a visual analog scale. They completed a report 3 times daily during the screening and baseline periods up to Week 2, followed by evening-only reports during the 10-week, open-label treatment period. A secondary endpoint of Study D was the evaluation of serious adverse events (SAEs) and other safety parameters in RA patients treated with adalimumab. SAEs but not AEs were collected for each patient from enrollment until 70 days following discontinuation of adalimumab. All SAEs were followed until resolution or stabilization of the event was documented. Laboratory assessments were also conducted to monitor for any abnormalities. In this preliminary safety analysis, we evaluated the SAEs that have been currently reported, focusing on those SAEs of interest with anti-TNF therapy.

At baseline, Week 2, 4 and 12 study visits, the following measures were evaluated: 1) Physician's global assessment of disease activity; 2) Swollen and tender joint counts; 3) C-reactive protein; 4) SF-36 Health Survey; 5) HAQ; 6) FACIT-Fatigue Health Thermometer; 7) VAS-Functional Limitation; 8) VAS-Morning Stiffness; 9) Safety Assessments; and 10) Clinical laboratory assessments were done at screening and Week 12, or if patient withdrew from the study for any reason.

An adverse event is labeled as a serious adverse event (SAE) based on the following regulatory criteria/definition: Fatal; Life-threatening; Requires inpatient hospitalization; Prolongs hospitalization; Results in congenital anomaly/birth defect; Causes persistent or significant disability/incapacity; Important medical event that jeopardizes the patient and requires medical/surgical intervention to prevent another serious outcome.

Only serious adverse events (SAEs) were collected from enrollment until 70 days following completion or withdrawal from the study. SAEs were coded using the Medical Dictionary for Regulatory Activities (MedDRA). Investigators were required to report SAEs within 24 hours of occurrence or knowledge of the event. All SAEs were followed until resolution or stabilization of the event was documented.

Between August 2004 and November 2005, 1938 patients enrolled in the study and 1807 patients completed the 12-week trial. FIG. 18 shows the disposition of the study while Table 92 demonstrates baseline demographics for patients who participated in the Study D. As of Mar. 30, 2006, a total of 69 SAEs were reported for 61 patients who have received at least one dose of blinded or open-label study drug (Table 93). There were no cases of lymphoma, tuberculosis, demyelinating disease, or systemic lupus erythematosus/lupus-like syndrome observed in either treatment group The numbers and percentages of SAEs of interest are reported in the Table 94 below. Since the ongoing Study D study has not been unblinded, neither total patient-years of adalimumab exposure nor safety data for the placebo cohort were available at the time of this analysis.

TABLE 92

Baseline Demographics

| Characteristics | Placebo n = 962 | Adalimumab n = 976 |
|---|---|---|
| Age, mean (years) | 55 | 54 |
| Sex (% male) | 23 | 21 |
| Disease Duration, median (years) | 3 | 3 |
| Patients on concomitant DMARDs (%) | 80 | 84 |
| Education, mean (years) | 13 | 13 |

TABLE 93

Serious Adverse Events Observed in Study D

| | Double-Blind Period Baseline - Week 2 | | Open-Label Period Weeks 2-12* All Patients |
|---|---|---|---|
| No. of Patients (%) | Placebo N = 962 n (%) | Adalimumab N = 976 n (%) | Adalimumab 40 eow N = 1905 n (%) |
| Any SAE | 3 (0.3) | 3 (0.3)† | 55 (2.9) |
| Any serious infection | 0 | 1 (0.1) | 12 (0.6) |
| Pneumonia | 0 | 0 | 3 (0.2) |
| Cellulitis | 0 | 1 (0.1) | 2 (0.1) |
| Septic Arthritis | 0 | 0 | 1 (0.1) |
| Malignancies | 0 | 0 | 5 (0.3)‡ |
| Lymphoma | 0 | 0 | 0 |

*Includes SAEs reported during the 70-day post-study period.
†1 case each of acute cholecystitis, rash, and cellulitis.
‡1 case each of malignant melanoma, colon cancer, ovarian granulosa-theca cell tumor, prostate cancer, and malignant neoplasm.

TABLE 94

Numbers and Percentages of Patients with SAEs of Interest

| Serious Adverse Events of Interest | Adalimumab 40 eow N = 1920 Number of Patients (%) |
|---|---|
| Serious Infections | 10 (0.5) |
| Pneumonia | 3 (0.2) |
| Cellulitis | 3 (0.2)* |
| Urinary Tract Infection | 0 |
| Septic Arthritis | 1 (0.1) |
| Tuberculosis | 0 |
| Malignancies | 4 (0.2) |
| Lymphoma | 0 |
| Demyelinating Diseases | 0 |
| SLE/lupus-like syndrome | 0 |

*One case of cellulitis occurred after the single, blinded dose, which could have been placebo.
The 4 malignancies observed were colon cancer, melanoma, prostate cancer, and granulosa cell tumor of the ovary.

In conclusion, in this preliminary analysis of Study D, no cases of lymphoma, tuberculosis, or demyelinating diseases were observed with adalimumab treatment. Further, the types and rates of SAEs observed were similar to what has been observed in other clinical trials of adalimumab in RA.

EXAMPLE 12

Cost Effectiveness of the 3 TNF Antagonists Vs. Abatacept in the Treatment of Moderate to Severe Rheumatoid Arthritis (RA)

For RA, TNF antagonists have been shown to significantly reduce the signs and symptoms of the disease, inhibit disease progression, and improve patients' quality of life (QOL). Adalimumab (Ada), etanercept (Eta), and infliximab (Inf) in combination with methotrexate have each demonstrated substantial advantages in each of these areas compared with traditional DMARDs. Abatacept (Abat), a selective T-cell co-stimulator, has recently been added to the RA armamentarium for patients who fail therapy with traditional DMARDs and TNF antagonists.

The objective of this analysis was to model, from a US managed-care perspective, the lifetime cost effectiveness of each of these 4 therapies as first-line biologic treatment for long-standing moderate to severe RA.

The study was performed using a published cost-effectiveness model developed at the University of Sheffield that simulates patients' responses to successive traditional DMARD and biologic therapies to estimate health and economic outcomes following treatment with each of the TNF antagonists based on efficacy data from key clinical studies in RA2, 3, 4, 5 (Bansback et al. Ann Rheum Dis. 2005; 64:995, incorporated by reference herein). The TNF antagonists were each modeled to yield health outcomes based on efficacy data from key clinical studies in RA. Adjustments for control drug response were made following the method proposed by Choi et al as follows (adjusted response for biologic in trial B (Bio B) applied to MTX response in trial A [MTX A]):

Marginal response Bio B: (Response Bio B−Response MTX B)/(1−Response MTX B).

Adjusted response: Response MTX A+Marginal response Bio B×[1−Response MTX A].

Initial response was determined by a Monte-Carlo patient-level simulation of ACR responses, with a minimum of ACR50, at 6 months after initiation of each treatment, determining adequate response. Following response, benefit to patients was linked to a reduction in patients' health assessment questionnaire (HAQ) scores (Table 95). HAQ scores were modeled to subsequently increase (i.e, physical function deteriorates) over variable durations of continued response compared with non-response. Eventual withdrawal from biologic therapy (followed by treatment with traditional DMARDs) and a reversal in original HAQ improvement were modeled to follow.

Utility values were assigned to patients in both arms of the model based on a regression equation associating patients' HAQ scores with their valuations of QOL measured by the Health Utility Index Mark 3. Costs included those of all drugs, monitoring and adverse events, as well as other direct health care costs, including hospitalizations, which were calculated by applying published relationships between HAQ scores and US health care costs. Mortality was based on US life tables and relative risks, which were also dependent on HAQ. Discounting was performed at 3% for both costs and outcomes.

TABLE 95

HAQ Progression and Treatment Withdrawal Rates

| | | | | |
|---|---|---|---|---|
| HAQ improvement on initial response12* | <ACR20 | ACR 20-50 | ACR 50-70 | >ACR70 |
| | 6.4 ± 2.4 | 34.7 ± 4.8 | 57.0 ± 4.9 | 64.6 ± 4.8 |
| HAQ progression (per 6 months)13, 14* | Non response | DMARD response | | Biologic response |
| | 0.132 | 0.044 | | 0.044 |
| Withdrawal from treatment (per 6 months)8* | DMARD | Adalimumab/Etanercept | | Infliximab/Abatacept |
| | 59.7 ± 4.8 | 13.2 ± 2.6 | | 15.9 ± 3.1 |
| Relative risk for mortality by HAQ point11† | 2.73 (95% confidence interval: 1.86, 4.02) | | | |
| Utility7‡ | 0.76 ± 0.023 − 0.28 ± 0.003 × HAQ | | | |

Values are averages ± standard errors unless otherwise stated.
*parameter assigned beta distribution.
†parameter assigned log-normal distribution.
‡parameter assigned bivariate normal distribution.

Disease progression is associated with increasing HAQ scores (ie, deteriorating physical function). During periods of response disease progression was modeled to be less rapid compared with non-response as shown in Table 95. Reversals in original HAQ improvements were modeled to follow eventual withdrawal (determined at 6-month intervals) from therapy (followed by treatment with traditional DMARDs).

Also shown in Table 95, utility values were assigned to patients, irrespective of treatment, based on a regression equation associating patients' prevailing HAQ scores with quality of life as measured by the Health Utility Index Mark 3 in order to generate quality-adjusted life-years (QALYs) and incremental cost-effectiveness ratios (ICER).

Transition-state model: Health economics outcomes were monitored in 1,000 hypothetical patients. Treatment success or failure was assessed in 6-month cycles where patients were transitioned to other DMARDs if they failed to reach a minimum ACR50 criteria (FIG. 19). All patients modeled had previously been treated with MTX. Up to 7 further DMARDs were used in sequence (including MTX in combinations with other DMARDs). In biologic strategies these DMARD sequences followed failure of, or withdrawal from biologic therapy (FIG. 62). As infliximab was subject to dose increases we modeled a second infliximab strategy where loss of response led to re-treatment with 10 mg/kg.

When a patient did not show adequate response to therapy (defined by ≥ACR 50), or withdrew subsequent to an initial response, treatment was switched to the next DMARD (or a 10-mg/kg infliximab dosage in the case of withdrawal from 3-mg/kg infliximab strategy). The likelihood of response decreased with time (odds ratio=0.98 per year).

All patients were monitored throughout their lifetime. Total costs included those for all drugs, monitoring, adverse events (Table 96), and other direct health care costs (eg, hospitalizations), which were calculated by applying published relationships between HAQ scores and US health care costs.

Mortality was based on US life tables adjusted for increased risk associated with higher HAQ scores. Discounting was performed at 3% for both costs and outcomes.

TABLE 96

Summary Model Costs (US $)

|  | Drug Cost | | Monitoring | | |
|---|---|---|---|---|---|
|  | 1st 6-month period | Subsequent 6-month periods | 1st 6-month period | Subsequent 6-month periods | Adverse Events All periods |
| Adalimumab* | 7993 | 7993 | 411 | 275 | 396 |
| Abatacept* | 10995 | 9645 | 1496 | 1258 | 565 |
| Etanercept* | 7993 | 7993 | 411 | 275 | 383 |
| Infliximab (3 mg/kg)* | 8478 | 5579 | 998 | 636 | 565 |
| Infliximab (3/10 mg/kg)* | 8478 | 12758 | 998 | 636 | 565 |
| Leflunomide | 2657 | 2657 | 395 | 275 | 348 |
| Leflunomide* | 2852 | 2852 | 406 | 275 | 348 |
| Sulfasalazine* | 280 | 280 | 406 | 275 | 348 |
| Cyclosporin* | 2322 | 2322 | 406 | 275 | 348 |
| Sulfasalazine + Cyclosporin | 2407 | 2407 | 406 | 275 | 348 |
| Hydroxychloroquine* | 552 | 552 | 406 | 275 | 348 |
| Gold | 1306 | 1306 | 416 | 334 | 348 |

*Therapy in combination with methotrexate

As shown in Table 97 the adalimumab strategy achieved the greatest Quality-Adjusted Life-Years (QALYs) of any single anti-TNF sequence (2.73 QALYs after discounting). An additional strategy was modeled for infliximab in which patients who failed to respond to 3 mg/kg were re-treated with 10 mg/kg. This treatment yielded fewer QALYs, vs. the single treatment sequence of adalimumab, at an extra cost of over $2,000. Adalimumab had cost per QALY vs. etanercept, of approximately $30,000, and had cost-per-QALY ratios vs. infliximab (3 mg/kg) of $37,500. Abatacept yielded fewer QALYs than adalimumab, at additional cost, despite patients remaining on abatacept far less than they did for the other biologics.

TABLE 97

Health Outcomes Based on Key RA Clinical Study Results of the TNF Antagonists and Abatacept

|  | Traditional DMARDs | Adalimumab | Etanercept | Infliximab 3 mg/kg | Infliximab 3 & 10 mg/kg | Abatacept |
|---|---|---|---|---|---|---|
| QALYs | 1.70 | 2.73 | 2.49 | 2.14 | 2.23 | 2.20 |
| Total cost ($) | 116,065 | 157,052 | 150,096 | 134,966† | 159,343 | 159,149 |
| ICER* for Traditional DMARDs vs. Other ($/QALY) |  | 39,901 | 42,820 | 42,748 | 80,844 | 85,607 |
| ICER for adalimumab vs Other ($/QALY) | 39,901 |  | 29,922 | 37,749 | Dominant | Dominant |

*ICER = Incremental Cost-Effectiveness Ratio.

Table 98 shows a Choi adjustment: the marginal response of each biologic vs. MTX was applied to the MTX response in Study I. For example: etanercept:

Marginal ACR50 response for etanercept=(39−3)/(100−3)= 37%

Applied to MTX response in Study I=8+(37×[100−8])= 42%

TABLE 98

Efficacy Data With Choi Adjustment

|  | Methotrexate arm | | | Biologic arm | | | Choi Adjusted Biologic | | |
|---|---|---|---|---|---|---|---|---|---|
| ACR | 20 (%) | 50 (%) | 70 (%) | 20 (%) | 50 (%) | 70 (%) | 20 (%) | 50 (%) | 70 (%) |
| Adalimumab | 15 | 8 | 5 | 67 | 55 | 27 | 67 | 55 | 27 |
| Etanercept | 27 | 3 | 0 | 71 | 39 | 15 | 66 | 42 | 19 |
| Infliximab (3 mg/kg) | 20 | 5 | 0 | 50 | 29 | 11 | 47 | 31 | 15 |
| Infliximab (10 mg/kg) | 20 | 5 | 0 | 58 | 26 | 11 | 55 | 28 | 15 |
| Abatacept | 33 | 11 | 3 | 64 | 32 | 12 | 54 | 30 | 14 |

All therapies were given in combination with methotrexate.

Beta distributions were assigned to all efficacy parameters and derived based on numbers in each trial (sampling was conditional on successive ACR categories, e.g. ACR 50 sampled as a proportion of ACR 20 responders).

Also shown in Table 97, Etanercept, abatacept, and infliximab (3 mg/kg) yielded 2.49, 2.20, and 2.14 QALYs, respectively. Re-treatment strategy of patients who failed infliximab (3 mg/kg) with 10 mg/kg yielded marginally greater QALYs than the 3 mg/kg dosage alone, but fewer QALYs than adalimumab.

As shown in Table 99, Adalimumab was marginally more costly than etanercept and infliximab (3 mg/kg) because of its better modeled ACR response and longer time on treatment. Adalimumab provided 0.24 more QALYs (cost per QALY, $29,922) than etanercept and 0.59 more QALYs (cost per QALY, $37,749) than infliximab, respectively. Adalimumab dominated both abatacept and infliximab strategies while etanercept and infliximab (3 mg/kg) were extendedly dominated by DMARDs and adalimumab combination.

An extendedly dominated strategy exists where a linear combination of two other strategies can produce at least as many QALYs at lower total cost.

ranged (in accordance with longevity in years) in relation to the first treatment in sequence from (low years) DMARDS (approximately 0.8)/Abatacept (approximately 2)/Infliximab (3 mg/kg) (approximately 2)/etanercept (approximately 3) adalimumab (approximately 3.8) (high years). The longer acting biologics were associated with far lower total costs per year on biologic. The scatter plot cost-utility plane, shows the distribution of incremental costs and QALYs for all biologic strategies compared to traditional DMARDs. Parameter values were randomly sampled from their assigned distributions over 1,000 probabilistic iterations of the model. Points with steeper gradients from the origin have higher cost per QALY ratios vs. DMARDs.

TABLE 99

Cost Effectiveness Results

|  | DMARDs | Infliximab (3 mg/kg) | Abatacept | Infliximab (3-10 mg/kg) | Etanercept | Adalimumab |
| --- | --- | --- | --- | --- | --- | --- |
| Drug costs ($) | 16,517 | 36,553 | 52,098 | 53,314 | 55,176 | 63,056 |
| Monitoring ($) | 6,418 | 7,972 | 10,412 | 8,805 | 6,432 | 6,540 |
| Adverse events ($) | 9,368 | 9,214 | 10,306 | 10,372 | 9,185 | 9,313 |
| Other Direct Costs ($) | 83,762 | 81,227 | 86,333 | 86,852 | 79,304 | 78,142 |
| Total Costs ($) | 116,065 | 134,966 | 159,149 | 159,343 | 150,096 | 157,052 |
| QALYs | 1.70 | 2.14 | 2.20 | 2.23 | 2.49 | 2.73 |
| ICER vs DMARDs ($/QALY) |  | 42,748 | 85,607 | 80,844 | 42,820 | 39,901 |
| ICER for adalimumab vs Other ($/QALY) | 39,901 | 37,749 | dominant | dominant | 29,922 | — |

All biologic therapies were given in combination with methotrexate.

Overall, patients were modeled to remain on adalimumab and methotrexate therapy considerably longer than on other biologic combinations. The model used a 6-month cycle. In the model, ACR response is determined 6 months after treatment, and subsequent withdrawal at 6-month intervals. In addition, following withdrawal, patients were switched to non-biologic DMARDs or rescue therapy. The longer acting biologics are associated with far lower total costs per year. The average time on the first treatment (years, 95% CI)

Adalimumab had a 62% probability of being cost effective at a minimum willingness to pay (WTP) of $50,000 per QALY in this analysis, rising to 83% at a WTP of $100,000 per QALY (Table 100).

TABLE 100

Cost effectiveness Probability for Each Strategy at Given WTP

| WTP/QALY | DMARDs | Adalimumab | Etanercept | Infliximab (3 mg/kg) | Infliximab (3-10 mg/kg) | Abatacept |
| --- | --- | --- | --- | --- | --- | --- |
| $40,000 | 40 | 22 | 4 | 34 | 0 | 0 |
| $50,000 | 6 | 62 | 14 | 18 | 0 | 0 |
| $60,000 | 1 | 75 | 16 | 8 | 0 | 0 |

All biologic therapies were given in combination with methotrexate.

In conclusion, both Ada and Eta have marked advantages over Inf and Abat. Adalimumab and etanercept demonstrated better cost effectiveness profiles than infliximab and abatacept. Adalimumab was superior to etanercept in terms of QALYs (0.24 more) at moderate additional cost ($6,956). The cost per QALY of adalimumab vs. etanercept was approximately $30,000. A combination of DMARDs and adalimumab could yield equivalent QALYs to etanercept at lower total cost suggesting that etanercept is extendedly dominated. Superior TNF-antagonist cost effectiveness to abatacept indicates that Abat therapy should be considered only after substantial trials of first-line trad DMARDs and TNF-antagonist therapies have not yielded satisfactory results.

EXAMPLE 13

Early Clinical Response in Venezuelan Patients with Rheumatoid Arthritis (RA) Treated with Adalimumab The objective of the study described herein was to assess early response to adalimumab in key clinical efficacy and functional measures in a cohort of Venezuelan patients with moderate to severe rheumatoid arthritis (RA) from a multi-center trial.

A group of 77 patients from 9 centers in Venezuela received adalimumab 40 mg every other week (eow) in addition to concomitant methotrexate (MTX) therapy in a prospective, open-label, 3-month trial. Of these, 65 completed the 12-week, open-label study. Inclusion criteria in this trial included age>18 years, active RA for ≥3 months (DAS28≥3.2) diagnosed by ACR criteria, and unsatisfactory response to at least 3 months of MTX monotherapy. Baseline disease severity indices were consistent with those of patients with moderate to severe RA (Table 101). The Mean age was 48 and the mean disease duration was 10 years.

Patients were screened for latent tuberculosis (PPD and chest X-ray). Selected efficacy measures, including indicators of clinical remission, were evaluated after 2 and 12 weeks of therapy. Regular visits for safety and efficacy monitoring were scheduled every 2 weeks until Week 12.

Efficacy (including indicators of clinical remission) and safety assessments were performed at Weeks 0, 2, 6, and 12. Outcomes measured included: Disease Activity Score 28 (DAS28); Tender and Swollen Joint counts (TJC, SJC); Health Assessment Questionnaire-Disability Index (HAQ-DI); Patients' assessment of pain using a visual analog scale (VAS); C-reactive protein (CRP); and Erythrocyte sedimentation rate (ESR). Clinical remission criteria was: DAS28<2.6; HAQ<0.5; TJC=0, SJC=0; and CRP<1 mg/dL. Outcomes of adalimumab therapy at Weeks 0 (baseline), 2, 6, and 12 were compared. See FIG. 20 for the study design.

Table 101 below shows that the benefits of adalimumab were evident as early as 2 weeks following first dose. Patients had continued to improve further by Week 12 (Table 102). Mean HAQ improved by −0.5 following a single dose of adalimumab, an improvement greater than previously reported in clinical trials of TNF antagonists. In addition, by Weeks 2 and 12, 9.2% and 29.2% of patients had achieved DAS28<2.6. By Week 12, approximately one-third of patients had achieved additional criteria for clinical remission: TJC=0 (32.3%), SJC=0 (46.2%), HAQ<0.5 (43.1%), and normal CRP concentrations (<1 mg/dL) (40.3%).

TABLE 101

Clinical Response to Adalimumab

| Efficacy Criteria | Baseline (N = 77) | Week 2 (N = 76) | Week 12 (N = 65) |
|---|---|---|---|
| DAS28 | 5.6 | 4.2 | 3.1 |
| TJC28 | 14 | 7 | 3 |
| SJC28 | 13 | 7 | 2 |
| HAQ (0-3) | 1.7 | 1.2 | 0.7 |
| Pain on VAS (0-100 mm) | 64 | 37 | 20 |
| ESR (mm/1$^{st}$ hour) | 40 | 31 | 28 |
| CRP (mg/dL) | 2.4 | N/A | 1.5* |

Mean values. p < 0.05 for all Week-2 and Week-12 results vs. baseline.
*Data available for 49 patients at Week 12.

TABLE 102

HAQ Improvement Through Week 12

| | Week 2 (n = 76) | Week 6 (n = 71) | Week 12 (n = 65) |
|---|---|---|---|
| Mean change from baseline | −0.50† | −0.78† | −0.99† |

†p < 0.001 vs. baseline, Wilcoxon's test.
MCID (minimum clinically important difference) = −0.22
Observed data.

TABLE 103

DAS28 Improvement Through Week 12

| | Week 0 (n = 77) | Week 2 (n = 76) | Week 6 (n = 72) | Week 12 (n = 65) |
|---|---|---|---|---|
| Mean DAS28 Scores | 5.6 | 4.2* | 3.4*† | 3.1* |

*p < 0.001 vs. baseline;
†p < 0.001 vs. Week 2, Wilcoxon's test.
Observed data.

TABLE 104

Tender and Swollen Joint Counts Through Week 12

| | Baseline (n = 77) | Week 2 (n = 76) | Week 6 (n = 72) | Week 12 (n = 65) |
|---|---|---|---|---|
| Tender Joint Count | 14.4 | 6.9* | 3.9*† | 2.7*‡ |
| Swollen Joint Count | 13.1 | 6.9* | 3.4*§ | 1.9* |

*p < 0.001 vs. baseline;
†p = 0.002 vs. Week 2;
‡p = 0.04 vs. Week 6;
§p < 0.001 vs. Week 2, Wilcoxon's test.
Observed data.

TABLE 105

Reduction of Pain as Assessed by VAS Through Week 12

| | Week 2 (n = 76) | Week 6 (n = 72) | Week 12 (n = 65) |
|---|---|---|---|
| Mean Change from Baseline | −2.7 | −3.7 | −4.4 |

TABLE 106

Percentages of Patients with CRP Normalization Through Week 12

|  | Week 6 (n = 80) | Week 12 (n = 49) |
|---|---|---|
| % of Patients | 49 | 40 |

Observed data.

TABLE 107

Percentages of Patients Who Achieved Clinical Remission as Assessed by Clinical Remission Indicators

| | % of Patients | | | |
|---|---|---|---|---|
| | HAQ < 0.5 (n = 76) | DAS28 < 2.6 (n = 76) | TJC = 0 (n = 76) | SJC = 0 (n = 76) |
| Week 2 | 14 | 9 | 9 | 16 |
| Week 12 | 43 | 29 | 32 | 46 |

Reductions in DAS28 scores were rapid and maintained through 12 weeks of adalimumab treatment (Table 103). Rapid reductions in TJC and SJC were observed when adalimumab was added to existing MTX therapy (Table 104). Patients reported a substantial reduction in pain, 43% and 69% after 2 and 12 weeks of adalimumab therapy, respectively (Table 105).

The percentages of patients demonstrating CRP normalization (<1 mg/dL) (Table 106) as well as decreasing ESR values (data not shown) after initiation of adalimumab 40 mg eow and after 12 weeks of therapy were maintained through Week 12. By Week 2, 14.5% and 9.2% of patients had achieved HAQ<0.5 and DAS28<2.6, respectively. The corresponding percentages for Week 12 were 43.1% and 29.2% (Table 107). Approximately one-third of patients achieved criteria for clinical remission: TJC=0 (32.3%), SJC=0 (46.2%) (Table 107).

In conclusion, under clinical trial conditions, Venezuelan patients with RA showed rapid and significant clinical improvements after a single dose of 40-mg adalimumab, including a substantial decrease in HAQ scores. Further, cumulative improvement was observed at Week 12, including a substantial percentage of patients achieving clinical remission based on DAS28 and other criteria. In addition, supplementing adalimumab to insufficient concomitant methotrexate therapy provides significant improvement in the signs and symptoms of RA. Thus, adalimumab provides an effective treatment for Hispanic, e.g., Venezuelan, patients suffering from RA.

EXAMPLE 14

Resource Utilization and Costs of Severe Rheumatoid Arthritis (RA) from Societal and Patient Perspectives The following study was performed to investigate resource utilization and costs for late-stage rheumatoid arthritis (RA) patients from societal and patient perspectives in several European countries.

Resource utilization was retrospectively collected from 505 patients with active, severe RA from a period prior to their enrollment in a multinational, open-label, follow-up clinical trial of adalimumab, a fully human, anti-tumor necrosis factor (anti-TNF) monoclonal antibody. At baseline, these patients had severe RA, had previously failed a mean of 3.7 disease-modifying anti-rheumatic drugs (DMARDs), and had a mean RA disease duration of 11 years. Data on 54 resource utilization items were collected, including direct costs (eg, hospitalizations, procedures, medications); direct non-medical costs (eg, transportation, devices); and indirect costs (eg, productivity loss, family support) for 6 months prior to inclusion in the study using a methodology recently recommended in a comprehensive review paper on the cost of RA (Hubertus et al. (2005) *Pharmacoeconomics* 23:243). In brief, the hierarchy of resource utilization assessment was as follows: Level 1 was the total, which was divided at level 2 into direct and indirect. At level 3, direct was subdivided into inpatient and outpatient. At level 4, outpatient was divided into direct medical and direct nonmedical. At level 5, inpatient from level 3 was divided into hospitalizations and rehabilitation. Level 4 direct medical was divided at level 5 into doctor, medications, and specific procedure. Level 4 direct nonmedical was divided at level 5 into other treatments, technical work and aids, personal help, and transportation. At level 5, level 2 indirect was subdivided into unfit for work. Resources were valuated using German prices (in 2004 euros). A human-capital approach was employed to estimate productivity losses.

Specific sets of health economic questionnaires (HEQs) were used by investigators (1-HEQ) and patients (P-HEQ) for the assessment of resource utilization and costs for late-stage rheumatoid arthritis (RA) patients. The data derived from 1-HEQ included: hospitalization; rehabilitation/recuperation; procedures performed; specific examinations and lab tests; outpatient essential RA related examinations; and drug consumption. The data derived from P-HEQ included: hospitalizations; outpatient visits; physical/occupational therapy; alternative treatment; medical devices; transportation; personal support; professional status; productivity loss; working time; and early retirement/unemployment.

A total of 505 patients were included in this analysis. These patients had severe RA, and had previously failed a mean of 3.7 disease modifying antirheumatic drugs (DMARDs), and also had a mean RA disease duration of 11 years. Mean societal total cost during the 6-month period before anti-TNF therapy was initiated was € 12 750 per patient per year (annualized) (Table 108), with 54% from direct non-medical cost, 28% from indirect cost (including reduced functionality at work, 52%; sick leave, 9%; and early retirement because of RA, 39%), and 19% from direct medical cost. In addition, 49% of the total direct cost was a result of hospitalizations. Mean total cost from the patients' perspective was 2121 € per year—with 96% from direct non-medical cost, of which 61% was for home support. More specifically, direct non-medical costs—societal perspective were 81% personal assistance, 19% medical device, and 9% transportation. Indirect costs from a societal perspective included 9% sick leave, 52% reduced functionality at work, and 39% early retirement. Patients relied on a number of aids and devices to manage daily life (Direct nonmedical cost to patient included 61% personal assistance, 18% medical devices, and 21% transportation).

TABLE 108

| Category | Costs per patient per year* E (%) |
|---|---|
| Direct non medical costs | 6,854 (54) |
| Indirect costs | 3,529 (28) |
| Direct medical costs | 2,368 (19) |
| Total | 12,750 |

In conclusion, total cost from a societal perspective in this study of late-stage RA patients is higher than similar data reported in the literature for Europe (Hubertus et al.). Total costs from the patients' perspective were much higher than previously reported (Huelsemann et al. (2005) *Ann Rheum Dis* 64:1456), demonstrating the economic burden of the disease on the patient—an often neglected focus in RA research.

EXAMPLE 15

Clinical Response by Day 1 with Adalimumab in Patients with Active Rheumatoid Arthritis Study D (HERO)

Adalimumab, a fully human monoclonal antibody targeting TNF, is approved for the treatment of rheumatoid arthritis, psoriatic arthritis, and ankylosing spondylitis in the United States, Europe, and elsewhere. Pivotal trials have proven the efficacy of and rapid response to adalimumab (as early as one week after study drug initiation) in patients with RA (Weinblatt M E, et al. *Arthritis Rheum.* 2003; 48:35-45; van de Putte L B A, et al. *Ann Rheum Dis.* 2004; 63:508-16, and van de Putte L B A, et al. *Ann Rheum Dis.* 2003; 62: 1168-77). These trials used a host of clinical, physician, and patient-reported outcome (PRO) measures at each study visit to demonstrate responses to therapy. Although these assessments detect response to therapy at time of first study visit, earlier improvement cannot be measured reliably without potential for recall bias.

Patient-reported outcomes (PRO) can be used to determine very early responses to therapy. The purpose of this study was to determine the early time course of response to adalimumab (ADA) using PRO measures recorded in electronic diaries in Study D (HERO).

Study D was a randomized, double-blind (first dose), placebo (PBO)-controlled, multi-center, Phase IV study of ADA 40 mg sc every other week in patients with active RA. Its emphasis was on early response markers and PROs. After screening, all eligible patients received a blinded dose of study medication, followed by 10 weeks (wks) of open-label (OL) ADA, beginning at week 2. The study design is depicted in FIG. 21. Patients were trained to use an electronic diary (e-diary) to report their global assessments of disease activity (Pt. Global), pain, function, fatigue and morning stiffness (presence, duration and severity) using a 0-100 visual analog scale (VAS), with higher values reflecting worse symptoms. During the screening and blinded first 2 weeks post-baseline, patients completed three reports per day (morning 5-10 am, afternoon 2-4 pm, and evening 8-11:45 pm), followed by evening-only reports during the 10-wk OL period. At baseline, Week 2, Week 4, and Week 12 study visits, the following assessments were performed and recorded on paper: Short Form 36 (SF-36) Health Survey, Health Thermometer, Functional Assessment of Chronic Illness Therapy-Fatigue (FACIT-F) scale, Health Assessment Questionnaire (HAQ), Physician's global assessment of disease activity, Swollen and Tender Joint Counts, C-reactive protein, VAS—Functional Limitation, and VAS—Morning Stiffness. The degree and timing of improvement in e-diary based PROs between PBO and ADA groups were determined during the blinded first 2 weeks of the study and after patients switched to OL therapy. Evening report scores were used for this analysis. Baseline values are from the last evening report (Day −1) prior to start of treatment.

A total of 1,880 patients (953 ADA, 927 PBO) enrolled at 204 study sites had e-diary data available for analysis. The study disposition is depicted in FIG. 22. In the overall Study D population, there were no significant differences between the two treatment arms in terms of baseline demographics. Table 109 lists the baseline demographics data for the 1880 patients included in this analysis. There were no significant differences between the two treatment groups in terms of baseline e-diary evening assessments, except for duration of morning stiffness (p=0.012), as shown in Table 110. Compliance with the e-diary was greater than 90% from screening to the end of the study.

TABLE 109

Baseline Demographics

| Characteristics | Placebo n = 927 | Adalimumab n = 953 |
|---|---|---|
| Age (mean, years) | 54.5 | 54.0 |
| Sex (% male) | 23.0 | 21.3 |
| Disease duration (mean, years) | 6.9 | 7.0 |
| Patients on concomitant DMARDs (%) | 78.9 | 82.5 |
| Education categories (%) | | |
| 0-8 yrs | 3.5 | 3.6 |
| 9-11 yrs | 9.3 | 9.1 |
| 12 yrs | 36.9 | 39.7 |
| 13-15 yrs | 30.8 | 26.0 |
| =16 yrs | 19.5 | 21.6 |

TABLE 110

Baseline e-Diary Assessments

| VAS scores (0-100) | Placebo | Adalimumab |
|---|---|---|
| e-PaGA | 50.6 | 49.8 |
| Pain | 50.9 | 50.9 |
| Function | 51.1 | 50.6 |
| Fatigue | 56.4 | 55.2 |
| Presence of AM stiffness (%) | 93.5 | 91.7 |
| Duration of AM stiffness (minutes) | 140.7 | 161.7 |
| Severity of AM stiffness | 53.3 | 51.3 |

Statistically significant separation from the PBO patients occurred after 1 day of treatment for all variables (P<0.001) (Table 111), with mean 14-day improvement differences ranging from 4.7 units (fatigue) to 7.6 units (stiffness) (P<0.001) (see Table 112). Adalimumab patients experienced significantly shorter periods of morning stiffness compared with placebo patients by Day 1 (mean decrease of 32.8 minutes for adalimumab patients vs. 0.3 minutes for placebo patients). Improvement in e-diary assessments at Weeks 2 and 12 are depicted in Table 113. Based on the e-diary assessments, the improvements in symptom severity PROs of the adalimumab group were significantly better than the placebo group for every day of the entire 2-week double-blind period. Placebo patients who switched to open-label adalimumab had similar symptom improvements as the adalimumab group. FIG. 23 depicts the time course of mean change in e-diary assessments to Week 12. The effect of adalimumab treatment on patient pain, functional disability, fatigue and AM morning stiffness severity during the double-blind period of 14 days followed by open-label adalimumab are shown in FIG. 24, FIG. 25, FIG. 26 and FIG. 27 respectively.

Baseline morning scores were approximately 3 units greater than evening scores, but response to treatment was similar. Improvement in Pt. Global continued throughout the OL period (see FIG. 28). Improvement in evening PROs are shown in Table 111 below.

TABLE 111

Improvement in Evening PROs in Study D

| | | Adalimumab Arm | | |
|---|---|---|---|---|
| | | All Patients | Improvement difference | Improvement difference |
| PRO* | Baseline (S.D.) | Mean Change from Baseline at Week 12 (95% CI) | from placebo at Day 1 (95% CI) | from placebo over 14 days (95% CI) |
| Pt. Global | 50.1 (22.9) | −19.3 (−20.5 to −18.2) | 5.0 (2.4-7.7) | 6.1 (4.9-7.3) |
| Pain | 50.8 (23.8) | −20.2 (−21.4 to −19.1) | 5.7 (2.8-8.6) | 7.1 (5.9-8.4) |
| Function | 50.8 (23.7) | −19.5 (−20.6 to −18.3) | 5.5 (2.7-8.2) | 6.5 (5.3-7.7) |
| Fatigue | 55.8 (25.4) | −19.7 (−20.9 to −18.5) | 3.7 (0.8-6.5) | 4.7 (3.5-5.9) |
| Stiffness | 52.3 (25.9) | −25.6 (−27.0 to −24.3) | 4.3 (1.2-7.5) | 7.6 (6.3-9.0) |

*Mean values

TABLE 112

Improvements in e-Diary Assessments at Day 1

| | Mean Improvement from Baseline | | | | |
|---|---|---|---|---|---|
| | e-PaGA | Pain | Function | Fatigue | AM Stiffness Severity |
| Placebo | 0.9 | 1.1 | 1.4 | 2.0 | 3.5 |
| Adalimumab | 5.7* | 6.7* | 6.7* | 5.3* | 7.3* |

*p < 0.001 vs. placebo

TABLE 113

Improvement in e-Diary Assessments at Weeks 2 and 12

| | % Improvement | | | | |
|---|---|---|---|---|---|
| | e-PaGA | Pain | Function | Fatigue | AM Stiffness (Severity) |
| | Week 2 Double-blind period | | | | |
| Placebo Arm | −1.9 | −5.4 | −5.0 | −2.0 | 9.5 |
| Adalimumab Arm | 16.9* | 16.9* | 17.7* | 10.3* | 24.8* |
| | Week 12 Open-label period | | | | |
| Placebo Arm | 30.3 | 20.6 | 18.7 | 23.6 | 49.3 |
| Adalimumab Arm | 33.2 | 33.3 | 32.5 | 23.7 | 47.7 |

*p < 0.001 vs. placebo

In conclusion, statistically significant responses to ADA in patients with RA occurred very quickly after the first dose. Recognition of this rapid response was made possible by the use of an e-diary which allowed real-time data capture of PROs on a daily basis. Almost half of the overall benefit from ADA was observed during the first 14 days.

EXAMPLE 16

A Comparison of Patient and Physician Measures in Assessing Treatment Response in Rheumatoid Arthritis: Results from Study D In clinical trials and in clinical practice, many variables are used to capture treatment effect. Assessments used to detect the existence of treatment effect must have a strong effect size (ES). For assessments used to determine the magnitude of improvement, the "truth" of the measure is more important than the effect size. Truth is compromised when non-treatment effects contribute to the total treatment effect (Table 114). The true component is the effect attributable to treatment. The false components are placebo effect and the effects attributed to regression to the mean and to the natural course of illness; the latter effects are time dependent.

TABLE 114

Truth: Non-Treatment Effects Contribute to the Total Treatment Effect

| Effect | Received Treatment | Received Placebo |
|---|---|---|
| True Effect | Yes | No |
| Placebo Effect | Yes | Yes |
| Regression to the mean effect | Depends on duration | Depends on duration |
| Course of illness effect | Depends on duration | Depends on duration |

Long term observations in clinical trials typically do not allow for the regression to the mean and course of illness effects to be factored out, and these time-dependent effects cannot be separated from true placebo effect. Early assessments allow for only treatment and placebo effects to influence results.

The purpose of this study was to determine which variables best measure treatment effect. In Study D, the rapid improvement that occurs with anti-TNF therapy was used to evaluate response variables two weeks after starting adalimumab (ADA). Early assessments do not include improvement that may occur with time as a function of regression to the mean, leaving only treatment and placebo (PBO) effects to influence results.

Study D was a randomized, double-blind, PBO-controlled, multi-center, Phase IV study of ADA 40 mg every other week (wk) in patients (pts) with active RA, with emphasis on patient-reported outcomes (PROs) and early response. The study design is depicted in FIG. 21.

Patients were trained to use a Palm® OS-based e-diary to report on the following using a 0-100 visual analog scale (VAS): Patient's Global Assessment of disease activity (e-PaGA), pain, function, fatigue, morning stiffness (AM Stiffness), presence of AM stiffness, duration of AM stiffness (minutes), and severity of AM stiffness. During screening and the blinded first 2 weeks of the study, patients were prompted to complete 3 sets of reports per day (morning 5-10 AM, afternoon 2-4 PM, and evening 8-11:45 PM). Once patients were switched to open-label adalimumab at Week 2, they were prompted to complete only daily evening reports until the end of the study.

Patients received a blinded dose of study drug, followed by 10 weeks of open-label (OL) ADA at Week 2. Physician measures, C-reactive protein (CRP) and PROs were collected at baseline, Weeks 2, 4, and 12. Patient Activity Score (PAS) was based on Health Assessment Questionnaire (HAQ) disability score, pain on a visual analog scale (VAS) and patient global VAS. Week 2 blinded data was evaluated to determine how well each variable captured ADA or PBO effect.

This analysis evaluated early assessments from the Week 2 blinded data in order to determine how well selected variables could capture treatment (adalimumab) and placebo effects. Effect sizes (ES), for both placebo group and the adalimumab group, were determined by the following function: (Baseline score—Week 2 score)/pooled standard deviation. To assess magnitude of treatment effect, effect sizes (ES) (standardized responses) was calculated at Week 2 for PBO (ES[P]) and for ADA, labelled ES[T+P] was calculated as there is a true (T)

treatment effect and a PBO component (P) in each observed response. Kendall's Tau-a was calculated between type of treatment (ADA or PBO) and change in study variables. Variables with higher Tau-a scores have greater ability to detect treatment effect. The area under the Receiver Operating Curve (AUC), a standardized multivariable measure of treatment effect, was used to compare groups of variables.

In the ADA arm, ACR 20/50/70 response rates were 24/13/9 at Week 2 and 58/47/40 at Week 12. Greatest PBO effect (ES[P]) was found for DAS-28, physician global (MD global), VAS stiffness and tender joint count (TJC). Only CRP was without PBO effect. ADA treatment ES (ES [T+P]) was greatest for MD global, DAS-28 and VAS stiffness. The results are shown in Table 115.

TABLE 115

Magnitude of Treatment Effect

| Variable | Mean All pts. (Baseline) | Mean All pts (Week 12) | ES (T + P) (Week 2) | ES (P) (Week 2) | Tau-a (Week 2) |
|---|---|---|---|---|---|
| CRP (mg/dL) | 1.40 | 0.70 | 0.47 | −0.01 | 0.213 |
| PAS (0-10) | 5.07 | 2.99 | 0.54 | 0.16 | 0.142 |
| VAS Pain (0-10) | 5.79 | 3.22 | 0.60 | 0.17 | 0.139 |
| DAS-28 | 3.89 | 2.55 | 0.63 | 0.29 | 0.135 |
| VAS Stiffness (0-10) | 5.59 | 2.75 | 0.62 | 0.24 | 0.123 |
| Pt. Global (0-10) | 5.28 | 3.00 | 0.50 | 0.14 | 0.118 |
| MD Global (0-10) | 5.65 | 2.43 | 0.72 | 0.29 | 0.116 |
| HAQ-II (0-3) | 1.19 | 0.83 | 0.32 | 0.09 | 0.100 |
| MD HAQ (0-3) | 0.94 | 0.61 | 0.34 | 0.11 | 0.099 |
| HAQ (0-3) | 1.24 | 0.82 | 0.31 | 0.11 | 0.094 |
| VAS Fatigue (0-10) | 5.78 | 3.54 | 0.35 | 0.15 | 0.087 |
| SJC (0-28) | 9.70 | 4.46 | 0.41 | 0.21 | 0.085 |
| TJC (0-28) | 12.28 | 5.22 | 0.40 | 0.23 | 0.068 |
| VAS QOL (0-10) | 0.76 | 0.82 | −0.30 | −0.04 | −0.075 |
| FACIT Fatigue (0-52) | 28.07 | 34.82 | −0.35 | −0.14 | −0.078 |

A total of 1938 patients enrolled in Study D. This analysis evaluated data from 1891 patients who completed at least the baseline and Week 2 assessments. No significant differences existed between groups at baseline (see Table 116).

TABLE 116

Study D Baseline Demographics and Disease Characteristics

| Variable | Mean Adalimumab | SD | Mean Placebo | SD |
|---|---|---|---|---|
| N | 958 | | 933 | |
| Age (years) | 54.0 | 12.5 | 54.5 | 12.9 |
| Sex (% male) | 21.23 | | 23.0 | |
| Physician & Laboratory Measures | | | | |
| Physician global (0-10) | 5.6 | 2.0 | 5.7 | 2.1 |
| Swollen joint count (0-28) | 9.7 | 6.4 | 9.7 | 6.4 |
| Tender joint count (0-28) | 12.2 | 8.2 | 12.4 | 7.9 |
| CRP (mg/100 ml) | 1.4 | 2.3 | 1.4 | 2.1 |
| DAS28 | 3.9 | 1.0 | 3.9 | 1.0 |
| Patient Self-report Measures | | | | |
| PaGA (0-10) | 5.3 | 2.3 | 5.3 | 2.3 |
| Pain (0-10) | 5.7 | 2.4 | 5.9 | 2.4 |
| PAS (0-10) | 5.0 | 2.0 | 5.1 | 2.0 |
| VAS functional disability (0-10) | 5.2 | 2.3 | 5.3 | 2.3 |
| Fatigue (0-10) | 5.7 | 2.7 | 5.9 | 2.7 |
| Stiffness (0-10) | 5.6 | 2.6 | 5.7 | 2.6 |
| HAQ (0-3) | 1.2 | 0.6 | 1.3 | 0.6 |
| HAQ2 (0-3) | 1.2 | 0.6 | 1.2 | 0.6 |
| MDHAQ (0-3) | 0.9 | 0.5 | 1.0 | 0.5 |
| FACIT fatigue (0-52) | 28.4 | 10.0 | 28.0 | 9.7 |

The superior efficacy of adalimumab vs. placebo through Week 12 is evident in ACR 20/50/70 responses and improvements in e-diary patient assessments (see FIGS. 21 and 25). Effect size should be approximately 0 for placebo-treated patients if there is no placebo effect. CRP was the only variable without placebo effect (see Table 117). Adalimumab treatment ES were greatest for MD global, VAS stiffness and DAS28.

TABLE 117

Effect Sizes and Kendall's Tau-a at the End of the Double Blind Period (Week 2)

| Variable | Mean All patients (baseline) | Adalimumab Effect Size (Week 2) | Placebo Effect Size (Week 2) | Tau-a (Week 2) |
|---|---|---|---|---|
| CRP (mg/dL) | 1.40 | 0.47 | −0.01 | 0.21 (0.19-0.24) |
| PAS (0-10) | 5.07 | 0.54 | 0.16 | 0.14 (0.12-0.17) |
| VAS Pain (0-10) | 5.79 | 0.60 | 0.17 | 0.14 (0.11-0.16) |
| DAS-28 | 3.89 | 0.63 | 0.28 | 0.14 (0.11-0.16) |
| VAS Stiffness (0-10) | 5.59 | 0.62 | 0.24 | 0.12 (0.10-0.15) |
| Patient Global (0-10) | 5.28 | 0.50 | 0.14 | 0.12 (0.09-0.14) |
| MD Global (0-10) | 5.65 | 0.72 | 0.29 | 0.12 (0.09-0.14) |
| HAQ-II (0-3) | 1.19 | 0.32 | 0.09 | 0.10 (0.07-0.13) |
| MD HAQ (0-3) | 0.94 | 0.34 | 0.11 | 0.10 (0.07-0.13) |
| HAQ (0-3) | 1.24 | 0.31 | 0.11 | 0.09 (0.07-0.12) |
| VAS Fatigue (0-10) | 5.78 | 0.35 | 0.15 | 0.09 (0.06-0.11) |
| SJC (0-28) | 9.70 | 0.41 | 0.21 | 0.08 (0.06-0.11) |
| TJC (0-28) | 12.28 | 0.40 | 0.23 | 0.07 (0.04-0.9) |
| VAS QOL (0-10) | 0.76 | −0.30 | −0.04 | −0.08 (−0.05-(−)0.10) |
| FACIT Fatigue (0-52) | 28.07 | −0.35 | −0.14 | −0.08 (−0.05-(−)0.10) |

CRP is the best at distinguishing treatment effect.
Measures in bold are statistically indistinguishable.
Measures that are italicized are the poorest at distinguishing treatment effect.

Looking at the ratio of placebo ES to treatment ES, the variables with the greatest placebo ES were TJC, SJC, DAS28, VAS fatigue, and MD global (see Table 118). As assessed by Tau-a, the metrics that best distinguished treatment effects were CRP, PAS, VAS Pain, and DAS28 (Table 117). The addition of CRP to PAS (PAS+CRP) substantially improves the ability to detect treatment effect compared to DAS28 or PAS alone. The area under the curve (AUC) was 0.64 for either PAS or DAS-28. However, combining PAS+CRP increased the AUC to 0.71. However, when considering the confidence intervals, three groups were seen with respect to Kendall's Tau-a: 1) CRP was the best identifier of treatment effect; 2) variables that were statistically indistinguishable from each other (in bold); and 3) variables that were poorest in distinguishing treatment effect (italicized). CRP best distinguishes treatment effect, while physician-based variables perform worst at the end of a 2-week double blind period. However, at the end of the 12-week open-label period, overall effect sizes are greatest for MD Global (1.57), DAS-28 (1.28), VAS Stiffness (1.10), VAS Pain (1.04) and PAS (1.00) as the increasing effect of adalimumab treatment becomes recognized.

TABLE 118

Ratio of Placebo ES to Treatment ES

| | Percent |
|---|---|
| CRP | −2.1 |
| VAS QOL | 13.3 |
| Patient Global | 28.0 |
| HAQ-II | 28.1 |
| Pain | 28.3 |
| PAS | 29.6 |
| MD HAQ | 32.4 |
| HAQ | 35.5 |
| VAS Stiffness | 38.7 |
| FACIT Fatigue | 40.0 |
| *MD Global | 40.3 |
| *VAS Fatigue | 42.9 |
| *DAS28 | 44.4 |
| *Swollen Joint Count | 51.2 |
| *Tender Joint Count | 57.5 |

*Variables with greatest placebo effect size

In conclusion, physician and patient-based measures have PBO components that can limit their usefulness. At Week 2 of this study, certain pt-based measures were equal or superior to individual physician variables and DAS-28 in determining efficacy, due to increased PBO effect in physician measures. The PAS+CRP combination is an effective and less biased way to evaluate early improvement and appears to be suitable for clinical practice use.

EXAMPLE 17

HAQ and FACIT-F are Better Predictors of Societal Costs of Rheumatoid Arthritis than DAS28

Health economists and outcomes researchers are currently debating which patient-reported measures best predict clinical and health economic outcomes. Changes in HAQ scores for patients with RA have been shown to predict future disability, health-related quality of life (HRQoL), and long-term costs (Kobelt G, et al. Rheumatology. 2005; 44:1169-75). This analysis investigated the differences between several patient-reported outcomes (PROs) in predicting future costs and/or changes in HRQoL in RA. Adalimumab, a fully human monoclonal antibody targeting TNF, is approved for the treatment of rheumatoid arthritis, psoriatic arthritis, and ankylosing spondylitis in the United States, Europe, and elsewhere.

The objective of this analysis was to investigate the differences between several patient-reported outcomes (PROs) in predicting future costs and/or QOL in rheumatoid arthritis (RA).

This study analyzed data on 505 patients who had received adalimumab therapy during one of six Phase II/III studies (most patients under double-blind, randomized conditions for at least 26 weeks of treatment). These patients were enrolled in a long-term, open-label health economic extension study (40 mg adalimumab every other week) and followed for up to 144 weeks (FIG. 29). Patients and/or investigators were asked to fill out several HRQoL-related instruments at baseline and multiple time points during the study: Health Assessment Questionnaire (HAQ); Functional Assessment of Chronic Illness Therapy—Fatigue Scale (FACIT-F); Health Utilities Index (HUI3); and Short form-36 questionnaire (SF-36). Among other clinical outcomes, investigators assessed DAS28 at baseline and at multiple times during the study. In addition, patients and investigators were asked to document resource utilization during the study.

Two linear regression models were constructed: one to determine prognostic factors for health-related QOL and one to determine progressive factors for costs from a societal perspective, which included direct medical costs, indirect costs (lost productivity) and costs to the patient.

A correlation analysis using Spearman correlation coefficients was conducted for the following data at baseline: TJC68 (tender joint count based on 68 joints); SJC66 (swollen joint count based on 66 joints); DAS28 (modified disease activity score) Disease activity by patient on a visual analog scale (VAS); Pain VAS by patient Disease activity by physician; Morning stiffness; ACR-rank (ie, no response=0, ACR20=1, ACR50=2, ACR70=3). Using correlation analyses, the factors influencing HRQoL outcome and costs per patient were pre-examined. The analyses were performed on all major covariates to check for possible associations between the covariates. Any correlations between explanatory variables which achieved correlation coefficients of r=0.5 or higher were to be removed from the selected statistical model for the analysis of influences of medical parameters and effectiveness factors on HRQoL and costs.

The following HRQoL outcome variables were modeled separately for DAS28: Quality adjusted life year calculated for HUI values over time (QALY HUI), Area under the curve for HUI over time (AUC HUI), Area under the curve for FACIT-F (AUC FACIT), Area under the curve for SF-36 mental component score over time (AUC SF-36 MCS), Area under the curve for SF-36 physical component score over time (AUC SF-36 PCS), and Area under the curve for HAQ over time (AUC HAQ). The explanatory variable DAS28 or the clinical parameters (TJC, SJC, disease activity, pain, morning stiffness) were removed from the model if they did not show an influence on HRQoL outcome (p>0.1). Those variables with a p-value=0.1 were considered as prognostic or progressive in the final model. Models were calculated using SAS Software (SAS 8.2).

Number of previously failed DMARDs, mean age, RA duration, TJC and SJC clearly indicate the severity of RA in these patients (Table 119). Baseline patient characteristics were: female, 77%; age, 55 years; % working, 30.1%; working time in employed patients, 30.89 hours per week; duration of disease, 12.36 years; TJC (0-68), 14.58; SJC (0-66), 8.23; HAQ score, 1.15; DAS28 (0-10), 4.58; DMARDs failed, 3.7; and body mass index, 25.06 (all mean values except % gender, working). The correlation analysis of baseline data using Spearman correlation coefficients showed that all input parameters analyzed were statistically significantly correlated with each other (p<0.0001).

TABLE 119

Baseline Demographics and Disease Activity

| Variable | | Study 8 population (n = 505) |
|---|---|---|
| Female | n (%) | 390 (77.2) |
| Age (years) | median (range) | 55.0 (22-82) |
| Weight (kg) | Mean ± SD | 69.12 ± 12.90 |
| Height (cm) | Mean ± SD | 166.06 ± 8.90 |
| Caucasian | n (%) | 498 (98.6) |
| BMI (kg/m$^2$) | Mean ± SD | 25.06 ± 4.34 |
| Employed | n (%) | 152 (30.1) |
| Retired | n (%) | 220 (43.6) |

TABLE 119-continued

Baseline Demographics and Disease Activity

| Variable | | Study 8 population (n = 505) |
|---|---|---|
| RA duration | Mean ± SD | 12.36 ± 7.69 |
| No. of previous DMARDs failed | Mean ± SD | 3.7 ± 1.82 |
| TJC (0-68) | Mean ± SD | 14.58 ± 14.89 |
| SJC (0-68) | Mean ± SD | 8.23 ± 8.18 |
| DAS28 | Mean ± SD | 4.58 ± 1.58 |

The correlation analysis of baseline data using Spearman correlation coefficients showed that all input parameters analyzed were statistically significantly correlated with each other (p<0.0001). For each of the HRQoL variables, the DAS28 at baseline had an influence on the outcome of the respective HRQoL variable. In addition, RA duration, age, and professional status at baseline were determined as explanatory factors for HRQoL outcome. As for the progressive factors model, DAS28, RA duration, age, and professional status were determined as explanatory factors for the outcome of HRQoL variables in the analysis with DAS28 response (Table 120). For all HRQoL variables analyzed, DAS28 was the factor with the strongest influence on HRQoL outcome.

TABLE 120

Progressive HRQoL analysis with DAS28 Response - Generalized Linear Model (N = 505)

| | n | Progressive factors determined by stepwise regression | Pr > F |
|---|---|---|---|
| QALY HUI | 415 | DAS28 mean | <0.0001 |
| | | RA duration | 0.0012 |
| | | age | 0.0160 |
| AUC HUI | 344 | DAS28 mean | <0.0001 |
| | | RA duration | 0.0797 |
| | | professional status | 0.0140 |
| AUC FACIT | 422 | DAS28 mean | <0.0001 |
| AUC SF-36 physical component score | 443 | DAS28 mean | <0.0001 |
| | | RA duration | 0.0235 |
| | | age | 0.0830 |
| | | professional status | 0.0065 |
| AUC SF-36 mental component score | 456 | DAS28 mean | 0.0006 |
| AUC HAQ | 456 | DAS28 mean | <0.0001 |
| | | RA duration | <0.0001 |
| | | professional status | <0.0001 |
| | | sex | <0.0001 |

AUC = area under the curve, DAS28 = Modified Disease Activity Score 28, DMARD = Disease Modifying Anti-Rheumatic Drug, n = observations used for the analysis, SF 36 = Short form-36 questionnaire, SS = sum of squares.

Pr > F represents the p-value, i.e. the probability (Pr) that SS is greater than the quantil of an F-distribution (F).

The results for the progressive cost analyses are summarized in Table 121. Since the explanatory variables that were used in the model (AUC HAQ, AUC FACIT, and DAS28) were all strongly correlated with each other, it was decided to analyze separate models, based on just one independent variable each. The analysis shows that the costs for RA from the societal perspective are strongly influenced by the outcome variables. AUC HAQ and AUC FACIT (p<0.01) however, are not strongly influenced by the clinical variable DAS28 over time (p>0.1).

TABLE 121

Progressive cost analysis

|  | n | Progressive factors determined by stepwise regression | Pr > F |
|---|---|---|---|
| Costs from societal perspective | 505 | AUC HAQ | 0.0007 |
| Costs from societal persective | 463 | AUC FACIT | <0.0001 |
| Costs from societal perspective | 461 | DAS28 | 0.1493 |

Pr > F represents the p-value, i.e. the probability (Pr) that SS is greater than the quantil of an F-distribution (F).

Based on the correlation analysis, the DAS 28 at baseline was chosen as the most representative factor for the correlated parameters. The first model showed that, for each of the QOL variables, the DAS28 at baseline had an influence on the outcome of the respective variable. The second model on costs showed that the costs for RA from the societal perspective were strongly influenced by HAQ and FACIT-F values (p<0.001). However, they were not strongly influenced by the DAS28 score (p>0.1).

In this observational study over 3 years, the DAS28 has proven to be an important tool in predicting QOL in patients with severe RA. However, HAQ and FACIT-F are better predictors of long-term societal costs, and RA patients with unmitigated fatigue are costly to treat in the long term.

EXAMPLE 18

Treatment with Adalimumab (HUMIRA®) is Well-Tolerated and Efficacious in Patients with Active RA in Various Age Groups Including Patients with Late-Onset RA—Subanalysis of 6610 Patients in Study A Limited data exist about the impact of age on safety and efficacy of anti-TNF therapy in patients with active RA. The recently completed Study A provides a large database to examine this question.

Adults aged=18 with active RA and prior insufficient response to disease-modifying antirheumatic drugs (DMARDs) received adalimumab (ADA) 40 mg sc every other week for 12 weeks in Study A, with an optional extension phase until ADA was commercially available. Efficacy and routine safety evaluations were conducted at Weeks 2, 6, and 12, and every 8 weeks thereafter. Efficacy outcomes were analyzed by 4 age groups and by late-onset RA [RA beginning at age>60 yrs (LORA)] at Week 12. Adverse events (AE) were collected throughout the entire treatment period (up to a maximum of 96 weeks).

Baseline characteristics in patients of age (n)<40 yrs (1,002), 40-<65 yrs (4,125), 65-<75 yrs (1,245), and =75 yrs (238) varied with increasing values from young to elderly in means of disease duration (7-14 yrs), disability index of the Health Assessment Questionnaire (HAQ) (1.45-2.00 units), Disease Activity Score 28 (DAS28) (5.8-6.3), percentage of patients receiving steroids (68-77%), and percentage receiving adalimumab monotherapy (24-35%). Co-morbidities were more frequent with increasing age and contributed to occurrences of AEs. With respect to the LORA-group the mean baseline HAQ was 1.64 in 266 pts with disease duration=3 yrs and 1.76 in 492 pts with disease duration>3 yrs. Respective DAS28 values were 6.3 and 6.2. Overall, the mean exposure to ADA was 233 days, up to a maximum of 96 weeks. Key efficacy outcomes at Week 12, withdrawal rates, and safety results for the complete treatment period are presented (Table 122). Except for ACR20, all efficacy values continued to improve beyond Week 12 in all age groups. Patients with LORA of short duration achieved better results than patients with LORA>3 yrs.

TABLE 122

Adalimumab Efficacy and Safety by Age Group and Disease Duration for Late-Onset RA

|  | Age < 40 yrs n = 1002 | Age 40-<65 yrs n = 4125 | Age 65-<75 yrs n = 1245 | Age = 75 yrs n = 238 | LORA = 3 yrs n = 266 | LORA > 3 yrs n = 492 |
|---|---|---|---|---|---|---|
| Efficacy at Week 12 |  |  |  |  |  |  |
| ACR20 (%) | 74 | 68 | 68 | 61 | 75 | 63 |
| ACR50 (%) | 49 | 40 | 35 | 35 | 44 | 34 |
| ACR70 (%( ) | 26 | 18 | 15 | 12 | 21 | 12 |
| Mean Change in DAS28* | −2.3 | −2.1 | −2.1 | −1.9 | −2.3 | −2.0 |
| Mean Change in HAQ* | −0.61 | −0.54 | −0.48 | −0.37 | −0.59 | −0.43 |
| Total withdrawals[†] |  |  |  |  |  |  |
| Due to loss of efficacy (%) | 7 | 7 | 6 | 6 | 5 | 6 |
| Due to AE (%) | 8 | 10 | 13 | 19 | 9 | 17 |
| Safety, complete period[†] |  |  |  |  |  |  |
| Pts with Severe AE (%) | 5.9 | 8.4 | 12.1 | 16.0 | 9.8 | 12.6 |
| Pts with Serious Infection (% pts) | 2.2 | 2.6 | 4.8 | 5.9 | 3.4 | 4.5 |

Observed values *p < 0.001.
[†]Up to a maximum of 96 weeks.

Adalimumab led to clinically significant improvement in disease activity and physical function in all age groups and patients with LORA. Adalimumab was generally well-tolerated with an expected increase of severe AEs in pts of higher age. The benefit-risk ratio in elderly patients was generally positive.

EXAMPLE 19

Disease Activity and Physical Function Improve Significantly in Most Patients with RA Receiving Adalimumab for Up to 6 Years Irrespective of ACR20 Response Significant improvements in disease activity and physical function have been demonstrated in a majority of patients with RA treated with adalimumab plus methotrexate (MTX) in randomized clinical trials (RCTs) and open-label extension studies. Although the ACR response rate is a key measure of therapeutic efficacy in RCTs, it is unclear what clinical benefits are achieved by patients on long-term therapy who do not reach ACR20 responses.

The objective of this study was to determine, in an open-label extension study of adalimumab and MTX, the extent to which there were significant improvements in various aspects of disease activity in patients who did not fulfill ACR20 response criteria.

Patients enrolled in Study I, Study 1, Study K, Study 6, and Study 7 RCTs were eligible to enter an extension study of adalimumab 40 mg eow sc and MTX. Efficacy and safety were evaluated in all patients' last visits for up to 6 years, including those who withdrew for any reason. The clinical characteristics of patients who did or did not achieve an ACR20 response and who continued or did not continue on long-term treatment were evaluated.

Of 1465 patients treated with adalimumab plus MTX for up to 6 years (mean±SD exposure of 45±24 months), 64%, 43% and 25% achieved ACR20, 50 and 70 responses, respectively, at their last visits. The remission parameters at last visit were DAS28<2.6: 34%; TJC68=0: 24%; SJC66=0: 23%; and HAQ=0: 20%. Rates and types of adverse events of all patients (5501 patient-years) were consistent with previous reports. The ACR20 non-responders were categorized as follows: 1) patients who continued in the study; 2) patients who discontinued (d/c) because of AEs or other reasons; and 3) patients who d/c because of lack of efficacy (LOE). Despite the lack of ACR20 response, the first two categories showed significant improvements in DAS28 and most of the core components of the ACR index (Table 123). Baseline characteristics were similar between all groups.

In conclusion, Adalimumab plus MTX induced sustained ACR20 response in 64% and remission in >20% of patients treated for up to 6 years. Patients not meeting the ACR20 response criteria who either continued on long-term adalimumab therapy or withdrew for reasons other than inefficacy showed significant improvements in individual facets of disease activity, including functional status.

EXAMPLE 20

Remission and Major Clinical Response in Patients with Active Rheumatoid Arthritis (RA) after Treatment with Adalimumab (HUMIRA®)

Concepts of improvement and current disease state are important to consider. While it is important to show how much RA patients have improved with therapy, it is even more important to demonstrate that they have achieved very low degrees of disease activity, including remission (Dougados M. *J Rheumatol* 2006; 32:1-2). Since the advent of tumor necrosis factor (TNF) antagonists, clinical remission has become a reachable treatment goal for patients with RA.

The objective of this study was to investigate the effectiveness of adalimumab treatment measured by five selected clinical remission criteria or MCR in relation to baseline and treatment characteristics, respectively, in a large RA population.

Since the introduction of TNF antagonists, clinical remission activity and a major clinical response (MCR) have become attainable therapeutic goals for patients with active RA. Different definitions of clinical remission have been provided by EULAR, ACR, and the FDA. We determined the proportions (%) of patients who participated in the recently completed Study A and who achieved remission or MCR using several criteria.

Methods
  Patients with active RA and prior disease modifying antirheumatic drug (DMARD) therapy enrolled in the Study A trial (see FIG. 1 for study design)
    Adalimumab was administered (40 mg every other week [eow] sc) for 12 weeks in addition to current antirheumatic therapy
    Patients optionally continued therapy until adalimumab was commercially available
    Effectiveness and safety evaluations were conducted at Weeks 2, 6, 12, and every 8 weeks thereafter
  Inclusion criteria included
    Age=18 years
    RA (defined by American College of Rheumatology criteria) for =3 months

TABLE 123

Last Visit Outcomes in ACR20 Responders and Non-Responders (NR) to Adalimumab Plus MTX

|  | Patients % (n) | TJC68* | SJC66* | Patient Global* | Physician Global* | HAQ* | CRP* | DAS28 |
|---|---|---|---|---|---|---|---|---|
| Baseline | 100 (1465) | 28 | 20 | 53 | 59 | 1.4 | 18 | 5.7 |
| Responders | 64 (937) | 5† | 4† | 20† | 14† | 0.7† | 8† | 2.8† |
| NR Continued | 15 (226) | 16† | 11† | 41† | 29† | 1.1† | 10‡ | 4.1† |
| NR d/c, AE, Other | 15 (213) | 20† | 13† | 51 | 40† | 1.4† | 15 | 4.6† |
| NR d/c, LOE | 6 (89) | 28 | 19 | 64 | 56‡ | 1.6 | 22 | 5.6 |

*Mean values.
†P < 0.001,
‡P < 0.01, vs. baseline in same category.

Unsatisfactory response or intolerance to at least one prior DMARD

Active RA defined as Disease Activity Score 28 (DAS28)=3.2

Five different criteria defining clinical remission in RA were used. The percentage of patients was calculated who achieved:

DAS28<2.6 based on ESR (Fransen J, et al. *Rheum* 2004; 43:1252)

Simplified Disease Activity Index (SDAI)<5 or SDAI≤3.3 (Aletaha D and Smolen J. *Clin Exp Rheumatol* 2005; 23(suppl 39):S100)

Clinical Disease Activity Index (CDAI)≤2.8 (Aletaha D and Smolen J. *Clin Exp Rheumatol* 2005; 23(suppl 39):S100)

Tender+Swollen Joint Count (TJC+SJC)=0

TJC+SJC+normal ESR first hour (defined as <20 mm in men and <30 in women) (Mäkinen H, et al. *Ann Rheum Dis* 2005, 64:1410)

Major Clinical Response

ACR70 response for ≥6 continuous months (www.fda.gov) in patients who continued up to Week 52

Time points for calculation of clinical remission (DAS28<2.6, SDAI≤3.3, CDAI≤2.8, TJC+SJC=0, TJC+SJC+normal ESR) at:

Week 12

Individual last observed value (mean treatment duration, 7 months)

Any time during the entire treatment phase

Two subsequent time-points at least 6 weeks apart.

The number of patients with available values at different time-points was used to calculate percentages Further subanalysis for DAS28<2.6 remission criteria by baseline categories:

DAS28 (categories:=5.1, >5.1)

Health assessment questionnaire disability index (HAQ DI) (categories: <1.0, 1.0-<1.5, 1.5-<2.0, >2.0)

Concomitant DMARD therapy (yes, no)

Generally, adults with active RA despite therapy with disease-modifying antirheumatic drugs (DMARDs) received adalimumab (ADA) 40 mg sc every other week for 12 weeks in the ReAct trial, with an optional extension phase until ADA was commercially available. Efficacy and routine safety evaluations were conducted at Weeks 2, 6, and 12, and every 8 weeks thereafter. Criteria for remission were Disease Activity Score (DAS28)<2.6; tender and swollen joint counts (TJC, SJC)=0, alone or in addition to a normal ESR (ESR<20 (male) or <30 (female) mm/1$^{st}$ hour; ACR70 and SDAI (Simplified Disease Activity Index)<5 measured at Week 12, at last observation, and at any time during the treatment period. Maintenance of remission was evaluated by two subsequent time points with an interval of at least 6 weeks. For pts who received ADA therapy for at least 52 weeks, the proportion who fulfilled ACR70 for 6 months was calculated (MCR). Data were stratified by baseline (BL) DAS28 and by concomitant DMARDs.

Results

Clinical study Results:

6,147 (93%) of 6,610 patients remained in ReAct through Week 12

A great percentage of patients (79%) remained in treatment up to a maximum of 96 weeks Mean treatment duration was 7 months

TABLE 124

| Baseline characteristics | |
|---|---|
| Total patients enrolled in Study A | 6,610 |
| Age (years) | 54 |
| Female (%) | 71 |
| Rheumatoid factor + (%) | 73 |
| Disease duration (years) | 11 |
| # of prior DMARDs | 3 |
| DAS28 | 6.0 |
| HAQ DI | 1.64 |
| TJC28 | 14 |
| SJC28 | 10 |

*Mean values of continuous data.

Of 6,610 patients enrolled, 81% were female, 73% were RF+, 74% were receiving concomitant (concom) DMARDs; and 71% were receiving steroids. Mean baseline characteristics included age, 54 yrs; disease duration, 11 yrs; DAS28, 6.0; and HAQ, 1.64 (Table 124). The mean exposure to ADA was 233 days, up to a maximum of 96 weeks. The number of participants decreased over time because of regular termination or withdrawals. Based on available joint count data, there were 6,235 pts at Week 12; 4,119 at Week 28, and 3,021 at Week 36. Of 1,251 pts at Week 52, 164 (13%) had sustained ACR70 without interruption for at least 6 months (MCR).

TABLE 125

Proportion (%) of Patients in Remission or with Continuous Good Clinical Response (Observed Values)

| | Week 12 | Last Observation | Any Time | 2 Consecutive Visits* |
|---|---|---|---|---|
| All patients (6,610)† | | | | |
| DAS28 < 2.6 | 20 | 25 | 38 | 21 |
| TJC + SJC = 0 | 12 | 19 | 30 | 16 |
| TJC + SJC = 0, normal ESR | 10 | 15 | 25 | 12 |
| ACR70 (%) | 18 | 25 | 38 | 21 |
| SDAI < 5 | 18 | 24 | 35 | 19 |
| DAS28 < 2.6 by BL subgroups (n†) | | | | |
| DAS28 = 5.1 (1,282†) | 40 | 44 | 63 | 40 |
| DAS28 > 5.1 (5,328†) | 15 | 21 | 32 | 16 |
| No concom DMARDs (1,731†) | 13 | 18 | 28 | 14 |
| =1 concom DMARDs (4879†) | 22 | 28 | 42 | 24 |

*At least 6 weeks apart
†Baseline n only; denominators by time point are not shown.

As shown in Tables 125-127, the percentages of patients (%) who achieved clinical remission increased beyond Week 12, irrespective of the assessment method. Nearly one-third of the patients achieved remission using various definitions during the adalimumab treatment phase (Table 127). Greater percentages of patients with low HAQ DI scores at baseline achieved and maintained a DAS28<2.6 compared to patients who were more disabled at study entry (Table 128). About half of the patients with a baseline HAQ DI of 1.0-≤1.5 experienced clinical remission during the Study A study (Table 128). A greater percentage of patients with lower DAS28 at baseline (DAS28≤5.1) achieved and maintained remission status compared to patients who had high disease activity (DAS28>5.1) at all time-points (Table 129). A greater percentage of patients with concomitant DMARD(s)

achieved and maintained remission status compared to patients treated with adalimumab monotherapy at all timepoints (Table 130).

TABLE 126

Percentages of Patients Achieving Clinical Remission at Week 12 and at Last Observed Time Point

| | % of Patients | |
|---|---|---|
| | Week 12 | LV |
| DAS28 < 2.6 | 20 | 25 |
| SDAI = 3.3 | 11 | 16 |
| CDAI = 2.8 | 11 | 17 |
| TJC + SJC = 0 | 12 | 19 |
| TJC + SJC = 0; ESR normal | 10 | 15 |

LV = last observed value

TABLE 127

Percentages of Patients Achieving Clinical Remission During Adalimumab Treatment

| | % of Patients | |
|---|---|---|
| | Remission at Any Time | Continuous Remission = 6 Weeks Apart |
| DAS28 < 2.6 | 38 | 21 |
| SDAI = 3.3 | 24 | 12 |
| CDAI = 2.8 | 27 | 14 |
| TJC + SJC = 0 | 30 | 16 |
| TJC + SJC = 0; ESR normal | 25 | 12 |

TABLE 128

Percentages of Patients with DAS28 < 2.6 During Adalimumab Treatment in Relation to Baseline HAQ DI

| | % of Patients | | | |
|---|---|---|---|---|
| | HAQ DI < 1.0 (n = 1034) | HAQ DI 1.0-<1.5 (n = 1275) | HAQ DI 1.5-<2.0 (n = 1603) | HAQ DI = 2.0 (n = 2,118) |
| Week 12 | 33 | 26 | 17 | 12 |
| Any time | 58 | 47 | 37 | 25 |
| Twice subsequently | 37 | 27 | 19 | 11 |

Anytime = remission measured any time during the treatment period.
Twice subsequently = maintenance of remission was evaluated by two subsequent time points with an interval of at least 6 weeks.

TABLE 129

Percentages of Patients with DAS28 < 2.6 During Adalimumab Treatment in Relation to DAS28 at Entry

| | % of Patients | |
|---|---|---|
| | DAS28 = 5.1 (n = 1266) | DAS28 = 5.1 (n = 5207) |
| Week 12 | 40 | 15 |
| Any time | 63 | 32 |
| Twice subsequently | 40 | 16 |

Anytime = remission measured any time during the treatment period.
Twice subsequently = maintenance of remission was evaluated by two subsequent time points with an interval of at least 6 weeks.

TABLE 130

Percentages of Patients with DAS28 < 2.6 During Adalimumab Treatment in Relation to Concomitant DMARD Use

| | % of Patients | |
|---|---|---|
| | 0 Concomitant DMARD (n = 1672) | =1 Concomitant DMARD(s) (n = 4801) |
| Week 12 | 13 | 22 |
| Any time | 28 | 42 |
| Twice subsequently | 14 | 24 |

Anytime = remission measured any time during the treatment period.
Twice subsequently = maintenance of remission was evaluated by two subsequent time points with an interval of at least 6 weeks.

More than ⅓ of the patients achieved a DAS28<2.6 at any time during therapy, and more than ⅕ had sustained remission based on DAS28 or ACR70 in 2 consecutive visits. Nearly ⅔ of patients with a DAS28=5.1 at study entry experienced clinical remission.

Of 1,251 patients treated with adalimumab for 52 weeks during the Study A trial, 164 (13%) patients achieved a major clinical response, which is an ACR70 response for ≥6 continuous months.

In conclusion, in a large cohort of patients with long-standing, active RA in real-life clinical practice, adalimumab provided clinical remission in a substantial percentage of patients, irrespective of the assessment method. To similar degrees, remission was observed across different definitions of clinical remission and maintained up to Week 12 and at last observed time point. The percentages of patients who experienced clinical remission were greater with adalimumab/DMARD combination therapy vs. adalimumab monotherapy. Less-disabled RA patients with moderate disease activity had a better chance of achieving clinical remission. Despite established and long standing RA, adalimumab therapy led to clinical remission or continuous good clinical response in a considerable proportion of patients even in a real life setting.

EXAMPLE 21

Adalimumab Clinical Trial Safety in Multiple Indications and Reduction in Mortality in Rheumatoid Arthritis The objective of this study was to evaluate the safety of adalimumab (ADA) in global clinical trials for multiple indications.

Safety data were routinely collected in all ADA clinical trials for various diseases (Table 131). Rates of serious adverse events (SAE) of interest to physicians prescribing anti-TNF therapy were assessed per 100 patient-years (E/100PY). These rates were compared to previously reported rates in ADA RA clinical trials.

TABLE 131

Adalimumab Clinical Trials and Studies

| Indication | Clinical Trials Included |
|---|---|
| RA | Rheumatoid arthritis clinical trials: All Phase I-III randomized controlled trials (RCTs), open-label extensions (OLE), and OL Phase IIIb clinical trials, except the early RA trial |
| PsA | Psoriatic arthritis clinical trials: a 24-wk Phase III RCT in NSAID non-responders, a 12-wk Phase III |

TABLE 131-continued

Adalimumab Clinical Trials and Studies

| Indication | Clinical Trials Included |
|---|---|
| | study in DMARD non-responders, an OLE for completers of the 2 studies |
| AS | Ankylosing spondylitis clinical trials: 2 ongoing Phase III multicenter studies in US, EU, and Canada, each composed of a 24-wk RCT phase and an 80-wk OLE |
| Ps | Psoriasis clinical trials: a 12-wk Phase II RCT and 48-wk OLE |
| JIA | Juvenile idiopathic arthritis clinical trials: the 16-wk OL lead-in and 32-wk RCT phases of a multicenter Phase III randomized, double-blind stratified parallel-group study in children with polyarticular JIA |
| CD | Crohn's disease clinical trials: 4 Phase II/III multicenter RCT trials and an OLE |

As of Apr. 15, 2005, the ADA RA clinical trial safety database included data for 10,050 patients (12,506 PY) of ADA exposure (Schiff M H, et al. Ann Rheum Dis 2006; doi:10.1136/ard.2005.043166). Serious infection rate (5.05/100PY) was comparable to that reported on Aug. 31, 2002 (4.9/100PY) and to published reports of anti-TNF naïve RA populations (Singh G, et al. Arthritis Rheum 1999; 42(Suppl): S242 and Doran M F, et al. Arthritis Rheum 2002; 46:2287-9). Table 132 summarizes the number of patients, PY of exposure and rates of SAE of interest for ADA-treated patients in multiple indications. In RA clinical trials, the calculated standardized mortality ratio of 0.67 (95% CI, 0.53-0.83) was much lower than previously reported for the RA population prior to the advent of anti-TNF therapy (Gabriel S E, et al. Arthritis Rheum 2003; 48(1):54-58 and Wolfe F, et al. Arthritis Rheum 1994; 37(4):481-94).

TABLE 132

Serious Adverse Events of Interest (E/100PY)

| Indication | RA[1] | PsA | AS | Ps | JIA | CD |
|---|---|---|---|---|---|---|
| Exposure (PY) | 12,506 | 484 | 423 | 135 | 99 | 1506 |
| Patients (N) | 10,050 | 395 | 393 | 142 | 171 | 1459 |
| Serious Infections | 5.05 | 2.07 | 1.18 | 0.74 | 4.04 | 5.98 |
| Tuberculosis | 0.27 | 0.00 | 0.00 | 0.00 | 0.00 | 0.20 |
| Lymphomas | 0.12 | 0.41 | 0.24 | 0.00 | 0.00 | 0.07 |
| Demy-elinating Disease | 0.08 | 0.00 | 0.00 | 0.00 | 0.00 | 0.13 |
| SLE/Lupus-like Syndrome | 0.10 | 0.00 | 0.00 | 0.00 | 0.00 | 0.07 |
| CHF | 0.28 | 0.00 | 0.00 | 0.00 | 0.00 | 0.00 |

In conclusion, adalimumab therapy showed consistent safety profiles in global clinical trials for TNF-mediated diseases. SAE rates of interest did not differ significantly across these clinical trials in multiple indications. In RA clinical trials, evidence suggests a decrease in mortality in adalimumab-treated patients compared to a sex and age matched non-RA population.

EXAMPLE 22

Screening Outcomes for Latent TB in Worldwide Adalimumab Clinical Trials

TNF is important in granuloma formation and homeostasis during *Mycobacterium tuberculosis* (TB) infection.[1] TNF-deficient animals produced by TNF gene knockout[2] or by administration of TNF antagonists[3,4] cannot develop or maintain granulomas, and mycobacterial infections result. TB cases have been reported following treatment with each of the three TNF antagonists. 5-8 Screening for TB infection is recommended for patients who receive anti-TNF therapy[9]. Isoniazid (INH) is used for treatment and prophylaxis of active TB.

The objective of the following study was to assess the incidence of TB cases in adalimumab clinical trials and the effectiveness of isoniazid (INH) and other prophylaxis in preventing reactivation in high-risk patients, and to evaluate the effect of screening on the incidence of TB in adalimumab clinical trials and the effectiveness of INH in preventing reactivation of latent TB in high-risk patients Patients with RA, AS, CD, PsA, and Ps participated in many Phase II, III, IIIb, and open-label extension adalimumab clinical trials. Data were collected from these previous trials, and reviewed for the incidence of TB and effectiveness of isoniazid (INH) prophylaxis in preventing TB reactivation in high-risk patients. TB rates for rheumatoid arthritis (RA), ankylosing spondylitis (AS), Crohn's disease, psoriatic arthritis (PsA), and psoriasis (Ps) were calculated for the periods before screening (primarily Phase I) and after screening. Screening included clinical interviews, PPD tests (PPD+ defined by local/country-specific guidelines), and chest X-rays (most patients). Overall TB rates were calculated prior to implementation of TB screening (pre-screening), and after implementation of TB screening (post-screening). INH or other prophylaxis was given for PPD+ and LTB-reactivation high-risk patients (investigator identified).

TB screening methods varied by location and generally followed local/country-specific guidelines at the discretion of individual investigators. These included one or more of the following: clinical interviews/patient histories; tuberculin skin test with purified protein derivative (PPD); and chest X-ray.

Incidence of TB in the Research in one of the large, open-label, Phase IIIb adalimumab trials for RA was evaluated (Study A). Study A provided a unique perspective on the effectiveness of TB screening, as the trial was one of the largest clinical trials using a TNF antagonist and was designed to follow real-life clinical practice. In Study A, patients with active RA received adalimumab 40 mg subcutaneous every other week (eow) for 12 weeks. Patients could elect to enter an extension phase and receive adalimumab until it was commercially available to them. Upon enrollment, all patients were screened by various methods for TB. Study A patients at high-risk for latent TB reactivation (identified by investigators) were administered INH (5 mg/kg/d×9 months, max. 300 mg/d). A total of 6,610 patients were enrolled in Europe and Australia, where the incidence of TB is more prevalent than other countries Differences in adalimumab clinical trials before and after TB screening was implemented are shown in Table 133.

TABLE 133

Characteristics of Adalimumab Clinical Trials Pre- and Post-Implementation of TB Screening

| Pre-Screening* | Post-Screening* |
|---|---|
| Phase I and early Phase II studies | Phase II-IIIb studies |
| Dose finding studies; many patients received >40 mg eow | Most received 40 mg eow sc dosing |

TABLE 133-continued

Characteristics of Adalimumab Clinical Trials Pre- and Post-Implementation of TB Screening

| Pre-Screening* | Post-Screening* |
|---|---|
| Patients from Europe | Geographically diverse: patients From North America, Europe and Australia |

*Pre-screening-prior to implementation of TB screening; Post-screening-after implementation of TB screening The number of patients and total years of exposure to adalimumab were greater in Europe and Australia than North America. Adalimumab exposure in clinical trials by region included the following (Table 134):

TABLE 134

|  | Patients n (%) | Exposure PYs (%)* |
|---|---|---|
| North America | 5,501 (39%) | 8,397 (48%) |
| Europe and Australia | 8,451 (61%) | 9,161 (52%) |

Across all indications from worldwide adalimumab clinical trials, implementation of screening procedures resulted in an approximately 82% reduction in the incidence of TB cases. The impact of screening on TB rates (based on 17,870 PYs from worldwide adalimumab clinical trials) saw an 82% decrease in the number of events per 100-PY. Pre-screening showed 8 cases in 534 exposures (PYS), resulting in 1.5 events per 100-PY (events per 100-PY included cases for which screening was not performed because of enrollment in early Phase I/II clinical trials before implementation of TB screening). Post-screening identified 46 cases in 17,336 exposures (PYs), resulting in 0.27 events per 100-PY.

Differences in TB rates between North American and Europe/Australia after screening was implemented: there were 0.04 events per 100-PY in North America (6 cases in 8,397 exposures (PYs), while there were 0.32 events per 100-PY in Europe and North America (29 cases in 9,161 exposures (PYs). This data was based on 17,558 exposure PYs in North America, Europe, and Australia (excluding PYs from patients in Asia). For the TB cases that occurred after screening procedures were implemented, the incidence was approximately 8-fold higher in Europe and Australia compared with North America.

Of the 54 total TB cases observed in adalimumab clinical trials examined in the study, 30 (56%) were culture positive and 33 (61%) were extrapulmonary disease cases. All cases resolved, as described below in Table 135.

TABLE 135

Summary of Cases Observed

| Total cases | 54 |
|---|---|
| Culture positive | 30 (56%) |
| Mean age | 59 years |
| Extrapulmonary | 33 (61%) |
| Median days from treatment to diagnosis (range) | 232 days (29-1,636) |
| Outcome resolved | 54* |

Data through November 2005. Based on 17,558 PYs from adalimumab clinical trials in North America, Europe, and Australia.
*Three patients died; two of unrelated causes and the third refused treatment for TB.

Study A was an open-label adalimumab trial with 6,610 RA patients, and provided insight into the effective management for reactivation of latent TB in patients receiving anti-TNF therapy. At enrollment, all patients were screened for latent TB using various methods. Screening identified high-risk patients for which INH prophylaxis was required. 16.4% of ReAct patients had positive PPD skin tests (=5 mm), whereas only 3% exhibited abnormal chest X-rays. Results of TB screening in Study A (based on 6,610 patients from Europe and Australia) included the following: PPD (≥10 mm), 11.6% positive and 88.4% negative; PPD (≥5 mm), 16.4% positive and 83.6% negative; and chest x-ray, 3% abnormal and 97% normal.

Only 5 out of 835 (0.60%) RA patients from Study A who received INH prophylaxis developed TB* (Table 136) (*The number of patients who developed TB is lower than a previously reported study (Ferebee S H. *Bibl Tuberc* 1970; 26:28-106). Reasons for INH prophylaxis are also presented in Table 136. The range of time between initiation of INH prophylaxis and adalimumab treatment varied greatly from 0 days to >43 days (Table 136).

TABLE 136

INH Prophylaxis in ReAct

| 835 RA Patients Received INH | Time Between Initiation of INH and Adalimumab |
|---|---|
| PPD positive: 621 (74.4%) | 0-14 days 4.5% |
| With chest X-ray indicative of past TB: 121 (14.5%) | 15-28 days 22.3% |
| With both abnormal: 76 (9.1%) | 29-42 days 50.2% |
| Other reasons: 17 (2.0%) | >43 days 23.0% |

Based on 6,610 patients from Europe and Australia. Compliance was not measured.

Three cases of TB were reported in CD patients. No cases of TB were reported among adalimumab-treated patients with AS, PsA, or Ps.

To summarize the results, 14,563 patients (17,870 patient-years [PYs] of exposure) were treated with adalimumab in clinical trials (8,397 PYs [NA] and 9,161 PYs [Europe]). Before screening, there were 8 TB cases in 534 PYs (0.015/PY). None of these patients received prophylaxis. After screening there were 46 TB cases in 17,336 PYs (0.0027/PY). Six were in NA (0.00047/PY), and 29 were in Europe (0.0032/PY). No patients who received adalimumab for Ps, PsA, or AS developed TB at this cutoff. Median time to TB development (in days) was 232 (range: 29-1,636). There were 30/54 (56%) culture-confirmed cases, and 33/54 (61%) extrapulmonary disease cases. The ratio of TB prior to screening to after screening represents an 82% reduction in TB development rate. In a subanalysis of 6,610 European patients screened uniformly, 12% and 16% were classified as PPD+ by=10-mm and 5-mm induration cutoffs. A total of 835 high-risk patients were identified (most were PPD+) and received INH prior to the study drug. Five patients (1%) developed TB despite INH prophylaxis.

In conclusion, TB screening resulted in substantial reduction in a LTB reactivation rate. TB rates were approximately seven-fold lower in NA than in Europe. Patients identified as high-risk for TB, and given prophylaxis prior to adalimumab treatment, rarely had LTB reactivation. Prior to initiation of any TNF antagonist, all patients should be screened for LTB. Incidence of TB reactivation decreased by approximately 82% in adalimumab clinical trials when TB screening was implemented. PPD status was positive in 16.4% of the ReAct patient population, whereas chest X-rays were abnormal in only 3% of patients. No cases of TB were reported in patients with AS, PsA, or Ps. INH prophylaxis was effective in preventing reactivation of latent TB in 99.4% of ReAct patients who received anti-TNF therapy.

1. Flynn J L, et al. *Annu Rev Immunol* 2001; 19:93-129.
2. Smith S, et al. *Infect Immun* 2002; 70:2082-2089.

3. Flynn J L, et al. *Immunity* 1995; 2:561-572.
4. Garcia I, et al. *Eur J Immunol* 1997; 27:3182-3190.
5. Keane, et al. *New Engl J Med* 2001; 345:1098-1104.
6. Mohan, et al. *Clin Infect Dis* 2004; 39:295-299.
7. Gomez-Reino, et al. *Arthritis Rheum* 2003; 48:2122-2127.
8. Schiff et al. *Ann Rheum Dis* 2006; 65(7):889-894.
9. Furst D E, et al. *Ann Rheum Dis* 2005; 64:iv2-iv14.

EXAMPLE 23

Efficacy of Adalimumab (Humira®) in Clinical Practice: Patients with Moderate Disease Activity were Compared to Those with Severe Disease Activity The objective of this study was to compare the efficacy of adalimumab in patients with moderate and severe disease activity.

The following study was an open-label, multi-center, Phase IIIb study. Patients with moderate to severe rheumatoid arthritis who had an inadequate response to standard antirheumatic therapy were treated with adalimumab 40 mg every other week in addition to their pre-existing therapies. Patients with moderately to severely active RA who had an inadequate response to standard therapy, including methotrexate (MTX), were enrolled in this study. Patients were treated for 12 weeks with subcutaneous adalimumab 40 mg every other week (eow) in addition to their pre-existing but inadequate therapies. Inclusion criteria included: ≥18 years old; RA defined by ACR criteria for >3 months; active RA (>5 swollen joints and one of: RF+, 1 or more joint erosions, HAQ score>1); unsatisfactory response or intolerance to therapy as per provincial guidelines required for biologic therapy; and concomitant prednisone had to be <10 mg/day.

Effectiveness assessments included Disease Activity Score 28 (DAS28), ACR20/50/70 (including 0-28 SJC and TJC scores), and the Health Assessment Questionnaire (HAQ). Efficacy was assessed at baseline, 12 weeks, and 24 weeks of the study. Results for patients with moderate RA vs. patients with severe RA as defined by baseline DAS28 scores (moderate RA=3.2<DAS28=5.1 and severe RA=DAS28>5.1) were compared.

A total of 879 patients enrolled in the study. Totals of 772 and 238 patients were followed for 12 and 24 weeks, respectively. The study design included 879 patients during the open label treatment period, which was 12 weeks. During the open label period, patients received 40 mg of adalimumab every other week (eow), subcutaneously. The 12-week continuation period of the study included 772 patients, and occurred following the 12 week open label treatment period.

Baseline characteristics were: mean age=54.4 years; % female=78.7; mean RA duration=12.5 years; % with moderate (3.2<DAS28≤5.1) and severe (DAS28>5.1) disease activity=8 and 80, respectively; mean DAS28 scores for patients with moderate and severe disease activity=4.5±0.5 and 6.6±0.8, respectively; mean HAQ score for patients with moderate and severe disease activity=1.2±0.6 and 1.7±0.6, respectively. The baseline characteristics of the subgroup of patients who completed Week 24 were comparable to those of the overall study population. Baseline demographics are provided in Table 137 and 138:

TABLE 137

Baseline Demographics and Disease Severity

| Characteristics* | Moderate n = 162 | Severe n = 700 | Moderate and Severe N = 862 |
|---|---|---|---|
| Age (years) | 52.8 ± 11.8 | 54.8 ± 11.4 | 54.4 ± 11.5 |
| Female (%) | 123 (75.9) | 556 (79.4) | 679 (78.8) |
| Disease duration (years) | 12.9 ± 9.8 | 12.2 ± 9.5 | 12.3 ± 9.6 |
| CRP (mg/L)‡ | 8.5 ± 12.1 | 24.6 ± 32.0 | 21.6 ± 30.0 |
| ESR (mm/hr)§ | 12.5 ± 10.5 | 35.0 ± 24.0 | 30.7 ± 23.8 |
| HAQ (0-3) | 1.2 ± 0.6 | 1.7 ± 0.6 | 1.6 ± 0.6 |
| DAS28 | 4.5 ± 0.5 | 6.6 ± 0.8 | 6.2 ± 1.1 |
| SJC (0-28) | 10.5 ± 4.0 | 13.9 ± 5.3 | 13.3 ± 5.2 |
| TJC (0-28) | 8.0 ± 5.5 | 16.7 ± 6.2 | 15.1 ± 7.0 |
| RF > 20 IU/ml, n (%) | 110 (67.9) | 544 (77.7) | 654 (75.9) |

*Mean values ± SD, except percentages.
§Normal values for men and women are <20 mm/hr and <30 mm/hr, respectively.
‡Normal value is <10 mg/L.

TABLE 138

Baseline Demographics: Prior Antirheumatic Therapies

| Characteristics* | Moderate n = 162 | Severe n = 700 | P-value |
|---|---|---|---|
| % Failed 0 DMARD | 0.6 | 2.4 | 0.222 |
| % Failed 1 DMARDs | 3.1 | 6.1 | 0.181 |
| % Failed 2 DMARDs | 3.7 | 6.9 | 0.153 |
| % Failed >3 DMARDs | 92.6 | 84.6 | 0.008 |
| % Failed prior BDMARD | 19.8 | 29.3 | 0.015 |
| % Failed prior TNF inhibitor | 13.6 | 24.9 | 0.041 |
| % Failed infliximab | 6.2 | 8.9 | >0.999 |
| % Failed etanercept | 7.4 | 16.7 | 0.055 |

Both groups achieved statistically significant improvement in DAS28 scores at 12 weeks. Patients with severe disease activity demonstrated even greater decreases in DAS28 scores. DAS28 results are described below in Table 139.

TABLE 139

Course of DAS28 Scores for Patients with Moderate vs. Severe Disease Activity at Baseline

| | Time course | | | |
|---|---|---|---|---|
| | Baseline | Week 4 | Week 8 | Week 12 |
| Moderate disease activity Mean score | 6.6 | 5.1 | 4.7 | 4.5‡ |
| Severe disease activity Mean score | 4.5 | 3.5 | 3.3 | 3.1‡§ |

‡p < 0.001 for within-group comparison (follow-up visit vs. baseline).
§p < 0.005 for change between groups from Week 12 to baseline.

At 12 weeks, significantly more patients with moderate disease activity at baseline achieved clinical remission (DAS28<2.6) and other scores indicating remission and low disease activity (described in more detail below). Patients with severe disease activity demonstrated greater reductions in DAS28 scores than patients with moderate disease.

At Week 12, more patients with severe disease activity at baseline achieved an ACR20. At Week 12, ACR50 and ACR70 response rates were comparable between groups.

Both groups achieved statistically significant improvement in HAQ scores at 12 weeks. Patients with severe disease activity demonstrated greater reductions in DAS28 scores than patients with moderate disease. At 12 weeks, significantly more patients with moderate disease activity at baseline achieved HAQ scores indicating no physical limitations and other predefined target scores of the HAQ. HAQ score results are also presented below in Tables 140 and 141.

TABLE 140

Course of Mean HAQ Scores for Patients with Moderate vs. Severe Disease Activity at Baseline

| | | Time course | | | |
|---|---|---|---|---|---|
| | | Baseline | Week 4 | Week 8 | Week 12 |
| Mean HAQ score | Moderate disease activity | 1.7§ | 1.3 | 1.2 | 1.1‡§ |
| | Severe disease activity | 1.2 | 0.9 | 0.9 | 0.8‡ |

‡$p < 0.001$ for within-group comparison (Week 12 vs. baseline).
§$p < 0.005$ for between-group comparison (Week 12 vs. baseline).

TABLE 141

Percentages of Patients with Moderate vs. Severe Disease Activity by Categories of HAQ Score

| | | HAQ < 1.0 | HAQ < 0.5 | HAQ = 0 |
|---|---|---|---|---|
| % patients | Moderate disease activity | 60.0* | 40** | 18.6*** |
| | Severe disease activity | 43.6 | 22.3 | 10.6 |

*$p < 0.005$, $p < 0.005$, *$p < 0.014$ for between-group comparisons.

Overall, the results show that patients that had a moderate or a severe disease activity at baseline showed improvements of 1.5±1.1 and 2.1±1.4 in the DAS28 at 12 weeks ($p<0.001$ each group vs. baseline), respectively. Improvements in the HAQ scores for the same groups at 12 weeks were 0.4±0.4 and 0.5±0.6 ($p<0.001$ each groups vs. baseline). Significantly more patients that had a moderate than a severe disease activity at baseline achieved low disease activity and clinical remission at week 12, DAS28<3.2=55.4% vs. 19.5% $p<0.001$ and DAS28<2.6=31.7% vs. 11.0% $p<0.001$, respectively. In addition, DAS28<2.4=23.7% for moderate disease activity and 7.6% for severe disease activity ($p<0.005$). As well, significantly more patients with moderate than with severe disease activity at baseline achieved a HAQ<1.0, (60.0% vs. 43.6% p=0.001). Importantly, those effects were observed despite comparable improvements between the groups. Indeed, 51.0%, 25.2% and 12.6% of the patients that had a moderate disease activity at baseline achieved ACR20/50/70 responses at week 12. 61.1%, 32.4% and 13.0% of the patients that had a severe disease activity at baseline achieved ACR20/50/70 responses. Between groups analyses showed a differences in ACR20 response rates (p=0.03).

In conclusion, significantly more patients with moderate than with severe disease activity at baseline achieved clinical remission, as defined by DAS28<2.6, and HAQ<0.1. During the first 12 weeks, patients with severe disease activity at baseline experienced greater reductions in the signs and symptoms of the disease. More patients with moderate disease activity at baseline achieved clinical remission (DAS28<2.6) and a level of no functional limitations (HAQ=0). The treatment effects of adalimumab were comparable between both sub-groups of patients. These observations support the utility of adalimumab therapy in RA patients early in the disease course. Adalimumab therapy led to good outcomes in both subgroups, with patients with moderate RA achieving even better results. Adalimumab should be used in both patient populations. Its use in patients with moderate disease, before they reach more severe disease states, may increase the likelihood of achieving clinical remission.

EXAMPLE 24

Real Life Evaluation of Rheumatoid Arthritis in Patients Taking HUMIRA: Analysis at 6 Months of Adalimumab Therapy The following study addresses the long-term effectiveness of adalimumab in the clinical care setting. Thus, the objective of the study was to describe the clinical effectiveness, functional status and disease activity of rheumatoid arthritis patients receiving adalimumab therapy (HUMIRA™) over a two year period.

The study was a multi-center, open-label observational study of adalimumab used in routine practice. A total of 1000 patients will be enrolled from approximately 150 sites.

Eligible participants are =18 years of age, either naïve to adalimumab therapy are receiving adalimumab therapy for less than 4 months and have moderate to severe active disease. Physicians collected baseline demographics and medical history including previous and concomitant anti-rheumatic medication and comorbidities. Physicians also completed a DAS28 while patients completed a HAQ-DI, RADAI and global assessment at every 6 months. Eligibility criteria included:
=18 years of age
Moderately to severely active RA
Naïve to adalimumab therapy OR receiving adalimumab therapy=4 months
Inadequate response to one or more DMARDs
Written and informed consent Preliminary analysis included 127 patients who received adalimumab therapy for =6 months. Data collected by the patients and physician included the following:
Physician: comorbidities; previous antirheumatic therapies; concomitant antirhemautic therapies; previous DAS28 or HAQ; and DAS28 score.
Patient: HAQ; RADAI; and global.

This initial analysis reports on the 127 patients who had received=6 months of adalimumab therapy at the time of the analysis. 78.4% were female and 89.8% were Caucasian, with a mean age of 57.0 and a mean disease duration of 10.5 years. Baseline disease measures were DAS28=5.41, HAQ=1.54, and RADAI=5.33. Baseline demographics are shown in Table 142.

TABLE 142

Baseline Patient Demographics and Clinical Characteristics (N = 127)

| Age (mean ± SD) | 57.0 ± 12.1 |
|---|---|
| Disease duration (mean ± SD) | 10.5 ± 10.0 |
| Characteristics | N (%) |
| Female | 100 (78.7) |
| Caucasian | 114 (89.8) |
| Disease Status | Mean ± SD |
| DAS28 | 5.41 ± 1.41 |
| HAQ pain (0-3) | 1.74 ± 0.75 |
| HAQ DI (0-3) | 1.54 ± 0.71 |
| RADAI (0-10) | 5.33 ± 1.84 |
| Patient Global | 3.20 ± 0.82 |

TABLE 142-continued

Baseline Patient Demographics and Clinical Characteristics (N = 127)

| | |
|---|---|
| Previous biologics | 0.50 ± 0.77 |
| Previous DMARDS | 3.28 ± 1.19 |
| Current antirheumatic therapies | 2.09 ± 1.11 |

The results show that mean decrease (improvement) from baseline to 6 months in DAS28 was 1.35 (p<0.001, n=101), with 66% of patients reaching a EULAR response of good or moderate, 16% achieving low disease activity (2.6=DAS28=3.2), and 18% reaching clinical remission (DAS28<2.6). HAQ improved by 0.36 (p<0.001, n=124). A minimum clinically important improvement of at least 0.22 in the HAQ was observed for 55% of patients (n=124). Mean HAQ DI and HAQ pain scores are shown in Table 143.

TABLE 143

Mean HAQ DI and HAQ Pain Scores at Baseline and 6 Months of Adalimumab Therapy

| | HAQ DI (0-3) | HAQ Pain (0-3) |
|---|---|---|
| Baseline | 1.54 | 1.74 |
| 6 Months | 1.18* | 1.29* |

*p < 0.001

DAS improvements are shown in Tables 144 and 145.

TABLE 144

Mean DAS28 scores, TJC, and SJC at Baseline and 6 Months of Adalimumab Therapy

| | DAS score (0-9.4) | Total Joint Count (0-28) | Swollen Joint Count (0-28) |
|---|---|---|---|
| Baseline | 5.41 | 11.01 | 9.33 |
| 6 Months | 4.06* | 6.27* | 4.28* |

*p < 0.001

TABLE 145

Mean DAS28 scores and Changes in DAS28 Scores by Disease Activity at Baseline and 6 Months of Adalimumab Therapy

| | Disease activity | | |
|---|---|---|---|
| | Low DAS28 (<3.2) | Moderate DAS28 (>3.2 and <5.1) | High DAS28 (>5.1) |
| Baseline | 2.49 | 4.48 | 6.26 |
| 6 Month | 2.2 | 3.5** | 4.67** |
| Δ Change | −0.29 | −0.99* | −1.6* |

*p < 0.001,
** p < 0.05

The RADAI score decreased (improved) by 1.43 (p<0.0001, n=125), and the patient global decreased (improved) by 0.55 (p<0.0001, n=125). The improvement in the mean RADAI score is shown below in Table 146. Correlation of RADAI and DAS28 scores after 6 months of adalimumab therapy (n=100) is shown in FIG. 30.

TABLE 146

Mean RADAI, Total Joint Count, Total Joint Score, and Stiffness Score at Baseline and 6 Months of Adalimumab Therapy

| | RADAI score (0-10) | Total Joint Count (0-16) | Total Joint Score (0-3) | Stiffness (0-6) |
|---|---|---|---|---|
| Baseline | 5.33 | 9.64 | 1.71 | 2.43 |
| 6 Months | 3.9* | 7.87* | 1.46* | 1.96** |

*p < 0.001,
**p < 0.05

Improvements in global scores over 6 months are shown in Table 147.

TABLE 147

Percentages of Patients with Various Global Scale Scores at Baseline and 6 Months of Adalimumab Therapy

| | Very poor | Poor | Fair | Good | Very good |
|---|---|---|---|---|---|
| % pts baseline | 5% | 27% | 56% | 9% | 4% |
| % pts 6 months | 5% | 9% | 42% | 35% | 10% |

Moreover, 54% of patients indicated that their symptoms had improved. In addition, 35% of patients had previous experience with an RA biologic (TNF antagonist, 95%; IL-1 receptor antagonist, 20%; both, 14%), and 94% had received=2 DMARDs before initiating adalimumab (mean=3.28). The most common previous DMARDs were methotrexate (48%), leflunomide (40%), and hydroxychloroquine (24%). Currently, 67% of patients are receiving=2 or more DMARDs concomitantly, with methotrexate and prednisone accounting for 70% and 33%, respectively. Correlation between EULAR responses and DAS28 scores are shown below in Table 148. Biologic and DMARD use prior to and during adalimumab therapy is shown in Tables 149-151.

TABLE 148

Patients with Good, Moderate, or No EULAR Response of DAS28 Following 6 Months of Adalimumab Therapy

| | Improvement in DAS28 from Baseline | | |
|---|---|---|---|
| N = 101 | >1.2 | >0.6 and <1.2 | <0.6 |
| ≤3.2 | 26% good | 38% moderate | 37% none |
| >3.2 and ≤5.1 | 38% moderate | 38% moderate | 37% none |
| >5.1 | 38% moderate | 37% none | 37% none |

TABLE 149

Biologic Use Prior to Adalimumab Therapy

| Previous Biologic Use (N = 127) | N (%) |
|---|---|
| No Previous Biologic Use | 83 (65.4) |
| Previous Biologic Use | 44 (34.6) |
| TNF Antagonist | 42 (95.5) |
| IL-1 Receptor Antagonist | 9 (20.5) |
| Both | 6 (13.6) |

TABLE 150

DMARD Use Prior to Adalimumab Therapy

| Previous DMARD Use | N (%) |
|---|---|
| Methotrexate | 43 (47.8) |
| Leflunomide | 36 (40.0) |
| Hydroxychloroquine | 22 (24.4) |
| Plaquenil | 18 (20.0) |
| Sulfasalazine | 17 (18.9) |
| Prednisone | 13 (14.4) |

TABLE 151

Concomitant DMARD Use During Adalimumab Therapy

| Current DMARD Use | N (%) |
|---|---|
| Methotrexate | 85 (69.7) |
| Prednisone | 40 (32.8) |
| Plaquenil | 29 (23.8) |
| Leflunomide | 22 (18.0) |
| Celebrex | 15 (12.3) |
| Sulfasalazine | 12 (9.8) |

In conclusion, the patients in the above study are representative of a moderate to severe RA population. At baseline, they had moderate to severe disease activity (DAS28), and established, long-standing disease. The majority had previously received=2 DMARDs, and even a previous RA biologic before initiating adalimumab. After 6 months of adalimumab therapy, most patients had achieved clinically important improvements in disease activity and physical function. 66% of patients obtained a EULAR response of good or moderate, with 18% achieving clinical remission (DAS28<2.6) and 16% reaching a low disease activity (2.6=DAS28=3.2). After 6 months of treatment, most patients had achieved clinically important improvements in both disease activity and physical function.

EXAMPLE 25

Improvement and Long-Term Maintenance of Quality of Life During Treatment with Adalimumab in Severe Rheumatoid Arthritis Measurement of patient reported outcomes (PRO) are relevant to an overall health care quality assessment (FDA et al, 2006). Although improvements in clinical parameters with novel biologic therapies have been established in RA, the impact of biologics on certain PROs in this disease requires further research. There are data to support the impact of biologics on HAQ and the SF-36; however, little or no information on other aspects of HRQL, such as special facets of quality of life (e.g., fatigue) or health-related utility, are available. Evaluation of fatigue in RA patients is especially important because clinically significant oppressive fatigue is present in 40% to 80% of RA patients and research supports an association between disability and fatigue (Rupp et al 2004). Also, from the perspective of the patient, a reduction of fatigue constitutes an important component of disease remission. It is not surprising that the Outcome Measures in Rheumatoid Arthritis Clinical Trials (OMERACT) group devoted discussion during a recent patient-perspective workshop to the relative impact of fatigue on patients.

In the current study, a number of PRO were applied measures simultaneously in a 3-year single-study setting. The aim is to analyze these results from patients with long-standing severe RA, focusing on measurement of fatigue and health utility.

This long-term, open-label health outcomes extension study (Study 8) included 505 patients with long-standing RA who had received adalimumab therapy during one of six Phase II/III studies, of which most were double-blind, randomized, placebo-controlled studies of at least 26 weeks in duration (FIG. 31). Patients received adalimumab 40 mg every other week and were followed for up to 144 weeks. The study was performed at 47 investigational sites in three countries, and conducted in conjunction with another clinical study, which was a multicenter, open-label study evaluating the clinical effectiveness of adalimumab in patients with RA.

The following example provides the largest of the preceding randomized dose-finding studies, and was a pivotal 6-month, Phase III, placebo-controlled study. Because data in the below study were collected in a manner similar to this study, data from patients in the placebo and adalimumab treatment arms were analyzed as a subgroup in this study. The subgroups described below refer to the current study, unless otherwise indicated.

Sociodemographic and medical history data were assessed at the baseline visit. Clinical examination findings (e.g., joint examination, morning stiffness), disease assessments (patients' and physicians' global assessment of disease activity and patients' assessment of pain), and HRQL data were recorded every 8 weeks.

Patients with RA, as defined by the 1987-revised American College of Rheumatology (ACR) criteria (Arnett et al 1988), were included in the study. Exclusion criteria included the following: 1) pregnant or breastfeeding females; 2) known human immunodeficiency virus (HIV)-positive status; 3) a history of alcohol or drug abuse within 6 months prior to study entry; 4) ongoing or active clinically relevant infection or any major episode of infection requiring hospitalization or treatment with intravenous antibiotics (within 30 days) or oral antibiotics (within 15 days); and 5) underlying cardiac, pulmonary, metabolic, renal, or gastrointestinal conditions; chronic or latent infectious diseases; immune deficiency; or abnormal laboratory values that, in the opinion of the investigator or the medical monitor, placed the patient at an unacceptable risk.

The SF-36 is the most widely used generic measure of HRQL. It covers eight areas of health status, including physical functioning, role-physical, bodily pain, general health, vitality, social functioning, role-emotional, and mental health. The SF-36 scores range between 0 (worst) and 100 (best). In addition, physical component summary (PCS) and mental component summary (MCS) scores can be derived. In RA, minimum clinically important differences (MCIDs) were defined as a 5- to 10-point change from baseline for the SF-36 subdomains and a 2.5- to 5-point change from baseline for the PCS and MCS (Kosinski et al, 2000).

Studies showed that patients regard oppressive fatigue as a major determinant of their overall HRQL (Kirwan et al 2005). The FACIT-Fatigue was used to assess fatigue in patients enrolled in this study. The FACIT-Fatigue scale includes 13 specific items linked with fatigue: fatigue, weakness, listlessness, tiredness, trouble with starting things, trouble with finishing things, energy, activity, sleep, eating, help doing activities, frustration, and social activities. FACIT-Fatigue scores range from 0 to 52, with higher scores representing less fatigue. The instrument has been validated for the general population and for patients with RA. The MCID for FACIT-Fatigue in RA was determined to be at least a 4-point change from baseline (Cella et al, 2005).

The health-related utility of patients suffering from RA was evaluated using the HUI3. The first component of the HUI3 is a multi-attribute health status classification system that is used to describe the health status of the patient (e.g., emotion or pain). The second component is a multi-attribute utility function that is used to value the health status as measured within the corresponding multi-attribute health status classification system. These scores can be directly converted into quality-adjusted life years (QALYs). Health utility scores range from 0 to 1, with 1 denoting perfect health and 0 denoting death. The construction of the scale is one of preference or desirability. The more preferable or desirable a health state, the higher its utility. In addition, negative scores are possible and represent health states considered worse than death. Score changes of 0.03 are considered clinically important (Horsman et al, 2003).

All patients enrolled in the study were included in the full analysis set. For dichotomous and categorical variables, absolute and relative frequencies were calculated. Metric parameters are described by mean, standard deviation, and/or standard error of the mean. HRQL data are presented as observed cases. A last-observation-carried-forward approach was used in some analyses for the subgroup of patients from study DE026 who participated in the placebo-controlled study with 40 mg adalimumab every other week for 26 weeks (n=99). All statistical analyses were performed using SAS® Version 8.2 (SAS Institute Inc., Cary, N.C., USA).

Patients

A total of 505 patients were enrolled in the study, with the greatest percentage of patients enrolled in Germany (n=153). Patients were recruited from several preceding dose-finding studies; the majority of patients originated from (FIG. 31).

On average, patients participated in the health outcomes study for 1.6 years (mean: 1.57±0.63 years, median: 1.8 years). Baseline patient characteristics are provided for two patient populations (Table 152): the current subgroup and the overall Study 8 population. Baseline data for the subgroup (n=99) capture data from patients who were naïve to biologic treatment and who received the same adalimumab dosage regimen (adalimumab 40 mg every other week) as the overall population for 26 weeks. Data from the cohort are included in the entire study population (N=505). There were no statistically significant differences between placebo and adalimumab groups at baseline from the study for all measures.

TABLE 152

Baseline demographic data from subgroup and overall Study 8 population

| Variable | | Subgroup receiving 40 mg adalimumab for 26 weeks prior to DE033 (n = 99) | Overall Study 8 population (N = 505) |
|---|---|---|---|
| Female | n (%) | 79 (79.8) | 390 (77.2) |
| Age (y) | Median (range) | 54 (19-80) | 55[a] (22-82) |
| Weight (kg) | Mean ± SD | 69.7 ± 13.92 | 69.12 ± 12.90 |
| Height (cm) | Mean ± SD | 165.9 ± 8.47 | 166.06 ± 8.90 |
| Caucasian | n (%) | 95 (96.0) | 498 (98.6) |
| BMI (kg/m²) | Mean ± SD | 25.4 ± 4.96 | 25.06[b] ± 4.34 |
| Employed[c] | n (%) | NA | 152 (30.1) |
| Retired | n (%) | NA | 220 (43.6) |

TABLE 152-continued

Baseline demographic data from subgroup and overall Study 8 population

| Variable | | Subgroup receiving 40 mg adalimumab for 26 weeks prior to DE033 (n = 99) | Overall Study 8 population (N = 505) |
|---|---|---|---|
| RA duration | Mean ± SD | 10.3 ± 7.05 | 12.36 ± 7.69 |
| Number of previous DMARDS failed | Mean ± SD | 3.8 ± 1.77 | 3.7 ± 1.82 |
| TJC (0-68)[d] | Mean ± SD | 33.81 ± 15.97 | 14.58 ± 14.89 |
| SJC (0-66)[d] | Mean ± SD | 21.02 ± 10.97 | 8.23 ± 8.18 |
| DAS28 | Mean ± SD | 5.39 ± 1.62 | 4.58 ± 1.58 |

[a]Eight patients missing.
[b]Two patients missing.
[c]Including self-employed.
[d]Baseline data for both cohorts differ, because patients in the overall population had already been treated with adalimumab.
BMI = body mass index.
DAS28 = Disease Activity Score 28;
DMARDs = disease-modifying antirheumatic drugs;
RA = rheumatoid arthritis;
SJC = swollen joint count;
TJC = total joint count.

Overall, most of the patients in the entire study group had long-standing severe RA, with a mean duration of 12.4 years and an average of up to four failed previous disease-modifying antirheumatic drugs. Approximately three quarters of patients were female, confirming a similar gender distribution of RA patients among industrialized countries.

Among the subgroup, there were no significant differences in baseline SF-36 scores between the placebo and adalimumab treatment groups. At Week 26, patients receiving adalimumab achieved significant improvement in all SF-36 subdomains; changes were statistically significant compared with placebo and compared with baseline (Table 153). Increases in all SF-36 subdomains in the subgroup were maintained over 3 years (Table 154). Table 155 provides a comparison of the baseline SF-36 scores for patients in the study (reflecting scores prior to adalimumab treatment), baseline SF-36 score of the entire study population, and SF-36 scores after 144 weeks of adalimumab treatment. SF-36 scores from the subgroup (Table 154) were consistent with SF-36 scores from the entire study population (Table 155). All increases in the SF-36 subdomains of the SF-36 were clinically relevant.

TABLE 153

Short Form 36 (SF-36) health profile scores at baseline and after 26 weeks of treatment with adalimumab or placebo in the subgroup (n = 99)

| PatientType | | SF-36 Domain Scores |
|---|---|---|
| Physical Functioning | Placebo (Baseline) | 28 |
| | Placebo (week 26) | 30 |
| | Adalimumab 40 mg eow (Baseline) | 26 |
| | Adalimumab (week 26) | 39 |
| Bodily Pain | Placebo (Baseline) | 26 |
| | Placebo (week 26) | 33 |
| | Adalimumab 40 mg eow (Baseline) | 24 |
| | Adalimumab (week 26) | 43 |
| Role-Physical | Placebo (Baseline) | 15 |
| | Placebo (week 26) | 23 |
| | Adalimumab 40 mg eow (Baseline) | 11 |
| | Adalimumab (week 26) | 34 |

TABLE 153-continued

Short Form 36 (SF-36) health profile scores at baseline and after 26 weeks of treatment with adalimumab or placebo in the subgroup (n = 99)

| Patient Type | | SF-36 Domain Scores |
|---|---|---|
| Role-Emotional | Placebo (Baseline) | 45 |
| | Placebo (week 26) | 45 |
| | Adalimumab 40 mg eow (Baseline) | 40 |
| | Adalimumab (week 26) | 57 |
| General Health | Placebo (Baseline) | 40 |
| | Placebo (week 26) | 41 |
| | Adalimumab 40 mg eow (Baseline) | 41 |
| | Adalimumab (week 26) | 49 |
| Mental Health | Placebo (Baseline) | 58 |
| | Placebo (week 26) | 60 |
| | Adalimumab 40 mg eow (Baseline) | 57 |
| | Adalimumab (week 26) | 66 |
| Vitality | Placebo (Baseline) | 33 |
| | Placebo (week 26) | 36 |
| | Adalimumab 40 mg eow (Baseline) | 32 |
| | Adalimumab (week 26) | 47 |
| Social Functioning | Placebo (Baseline) | 53 |
| | Placebo (week 26) | 56 |
| | Adalimumab 40 mg eow (Baseline) | 48 |
| | Adalimumab (week 26) | 61 |

Adalimumab $P < 0.01$ vs. baseline and vs. placebo for all subdomains except role-physical, which was $P < 0.05$. The placebo-treated patients did not achieve statistical significance vs. baseline. Last observation carried forward. eow = every other week.
*United States population norms from Ware et al. 1997.

TABLE 154

Short Form 36 (SF-36) health profile scores in the subgroup over 3 years (n = 99)

| | Weeks | SF-36 Domain Scores |
|---|---|---|
| Physical Functioning | 0 | 25 |
| | 26 | 35 |
| | 50 | 35 |
| | 98 | 35 |
| | 170 | 35 |
| Bodily Pain | 0 | 24 |
| | 26 | 45 |
| | 50 | 40 |
| | 98 | 40 |
| | 170 | 40 |
| Role-Physical | 0 | 11 |
| | 26 | 35 |
| | 50 | 28 |
| | 98 | 30 |
| | 170 | 30 |
| Role-Emotional | 0 | 40 |
| | 26 | 58 |
| | 50 | 56 |
| | 98 | 54 |
| | 170 | 55 |
| General Health | 0 | 41 |
| | 26 | 49 |
| | 50 | 48 |
| | 98 | 47 |
| | 170 | 48 |
| Mental Health | 0 | 56 |
| | 26 | 66 |
| | 50 | 65 |
| | 98 | 66 |
| | 170 | 67 |
| Vitality | 0 | 32 |
| | 26 | 47 |
| | 50 | 44 |
| | 98 | 45 |
| | 170 | 47 |
| Social Functioning | 0 | 48 |
| | 26 | 60 |
| | 50 | 59 |
| | 98 | 58 |
| | 170 | 57 |

Adalimumab $P < 0.02$ vs. baseline for all domains except role-physical, which was $P < 0.05$, on and after week 26. Last observation carried forward.

TABLE 155

Change in SF-36 values over 3 years

| SF-36 domain | Baseline of subgroup (current study) | | | Baseline of overall Study 8 population | | | AUC for 144 weeks of treatment[a,b] | |
|---|---|---|---|---|---|---|---|---|
| | n | Mean ± SD | Median | n | Mean ± SD | Median | Mean ± SD | Median |
| Physical functioning | 97 | 25.81 ± 19.49 | 20.0 | 501 | 44.06 ± 25.34 | 45.0 | 44.93 ± 23.25 | 44.58 |
| Role physical | 95 | 11.05 ± 21.49 | 0.0 | 501 | 40.81 ± 41.34 | 25.0 | 39.74 ± 31.56 | 35.42 |
| Bodily pain | 98 | 24.03 ± 16.56 | 22.0 | 501 | 49.54 ± 21.73 | 51.0 | 50.16 ± 17.32 | 48.56 |
| General health | 95 | 41.23 ± 18.31 | 40.0 | 501 | 50.32 ± 20.10 | 47.0 | 50.03 ± 17.87 | 48.92 |
| Vitality | 98 | 31.85 ± 17.76 | 30.0 | 501 | 49.17 ± 20.94 | 50.0 | 49.50 ± 17.75 | 49.58 |
| Social functioning | 98 | 47.58 ± 22.82 | 50.0 | 501 | 68.65 ± 25.63 | 75.0 | 68.53 ± 20.77 | 68.75 |
| Role emotional | 95 | 40.35 ± 44.80 | 33.3 | 500 | 62.06 ± 43.77 | 100.0 | 59.91 ± 34.50 | 64.73 |
| Mental health | 98 | 56.95 ± 21.86 | 60.0 | 501 | 67.58 ± 19.76 | 72.0 | 66.68 ± 17.31 | 68.67 |
| Physical component score (PCS) | | NA | | 500 | 33.95 ± 9.72 | 33.3 | 33.47 ± 8.87 | 33.32 |

TABLE 155-continued

| | Change in SF-36 values over 3 years | | | | | | |
|---|---|---|---|---|---|---|---|
| SF-36 | Baseline of subgroup (current study) | | | Baseline of overall Study 8 population | | | AUC for 144 weeks of treatment[a,b] | |
| domain | n | Mean ± SD | Median | n | Mean ± SD | Median | Mean ± SD | Median |
| Mental component score (MCS) | | NA | | 500 | 49.36 ± 11.37 | 51.9 | 47.33 ± 10.60 | 48.60 |

[a]Area under the curve (AUC) values are based on the average value per visit throughout the whole study.
[b]Results demonstrate no significant changes from baseline of overall DE033 population and maintenance of effects of initial treatment.

In the subgroup, rapid and statistically significant improvements from baseline in FACIT-Fatigue scores were observed after 12 weeks of adalimumab treatment and were maintained for more than 3 years (FIG. 32). The FACIT-Fatigue score for adalimumab patients at baseline was 26.08 (±10.41) and increased to 34.63 (±11.67) at Week 26. From Week 26 to Week 170, FACIT-Fatigue scores remained stable (33.28±11.42 at Week 170). The difference between adalimumab and placebo and the differences in change from baseline between placebo and adalimumab treatments were both statistically significant and clinically meaningful at each time point assessed. For adalimumab-treated patients, mean improvements in FACIT-Fatigue scores were more than 4, indicating clinically meaningful improvements. The changes from baseline in fatigue scores for the placebo group were not statistically significant or clinically important. Results were robust to various methods of imputation for missing values.

In the subgroup, adalimumab-treated patients had a significant increase from baseline in the overall utility score at 26 weeks, which was maintained over 3 years (FIG. 33). HUI3 scores were 0.27 and 0.29 at baseline and 0.45 and 0.35 at Week 26 for adalimumab and placebo, respectively. The differences between adalimumab and placebo were statistically significant at 26 weeks. At Week 170, the utility score was 0.45 for adalimumab treatment. After adjusting for placebo, the adalimumab group experienced an increase of 0.11 in HUI3 scores, reflecting a clinically meaningful difference between treatment groups. Results were consistent regardless of whether or not imputation for missing values was conducted.

This health outcomes trial was conducted as a companion study to the adalimumab clinical trials in patients with long-standing RA. HRQL was assessed using specific quality-of-life questionnaires (SF-36, FACIT-Fatigue, HUI3). All HRQL measures reflected a rapid and statistically significant improvement from baseline in HRQL after initiation of adalimumab therapy.

Improvements in HRQL measures were considered clinically meaningful and were maintained for up to 3 years. Mean SF-36, FACIT-Fatigue, and HUI3 scores rapidly improved and remained stable during the entire treatment period. SF-36 scores indicated that patients with late-stage RA are especially impaired in their physical functioning, physical role, bodily pain, general health, and vitality. The maintenance of the utility values over time is important to clinical practice as disability and clinical parameters, such as joint and bone destruction, progress over time, especially among patients with long-standing RA, such as those enrolled in this study (Pollard et al, 2005).

This study provided the only information to date on the positive and clinically meaningful effects of long-term treatment with adalimumab or any other TNF antagonist on certain facets of HRQL. This was the first trial to measure long-term effects of a TNF antagonist on fatigue. Measuring fatigue as a marker of impairment proved to be valid; FACIT-Fatigue results significantly correlated with other more well-established HRQL measures. To date, the HUI3 previously has been used only once in a clinical trial of RA patients receiving TNF-antagonist treatment. Consistent with the results of this study, adalimumab provided significant improvement in HUI3 in patients with long-standing RA during the 12-month duration of the study (Torrance et al, 2004).

This study clearly demonstrated that, with the evaluated instrument, even relatively small improvements can be observed. The strengths of this study are the long study duration, the size of the cohort, the parallel assessment of multiple PRO outcomes measures in identical time frames, the multinational approach in industrialized countries (all with existing high treatment standard for RA patients), and the combination of PRO results within a clinical trial.

In addition to the HAQ, a measure routinely incorporated in clinical trials, this study supports the use of at least two additional measures to further characterize the burden of disease imposed on patients. These are the SF-36 and the FACIT-Fatigue. The SF-36 can be used to gain utilities and reflects eight different facets of HRQL. Each of these facets describes an area in which patients with RA exhibit significant impairment as compared with the general population. The FACIT-Fatigue also provides researchers insight into one of the issues of particular concern to patients: oppressive fatigue.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

What is claimed:

1. A method for treating an adult patient having moderate to severe active rheumatoid arthritis (RA), wherein the patient is nonresponsive to treatment with etanercept and infliximab, the method comprising administering 40 mg of adalimumab to the patient every other week to thereby treat the moderate to severe active RA.

2. The method of claim 1, wherein treatment is assessed by an improvement in EULAR score.

3. The method of claim 1, wherein treatment is assessed by achieving an ACR20 response.

4. The method of claim 1, wherein adalimumab is administered to the patient by subcutaneous injection.

5. The method of claim 1, wherein said 40 mg adalimumab is comprised in a pre-filled syringe for subcutaneous injection.

6. The method of claim 1, wherein said 40 mg adalimumab is formulated at a concentration of 50 mg/ml.

* * * * *

SEQUENCE LISTING

<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: VARIANT
<222> LOCATION: 9
<223> OTHER INFORMATION: Xaa = Thr or Ala

```
<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
1               5

<210> SEQ ID NO 9
<211> LENGTH: 107
```

```
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Tyr
                 85                  90                  95

Ala Phe Gly Gln Gly Thr Lys Val Glu Ile Lys
             100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Asp Trp Val
         35                  40                  45

Ser Ala Ile Thr Trp Asn Ser Gly His Ile Asp Tyr Ala Asp Ser Val
 50                  55                  60

Glu Gly Arg Phe Ala Val Ser Arg Asp Asn Ala Lys Asn Ala Leu Tyr
 65                  70                  75                  80

Leu Gln Met Asn Ser Leu Arg Pro Glu Asp Thr Ala Val Tyr Tyr Cys
                 85                  90                  95

Thr Lys Ala Ser Tyr Leu Ser Thr Ser Ser Ser Leu Asp Asn Trp Gly
             100                 105                 110

Gln Gly Thr Leu Val Thr Val Ser Ser
         115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
 1               5

<210> SEQ ID NO 12
<211> LENGTH: 9
<212> TYPE: PRT
```

```
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
 1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5

<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
 1               5

<210> SEQ ID NO 18
<211> LENGTH: 9
<212> TYPE: PRT
<213> ORGANISM: Artificial Sequence
```

```
<220> FEATURE:
<223> OTHER INFORMATION: VLLOG7 light chain variable region CDR3

<400> SEQUENCE: 18

Gln Lys Tyr Asn Ser Ala Pro Tyr Asn
 1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

Gln Lys Tyr Thr Ser Ala Pro Tyr Thr
 1               5

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

Gln Lys Tyr Asn Arg Ala Pro Tyr Asn
 1               5

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3

<400> SEQUENCE: 21

Gln Lys Tyr Asn Ser Ala Ala Tyr Ser
 1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
 1               5

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
 1               5

<210> SEQ ID NO 24
<211> LENGTH: 9
<212> TYPE: PRT
<213> ORGANISM: Artificial Sequence
<220> FEATURE:
```

```
<223> OTHER INFORMATION: VL0.1F4 light chain variable region CDR3

<400> SEQUENCE: 24

Gln Lys Tyr Ile Ser Ala Pro Tyr Thr
 1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
 1               5

<210> SEQ ID NO 26
<211> LENGTH: 9
<212> TYPE: PRT
<213> ORGANISM: Artificial Sequence
<220> FEATURE:
<223> OTHER INFORMATION: L0E7.A light chain variable region CDR3

<400> SEQUENCE: 26

Gln Arg Tyr Asn Arg Ala Pro Tyr Ala
 1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
 1               5                   10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
 1               5                   10

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
 1               5                   10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3
```

```
<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
1               5                   10

<210> SEQ ID NO 36
<211> LENGTH: 321
<212> TYPE: DNA
<213> ORGANISM: Artificial Sequence
<220> FEATURE:
<223> OTHER INFORMATION: adalimumab light chain variable region
```

```
<400> SEQUENCE: 36
gacatccaga tgacccagtc tccatcctcc ctgtctgcat ctgtagggga cagagtcacc        60
atcacttgtc gggcaagtca gggcatcaga aattacttag cctggtatca gcaaaaacca       120
gggaaagccc ctaagctcct gatctatgct gcatccactt tgcaatcagg ggtcccatct       180
cggttcagtg gcagtggatc tgggacagat ttcactctca ccatcagcag cctacagcct       240
gaagatgttg caacttatta ctgtcaaagg tataaccgtg caccgtatac ttttggccag       300
gggaccaagg tggaaatcaa a                                                 321

<210> SEQ ID NO 37
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 37
gaggtgcagc tggtggagtc tgggggaggc ttggtacagc ccggcaggtc cctgagactc        60
tcctgtgcgg cctctggatt cacctttgat gattatgcca tgcactgggt ccggcaagct       120
ccagggaagg gcctggaatg ggtctcagct atcacttgga atagtggtca catagactat       180
gcggactctg tggagggccg attcaccatc tccagagaca acgccaagaa ctccctgtat       240
ctgcaaatga acagtctgag agctgaggat acggccgtat attactgtgc gaaagtctcg       300
taccttagca ccgcgtcctc ccttgactat tggggccaag gtaccctggt caccgtctcg       360
agt                                                                     363
```